United States Patent [19]

Fung et al.

[11] Patent Number: 5,268,374
[45] Date of Patent: Dec. 7, 1993

[54] NON-PEPTIDE RENIN INHIBITORS

[75] Inventors: Anthony K. L. Fung, Gurnee; William R. Baker, Libertyville, both of Ill.; Yoek-Lin Armiger, Elk Creek, Va.; Saul H. Rosenberg, Libertyville, Ill.; Jacob J. Plattner, Libertyville, Ill.; Steven A. Boyd, Palatine, Ill.

[73] Assignee: Abbott Laboratories, Abbott Park, Ill.

[21] Appl. No.: 700,185

[22] PCT Filed: Oct. 3, 1989

[86] PCT No.: PCT/US89/04385

§ 371 Date: May 22, 1991

§ 102(e) Date: May 22, 1991

Related U.S. Application Data

[63] Continuation-in-part of Ser. No. 393,721, Aug. 14, 1989, abandoned, which is a continuation-in-part of Ser. No. 253,282, Oct. 4, 1988, abandoned.

[51] Int. Cl.$^5$ .................. A61K 37/43; C07K 5/08
[52] U.S. Cl. .................. 514/237.2; 514/316; 514/318; 514/326; 514/336; 514/340; 544/130; 546/208; 546/186; 548/518; 548/950; 548/953; 548/954; 548/962
[58] Field of Search .................. 544/130; 514/237.2, 514/316, 318, 326, 336, 340; 548/518, 950, 953, 954, 962; 546/208, 186

[56] References Cited

U.S. PATENT DOCUMENTS

| | | | |
|---|---|---|---|
| 4,548,926 | 10/1985 | Matsueda et al. | 514/19 |
| 4,657,931 | 4/1987 | Baran et al. | 514/616 |
| 4,680,284 | 7/1987 | Luly et al. | 514/18 |
| 4,713,445 | 12/1987 | Szelke et al. | 260/112.5 R |
| 4,725,584 | 2/1988 | Luly et al. | 514/19 |
| 4,727,060 | 2/1988 | Buhlmayer et al. | 514/18 |
| 4,755,592 | 7/1988 | Raddatz et al. | 530/323 |
| 4,758,584 | 7/1988 | Buhlmayer et al. | 514/400 |
| 4,782,043 | 11/1988 | Boger et al. | 514/11 |
| 4,812,442 | 3/1989 | Boger et al. | 514/83 |
| 4,837,204 | 6/1989 | Rosenberg et al. | 514/18 |
| 4,845,079 | 7/1989 | Luly et al. | 514/18 |

FOREIGN PATENT DOCUMENTS

| | | |
|---|---|---|
| 76222/87 | 2/1988 | Australia. |
| 184855 | 6/1986 | European Pat. Off.. |
| 189203 | 7/1986 | European Pat. Off.. |
| 0228192 | 7/1987 | European Pat. Off.. |
| 23020266 | 7/1987 | European Pat. Off.. |
| 0231919 | 8/1987 | European Pat. Off.. |
| 244083 | 11/1987 | European Pat. Off.. |
| 0310070 | 4/1989 | European Pat. Off.. |
| 0310071 | 4/1989 | European Pat. Off.. |
| 0310072 | 4/1989 | European Pat. Off.. |
| 0310073 | 4/1989 | European Pat. Off.. |
| 0311012 | 4/1989 | European Pat. Off.. |
| 3721855 | 9/1988 | Fed. Rep. of Germany. |
| WO87/02581 | 5/1987 | PCT Int'l Appl.. |
| WO87/02986 | 5/1987 | PCT Int'l Appl.. |
| WO88/05050 | 7/1988 | PCT Int'l Appl.. |

OTHER PUBLICATIONS

Chemical Abstracts Service; Abstract 110:24311t 1989 Corresponding to EP229667 (Abbott Labs).
Szelke, et al., Nature 299 555–557 (1982).
Boger, et al., Nature 303 81–84 (1983).
Richards, FEBS Lett. 247 113 (1989).
Hanson, Biochem. Biophys. Res. Commun. 132 155 (1985).
Moore, Biochem. Biophys. Res. Commun. 159 420 (1989).
Billich, J. Biol. Chem., 263 17905 (1988).

*Primary Examiner*—Marianne M. Cintins
*Assistant Examiner*—Catherine S. Kilby Scalzo
*Attorney, Agent, or Firm*—Steven R. Crowley

[57] ABSTRACT

The present invention relates to renin inhibiting compounds of the formula:

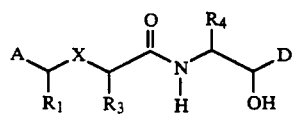

10 Claims, No Drawings

NON-PEPTIDE RENIN INHIBITORS

This is a continuation-in-part of U.S. patent application Ser. No. 393,721, filed Aug. 14, 1989, abandoned which is a continuation-in-part of U.S. patent application Ser. No. 253,282, abandoned, filed Oct. 4, 1988.

TECHNICAL FIELD

The present invention relates to novel compounds and compositions which inhibit renin, processes for making such compounds, synthetic intermediates employed in these processes, and a method of treating hypertension or congestive heart failure with such compounds or in combination with another antihypertensive agent. The present invention also relates to compositions and a method for treating glaucoma with such compounds and a method of inhibiting retroviral proteases and treating a retroviral infection with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharamacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. Sodium retention causes blood volume to increase, which leads to hypertension. AII is cleaved by an aminopeptidase to form angiotensin III (AIII), which, compared to AII, is a less potent vasoconstrictor but a more potent inducer of aldosterone release.

Angiotensinogen, the natural substrate for human renin has the following amino acid sequence.

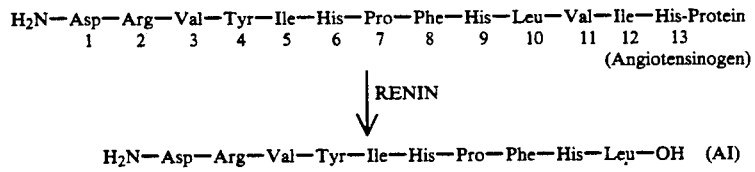

Renin cleaves angiotensinogen at the amide bond between amino acid residues 10 and 11 to give angiotensin I (AI).

Compounds which are inhibitors of renin generally comprise two parts. One part of the compound mimics the first 9 amino acid residues of angiotensinogen. The other part mimics the Leu-Val cleavage site of angiotensinogen and is designed to be non-cleavable by renin. When these two parts are combined in one compound, the compound binds to renin but is not cleaved.

Thus, renin is inhibited from acting on its natural substrate angiotensinogen.

Inhibitors of renin have been sought as agents for control of hypertension and as diagnostic agents for identification of cases of hypertension due to renin excess.

With these objectives in mind, the renin-angiotensin system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavorial and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (*Nature*, Vol. 303, p. 81, 1983). In addition, Szelke and co-workers have described polypeptide analogs containing a non-peptide link (*Nature*, Vol. 299, p. 555, 1982) which also cause potent renin inhibition and show a high specificity for this enzyme. Recent patents have disclosed novel small peptide renin inhibitors which contain novel dipeptide isosteres as transition state analogs (Szelke, et al., U.S. Pat. No. 4,609,643; Boger, et al., U.S. Pat. No. 4,668,770; Baran, et al., U.S. Pat. No. 4,657,931; Matsueda, et al., U.S. Pat. No. 4,548,926; Luly, et al., U.S. Pat. No. 4,645,759; and Luly, et al., U.S. Pat. No. 4,680,284).

The following references disclose peptide renin inhibitors which incorporate hydroxyl, substituted amide and heterocyclic derivatives of statine and statine analogs:

Luly, et al., U.S. Pat. No. 4,845,079, issued Jul. 4, 1989;

Fung, et al., PCT Patent Application No. WO88/05050, published Jul. 14, 1988;

Luly, et al., U.S. Pat. No. 4,725,584, issued Feb. 16, 1988;

Luly, et al., U.S. Pat. No. 4,680,284, issued Jul. 14, 1987;

Rosenberg, et al., U.S. Pat. No. 4,837,204, issued Jun. 6, 1989;

Baran, et al., U.S. Pat. No. 4,657,931, issued Apr. 14, 1987;

Matsueda, et al., U.S. Pat. No. 4,548,926, issued Oct. 22, 1985;

Morisawa, et al., European Patent Application No. 0228192, published Jul. 8, 1987;

Ten Brink, PCT Patent Application No. WO87/02986, published May 21, 1987;

Buhlmayer, et al., U.S. Pat. No. 4,727,060, issued Feb. 23, 1988;

Buhlmayer, et al., U.S. Pat. No. 4,758,584, issued Jul. 19, 1988;

Szelke, et al., U.S. Pat. No. 4,713,445, issued Dec. 15, 1987;

Raddatz, et al., U.S. Pat. No. 4,755,592, issued Jul. 5, 1988;

Raddatz, et al., Australian Patent Application No. AU 76222/87, published Feb. 4, 1988;

Ryono, et al., European Patent Application No. EP 0231919, published Aug. 12, 1987;

Hanson, Biochem. Biophys. Res. Commun. 132 155 (1985); Luly, European Patent Application No. EP0189203, published Jul. 30, 1986;

Hanson, et al., European Patent Application No. EP0310070, published Apr. 5, 1989;

Hanson, et al., European Patent Application No. EP0310071, published Apr. 5, 1989;

Hanson, et al., European Patent Application No. EP0310072, published Apr. 5, 1989;

Hanson, et al., European Patent Application No. EP0310073, published Apr. 5, 1989; and Gante, et al., German Patent Application No. DE3721855, published Sep. 22, 1988.

Boger, et al., U.S. Pat. No. 4,782,043, issued Nov. 1, 1988, discloses cyclic peptide renin inhibitors in combination with other antihypertensive agents.

Boger, et al., U.S. Pat. No. 4,812,442, issued Mar. 14, 1989, discloses tripeptide renin inhibitors in combination with other antihypertensive agents.

Watkins, PCT Patent Application No. WO87/02581, published May 7, 1987, discloses the use of renin inhibitors for the treatment of glaucoma.

Stein, et al., European Patent Application No. EP0311012, published Apr. 12, 1989, discloses renin inhibitors having a diol substituent which are anti-glaucoma agents.

Peptidyl inhibitors of HIV protease are disclosed by Moore, Biochem. Biophys. Res. Commun., 159 420 (1989); Billich, J. Biol. Chem., 263 1790S (1988); and Richards, FEBS Lett., 247 113 (1989).

Disclosure of the Invention

In accordance with the present invention, there are renin inhibiting compounds of the formula:

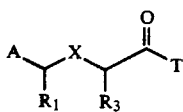

(1)

or a pharmaceutically acceptable salt, ester or prodrug thereof.

A is
(I) $R_5C(O)-(CH_2)_w-$ wherein
  1) w is 0 to 4 and
  2) $R_5$ is
    i) hydroxy,
    ii) alkoxy,
    iii) thioalkoxy,
    iv) amino or
    v) substituted amino;
(II) alkylsulfonyl, (aryl)sulfonyl or (heterocyclic)sulfonyl;
(III) aryl, arylalkyl, heterocyclic or (heterocyclic)alkyl; or
(IV) $R_{90}-$ or $R_{90}NHC(O)-$ wherein $R_{90}$ is a $C_1$ to $C_4$ straight or branched carbon chain substituted by a substituent selected from
  1) carboxy,
  2) alkoxycarbonyl,
  3) alkylsulfonyl,
  4) aryl,
  5) arylsulfonyl,
  6) heterocyclic or
  7) (heterocyclic)sulfonyl).

$R_1$ is
(I) hydrogen,
(II) loweralkyl,
(III) loweralkenyl,
(IV) cycloalkylalkyl,
(V) cycloalkenylalkyl,
(VI) aryloxyalkyl,
(VII) thioaryloxyalkyl,
(VIII) arylalkoxyalkyl,
(IX) arylthioalkoxyalkyl or
(X) a $C_1$ to $C_3$ straight or branched carbon chain substituted by a substituent selected from
  1) alkoxy,
  2) thioalkoxy,
  3) aryl and
  6) heterocyclic.

X is
(I) $CH_2$,
(II) CHOH,
(III) C(O),
(IV) NH,
(V) O,
(VI) S,
(VII) S(O),
(VIII) $SO_2$,
(IX) N(O) or
(X) $-P(O)O-$.

$R_3$ is
(I) loweralkyl,
(II) haloalkyl,
(III) loweralkenyl,
(IV) cycloalkylalkyl,
(V) cycloalkenylalkyl,
(VI) alkoxyalkyl,
(VII) thioalkoxyalkyl,
(VIII) (alkoxyalkoxy)alkyl,
(IX) hydroxyalkyl,
(X) $-(CH_2)_{ee}NHR_{12}$ wherein
  1) ee is 1 to 3 and
  2) $R_{12}$ is
    i) hydrogen,
    ii) loweralkyl or
    iii) an N-protecting group;
(XI) arylalkyl or
(XII) (heterocyclic)alkyl.

T is a mimic of the Leu-Val cleavage site of angiotensinogen.

The term "mimic of the Leu-Val cleavage site of angiotensinogen" as used herein includes

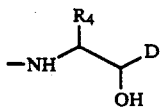

wherein
R₄ is
(I) loweralkyl,
(II) cycloalkylalkyl
(III) cycloalkenylalkyl or
(III) arylalkyl; and
D is

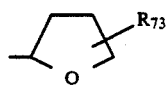

wherein R₇₃ is loweralkyl,

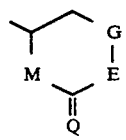

wherein
1) M is
  i) O,
  ii) S or
  iii) NH;
2) Q is
  i) O or
  ii) S;
3) E is
  i) O,
  ii) S,
  iii) CHR₇₃ wherein R₇₃ is loweralkyl,
  iv) C=CH₂ or
  v) NR₁₈ wherein R₁₈ is
    a) hydrogen,
    b) loweralkyl,
    c) hydroxyalkyl,
    d) hydroxy,
    e) alkoxy,
    f) amino or
    g) alkylamino;
and
4) G is
  i) absent,
  ii) CH₂ or
  iii) NR₁₉ wherein R₁₉ is hydrogen or loweralkyl, with the proviso that when G is NR₁₉, then R₁₈ is loweralkyl or hydroxyalkyl;

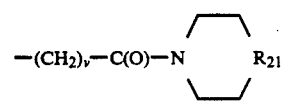

wherein
1) v is 0 or 1 and
2) R₂₁ is
  i) NH,
  ii) O, iii) S or
iv) SO₂; or
(IV) a substituted methylene group.

The term "mimic of the Leu-Val cleavage site of angiotensinogen" as used herein also includes the substituents (T) disclosed in the following references:

Luly, et al., U.S. Pat. No. 4,645,759, issued Feb. 24, 1987, which is hereby incorporated by reference, discloses mimics of the Leu-Val cleavage site of angiotensinogen having the formula (I)

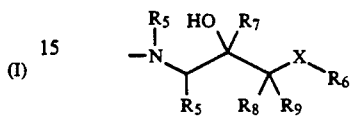

wherein R₄, R₅, R₆, R₇, R₈, R₉ and X are as defined therein;

Luly, et al., U.S. Pat. No. 4,652,551, issued Mar. 24, 1987, which is hereby incorporated by reference, discloses mimics of the Leu-Val cleavage site of angiotensinogen having the formula (II)

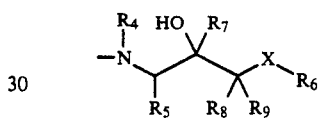

wherein R₄, R₅, R₆, R₇, R₈, R₉ and X are as defined therein;

Luly, et al., U.S. Pat. No. 4,680,284, issued Jul. 14, 1987, which is hereby incorporated by reference, discloses mimics of the Leu-Val cleavage site of angiotensinogen having the formula

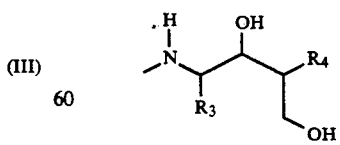

wherein R₃ is as defined therein;

Luly, et al., U.S. Pat. No. 4,725,584, issued Feb. 16, 1988, which is hereby incorporated by reference, discloses mimics of the Leu-Val cleavage site of angiotensinogen having the formula (III)

wherein R₃ and R₄ are as defined therein; Luly, et al., U.S. Pat. No. 4,725,583, issued Feb. 16, 1988, which is hereby incorporated by reference, discloses mimics of the Leu-Val cleavage site of angiotensinogen having the formula

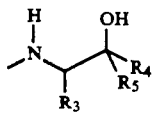

wherein R₃, R₄ and R₅ are as defined therein;
Rosenberg, et al., U.S. Pat. No. 4,837,204, issued Jun. 6, 1989, which is hereby incorporated by reference, discloses mimics of the Leu-Val cleavage site of angiotensinogen having the formula

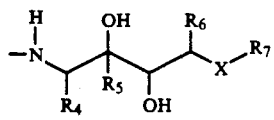

wherein R₄, R₅, R₆, R₇ and X are as defined therein;
Luly, et al., U.S. Pat. No. 4,845,079, issued Jul. 4, 1989, which is hereby incorporated by reference, discloses mimics of the Leu-Val cleavage site of angiotensinogen having the formula

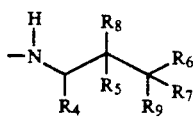

wherein R₄, R₅, R₆, R₇, R₈ and R₉ are as defined therein;
8. Sham, U.S. Pat. No. 4,826,958, issued May 2, 1989, which is hereby incorporated by reference, discloses mimics of the Leu-Val cleavage site of angiotensinogen having the formula

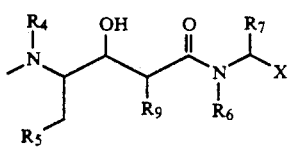

wherein R₄, R₅, R₆, R₇, R₉ and X are as defined therein;
Rosenberg et al., U.S. Pat. No. 4,857,507, issued Aug. 15, 1989, which is hereby incorporated by reference, discloses mimics of the Leu-Val cleavage site of angiotensinogen having the formula

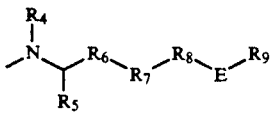

wherein R₄, R₅, R₆, R₇, R₈, R₉ and E are as defined therein;
Luly, et al., U.S. Pat. No. 4,826,815, issued May 2, 1989, which is hereby incorporated by reference, discloses mimics of the Leu-Val cleavage site of angiotensinogen having the formula

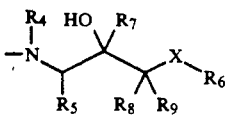

wherein R₄, R₅, R₆, R₇, R₈, R₉ and X are as defined therein;
Bender, et al., U.S. Pat. No. 4,818,748, issued Apr. 4, 1989, which is hereby incorporated by reference, discloses mimics of the Leu-Val cleavage site of angiotensinogen having the formula

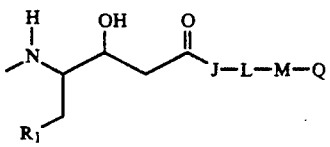

wherein R₁, J, L, M and Q are as defined therein;
Fuhrer, et al., U.S. Pat. No. 4,613,676, issued Sep. 23, 1986, which is hereby incorporated by reference, discloses mimics of the Leu-Val cleavage site of angiotensinogen having the formula

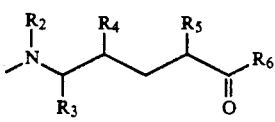

wherein R₂, R₃, R₄, R₅ and R₆ are as defined therein;
Riniker, et al., U.S. Pat. No. 4,595,677, issued Jun. 17, 1986, which is hereby incorporated by reference, discloses mimics of the Leu-Val cleavage site of angiotensinogen having the formula

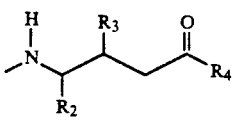

wherein R₂, R₃ and R₄ are as defined therein;
Buhlmayer, et al., U.S. Pat. No. 4,727,060, issued Feb. 23, 1988, which is hereby incorporated by reference, discloses mimics of the Leu-Val cleavage site of angiotensinogen having the formula

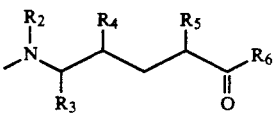

wherein R₂, R₃, R₄, R₅ and R₆ are as defined therein;
Buhlmayer, et al., U.S. Pat. No. 4,758,584, issued Jul. 19, 1988, which is hereby incorporated by reference, discloses mimics of the Leu-Val cleavage site of angiotensinogen having the formula

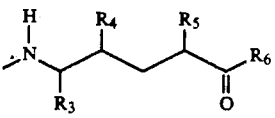

wherein R₂, R₃, R₄, R₅ and R₆ are as defined therein;
Szelke, et al., U.S. Pat. No. 4,609,643, issued Sep. 2, 1986, which is hereby incorporated by reference, discloses mimics of the Leu-Val cleavage site of angiotensinogen having the formula

—A—B—Z—W wherein A, B, Z and W are as defined therein;

Szelke, et al., U.S. Pat. No. 4,650,661, issued Mar. 17, 1987, which is hereby incorporated by reference, discloses mimics of the Leu-Val cleavage site of angiotensinogen having the formula

wherein A, B, Z and W are as defined therein;

Szelke, et al., U.S. Pat. No. 4,713,445, issued Dec. 15, 1987, which is hereby incorporated by reference, discloses mimics of the Leu-Val cleavage site of angiotensinogen having the formula

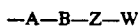

wherein A, B, Z and W are as defined therein;

Iizuka, et al., U.S. Pat. No. 4,656,269, issued Apr. 7, 1987, which is hereby incorporated by reference, discloses mimics of the Leu-Val cleavage site of angiotensinogen having the formula

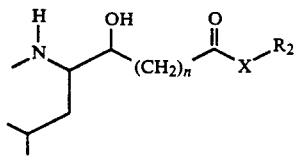

wherein n, X and $R_2$ are as defined therein;

Iizuka, et al., U.S. Pat. No. 4,711,958, issued Dec. 8, 1987, which is hereby incorporated by reference, discloses mimics of the Leu-Val cleavage site of angiotensinogen having the formula

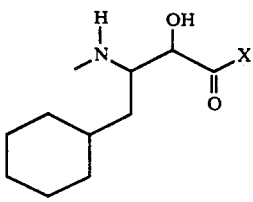

wherein X is as defined therein;

Kleinman, et al., U.S. Pat. No. 4,729,985, issued Mar. 8, 1988, which is hereby incorporated by reference, discloses mimics of the Leu-Val cleavage site of angiotensinogen having the formula

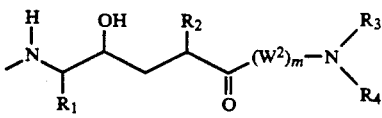

wherein $R_1$, $R_2$, m, $W^2$, $R_3$ and $R_4$ are as defined therein;

Hoover, U.S. Pat. No. 4,668,769, issued May 26, 1987, which is hereby incorporated by reference, discloses mimics of the Leu-Val cleavage site of angiotensinogen having the formula

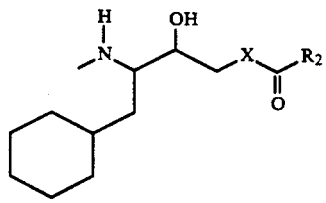

wherein X and $R_2$ are as defined therein;

Hoover, et al., U.S. Pat. No. 4,814,342, issued Mar. 21, 1989, which is hereby incorporated by reference, discloses mimics of the Leu-Val cleavage site of angiotensinogen having the formula

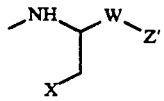

wherein X, W and $Z^1$ are as defined therein;

Bindra, et al., U.S. Pat. No. 4,749,687, issued Jun. 7, 1988, which is hereby incorporated by reference, discloses mimics of the Leu-Val cleavage site of angiotensinogen having the formula

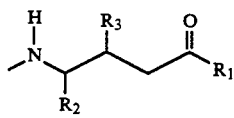

wherein $R_1$, $R_2$ and $R_3$ are as defined therein;

Hoover, et al., U.S. Pat. No. 4,814,342, issued Mar. 21, 1989, which is hereby incorporated by reference, discloses mimics of the Leu-Val cleavage site of angiotensinogen having the formula

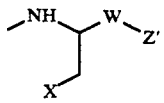

wherein X, W and $Z^1$ are as defined therein;

Matsueda, et al., U.S. Pat. No. 4,698,329, issued Oct. 6, 1987, which is hereby incorporated by reference, discloses mimics of the Leu-Val cleavage site of angiotensinogen having the formula

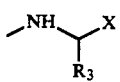

wherein $R_3$ and X are as defined therein;

Matsueda, et al., U.S. Pat. No. 4,548,926, issued Oct. 22, 1985, which is hereby incorporated by reference, discloses mimics of the Leu-Val cleavage site of angiotensinogen having the formula

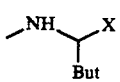

wherein But and X are as defined therein;

Wagnon, et al., U.S. Pat. No. 4,725,580, issued Feb. 16, 1988, which is hereby incorporated by reference, discloses mimics of the Leu-Val cleavage site of angiotensinogen having the formula

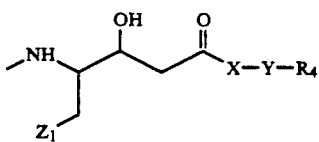

wherein $Z_1$, X, Y and $R_4$ are as defined therein;

Wagnon, et al., U.S. Pat. No. 4,746,648, issued May 24, 1988, which is hereby incorporated by reference, discloses mimics of the Leu-Val cleavage site of angiotensinogen having the formula

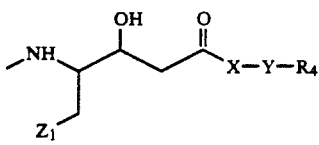

wherein $Z_1$, X, Y and $R_4$ are as defined therein;

Cazaubon, et al., U.S. Pat. No. 4,481,192, issued Nov. 6, 1984, which is hereby incorporated by reference, discloses mimics of the Leu-Val cleavage site of angiotensinogen having the formula —Statyl$_1$—Ala—Statyl$_2$—R′ wherein Statyl$_1$, Ala, Statyl$_2$ and R′ are as defined therein;

Hansen, et al., U.S. Pat. No. 4,722,922, issued Feb. 2, 1988, which is hereby incorporated by reference, discloses mimics of the Leu-Val cleavage site of angiotensinogen having the formula

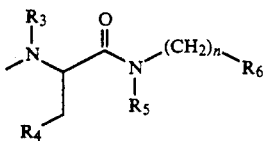

wherein $R_3$, $R_4$, $R_5$, n and $R_6$ are as defined therein;

Hansen, et al., U.S. Pat. No. 4,510,085, issued Apr. 9, 1985, which is hereby incorporated by reference, discloses mimics of the Leu-val cleavage site of angiotensinogen having the formula

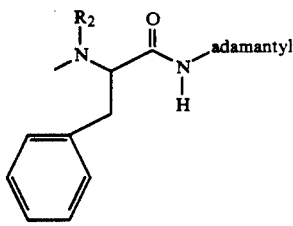

wherein $R_2$ is as defined therein;

Baran, et al., U.S. Pat. No. 4,657,931, issued Apr. 14, 1987, which is hereby incorporated by reference, discloses mimics of the Leu-Val cleavage site of angiotensinogen having the formula

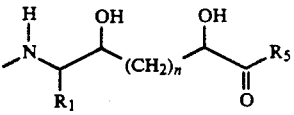

wherein $R_4$, n and $R_5$ are as defined therein;

Hansen, et al., U.S. Pat. No. 4,514,332, issued Apr. 30, 1985, which is hereby incorporated by reference, discloses mimics of the Leu-Val cleavage site of angiotensinogen having the formula

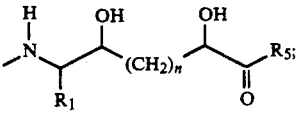

Natarajan, et al., U.S. Pat. No. 4,757,050, issued Jul. 12, 1988, which is hereby incorporated by reference, discloses mimics of the Leu-Val cleavage site of angiotensinogen having the formula

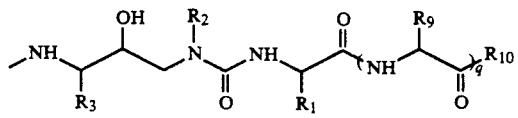

wherein $R_1$, $R_2$, $R_3$, q, $R_9$ and $R_{10}$ are as defined therein;

Gordon, U.S. Pat. No. 4,749,781, issued Jun. 7, 1988, which is hereby incorporated by reference, discloses mimics of the Leu-Val cleavage site of angiotensinogen having the formula

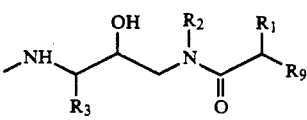

wherein $R_1$, $R_2$, $R_3$ and $R_9$ are as defined therein;

Ryono, et al., U.S. Pat. No. 4,665,193, issued May 12, 1987, which is hereby incorporated by reference, discloses mimics of the Leu-Val cleavage site of angiorensinogen having the formula

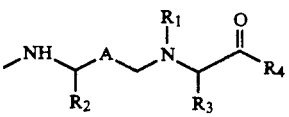

wherein $R_1$, $R_2$, $R_3$, $R_4$ and A are as defined therein;

Ryono, et al., U.S. Pat. No. 4,616,088, issued Oct. 7, 1986, which is hereby incorporated by reference, discloses mimics of the Leu-Val cleavage site of angiotensinogen having the formula

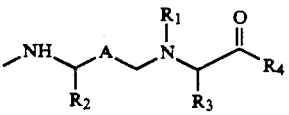

wherein $R_1$, $R_2$, $R_3$, $R_4$ and A are as defined therein;

Ryono, et al., U.S. Pat. No. 4,629,724, issued Dec. 16, 1986, which is hereby incorporated by reference, discloses mimics of the Leu-Val cleavage site of angiotensinogen having the formula

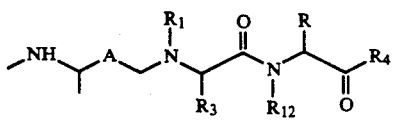

wherein $R_1$, $R_2$, $R_3$, $R_4$, $R$, $R_{12}$ and A are as defined therein;

Patel, U.S. Pat. No. 4,820,691, issued Apr. 11, 1989, which is hereby incorporated by reference, discloses mimics of the Leu-Val cleavage site of angiotensinogen having the formula

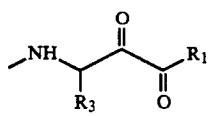

wherein $R_1$ and $R_3$ are as defined therein;

Thaisrivongs, U.S. Pat. No. 4,705,846, issued Nov. 10, 1987, which is hereby incorporated by reference, discloses mimics of the Leu-val cleavage site of angiotensinogen having the formula

wherein $E_{10}$, $F_{11}$, $G_{12}$, $H_{13}$, $I_{14}$ and Z are as defined therein;

Hudspeth, et al., U.S. Pat. No. 4,743,585, issued May 10, 1988, which is hereby incorporated by reference, discloses mimics of the Leu-Val cleavage site of angiotensinogen having the formula

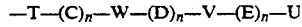

wherein T, C, W, D, V, E, U and n are as defined therein;

Hudspeth, et al., U.S. Pat. No. 4,735,933, issued Apr. 5, 1988, which is hereby incorporated by reference, discloses mimics of the Leu-Val cleavage site of angiotensinogen having the formula

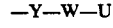

wherein Y, W and U are as defined therein;

Kaltenbronn, et al., U.S. Pat. No. 4,804,743, issued Feb. 14, 1989, which is hereby incorporated by reference, discloses mimics of the Leu-Val cleavage site of angiotensinogen having the formula

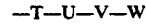

wherein T, U, V and W are as defined therein;

Pinori, et al., U.S. Pat. No. 4,560,505, issued Dec. 24, 1985, which is hereby incorporated by reference, discloses mimics of the Leu-Val cleavage site of angiotensinogen having the formula

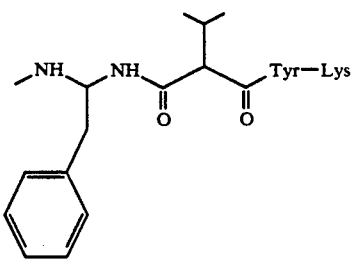

wherein Tyr and Lys are as defined therein;

Yamato, et al., U.S. Pat. No. 4,683,220, issued Jul. 28, 1987, which is hereby incorporated by reference, discloses mimics of the Leu-Val cleavage site of angiotensinogen having the formula

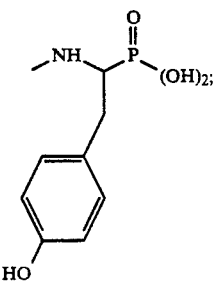

Boger, et al , U.S. Pat. No. 4,668,770, issued May 26, 1987, which is hereby incorporated by reference, discloses mimics of the Leu-val cleavage site of angiotensinogen having the formula

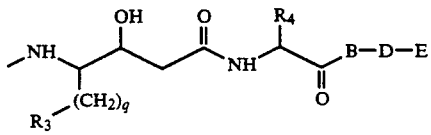

wherein $R_3$, $R_4$, q, B, D and E are as defined therein;

Boger, U.S. Pat. No. 4,668,663, issued May 26, 1987, which is hereby incorporated by reference, discloses mimics of the Leu-Val cleavage site of angiotensinogen having the formula

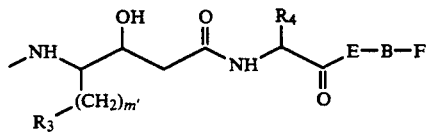

wherein $R_3$, $R_4$, m', E, B and F are as defined therein;

Bock, et al., U.S. Pat. No. 4,636,491, issued Jan. 13, 1987, which is hereby incorporated by reference, discloses mimics of the Leu-Val cleavage site of angiorensinogen having the formula

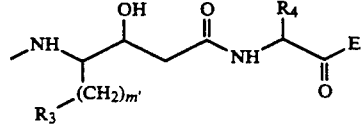

wherein $R_3$, $R_4$, m' and E are as defined therein;

Bock, et al., U.S. Pat. No. 4,663,310, issued May 5, 1987, which is hereby incorporated by reference, discloses mimics of the Leu-Val cleavage site of angiotensinogen having the formula

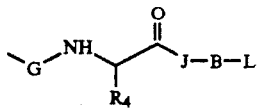

wherein G, R₄, J, B and L are as defined therein;

Boger, et al., U.S. Pat. No. 4,661,473, issued Apr. 28, 1987, which is hereby incorporated by reference, discloses mimics of the Leu-Val cleavage site of angiotensinogen having the formula

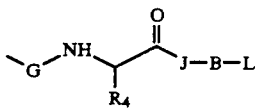

wherein G, R₄, J, B and L are as defined therein;

Veber, et al., U.S. Pat. No. 4,479,941, issued Oct. 30, 1984, which is hereby incorporated by reference, discloses mimics of the Leu-Val cleavage site of angiotensinogen having the formula

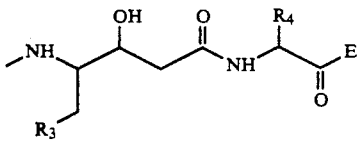

wherein $R_3$, $R_4$ and E are as defined therein;

Boger, et al., U.S. Pat. No. 4,470,971, issued Sep. 11, 1984, which is hereby incorporated by reference, discloses mimics of the Leu-Val cleavage site of angiotensinogen having the formula

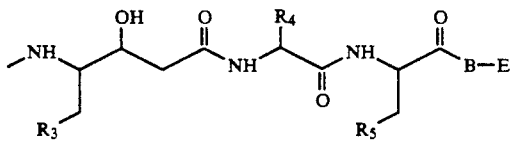

wherein $R_3$, $R_4$, $R_5$, B and E are as defined therein;

Veber, et al., U.S. Pat. No. 4,384,994, issued May 24, 1983, which is hereby incorporated by reference, discloses mimics of the Leu-Val cleavage site of angiotensinogen having the formula

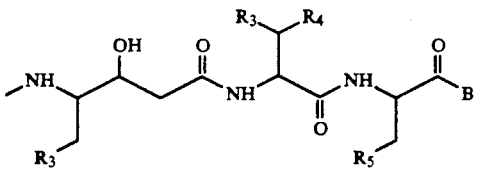

wherein $R_1$, $R_2$, $R_3$, $R_4$ and B are as defined therein:

Boger, et al., U.S. Pat. No. 4,812,442, issued Mar. 14, 1989, which is hereby incorporated by reference, discloses mimics of the Leu-Val cleavage site of angiotensinogen having the formula

—G—J wherein G and J are as defined therein;

Evans, U.S. Pat. No. 4,665,055, issued May 12, 1987, which is hereby incorporated by reference, discloses mimics of the Leu-Val cleavage site of angiotensinogen having the formula

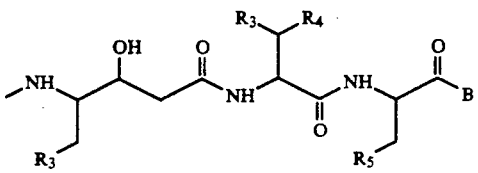

wherein $R_4$, $R_5$, B and C are as defined therein;

Evans, et al., U.S. Pat. No. 4,609,641, issued Sep. 2, 1986, which is hereby incorporated by reference, discloses mimics of the Leu-Val cleavage site of angiotensinogen having the formula

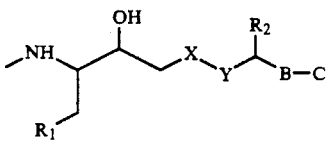

wherein $R_1$, $R_2$, X, Y, B and C are as defined therein;

Patchett, et al., U.S. Pat. No. 4,839,357, issued Jun. 13, 1989, which is hereby incorporated by reference, discloses mimics of the Leu-Val cleavage site of angiotensinogen having the formula

—G—J wherein G and J are as defined therein;

Boger, et al., U.S. Pat. No. 4,812,442, issued Mar. 14, 1989, which is hereby incorporated by reference, discloses mimics of the Leu-Val cleavage site of angiotensinogen having the formula

—G—J wherein G and J are as defined therein;

Boger, U.S. Pat. No. 4,665,052, issued May 12, 1987, which is hereby incorporated by reference, discloses mimics of the Leu-Val cleavage site of angiotensinogen having the formula

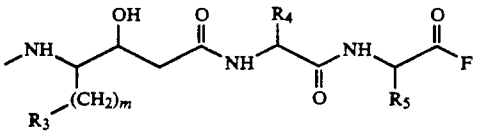

wherein $R_3$, $R_4$, $R_5$, m and F are as defined therein;

Veber, et al., U.S. Pat. No. 4,478,826, issued Oct. 23, 1984, which is hereby incorporated by reference, discloses mimics of the Leu-Val cleavage site of angiotensinogen having the formula

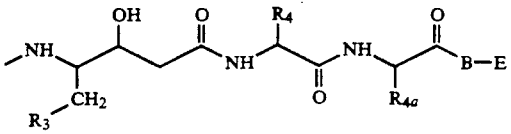

wherein $R_3$, $R_4$, $R_{4a}$, B and E are as defined therein;

Boger, et al., U.S. Pat. No. 4,485,099, issued Nov. 27, 1984, which is hereby incorporated by reference, discloses mimics of the Leu-Val cleavage site of angiotensinogen having the formula

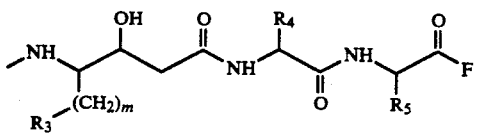

wherein $R_3$, $R_4$, $R_5$, m and F are as defined therein;

Boger, et al., U.S. Pat. No. 4,477,440, issued Oct. 16, 1984, which is hereby incorporated by reference, discloses mimics of the Leu-Val cleavage site of angiotensinogen having the formula

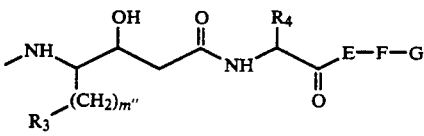

wherein $R_3$, $R_4$, m'', E, F and G are as defined therein;

Raddatz, et al., U.S. Pat. No. 4,721,776, issued Jan. 26, 1988, which is hereby incorporated by reference, discloses mimics of the Leu-Val cleavage site of angiotensinogen having the formula

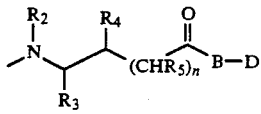

wherein $R_2$, $R_3$, $R_4$, $R_5$, n, B and D are as defined therein;

Holzemann, et al, U.S. Pat. No. 4,709,010, issued Nov. 24, 1987, which is hereby incorporated by reference, discloses mimics of the Leu-Val cleavage site of angiotensinogen having the formula

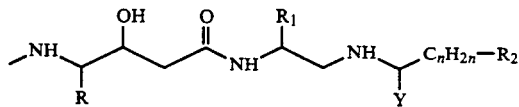

wherein R, $R_1$, $R_2$, n and Y are as defined therein;

Raddatz, et al., U.S. Pat. No. 4,812,555, issued Mar. 14, 1989, which is hereby incorporated by reference, discloses mimics of the Leu-Val cleavage site of angiotensinogen having the formula

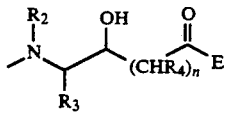

wherein $R_2$, $R_3$, $R_4$, n and E are as defined therein;

Raddatz, et al., U.S. Pat. No. 4,755,592, issued Jul. 5, 1988, which is hereby incorporated by reference, discloses mimics of the Leu-Val cleavage site of angiotensinogen having the formula

—W—E—W'—Y wherein W, E, W' and Y are as defined therein;

Raddatz, et al., U.S. Pat. No. 4,666,888, issued May 19, 1987, which is hereby incorporated by reference, discloses mimics of the Leu-Val cleavage site of angiotensinogen having the formula

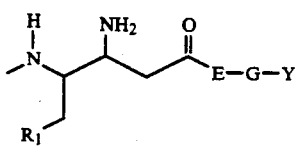

wherein $R_1$, E, G and Y are as defined therein;

Wagnon, et al., U.S. Pat. No. 4,840,935, issued Jun. 20, 1989, which is hereby incorporated by reference, discloses mimics of the Leu-Val cleavage site of angiotensinogen having the formula

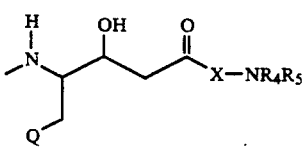

wherein $R_4$, $R_5$, Q and X are as defined therein;

Iizuka, et al., U.S. Pat. No. 4,841,067, issued Jun. 20, 1989, which is hereby incorporated by reference, discloses mimics of the Leu-Val cleavage site of angiotensinogen having the formula

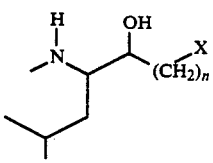

wherein n and X are as defined therein;

Raddatz, et al., U.S. Pat. No. 4,829,053, issued May 9, 1989, which is hereby incorporated by reference, discloses mimics of the Leu-Val cleavage site of angiotensinogen having the formula

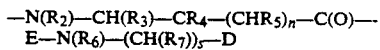

—N($R_2$)—CH($R_3$)—C$R_4$—(CH$R_5$)$_n$—C(O)—
E—N($R_6$)—(CH($R_7$))$_s$—D wherein n, s, $R_2$, $R_3$, $R_4$, $R_5$, $R_6$, $R_7$, E and D are as defined therein;

European Patent Application No. EP0264106, published Apr. 20, 1988, discloses mimics of the Leu-Val cleavage site of angiotensinogen having the formula

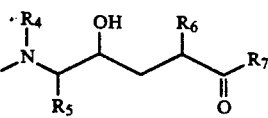

wherein $R_4$, $R_5$, $R_6$ and $R_7$ are as defined therein including $R_4$ is hydrogen or loweralkyl; $R_5$ is hydrogen, loweralkyl or an amino acid residue; $R_6$ is loweralkyl, cycloalkyl, cycloalkylalkyl or arylalkyl and $R_7$ is hydroxy, alkoxy, substituted alkoxy, amino, substituted amino or an N-heterocycle;

European Patent Application No. EP0272583, published Jun. 29, 1988, discloses mimics of the Leu-Val cleavage site of angiotensinogen having the formula

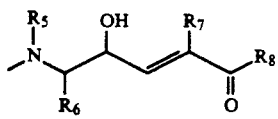

wherein $R_5$, $R_6$, $R_7$ and $R_8$ are as defined therein including $R_5$ is hydrogen or loweralkyl; $R_6$ is hydrogen, loweralkyl, cycloalkyl, cycloalkylalkyl, aryl, arylalkyl or an amino acid residue; and $R_7$ and $R_8$ are independently selected from hydrogen, loweralkyl, cycloalkyl, cycloalkylalkyl or arylalkyl;

European Patent Application No. EP0309766, published Apr. 5, 1989, discloses mimics of the Leu-Val cleavage site of angiotensinogen having the formula

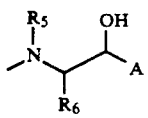

wherein $R_5$, $R_6$ and A are as defined therein including $R_5$ is hydrogen or loweralkyl; $R_6$ is hydrogen, loweralkyl, cycloalkyl, cycloalkylalkyl, aryl, aralkyl or heterocyclic; and A is —CH(OH)—(CH)$_q$—R$_7$ wherein q is 0–5 and $R_7$ is hydrogen, loweralkyl, cycloalkyl, cycloalkylalkyl, aryl, arylalkyl, heterocyclic, substituted thioalkyl, substituted sulfone, substituted sulfoxide, substituted amine, quaternized amine, heterocyclic, carboxyalkyl, alkoxycarbonylalkyl or amidoalkyl;

European Patent Application No. EP0300189, published Jan. 25, 1989, discloses mimics of the Leu-Val cleavage site of angiotensinogen having the formula

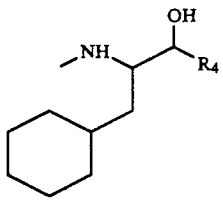

wherein $R_4$ is as defined therein including $R_4$ is loweralkyl;

European Patent Application No. EP0283970, published Sep. 28, 1988, discloses mimics of the Leu-Val cleavage site of angiotensinogen having the formula

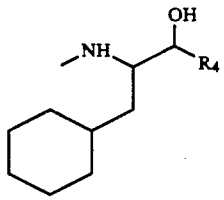

wherein $R_4$ is as defined therein including $R_4$ is loweralkyl;

European Patent Application No. EP0255082, published Feb. 3, 1988, discloses mimics of the Leu-Val cleavage site of angiotensinogen having the formula

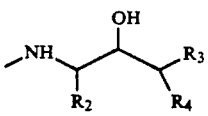

wherein $R_2$, $R_3$ and $R_4$ are as defined therein including $R_2$ is hydrogen, alkyl, cyclcoalkyl, cycloalkylalkyl, aryl or arylalkyl; $R_3$ is hydrogen, alkyl or arylalkyl; and $R_4$ is —X—(CH$_2$)$_{n'}$—R$_7$ wherein X is absent, O or S, n' is 0–4 and $R_7$ is hydrogen, hydroxy, amino, heteroaryl or —CH(R$_9$)—(CH$_2$)$_p$— Y—(CH$_2$)$_q$—R$_{10}$ wherein p, q, Y and R$_{10}$ are as defined therein;

European Patent Application No. EP0230242, published Jul. 29, 1987, discloses mimics of the Leu-Val cleavage site of angiotensinogen having the formula

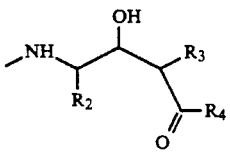

wherein $R_2$, $R_3$ and $R_4$ are as defined therein including $R_2$ is hydrogen, alkyl, cycloalkylalkyl, aryl or arylalkyl; $R_3$ is hydrogen, alkyl or alkenyl; and $R_4$ is —N(R$_5$)—CH(R$_6$)— (CH$_2$)$_n$—Ar or —N(R$_5$)—CH(R$_6$)—CH=CH—(CH$_2$)$_m$—Ar wherein n is 0–6, m is 0–4, $R_5$ is hydrogen or alkyl and $R_6$ is hydrogen, alkyl, hydroxyalkyl, alkoxyalkyl, thioalkoxyalkyl, carboxyalkyl, alkoxycarbonylalkyl, haloalkyl, alkylaminoalkyl, alkoxycarbonylaminoalkyl or arylalkoxycarbonylaminoalkyl;

European Patent Application No. EP0310015, published Apr. 5, 1989, discloses mimics of the Leu-Val cleavage site of angiotensinogen having the formula

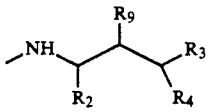

wherein $R_2$, $R_3$, $R_4$ and $R_9$ are as defined therein including $R_2$ is hydrogen, alkyl, cycloalkyl, cycloalkylalkyl, aryl or arylalkyl; $R_3$ is hydrogen, alkyl, aryl or arylalkyl; $R_9$ is hydroxy or fluoro; and $R_4$ is —(CH$_2$)$_p$—X—(CH$_2$)$_q$—R$_7$ wherein p is 0–4, q is 0–4, X is —CF$_2$—, —C(O)— or —CH(R$_8$)— wherein R$_8$ is alkyl, alkoxy, thioalkoxy, alkylamino, hydroxy, azido or halo and $R_7$ is hydrogen, hydroxy, amino, aryl or heteroaryl;

European Patent Application No. EP0315574, published May 10, 1989, discloses mimics of the Leu-Val cleavage site of angiotensinogen having the formula

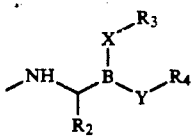

(B is a boron atom)
wherein $R_2$, X, Y, $R_3$ and $R_4$ are as defined therein including $R_2$ is hydrogen, alkyl, cycloalkyl, cycloalkylalkyl, aryl or hererocyclic; X and Y are independently selected from O or —N(R$_{13}$)— wherein $R_{13}$ is hydrogen, alkyl or substituted alkyl; and $R_3$ and $R_4$ are independently selected from hydrogen, alkyl or aryl; or the boron containing substituent is a boron containing cyclic group;

Japanese Patent Application No. J63275552, published Nov. 14, 1988 discloses mimics of the Leu-Val cleavage site of angiotensinogen having the formula

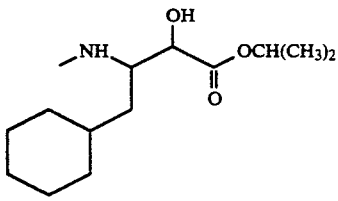

European Patent Application No. EP0252727, published Jan. 13, 1988, discloses mimics of the Leu-Val cleavage site of angiotensinogen having the formula

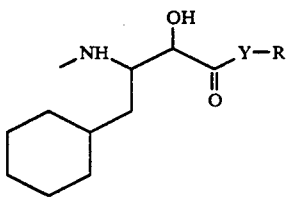

wherein Y and R are as defined therein including Y is O or NH and R is alkyl, cycloalkyl or halogenated alkyl;

European Patent Application No. EP0244083, published Nov. 4, 1987, discloses mimics of the Leu-Val cleavage site of angiotensinogen having the formula

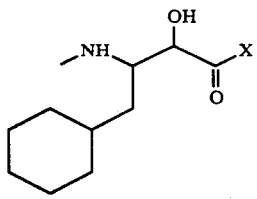

wherein X is as defined therein including X is alkoxy, alkyalamino, cyclcalkyloxy, morpholino and haloalkoxy.

European Patent Application No. EP0216539, published Apr. 1, 1987, discloses mimics of the Leu-Val cleavage site of angiotensinogen having the formula

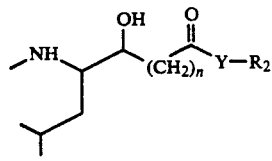

wherein n, Y and $R_2$ are as defined therein including n is 0-1, Y is O or NH and $R_2$ is alkyl;

European Patent Application No. EP0206807, published Dec. 30, 1986, discloses mimics of the Leu-Val cleavage site of angiotensinogen having the formula

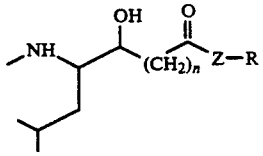

wherein n, Z and R are as defined therein including n is 0-1, Z is O or NH and R is alkyl;

European Patent Application No. EP0190891, published Aug. 13, 1986, discloses mimics of the Leu-Val cleavage site of angiotensinogen having the formula

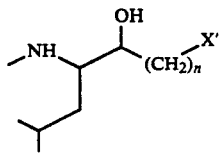

wherein n and X' are as defined therein including n is 0-1 and X' is alkoxycarbonyl, aralkoxycarbonyl, or $—C(O)NR_1R_2$ wherein R is hydrogen, alkyl or aralkyl and $R_2$ is alkyl or $—CH_2—Y—R$ wherein Y is O or NH and R is alkyl or aralkyl;

European Patent Application No. EP0181110, published May 14, 1986, discloses mimics of the Leu-Val cleavage site of angiotensinogen having the formula

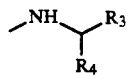

wherein $R_3$ and $R_4$ are as defined therein including $R_3$ is —CHO or —CH$_2$OH and $R_4$ is isobutyl or benzyl;

European Patent Application No. EP0297816, published Jan. 4, 1989, discloses mimics of the Leu-Val cleavage site of angiotensinogen having the formula

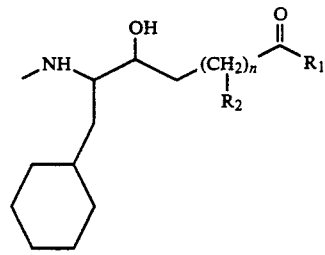

wherein n, $R_1$ and $R_2$ are as defined therein including n is 0-1, $R_1$ is —NH$_2$, alkylamino, alkoxy, or 2-alkoxycarbonylpyrrolidin-1-yl and $R_2$ is alkyl, alkenyl, haloalkenyl or azide substituted alkenyl;

European Patent Application No. EP0297815, published Jan. 4, 1989, discloses mimics of the Leu-Val cleavage site of angiotensinogen having the formula

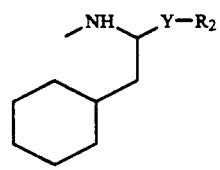

wherein Y and R₂ are as defined therein including Y is —CH(OH)— or —C(O)— and R₂ is —CF₂C(O)NHCH₃, —CF₃ or —CF₂C(CH₂CH(CH₃)₂)CO₂C₂H₅;

European Patent Application No. EP0212903, published Mar. 4, 1987, discloses mimics of the Leu-Val cleavage site of angiotensinogen having the formula

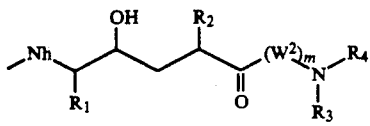

wherein m, R₁, R₂, R₃, R₄ and W² are as defined therein including m is 0–1, R₁ and R₂ are independently selected from hydrogen, alkyl, alkenyl, phenyl, naphthyl, cycloalkyl, cycloalkenyl, phenylalkyl, naphthylalkyl, cycloalkylalkyl and cycloalkenylalkyl, R₃ and R₄ are independently selected from alkyl, phenyl, naphthyl, cycloalkyl, adamantyl, phenylalkyl, naphthylalkyl, cycloalkylalkyl and adamantylalkyl; or R₃ is hydrogen and R₄ is —CH(R₇) (CH₂)ₚ(Q)ᵣCH(R₈) (CH₂)_q—T wherein p and q are independently selected from 0,1,2,3,4,5 and 6, r is 0–1, Q is —CH₂—, —CH=CH—, —O—, —NH—, —CH(OH)— or —C(O)—, Y is methyl, phenyl, —C(O)OR₉, —C(O)NR₉R₁₀, —C(O)NHC(O)OCH₂C₆H₅, —NH₂, —NHC(O)CH₂C₆H₅, —NHCH(CH₂C₆H₅)C(O)OR₉ or —NHCH(CH₂C₆H₅)C(O)NR₉R₁₀ wherein R₉ and R₁₀ are independently selected from hydrogen, alkyl, phenyl, cycloalkyl, phenylalkyl, cycloalkylalkyl or adamantyl, and R₇ and R₈ are independently selected from hydrogen, alkyl, phenyl, cycloalkyl, phenylalkyl, cycloalkylalkyl or adamantyl; or R₃ and R₄ taken together with the nitrogen to which they are attached form a pyrrole, indoline, isoindoline, piperidine, 1,2,3,4-tetrahydroquinoline, 1,2,3,4-tetrahydroisoquinoline, perhydroazepine or morpholine ring; and W² is —NHCH((CH₂)₃R₆)—C(O)— wherein R₆ is —NH₂, —NHC(=NH)NH₂ or —CH₂NH₂;

PCT Patent Application No. WO 88/03022, published May 5, 1988, discloses mimics of the Leu-Val cleavage site of angiotensinogen having the formula

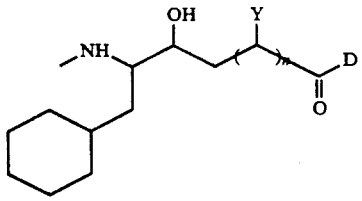

wherein n, Y and D are as defined therein including n is 0–1, Y is isobutyl, allyl or benzyl and D is 2-carboxypyrrolidin-1-yl or —ZR wherein Z is O or NH and R is alkyl, phenyl or substituted alkyl or substituted phenyl;

German Patent Application No DE3725137, published Aug. 6, 1986, discloses mimics of the Leu-Val cleavage site of angiotensinogen having the formula

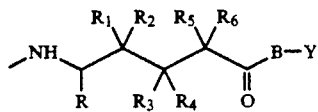

wherein R, R₁, R₂, R₃, R₄, R₅, R₆, B and Y are as defined therein including R is hydrogen, alkyl, cycloalkyl, cycloalkylalkyl, aryl, arylalkyl, heteroaryl or heteroarylalkyl, R₁ is hydroxy, alkoxy or aryloxy, R₂ is hydrogen or R₁ and R₂ taken together is oxo (=O), R₃, R₄, R₅ and R₆ are independently selected from hydrogen, fluoro, chloro, alkyl, cycloalkyl, cycloalkylalkyl, aryl, arylalkyl, heteroaryl and heteroarylalkyl, B is a peptide chain containing from 1 to 10 amino acid residues and Y is hydroxy or a protecting group for the peptide carboxy group;

British Patent Application No. GB2203740, published Oct. 26, 1988, discloses mimics of the Leu-Val cleavage site of angiotensinogen having the formula

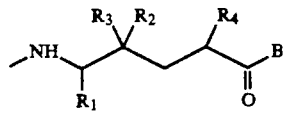

wherein R₁, R₂, R₃, R₄ and B are as defined therein including R₁ is a hydrophobic or hydrophilic side chain, R₂ is hydroxy or amino, R₃ is hydrogen or R₂ and R₃ taken together is oxo (=O), R₄ is a hydrophobic or hydrophilic side chain and B is —NHCH(R₆)C(R₇)(R₈)C(R₉)(R₁₀)CH₂C(O)NR₁₁R₁₂ wherein R₆ is R₁, R₇ and R₈ are the same as R₂ and R₃, R₉ and R₁₀ are independently selected from hydrogen and fluoro and R₁₁ and R₁₂ are independently selected from hydrogen, alkyl, arylalkyl, heteroarylalkyl and —CH(R₁₃)C(O)R₁₄ wherein R₁₃ is alkyl or hydroxyalkyl and R₁₄ is hydroxy, alkoxy, amino, alkylamino, aminomethylpyridyl or benzyl;

British Patent Application No. GB2200115, published Jul. 27, 1988, discloses mimics of the Leu-Val cleavage site of angiotensinogen having the formula

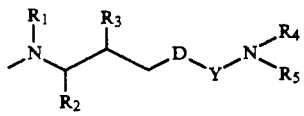

R₁, R₂, R₃, R₄, R₅, D and Y are as defined therein including R₁ is hydrogen or alkyl, R₂ is an amino acid side chain, R₃ is hydrogen, hydroxy, aryloxy or amino, R₄ and R₅ are independently selected from hydrogen, alkyl, arylalkyl, heteroarylalkyl and —CH(R₁₂)C(O)R₁₃ wherein R₁₂ is alkyl or hydroxyalkyl and R₁₃ is hydroxy, alkoxy, amino, alkylamino, aminomethylpyridyl or benzyl; or —NR₄R₅ represents pyrrolidinyl, piperidinyl, morpholinyl, piperazinyl or substituted piperazinyl; D is a bond, O, —N(R₁)— or —CH(R₁)— and Y is —C(O)—, —S(O)₂— or —P(O)—;

German Patent Application No. DE3830825, published Mar. 23, 1989, discloses mimics of the Leu-Val cleavage site of angiotensinogen having the formula

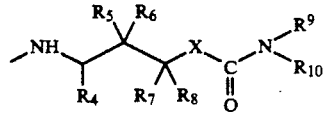

wherein R₄, R₅, R₆, R₇, R₈, R₉, R₁₀ and X are as defined therein including R₄ is a hydrophilic or hydrophobic amino acid side chain, R₅ is hydroxy or amino, R₆ is hydrogen or R₅ and R₆ taken together are oxo (=O), $R_7$ and $R_8$ are independently selected from hydrogen and fluoro, $R_9$ and $R_{10}$ are independently selected from hydrogen, alkyl and —CH($R_{11}$)C(O)$R_{12}$ wherein $R_{11}$ is alkyl or hydroxyalkyl and $R_{12}$ is hydroxy, alkoxy, amino, alkylamino, aminomthylpyridyl, benzyl or —NH—(CH$_2$CH$_2$O)$_m$—$R_1$ wherein m is 1–20 and $R_1$ is as defined therein; and X is a bond or O, NH or —C($R_{13}$)($R_{14}$)— wherein $R_{13}$ and $R_{14}$ are independently selected from hydrogen, fluoro or $R_4$;

Japanese Patent Application No. J62246546, published Oct. 27, 1987, discloses mimics of the Leu-Val cleavage site of angiotensinogen having the formula

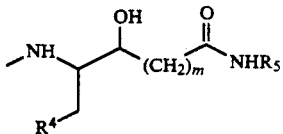

wherein m, $R_4$ and $R_5$ are as defined therein including m is 0–1, $R_4$ is alkyl, cycloalkyl or phenyl and $R_5$ is alkyl or substituted alkyl as defined therein;

European Patent Application No. EP0274259, published Jul. 13, 1988, discloses mimics of the Leu-Val cleavage site of angiotensinogen having the formula

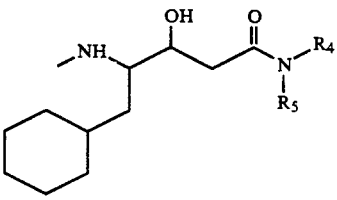

wherein $R_4$ and $R_5$ are as defined therein including $R_4$ is alkyl, hydroxyalkyl, (heterocyclic)alkyl, aminoalkyl, alkylaminoalkyl or dialkylaminoalkyl and $R_5$ is hydrogen or alkyl;

European Patent Application No. EP0228192, published Jul. 8, 1987, discloses mimics of the Leu-Val cleavage site of angiotensinogen having the formula

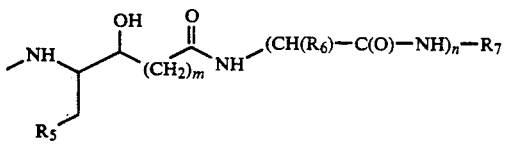

wherein m, n, $R_5$, $R_6$, and $R_7$ are as defined therein including m and n are independently selected from 0 and 1, $R_5$ is alkyl, cycloalkyl or phenyl, $R_6$ is alkyl and $R_7$ is alkyl or substituted alkyl as defined therein;

European Patent Application No. EP0273893, published Jul. 6, 1988, discloses mimics of the Leu-Val cleavage site of angiotensinogen having the formula

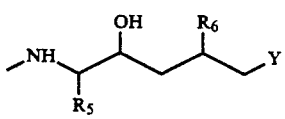

wherein $R_5$, $R_6$ and Y are as defined therein including $R_5$ is alkyl or cycloalkyl, $R_6$ is hydrogen or alkyl and Y is —SCH(CH$_3$)$_2$ or —S(O)$_2$CH(CH$_3$)$_2$;

European Patent Application No. EP0310070, published Apr. 5, 1989, discloses mimics of the Leu-Val cleavage site of angiotensinogen having the formula

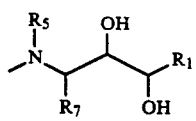

wherein $R_1$, $R_5$ and $R_7$ are as defined therein including $R_1$ is hydrogen, alkyl, haloalkyl, alkylcycloalkyl, alkylcycloalkenyl or alkoxycarbonyl, $R_5$ is hydrogen or alkyl and $R_7$ is cycloalkyl, phenyl, cycloalkylalkyl or phenylalkyl;

European Patent Application No. EP0310071, published Apr. 5, 1989, discloses mimics of the Leu-Val cleavage site of angiotensinogen having the formula

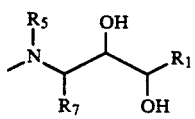

wherein $R_1$, $R_5$ and $R_7$ are as defined therein including $R_1$ is hydrogen, alkyl, haloalkyl, alkylcycloalkyl, alkylcycloalkenyl or alkoxycarbonyl, $R_5$ is hydrogen or alkyl and $R_7$ is cycloalkyl, phenyl, cycloalkylalkyl or phenylalkyl;

European Patent Application No. EP0310072, published Apr. 5, 1989, discloses mimics of the Leu-Val cleavage site of angiotensinogen having the formula

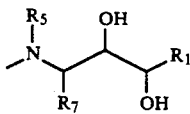

wherein $R_1$, $R_5$ and $R_7$ are as defined therein including $R_1$ is hydrogen, alkyl, haloalkyl, alkylcycloalkyl, alkylcycloalkenyl or alkoxycarbonyl, $R_5$ is hydrogen or alkyl and $R_7$ is cycloalkyl, phenyl, cycloalkylalkyl or phenylalkyl;

European Patent Application No. EP0310073, published Apr. 5, 1989, discloses mimics of the Leu-Val cleavage site of angiotensinogen having the formula

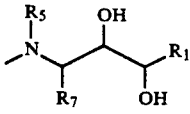

wherein $R_1$, $R_5$ and $R_7$ are as defined therein including $R_1$ is hydrogen, alkyl, haloalkyl, alkylcycloalkyl, alkylcycloalkenyl or alkoxycarbonyl, $R_5$ is hydrogen or alkyl and $R_7$ is cycloalkyl, phenyl, cycloalkylalkyl or phenylalkyl;

European Patent Application No. EP0313847, published May 3, 1989, discloses mimics of the Leu-Val cleavage site of angiotensinogen having the formula

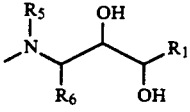

wherein $R_1$, $R_5$ and $R_6$ are as defined therein including $R_1$ is hydrogen, alkyl, haloalkyl, alkylcycloalkyl, alkylcycloalkenyl or alkoxycarbonyl, $R_5$ is hydrogen or alkyl and $R_6$ is cycloalkyl, phenyl, cycloalkylalkyl or phenylalkyl;

European Patent Application No. EP0296581, published Dec. 28, 1988, discloses mimics of the Leu-Val cleavage site of angiotensinogen having the formula

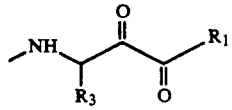

wherein $R_1$ and $R_3$ are as defined therein including $R_1$ is hydrogen, arylalkyl, aryl, (heterocyclic)alkyl or heterocyclic and $R_3$ is hydrogen, alkyl, haloalkyl, arylalkyl, (heterocyclic)alkyl, hydroxyalkyl, alkoxyalkyl, aminoalkyl, mercaptoalkyl, thioalkoxyalkyl, hydorxyalkoxyalkyl, aminoalkoxyalkyl, hydroxythioalkoxyalkyl, carboxyalkyl, aminothioalkoxyalkyl, guanidinoalkyl, aminocarbonylalkyl or imidazolylalkyl;

European Patent Application No. EP0231919, published Aug. 12, 1987, discloses mimics of the Leu-Val cleavage site of angiotensinogen having the formula

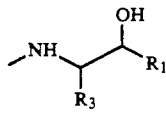

wherein $R_1$ and $R_3$ are as defined therein including $R_1$ is an N-heterocyclic ring and $R_3$ is hydrogen, alkyl, cycloalkylalkyl, haloalkyl, arylalkyl, (heterocyclic)alkyl, hydroxyalkyl, alkoxyalkyl, alkoxyalkyl, aminoalkyl, mercaptoalkyl, tioalkoxyalkyl, hydroxyalkoxyalkyl, aminoalkoxyalkyl, hydroxythioalkoxyalkyl, carboxyalkyl, aminothioalkoxyalkyl, guanidinoalkyl, aminocarbonylalkyl or imidazolylalkyl;

PCT Patent Application No. WO 87/05302, published May 3, 1989, discloses mimics of the Leu-Val cleavage site of angiotensinogen having the formula

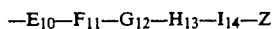

—$E_{10}$—$F_{11}$—$G_{12}$—$H_{13}$—$I_{14}$—Z wherein $E_{10}$, $F_{11}$, $G_{12}$, $H_{13}$, $I_{14}$ and Z are as defined therein including —$E_{10}$—$F_{11}$— is

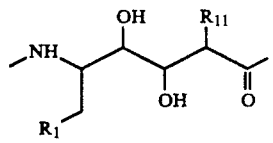

or

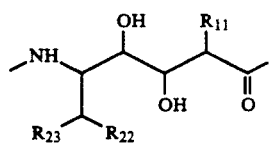

wherein $R_1$ is hydrogen, alkyl, aryl, cycloalkyl, heterocyclic, alkoxy or thioalkoxy, $R_{11}$ is hydrogen, alkyl, benzyl, cycloalkyl, hydroxyalkyl, cycloalkylalkyl, arylalkyl, (heterocyclic)alkyl, alkoxyalkyl or thioalkoxyalkyl, $R_{22}$ is hydrogen or alkyl and $R_{23}$ is hydroxyalkyl, aminoalkyl, aryl or alkyl, $G_{12}$ is absent or an amino acid residue, $H_{13}$ is absent or an amino acid residue, $I_{14}$ is absent or an amino acid residue and Z is hydroxy, substituted alkoxy, substituted amino or cyclic amino;

PCT Patent Application No. WO 87/02986, published May 21, 1987, discloses mimics of the Leu-Val cleavage site of angiotensinogen having the formula

—$E_{10}$—$F_{11}$—$G_{12}$—$H_{13}$—$I_{14}$—Z wherein $E_{10}$, $F_{11}$, $G_{12}$, $H_{13}$, $I_{14}$ and Z are as defined therein including —$E_{10}$—$F_{11}$— is

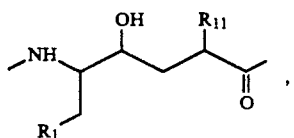

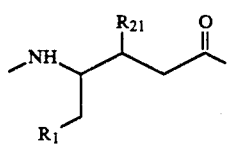

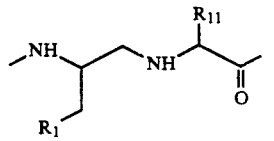

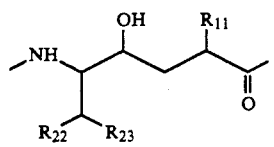

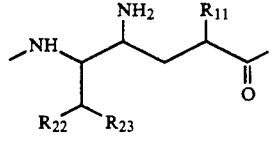

or

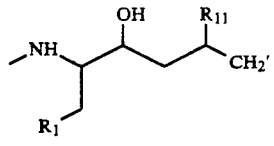

wherein $R_1$ is hydrogen, alkyl, aryl, cycloalkyl, heterocyclic, alkoxy or thioalkoxy, $R_{11}$ is hydrogen, alkyl, benzyl, cycloalkyl, hydroxyalkyl, cycloalkylalkyl, arylalkyl, (heterocyclic)alkyl, alkoxyalkyl or thioalkoxyalkyl, $R_{21}$ is hydroxy or amino, $R_{22}$ is hydrogen or alkyl and $R_{23}$ is hydroxy, amino, hydroxyalkyl, aminoalkyl, aryl or alkyl, $G_{12}$ is absent or an amino acid residue, $H_{13}$ is absent or an amino acid residue, $I_{14}$ is absent or an amino acid residue and Z is hydroxy, substituted alkoxy, substituted amino or cyclic amino;

PCT Patent Application No. WO 89/00161, published Jan. 12, 1989, discloses mimics of the Leu-Val cleavage site of angiotensinogen having the formula

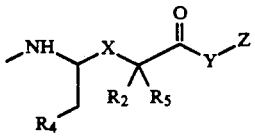

wherein $R_2$, $R_4$, $R_5$, X, Y and Z are as defined therein including $R_2$ is hydrogen or alkyl, $R_4$ is hydrogen, alkyl, cycloalkyl, aryl, heterocyclic, hydroxyalkyl or aminoalkyl, $R_5$ is hydrogen, alkyl, arylalkyl, (heterocyclic)alkyl or cycloalkyl, X is —CH(OH)—, —CH(NH$_2$)—, —C(O)—, —CH(OH)CH(OH)—, —CH(OH)CH$_2$—, —CH(NH$_2$)CH$_2$—, —C(O)—CH$_2$—, —CH$_2$—NH—, —CH$_2$—O— or —P(O)(A)B— wherein A is hydroxy or amino and B is absent, O, NH or CH$_2$, Y is absent or —NHCH(R$_5$)C(O)— and Z is hydroxy, substituted alkoxy, substituted amino or N-heterocyclic;

PCT Patent Application No. WO 88/07053, published Sep. 22, 1988, discloses mimics of the Leu-Val cleavage site of angiotensinogen having the formula

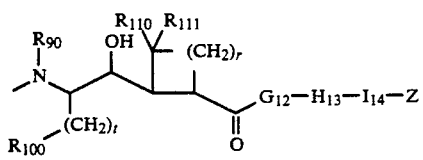

wherein r, t, $R_{90}$, $R_{100}$, $R_{110}$, $R_{111}$, $G_{12}$, $H_{13}$, $I_{14}$ and Z are as defined therein including r is 0–3, t is 0–3, $R_{90}$ is hydrogen or alkyl, $R_{100}$ is hydrogen, alkyl, aryl, cycloalkyl, heterocyclic, alkoxy or thioalkoxy, $R_{110}$ and $R_{111}$ are independently selected from hydrogen, alkyl, aryl, arylalkyl and halo, $G_{12}$ is absent, an amino acid residue or

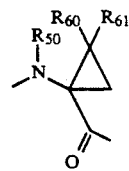

wherein $R_{50}$ is hydrogen, alkyl, arylalkyl, (heterocyclic)alkyl, cycloalkylalkyl or adamantyl, and $R_{60}$ and $R_{61}$ are independently selected from hydrogen, alkyl, aryl, arylalkyl, heterocyclic, (heterocyclic)alkyl, cycloalkyl, cycloalkylalkyl and adamantyl; or $R_{60}$ and $R_{61}$ taken together form a carbocyclic or heterocyclic spirocycle, $H_{13}$ is absent an amino acid residue or

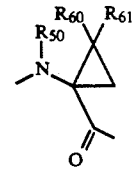

wherein $R_{50}$ is hydrogen, alkyl, arylalkyl, (heterocyclic)alkyl, cycloalkylalkyl or adamantyl, and $R_{60}$ and $R_{61}$ are independently selected from hydrogen, alkyl, aryl, arylalkyl, heterocyclic, (heterocyclic)alkyl, cycloalkyl, cycloalkylalkyl and adamantyl; or $R_{60}$ and $R_{61}$ taken together form a carbocyclic or heterocyclic spirocycle, $I_{14}$ is absent an amino acid residue or

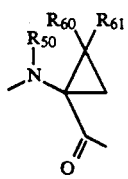

wherein $R_{50}$ is hydrogen, alkyl, arylalkyl, (heterocyclic)alkyl, cycloalkylalkyl or adamantyl, and $R_{60}$ and $R_{61}$ are independently selected from hydrogen, alkyl, aryl, arylalkyl, heterocyclic, (heterocyclic)alkyl, cycloalkyl, cycloalkylalkyl and adamantyl; or $R_{60}$ and $R_{61}$ taken together form a carbocyclic or heterocyclic spirocycle and Z is hydroxy, alkoxy, substituted alkoxy, amino, substituted amino or cyclic amino;

PCT Patent Application No. WO 88/02374, published Apr. 7, 1988, discloses mimics of the Leu-Val cleavage site of angiotensinogen having the formula

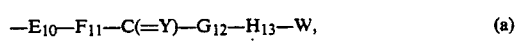   (a)

   (b)

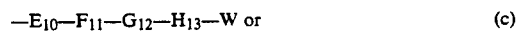   (c)

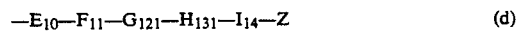   (d)

wherein $E_{10}$, $F_{11}$, $G_{12}$, $H_{13}$, $G_{121}$, $H_{131}$, $I_{14}$, W, Y and Z are as defined therein including —$E_{10}$—$F_{11}$— is

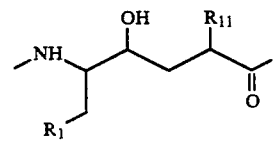

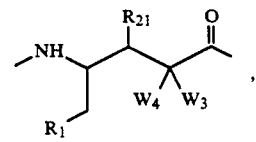

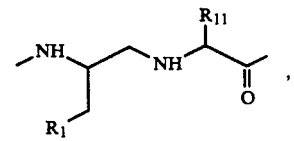

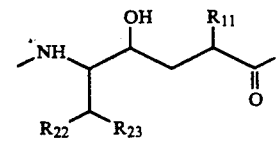

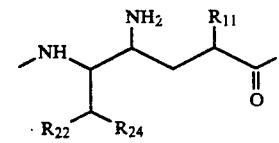

-continued

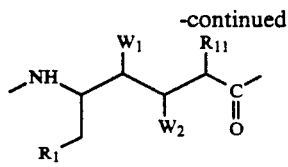

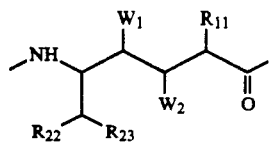

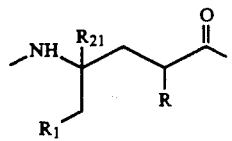

or

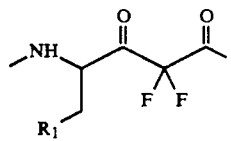

wherein R and $R_1$ are independently selected from alkyl, cycloalkyl, aryl, substituted alkyl as defined therein, alkoxy or thioalkoxy, $R_{11}$ is alkyl, cycloalkyl, aryl, substituted alkyl as defined therein, alkoxy, thioalkoxy, hydrogen, hydroxyalkyl, cycloalkylalkyl, arylalkyl, (heterocyclic)alkyl, alkoxyalkyl and thioalkoxyalkyl, $R_{22}$ is hydrogen or alkyl, $R_{23}$ is hydroxy, hydroxyalkyl, amino, aminoalkyl, aryl or alkyl, $R_{24}$ is aryl, amino, alkylamino, dialkylamino, trialkylamino, heterocyclic, hydroxy, alkoxy, alkanoyloxy, mercapto, carboxy, alkoxycarbonyl, dialkylaminoalkoxycarbonyl, aminocarbonyl, alkylaminocarbonyl, dialkylaminocarbonyl, cyclicamino, cycloalkylamino, guanidinyl, cyano, N-cyanoguanidinyl, cyanoamino, hydroxyalkylamino, di(hydroxyalkyl)amino, arylalkyl, aminoalkyl, alkylaminoalkyl, dialkylaminoalkyl, trialkylaminoalkyl, heterocyclicalkyl, hydroxyalkyl, alkoxyalkyl, alkanoyloxyalkyl, mercaptoalkyl, carboxyalkyl, alkoxycarbonylalkyl, dialkylaminoalkoxycarbonylalkyl, aminocarbonylalkyl, alkylaminocarbonylalkyl, dialkylaminocarbonylalkyl, cyclicaminoalkyl, cycloalkylaminoalkyl, guanidinylalkyl, cyanoalkyl, N-cyanoguanidinylalkyl, cyanoaminoalkyl, hydroxyalkylaminoalkyl or di(hydroxyalkyl)aminoalkyl, $W_1$ and $W_2$ are independently selected from hydroxy and amino, $W_3$ and $W_4$ are independently selected from hydrogen and fluoro, W is as defined therein, Y is O, S, NH or —N(alkyl)—, Z is as defined therein, $G_{12}$ is absent or an amino acid residue, $H_{13}$ is absent or an amino acid residue, $G_{121}$ is absent or an amino acid residue, $H_{131}$ is absent or an amino acid residue and $I_{14}$ is absent or an amino acid residue;

PCT Patent Application No. WO 86/06379, published Apr. 5, 1989, discloses mimics of the Leu-Val cleavage site of angiotensinogen having the formula

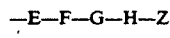

wherein E, F, G, H and Z are as defined therein including —E—F— is

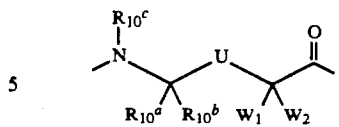

wherein $R_{10a}$ is hydrogen or alkyl, $R_{10b}$ is alkyl, cycloalkyl, cycloalkylalkyl, arylalkyl, (heterocyclic)alkyl, cycloalkenyl or cycloalkenylalkyl, $R_{10c}$ is hydrogen or alkyl, U is —C(O)—, —CH(OH)— or —CH(NH$_2$)— and $W_1$ and $W_2$ are independently selected from hydrogen, fluoro, chloro and bromo, G is absent or an amino acid residue, H is absent or an amino acid residue and Z is hydroxy, thiol, amino, substituted alkoxy, substituted thioalkoxy, substituted alkylamino, Lys—OH, Lys—NH$_2$, Ser—OH or Ser—NH$_2$;

European Patent Application No. EP0271862, published Jun. 22, 1988, discloses mimics of the Leu-Val cleavage site of angiotensinogen having the formula

—Y—W—U wherein Y, W and U are as defined therein including Y is Sta, Cysta or PhSta, W is Leu, Ile, N-MeLeu, Val or absent and U is —NHCH$_2$CH(CH$_3$)CH$_2$CH$_3$, —NHCH$_2$Ph, —NHCH(CH$_2$OH)CH(CH$_3$)CH$_2$CH$_3$, —NHCH$_2$CH(OH)CH$_2$SCH(CH$_3$)$_2$, —NHCH$_2$CH(OH)CH$_2$S(O)CH(CH$_3$)$_2$, —NHCH$_2$CH(OH)CH$_2$S(O)$_2$CH(CH$_3$)$_2$, —NHCH$_2$CH$_2$Ph, —NHCH$_2$(pyrid-2-yl), —NH$_2$, —NHCH$_2$CH=CH$_2$, —OEt, —OMe, —NH(piperidin-4-yl),

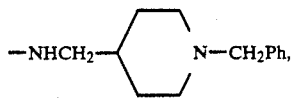

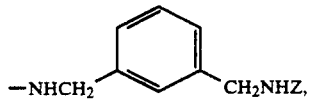

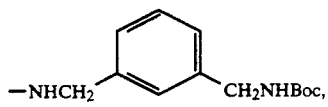

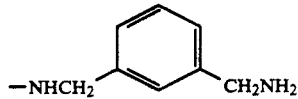

or

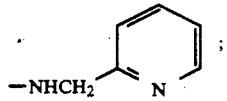

European Patent Application No. EP0275480, published Jul. 27, 1988, discloses mimics of the Leu-Val cleavage site of angiotensinogen having the formula

—W—U—V wherein W, U and V are as defined therein including W is Sta, PhSta or Cysta, U is absent, Leu, Ile, Val, N-

MeLeu or N-MeIle and V is —NHCH$_2$Ph, —NHCH$_2$-cyclohexyl, —NH(piperidin-4-yl), —NHCH$_2$(pyrid-2-yl), —NHCH$_2$CH(CH$_3$)CH$_2$CH$_3$, —OMe, —OEt, —NHCH(CH$_2$OH)CH(CH$_3$)CH$_2$CH$_3$, —NHCH$_2$CH$_2$-(morpholin-1-yl),

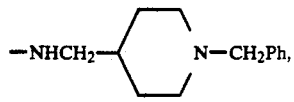

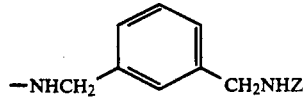

or

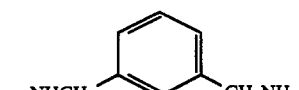

PCT Patent Application No. WO 88/03927, published Jun. 2, 1988, discloses mimics of the Leu-Val cleavage site of angiotensinogen having the formula

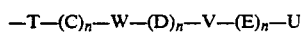

wherein T, C, W, D, V, E, U and n are as defined therein including n is 0–1, T is Sta, PhSta, Cysta, Leu, CyclohexylAla or Phe, W is absent, Leu, Gly or Ile, V is absent, Leu or Ile, C is —CH$_2$NH—, —CH(OH)CH$_2$—, or —CH(OH)—CH=CH—C(O)—, D is —CH$_2$NH—, E is —CH$_2$NH— or —CH$_2$N(Cbz)— and U is —NHCH$_2$Ph, —NHCH$_2$-cyclohexyl, —NH$_2$, —NH(piperidin-4-yl), —NHCH$_2$(pyrid-2-yl), —NHCH$_2$CH(CH$_3$)CH$_2$CH$_3$, —OMe, —OEt,

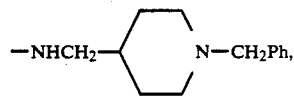

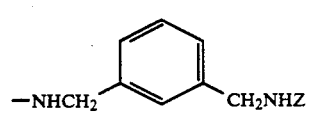

or

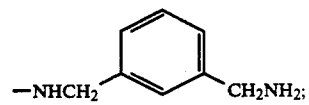

European Patent Application No. EP0314060, published May 3, 1989, discloses mimics of the Leu-Val cleavage site of angiotensinogen having the formula

wherein W and U are as defined therein including W is Sta, Cysta, PhSta, ChSta, DFKSta, DFKCys, DFKChs, ASta or ACys and U is —NHCH$_2$CH$_2$(morpholin-1-yl), —NHCH$_2$CH(CH$_3$)CH$_2$CH$_3$, —NHCH(CH$_2$OH)CH(CH$_3$)CH$_2$CH$_3$, —LeuNHCH$_2$Ph, —LeuNHCH$_2$-cyclohexyl, —LeuNH(piperidin-4-yl), —LeuNHCH$_2$(pyrid-2-yl) or

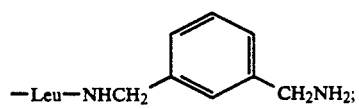

European Patent Application No. EP0310918, published Apr. 12, 1989, discloses mimics of the Leu-Val cleavage site of angiotensinogen having the formula

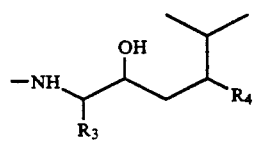

wherein R$_3$ and R$_4$ are as defined therein including R$_3$ is isobutyl, cyclohexylmethyl or benzyl and R$_4$ is phenyl, furyl, vinyl, ethyl or 1,2-dihydroxyethyl;

French Patent Application No. FR8700560, published Jul. 22, 1988, discloses mimics of the Leu-Val cleavage site of angiotensinogen having the formula

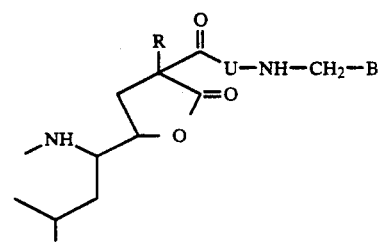

wherein R, U and B are as defined therein including R is hydrogen or hydroxyalkyl. U is Leu, Ala, Val or Ile and B is pyridyl European Patent Application No. EP0236948, published Sep. 16, 1987, discloses mimics of the Leu-Val cleavage site of angiotensinogen having the formula

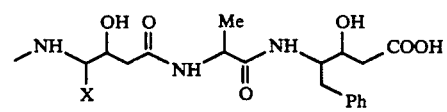

wherein X is as defined therein including X is isobutyl or benzyl;

European Patent Application No. EP0281316, published Sep. 7, 1988, discloses mimics of the Leu-val cleavage site of angiotensinogen having the formula

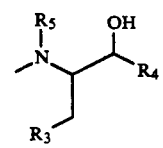

wherein R$_3$, R$_4$ and R$_5$ are as defined therein including R$_3$ is allyl, cyclohexyl or phenyl, R$_4$ is nitromethyl, alkoxycarbonyl or —CH$_2$S(O)$_n$—R$^d$ wherein n is 0–2 and R$^d$ is heterocyclic and R$_5$ is hydrogen or alkyl;

German Patent Application No. DE3825242, published Feb. 9, 1989, discloses mimics of the Leu-Val cleavage site of angiotensinogen having the formula

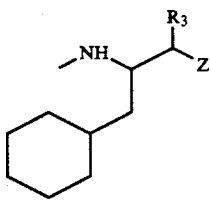

wherein R₃ and Z are as defined therein including R₃ is hydroxy or amino and Z is substituted carbonyl, substituted thiocarbonyl, substituted iminocarbonyl or unsubstituted or substituted phosphono, aminomethyl, thiomethyl, sulfinylmethyl, sulfonylmethyl or phosphonomethyl;

' European Patent Application No. EP0275101, published Jul. 20, 1988, discloses mimics of the Leu-Val cleavage site of angiotensinogen having the formula

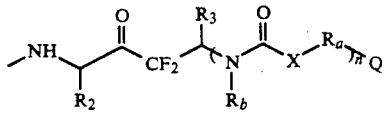

wherein $R_2$, $R_3$, $R_a$, $R_b$, n, X and Q are as defined therein including $R_2$ is an amino acid side chain, $R_3$ is hydrogen, alkyl, cyclohexyl, cyclohexylmethyl, phenyl, benzyl, 2-pyridylmethyl or an amino acid side chain, $R_a$ is an amino acid side chain, $R_b$ is hydrogen or alkyl or $R_a$ and $R_b$ taken together are —CH₂—CH₂—, n is 1-10, X is hydrogen, CH₂, alkoxy, substituted alkoxy, alkyl, phenyl, benzyl, cyclohexyl, cyclohexylmethyl or 2-pyridylmethyl and Q is hydrogen, alkyl, arylakyl, alkoxycarbonyl or an amino acid residue;

PCT Patent Application No. WO 89/01488, published Feb. 23, 1989, discloses mimics of the Leu-Val cleavage site of angiotensinogen having the formula

—E₁₀—F₁₁—G₁₂—H₁₃—I₁₄—Z wherein E₁₀, F₁₁, G₁₂, H₁₃, I₁₄ and Z are as defined therein including —E₁₀—F₁₁— is

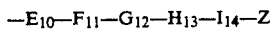

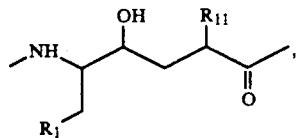

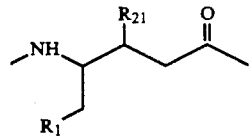

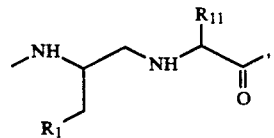

-continued

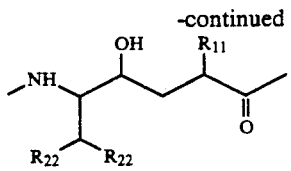

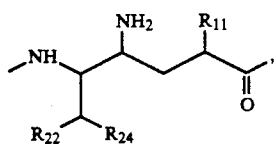

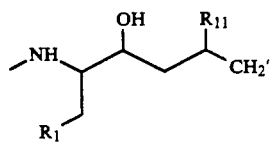

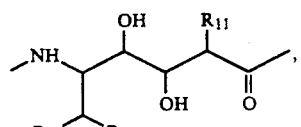

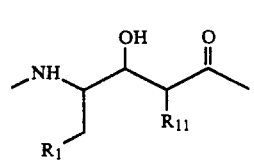

or

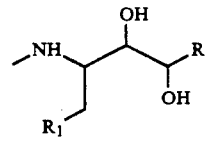

wherein R₁ is hydrogen, alkyl, aryl, cycloalkyl, heterocyclic, alkoxy or thioalkoxy, R₁₁ is hydrogen, alkyl, benzyl, cycloalkyl, hydroxyalkyl, cycloalkylalkyl, arylalkyl, (heterocyclic)alkyl, alkoxyalkyl or thioalkoxyalkyl, R₂₁ is hydroxy or amino, R₂₂ is hydrogen or alkyl and R₂₃ is hydroxy, amino, hydroxyalkyl, aminoalkyl, aryl or alkyl, R₂₄ is R₁ hydroxy, amino, hydroxyalkyl or aminoalkyl, G₁₂ is absent or an amino acid residue, H₁₃ is absent or an amino acid residue, I₁₄ is absent or an amino acid residue and Z is hydroxy, substituted alkoxy, substituted amino or cyclic amino;

European Patent Application No. EP0275101, published Jul. 20, 1988, discloses mimics of the Leu-Val cleavage site of angiotensinogen having the formula

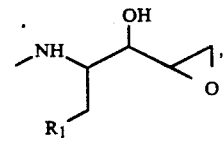

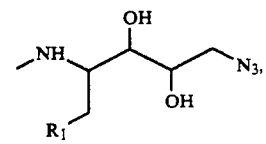

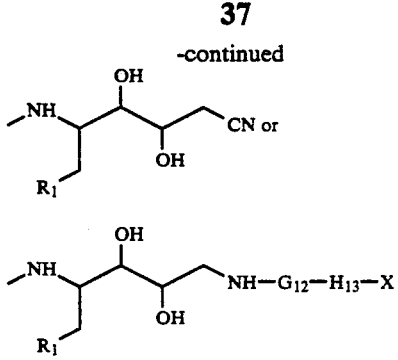

wherein $R_1$, $G_{12}$, $H_{13}$ and X are as defined therein including R1 is hydrogen, alkyl, aryl, cycloalkyl, heterocyclic, alkoxy or thioalkoxy, $G_{12}$ is absent, an amino acid residue or an amino acid residue wherein the alpha-amino group has been replaced by O, $H_{13}$ is absent, an amino acid residue or an amino acid residue wherein the alpha-amino group has been replaced by O and X is hydrogen, alkyl or substituted alkyl as defined therein;

European Patent Application No. EP0312291, published Apr. 19, 1989, discloses mimics of the Leu-Val cleavage site of angiotensinogen having the formula

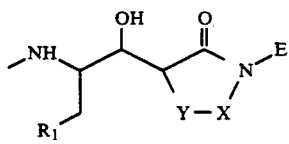

wherein $R_1$, Y, X and E are as defined therein including $R_1$ is hydrogen, alkyl, aryl, cycloalkyl, 1,3-dithiolan-2-yl or 1,3-dithian-2-yl, X is —$CH_2$—$C(R_{13})(R_{14})$— wherein $R_{13}$ and $R_{14}$ are independently selected from hydrogen, alkyl, alkenyl, carboxy, aminocarbonyl, substituted aminocarbonyl, substituted alkyl, alkanoyloxy, substituted aminocarbonyloxy, substituted carbonylamino, substituted aminocarbonylamino, substituted sulfinyl, substituted sulfonyl, substituted sulfide, amino, alkylamino, dialkylamino or heterocyclic, Y is $CH_2$, O, S, SO or $SO_2$ or X and Y taken together is —$(CH_2)_4$— and E is hydrogen, aryl, heterocyclic, alkyl, cycloalkyl or substituted alkyl;

European Patent Application No. EP0312283, published Apr. 19, 1989, discloses mimics of the Leu-Val cleavage site of angiotensinogen having the formula

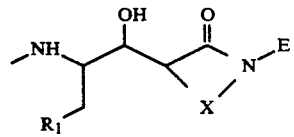

wherein R1, X and E are as defined therein including $R_1$ is hydrogen, alkyl, aryl, cycloalkyl, 1,3-dithiolan-2-yl or 1,3-dithian-2-yl, X is —$CH_2$—$C(R_{13})(R_{14})$— wherein $R_{13}$ and $R_{14}$ are independently selected from hydrogen, alkyl, alkenyl, carboxy, aminocarbonyl, substituted aminocarbonyl, substituted alkyl, alkanoyloxy, substituted aminocarbonyloxy, substituted carbonylamino, substituted aminocarbonylamino, substituted sulfinyl, substituted sulfonyl, substituted sulfide, amino, alkylamino, dialkylamino or heterocyclic and E is hydrogen, aryl, heterocyclic, alkyl, cycloalkyl or substituted alkyl;

European Patent Application No. EP0312158, published Apr. 19, 1989, discloses mimics of the Leu-Val cleavage site of angiotensinogen having the formula

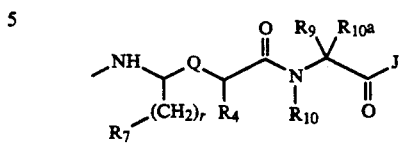

wherein r, $R_7$, $R_4$, $R_{10}$, $R_9$, $R_{10a}$, Q and J are as defined therein including r is 1–4, $R_7$ is alkyl, aryl or cycloalkyl, $R_4$ is hydrogen, alkyl, alkenyl, cycloalkyl, aryl or substituted alkyl, $R_{10}$ and $R_{10a}$ are independently selected from hydrogen and alkyl, $R_9$ is —$(CH_2)_s$—$NR_{11}R_{12}$ wherein s is 1–2 and $R_{11}$ and $R_{12}$ are independently selected from hydrogen, heterocyclic, aryl, cycloalkyl, alkyl, arylalkyl, (heterocyclic)alkyl, aminoalkyl, hydroxyalkyl, alkylaminoalkyl, dialkylaminoalkyl, carboxy, alkyl substituted by —$SO_3H$, aminocarbonylalkyl, alkylaminocarbonylalkyl or dialkylaminocarbonylalkyl, Q is —CH(OH)—, —CH(N($R_8$))—, —CH(OH)$CH_2$— or —CH(N($R_8$))$CH_2$— wherein $R_8$ is hydrogen, alkyl, formyl, alkanoyl, aroyl, alkoxycarbonyl, aryloxycarbonyl or araylalkoxycarbonyl and J is substituted alkylamino or substituted alkoxy;

European Patent Application No. EP03 2157, published Apr. 19, 1989, discloses mimics of the Leu-Val cleavage site of angiotensinogen having the formula

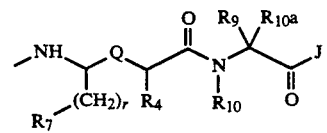

wherein r, $R_7$, $R_4$, $R_{10}$, $R_9$, $R_{10a}$, Q and J are as defined therein including r is 1–4, $R_7$ is alkyl, aryl or cycloalkyl, $R_4$ is hydrogen, alkyl, alkenyl, cycloalkyl, aryl or substituted alkyl, $R_{10}$ and $R_{10a}$ are independently selected from hydrogen and alkyl, $R_9$ is —$(CH_2)_s$—$NR_{11}R_{12}$ wherein s is 1–2 and $R_{11}$ and $R_{12}$ are independently selected from hydrogen, heterocyclic, aryl, cycloalkyl, alkyl, arylalkyl, (heterocyclic)alkyl, aminoalkyl, hydroxyalkyl, alkylaminoalkyl, dialkylaminoalkyl, carboxy, alkyl substituted by —$SO_3H$, aminocarbonylalkyl, alkylaminocarbonylalkyl or dialkylaminocarbonylalkyl, Q is —CH(OH)—, —CH(N($R_8$))—, —CH(OH)$CH_2$— or —CH(N($R_8$))$CH_2$— wherein $R_8$ is hydrogen, alkyl, formyl, alkanoyl, aroyl, alkoxycarbonyl, aryloxycarbonyl or araylalkoxycarbonyl and J is substituted alkylamino, substituted alkoxy, heterocyclic, heterocyclicamino or substitute guanidino;

European Patent Application No. EP0314239, published May 3, 1989, discloses mimics of the Leu-Val cleavage site of angiotensinogen having the formula

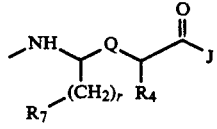

wherein r, $R_7$, $R_4$, Q and J are as defined therein including r is 1–4, $R_7$ is alkyl, aryl or cycloalkyl, $R_4$ is hydrogen, alkyl, alkenyl, cycloalkyl, aryl or substituted alkyl, Q is —CH(OH)—, —CH(N($R_8$))—, —CH(OH)$CH_2$— or —CH(N(R$_8$))CH$_2$— wherein R$_8$ is hydrogen, alkyl, formyl, alkanoyl, aroyl, alkoxycarbonyl, aryloxycarbonyl or araylalkoxycarbonyl and J is amino, hydroxy, substituted alkylamino or substituted alkoxy;

South African Patent Application No. 866642, published Feb. 24, 1987, discloses mimics of the Leu-Val cleavage site of angiotensinogen having the formula

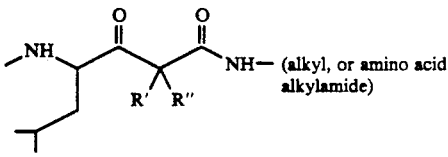

wherein R' and R" are as defined therein including R' is fluoro and R" is hydrogen or fluoro;

European Patent Application No. EP0273696, published Jul. 6, 1988, discloses mimics of the Leu-Val cleavage site of angiotensinogen having the formula

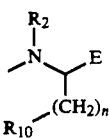

wherein n, R$_2$, R$_{10}$ and E are as defined therein including n is 0–5, R$_2$ is hydrogen or alkyl, R$_{10}$ is alkyl, cycloalkyl, cycloalkylalkyl, arylalkyl, (heterocyclic)alkyl, alkoxyalkyl, thioalkoxyalkyl, hydroxyalkyl or aminoalkyl and E is —CH(W)—G wherein W is hydroxy, amino, alkanoyloxy or alkanoyloxyalkyloxy and G is —Q—C(O)—T—U—V wherein Q is a bond or —CH(R$_{13}$)— wherein R$_{13}$ is hydrogen, aryl, alkyl, cycloalkyl or substituted alkyl, T and U are independently absent or selected from an amino acid residue and V is hydroxy, substituted alkoxy, amino or substituted amino;

European Patent Application No. EP0278158, published Aug. 17, 1988, discloses mimics of the Leu-Val cleavage site of angiotensinogen having the formula

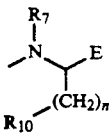

wherein n, R$_7$, R$_{10}$ and E are as defined therein including n is 0–3, R$_7$ is alkyl or substituted alkyl, R$_{10}$ is alkyl, cycloalkyl, cycloalkylalkyl, arylalkyl, (heterocyclic)alkyl, alkoxyalkyl, thioalkoxyalkyl, hydroxyalkyl or aminoalkyl and E is —CH(W)—G wherein W is hydroxy, amino, alkanoyloxy or alkanoyloxyalkyloxy and G is —Q—C(O)—T—U—V wherein Q is a bond or —CH(R$_{13}$)— wherein R$_{13}$ is hydrogen, aryl, alkyl, cycloalkyl or substituted alkyl, T and U are independently absent or selected from an amino acid residue and V is hydroxy, substituted alkoxy, amino or substituted amino;

German Patent Application No. DE3721855, published Sep. 22, 1988, discloses mimics of the Leu-Val cleavage site of angiotensinogen having the formula

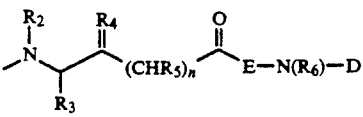

wherein n, R$_2$, R$_3$, R$_4$, R$_5$, R$_6$, E and D are as defined therein including n is 1–2, R$_2$ is hydrogen or alkyl, R$_3$ is hydrogen, alkyl, aryl, arylalkyl, (heterocyclic)alkyl, cycloalkyl, alkoxy or cycloalkylalkyl, R$_4$ is (H,OH), (H,NH$_2$) or O, R$_5$ is hydrogen or alkyl, R$_6$ is hydrogen or alkyl, E is 0–2 amino acid residues and D is —CH$_2$CHOHCH$_2$OH, substituted sulfonyl, substituted sulfonylalkyl, substituted carbonyl, substituted phosphonyl, phenyl, phenylalkyl, furyl, furylalkyl, thienyl, thienylalkyl, pyridyl, pyridylalkyl or other (heterocyclic)alkyl;

European Patent Application No. EP0309841, published Apr. 5, 1989, discloses mimics of the Leu-Val cleavage site of angiotensinogen having the formula

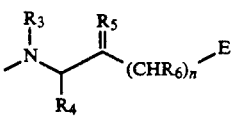

wherein n, R$_3$, R$_4$, R$_5$, R$_6$ and E are as defined therein including n is 1–2, R$_3$ is hydrogen or alkyl, R$_4$ is hydrogen, alkyl, aryl, arylalkyl, heterocyclic, (heterocyclic)alkyl, cycloalkyl, alkoxy or cycloalkylalkyl, R$_5$ is (H,OH), (H,NH$_2$) or O, R$_6$ is hydrogen, alkyl or alkenyl and E is —SR$_7$, —SOR$_7$, —SO$_2$R$_7$, —SO$_2$OR$_7$ or —SO$_2$NR$_7$R$_8$ wherein R$_7$ and R$_8$ are independently selected from R$_4$;

European Patent Application No. EP0292800, published Nov. 30, 1988, discloses mimics of the Leu-Val cleavage site of angiotensinogen having the formula

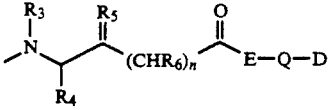

wherein n, R$_3$, R$_4$, R$_5$, R$_6$, E, Q and Y are as defined therein including n is 1–2, R$_3$ is hydrogen or alkyl, R$_4$ is hydrogen, alkyl, aryl, arylalkyl, heterocyclic, (heterocyclic)alkyl, cycloalkyl, cycloalkylalkyl or alkoxy, R$_5$ is (H,OH), (H,NH$_2$), or O, R$_6$ is hydrogen or alkyl, E is 0–2 amino acid residues, Q is O or NH and Y is H or substituted alkyl;

European Patent Application No. EP0249096, published Dec. 16, 1987, discloses mimics of the Leu-Val cleavage site of angiotensinogen having the formula

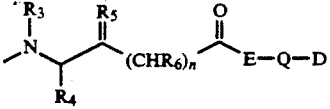

wherein n, R$_3$, R$_4$, R$_5$, R$_6$, E, Q and Y are as defined therein including n is 1–2, R$_3$ is hydrogen or alkyl, R$_4$ is hydrogen, alkyl, aryl, arylalkyl, heterocyclic, (heterocyclic)alkyl, cycloalkyl, cycloalkylalkyl or alkoxy, R$_5$ is (H,OR$_{12}$), (H,NR$_{12}$R$_{13}$), or O wherein R$_{12}$ and R$_{13}$ are independently selected from hydrogen and alkyl, $R_6$ is hydrogen or alkyl, E is 0-2 amino acid residues, Q is O or NH and Y is H or substituted alkyl; and European Patent Application No. EP0264795, published Apr. 27, 1988, discloses mimics of the Leu-Val cleavage site of angiotensinogen having the formula

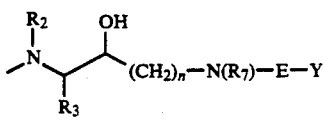

wherein n, R2, R3, R4, E and Y are as defined therein including n is 1-2, R2 is hydrogen or alkyl, R3 is hydrogen, alkyl, aryl, arylalkyl, heterocyclic, (heterocyclic)alkyl, cycloalkyl, cycloalkylalkyl or alkoxy, R4 is hydrogen or alkyl, E is —C(O)NH—, —C(S)NH—, —C(O)O—, —SO2—, —SO2NH—, or —PO(OA)O— wherein A is hydrogen or alkyl and Y is carboxy, carboxyalkyl, substituted carboxyalkyl, alkoxycarbonyl, alkoxycarbonylalkyl, substituted alkoxycarbonylalkyl, aminocarbonyl, substituted aminocarbonyl, aminocarbonylalkyl, substituted aminocarbonylalkyl, hydrogen, alkyl, aryl, arylalkyl, cycloalkyl or cycloalkylalkyl; or E-Y is pyrrolidinocarbonyl, piperidinocarbonyl, morpholinocarbonyl, pyrrolidinosulfonyl, piperidinosulfonyl or morpholinosulfonyl.

The term "substituted amino" as used herein refers to:
I) alkylamino,
II) dialkylamino,
III) (hydroxyalkyl)(alkyl)amino,
IV) (dihydroxyalkyl)(alkyl)amino,
V) alkoxycarbonylalkylamino,
VI) carboxyalkylamino,
VII) (amino)carboxyalkylamino,
VIII) ((N-protected)amino)carboxyalkylamino,
IX) (alkylamino)carboxyalkylamino,
X) ((N-protected)alkylamino)carboxyalkylamino,
XI) (dialkylamino)carboxyalkylamino,
XII) (amino)alkoxycarbonylalkylamino,
XIII) ((N-protected)amino)alkoxycarbonylalkylamino,
XIV) (alkylamino)alkoxycarbonylalkylamino,
XV) ((N-protected)alkylamino)alkoxycarbonylalkylamino,
XVI) (dialkylamino)alkoxycarbonylalkylamino,
XVII) (alkoxyalkyl)(alkyl)amino,
XVIII) (alkoxyalkoxyalkyl)(alkyl)amino,
XIX) di-(alkoxyalkyl)amino,
XX) di-(alkoxyalkoxyalkyl)amino,
XXI) di-(hydroxyalkyl)amino,
XXII) ((unsubstituted heterocyclic)alkyl)(alkyl)amino,
XXIII) ((substituted heterocyclic)alkyl)(alkyl)amino,

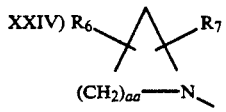

wherein aa is 1 to 5 and $R_6$ and $R_7$ are independently selected from
1) hydrogen,
2) hydroxy,
3) alkoxy,
4) thioalkoxy,
5) alkoxyalkoxy,
6) carboxy,
7) alkoxycarbonyl,
8) halogen,
9) amino,
10) alkylamino,
11) dialkylamino,
12) alkylsulfonylamino,
13) arylsulfonylamino,
14) alkylaminocarbonylamino,
15) alkylaminocarbonyloxy,
16) alkoxycarbonyloxy,

wherein dd is 1 to 5, and
18) $R_8$—Z— wherein
Z is O, S or NH and $R_8$ is a $C_1$ to $C_6$ straight or branched carbon chain substituted by a substituent selected from hydroxy, alkoxy, thioalkoxy, alkoxyalkoxy, amino, alkylamino, dialkylamino, carboxy, alkoxycarbonyl, aryl and heterocyclic;

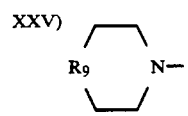

wherein $R_9$ is
1) O,
2) S,
3) $SO_2$ or
4) C=O; or

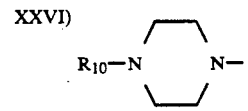

wherein $R_{10}$ is
1) hydrogen,
2) loweralkyl,
3) an N-protecting group or
4) $R_{11}$—C(O)— wherein $R_{11}$ is aminoalkyl, (N-protected)aminoalkyl, 1-amino-2-phenylethyl or 1-(N-protected)amino-2-phenylethyl.

The term "substituted methylene group" as used herein refers to:
(I) —$CHR_{13}R_{14}$ wherein
1) $R_{13}$ is
   i) hydroxy
   ii) hydroxy
and
2) $R_{14}$ is
   i) hydrogen,
   ii) loweralkyl,
   iii) hydroxy,
   iv) hydroxyalkyl,
   v) alkoxy,
   vi) alkoxyalkyl,
   vii) azido,
   viii) azidoalkyl,
   ix) amino,
   x) (N-protected)amino,
   xi) aminoalkyl, xii) (N-protected)aminoalkyl,
xiii) alkylamino,
xiv) (N-protected)(alkyl)amino,
xv) alkylaminoalkyl,
xvi) (N-protected)(alkyl)aminoalkyl,
xvii) dialkylamino,
xviii) dialkylaminoalkyl,
xix) carboxyalkyl,
xx) thioalkoxy,
xxi) thioalkoxyalkyl,
xxii) alkylsulfonyl,
xxiii) alkylsulfonylalkyl,
xxiv) thioaryloxy,
xxv) thioaryloxyalkyl,
xxvi) arylsulfonyl,
xxvii) arylsulfonylalkyl,
xxviii) (unsubstituted heterocyclic)alkyl or
xxvix) (substituted heterocyclic)alkyl
such that when $R_{13}$ is hydroxy then $R_{14}$ is not hydroxy, alkoxy, azido, amino, alkylamino, dialkylamino, (N-protected)amino, (N-protected)(alkyl)amino, thioalkoxy, alkylsulfonyl or arylsulfonyl, and such that when $R_{13}$ is hydrogen then $R_{14}$ is not hydrogen or loweralkyl;

(II) $-C(=CH_2)C(O)NHR_{15}$,
(III) $-C(OH)(R_{16})C(O)NHR_{15}$ or
(IV) $-CH(R_{16})C(O)NHR_{15}$ wherein
 1) $R_{15}$ is
  i) loweralkyl,
  ii) hydroxyalkyl,
  iii) alkoxyalkyl,
  iv) aminoalkyl,
  v) alkylaminoalkyl,
  vi) dialkylaminoalkyl,
  vii) aryl,
  viii) heterocyclic or
  ix) (heterocyclic)alkyl and
 2) $R_{16}$ is
  i) hydrogen,
  ii) loweralkyl,
  iii) hydroxyalkyl,
  iv) haloalkyl or
  v) azidoalkyl;

(V) 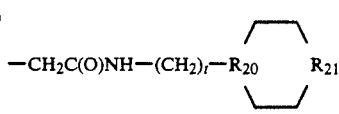

wherein
 1) t is 0 to 3,
 2) $R_{20}$ is
  i) $CH_2$ or
  ii) N and
 3) $R_{21}$ is
  i) NH,
  ii) O,
  iii) S or
  iv) $SO_2$,
such that when t is 0 then $R_{20}$ is $CH_2$ and when t is 1 to 3 then $R_{20}$ is N,
(VI) $-CH_2CH(R_{22})C(O)NHR_{23}$ wherein
 1) $R_{22}$ is
  i) loweralkyl or
  ii) cycloalkylalkyl
and
 2) $R_{23}$ is
  i) loweralkyl,
  ii) hydroxyalkyl,
  iii) alkoxyalkyl,
  iv) aminoalkyl,
  v) alkylaminoalkyl,
  vi) dialkylaminoalkyl,
  vii) aryl,
  viii) arylalkyl
  ix) heterocyclic,
  x) (heterocyclic)alkyl or xi) 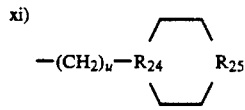

wherein
 a) u is 0 to 3,
 b) $R_{24}$ is $CH_2$ or N and
 c) $R_{25}$ is NH, O, S or $SO_2$,
such that when u is 0 then $R_{24}$ is $CH_2$ and when u is 1 to 3 then $R_{24}$ is N;

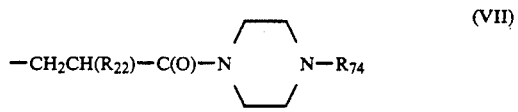 (VII)

wherein
 1) $R_{22}$ is as defined above and
 2) $R_{74}$ is
  i) hydrogen,
  ii) loweralkyl,
  iii) an N-protecting group or
  iv) $R_{75}-C(O)-$ wherein $R_{75}$ is aminoalkyl or (N-protected)-aminoalkyl;

 (VIII)

wherein
 1) $R_{26}$ is
  i) loweralkyl or
  ii) cycloalkylalkyl and
 2) $R_{27}$ is
  i) loweralkyl or
  ii) cycloalkylalkyl;
(IX) $-CH_2CH(R_{81})NHC(O)R_{82}$ or
$-CH_2CH(R_{81})NHS(O)_2R_{82}$ wherein
 1) $R_{81}$ is
  i) loweralkyl or
  ii) cycloalkylalkyl and
 2) $R_{82}$ is
  i) loweralkyl,
  ii) alkoxy,
  iii) alkylamino
  iv) dialkylamino,
  v) $-OR^*$ wherein $R^*$ is aminoalkyl, alkylaminoalkyl, dialkylaminoalkyl or (heterocyclic)alkyl or vi)

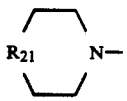

wherein $R_{21}$ is as defined above;

(X) —$CH_2NHC(O)R_{82}$ or —$CH_2NHS(O)_2R_{82}$ wherein $R_{82}$ is as defined above; or (XI) —$CF_2CH(OH)R_{83}$ wherein $R_{83}$ is loweralkyl, loweralkenyl, cycloalkyl, cycloalkenyl, cycloalkylalkyl, cycloalkenylalkyl, aryl, arylalkyl, heterocyclic or (heterocyclic)alkyl.

The chiral centers of the compounds of the invention may have either the "R", "S" or "R,S" configuration. The terms "R" and "S" configuration are as defined by IUPAC 1974 Recommendations for Section E, Fundamental Stereochemistry, Pure Appl. Chem. (1976) 45, 13–30.

The term "N-protecting group" or "N-protected" as used herein refers to those groups intended to protect nitrogen atoms against undesirable reactions during synthetic procedures or to prevent the attack of exopeptidases on the final compounds or to increase the solubility of the final compounds and includes but is not limited to acyl, acetyl, pivaloyl, t-butylacetyl, trichloroethoxycarbonyl, t-butyloxycarbonyl (Boc), benzyloxycarbonyl (Cbz) or benzoyl groups or an L- or D-aminoacyl residue, which may itself be N-protected similarly.

The term "loweralkyl" as used herein refers to straight or branched chain alkyl radicals containing from 1 to 6 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "loweralkenyl" as used herein refers to a loweralkyl radical which contains at least one carbon-carbon double bond.

The term "aminoalkyl" as used herein refers to —$NH_2$ appended to a loweralkyl radical.

The term "hydroxyalkyl" as used herein refers to —OH appended to a loweralkyl radical.

The term "alkylamino" as used herein refers to a loweralkyl radical appended to an NH radical.

The term "cycloalkyl" as used herein refers to an aliphatic ring having 3 to 7 carbon atoms.

The term "cycloalkylalkyl" as used herein refers to an cycloalkyl group appended to a loweralkyl radical, including, but not limited to cyclohexylmethyl and the like.

The term "cycloalkenyl" as used herein refers to an aliphatic ring having 3–7 carbon atoms and also having at least one carbon-carbon double bond including, but not limited to, cyclohexenyl and the like.

The term "cycloalkenylalkyl" as used herein refers to a cycloalkenyl group appended to a loweralkyl radical.

The terms "alkoxy" and "thioalkoxy" as used herein refer to $R_{30}O$— and $R_{30}S$—, respectively, wherein $R_{30}$ is a loweralkyl group or a cycloalkyl group.

The term "alkoxyalkoxy" as used herein refers to an alkoxy group appended to an alkoxy radical, including, but not limited to methoxymethoxy and the like.

The term "alkoxyalkyl" as used herein refers to an alkoxy group appended to a loweralkyl radical.

The term "(thioalkoxy)alkyl" as used herein refers to thioalkoxy appended to a loweralkyl radical.

The term "dialkylamino" as used herein refers to —$NR_{31}R_{32}$ wherein $R_{31}$ and $R_{32}$ are independently selected from loweralkyl groups.

The term "((alkoxy)alkoxy)alkyl" refers to an alkoxy group appended to an alkoxy group which is appended to a loweralkyl radical.

The term "(hydroxyalkyl)(alkyl)amino" as used herein refers to —$NR_{33}R_{34}$ wherein $R_{33}$ is hydroxyalkyl and $R_{34}$ is loweralkyl.

The term "(N-protected)(alkyl)amino" as used herein refers to —$NR_{34}R_{35}$ wherein $R_{34}$ is a loweralkyl group and $R_{35}$ is an N-protecting group.

The term "N-protected aminoalkyl" as used herein refers to $NHR_{35}$ appended to a loweralkyl group, wherein $R_{35}$ is an N-protecting group.

The term "alkylaminoalkyl" as used herein refers to $NHR_{36}$ appended to a loweralkyl radical, wherein $R_{36}$ is a loweralkyl group.

The term "(N-protected)(alkyl)aminoalkyl" as used herein refers to $NR_{35}R_{36}$, which is appended to a loweralkyl radical, wherein $R_{35}$ and $R_{36}$ are as defined above.

The term "dialkylaminoalkyl" as used herein refers to $NR_{39}R_{40}$ is appended to a loweralkyl radical wherein $R_{39}$ and $R_{40}$ are independently selected from loweralkyl.

The term "carboxyalkyl" as used herein refers to a carboxylic acid group (—COOH) appended to a loweralkyl radical.

The term "alkoxycarbonylalkyl" as used herein refers to $R_{41}COR_{42}$— wherein $R_{41}$ is an alkoxy group and $R_{42}$ is a loweralkyl radical.

The term "(amino)carboxyalkyl" as used herein refers to a loweralkyl radical to which is appended a carboxylic acid group (—COOH) and an amino group (—$NH_2$).

The term "((N-protected)amino)carboxyalkyl" as used herein refers to a loweralkyl radical to which is appended a carboxylic acid group (—COOH) and —$NHR_{43}$ wherein $R_{43}$ is an N-protecting group.

The term "(alkylamino)carboxyalkyl" as used herein refers to a loweralkyl radical to which is appended a carboxylic acid group (—COOH) and an alkylamino group.

The term "((N-protected)alkylamino)carboxyalkyl" as used herein refers to a loweralkyl radical to which is appended a carboxylic acid group (—COOH) and an —$NR_{43}R_{44}$ wherein $R_{43}$ is as defined above and $R_{44}$ is a loweralkyl group.

The term "(dialkylamino)carboxyalkyl" as used herein refers to a loweralkyl radical to which is appended a carboxylic acid group (—COOH) and —$NR_{45}R_{46}$ wherein $R_{45}$ and $R_{46}$ are independently selected from loweralkyl.

The term "(amino)alkoxycarbonylalkyl" as used herein refers to a loweralkyl radical to which is appended an alkoxycarbonyl group as defined above and an amino group (—$NH_2$).

The term "((N-protected)amino)alkoxycarbonylalkyl" as used herein refers to a loweralkyl radical to which is appended an alkoxycarbonyl group as defined above and —$NHR_{43}$ wherein $R_{43}$ is as defined above.

The term "(alkylamino)alkoxycarbonylalkyl" as used herein refers to a loweralkyl radical to which is appended an alkoxycarbonyl group as defined above and an alkylamino group as defined above.

The term "((N-protected)alkylamino)alkoxycarbonylalkyl" as used herein refers to a loweralkyl radical to which is appended an alkoxycarbonyl group as defined above and —$NR_{43}R_{44}$ wherein $R_{43}$ and $R_{44}$ are as defined above.

The term "(dialkylamino)alkoxycarbonylalkyl" as used herein refers to a loweralkyl radical to which is appended an alkoxycarbonyl group as defined above and —$NR_{43}R_{44}$ wherein $R_{43}$ and $R_{44}$ are as defined above.

The term "carboxyalkylamino" as used herein refers to —$NHR_{47}$ wherein $R_{47}$ is a carboxyalkyl group.

The term "alkoxycarbonylalkylamino" as used herein refers to —$NHR_{48}$ wherein $R_{48}$ is an alkoxycarbonylalkyl group.

The term "(amino)carboxyalkylamino" as used herein refers to —$NHR_{49}$ wherein $R_{49}$ is an (amino)carboxyalkyl group.

The term "((N-protected)amino)carboxyalkylamino" as used herein refers to —$NHR_{50}$ wherein $R_{50}$ is an ((N-protected)amino)carboxyalkyl group.

The term "(alkylamino)carboxyalkylamino" as used herein refers to —$NHR_{51}$ wherein $R_{51}$ is an (alkylamino)carboxyalkyl group.

The term "((N-protected)alkylamino)carboxyalkylamino" as used herein refers to —$NHR_{52}$ wherein $R_{52}$ is an ((N-protected)alkylamino)carboxyalkyl group.

The term "(dialkylamino)carboxyalkylamino" as used herein refers to —$NHR_{53}$ wherein $R_{53}$ is a (dialkylamino)carboxyalkyl group.

The term "(amino)alkoxycarbonylalkylamino" as used herein refers to —$NHR_{54}$ wherein $R_{54}$ is an (amino)alkoxycarbonylalkyl group.

The term "((N-protected)amino)alkoxycarbonylalkylamino" as used herein refers to —$NHR_{55}$ wherein $R_{55}$ is an ((N-protected)amino)alkoxycarbonylalkyl group.

The term "(alkylamino)alkoxycarbonylalkylamino" as used herein refers to —$NHR_{56}$ wherein $R_{56}$ is an (alkylamino)alkoxycarbonylalkyl group.

The term "((N-protected)alkylamino)alkoxycarbonylalkylamino" as used herein refers to —$NHR_{57}$ wherein $R_{57}$ is an ((N-protected)alkylamino)alkoxycarbonylalkyl group.

The term "(dialkylamino)alkoxycarbonylalkylamino" as used herein refers to —$NHR_{58}$ wherein $R_{58}$ is a (dialkylamino)alkoxycarbonylalkyl group.

The term "polyalkoxy" as used herein refers to —$OR_{59}$ wherein $R_{59}$ is a straight or branched chain containing 1-5, $C_{gg}$—O—$C_{hh}$ linkages wherein gg and hh are independently selected from 1 to 3, including, but not limited to methoxyethoxymethoxy, ethoxyethoxymethoxy and the like.

The term "(dihydroxyalkyl)(alkyl)amino" as used herein refers to a loweralkyl group which is disubstituted with —OH radicals, appended to an amino group, which amino group also has appended another loweralkyl group.

The term "di-(hydroxyalkyl)amino" as used herein refers to —$NR_{60}R_{61}$ wherein $R_{60}$ and $R_{61}$ are hydroxyalkyl residues.

The term "alkoxyalkyl(alkyl)amino" as used herein refers to —$NR_{62}R_{63}$ wherein $R_{62}$ is an alkoxyalkyl group and $R_{63}$ is a loweralkyl group.

The term "di-(alkoxyalkyl)amino" as used herein refers to —$NR_{64}R_{65}$ wherein $R_{64}$ and $R_{65}$ are alkoxyalkyl groups.

The term "(alkoxyalkoxyalkyl)(alkyl)amino" as used herein refers to —$NR_{66}R_{67}$ wherein $R_{66}$ is an alkoxyalkoxyalkyl group and $R_{67}$ is a loweralkyl group.

The term "di-(alkoxyalkoxyalkyl)amino" as used herein refers to —$NR_{68}R_{69}$ wherein $R_{68}$ and $R_{69}$ are alkoxyalkoxyalkyl groups.

The terms "((unsubstituted heterocyclic)alkyl)(alkyl)amino and ((substituted heterocyclic)alkyl)(alkyl)amino" as used herein refer to an amino radical substituted by a loweralkyl group and an (unsubstituted heterocyclic)alkyl group or a (substituted heterocyclic)alkyl group, respectively.

The term "(heterocyclic)alkyl" or "heterocyclic ring substituted alkyl" as used herein refers to a heterocyclic group appended to a loweralkyl radical, including but not limited to imidazolylmethyl and thiazolylmethyl.

The term "azidoalkyl" as used herein refers to —$N_3$ appended to a loweralkyl radical.

The term "alkylsulfonyl" as used herein refers to $R_{70}S(O)_2$— wherein $R_{70}$ is a loweralkyl residue.

The term "alkylsulfonylalkyl" as used herein refers to an alkylsulfonyl group appended to a loweralkyl radical, The term "aryl" as used herein refers to a monocyclic or bicyclic carbocyclic ring system having one or more aromatic rings including, but not limited to, phenyl, naphthyl, tetrahydronaphthyl, indanyl and the like; or "aryl" refers to a heterocyclic aromatic ring as defined below. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, carboalkoxy and carboxamide.

The term "arylalkyl" as used herein refers to an aryl group appended to a loweralkyl radical including, but not limited to, benzyl, naphthylmethyl and the like.

The terms "aryloxy" and "thioaryloxy" as used herein refer to $R_{71}O$— or $R_{71}S$—, respectively, wherein $R_{71}$ is an aryl group.

The terms "aryloxyalkyl" and "thioaryloxyalkyl" as used herein refer to an aryloxy group or a thioaryloxy group, respectively, appended to a loweralkyl radical.

The terms "arylalkoxy" and "arylthioalkoxy" as used herein refer to an aryl group appended to an alkoxy radical or a thioalkoxy radical, respectively, including, but not limited to, phenoxymethyl, thiophenoxymethyl and the like.

The terms "arylalkoxyalkyl" and "arylthioalkoxyalkyl" as used herein refer to an arylalkoxy group or an arylthioalkoxy group, respectively, appended to a loweralkyl radical.

The term "arylsulfonyl" as used herein refers to $R_{72}S(O)_2$— wherein $R_{72}$ is an aryl group.

The term "arylsulfonylalkyl" as used herein refers to an arylsulfonyl group appended to a loweralkyl radical.

The term "alkylsulfonylamino" as used herein refers to $R_{76}NH$— wherein $R_{76}$ is an alkylsulfonyl group.

The term "arylsulfonylamino" as used herein refers $R_{77}NH$— wherein $R_{77}$ is an arylsulfonyl group.

The term "(heterocyclic)sulfonyl" as used herein refers to $R_{72a}S(O)2$— wherein $R_{72a}$ is a heterocyclic group.

The term "alkylaminocarbonylamino" as used herein refers to $R_{78}NHCONH$— wherein $R_{78}$ is a loweralkyl group.

The term "alkylaminocarbonyloxy" is used herein refers to $R_{79}NHC(O)O-$ wherein $R_{79}$ is a loweralkyl group.

The term "alkoxycarbonyloxy" as used herein refers to $R_{80}OC(O)O-$ wherein $R_{80}$ is a loweralkyl group.

The term "halo" or "halogen" as used herein refers to Cl, Br, F or I substituents.

The term "haloalkyl" as used herein refers to a loweralkyl radical in which one or more hydrogen atoms are replaced by halogen including, but not limited to, fluoromethyl, 2-chloroethyl, trifluoromethyl, 2,2-dichloroethyl and the like.

The term "O-protecting group" as used herein refers to a substituent which protects hydroxyl groups and includes but is not limited to substituted methyl ethers, for example, methoxymethyl, benzyloxymethyl, 2-methoxyethoxymethyl, 2-(trimethylsilyl)ethoxymethyl and tehahydropyranyl; substituted ethyl ethers, for example, 2,2,2-trichloroethyl, t-butyl, benzyl and triphenylmethyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

The term "heterocyclic group" or "heterocyclic" as used herein refers to any 3- or 4-membered ring containing a heteroatom selected from oxygen, nitrogen and sulfur, or a 5- or 6-membered ring containing from one to three heteroatoms selected from the group consisting of nitrogen, oxygen, and sulfur; wherein the 5-membered ring has 0-2 double bonds and the 6-membered ring has 0-3 double bonds; wherein the nitrogen and sulfur heteroatoms may optionally be oxidized; wherein the nitrogen heteroatom may optionally be quaternized; and including any bicyclic group in which any of the above heterocyclic rings is fused to a benzene ring or another 5- or 6-membered heterocyclic ring independently as defined above. Heterocyclics in which nitrogen is the heteroatom are preferred. Fully saturated heterocyclics are also preferred. Preferred heterocyclics include: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, N-methyl piperazinyl, azetidinyl, N-methyl azetidinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclics can be unsubstituted or monosubstituted or disubstituted with substitutents independently selected from hydroxy, halo, oxo (=O), alkylimino (R*N= wherein R is a loweralkyl group), amino, alkylamino, dialkylamino, alkoxy, thioalkoxy, polyalkoxy, loweralkyl, cycloalkyl or haloalkyl.

The most preferred heterocyclics include imidazolyl, pyridyl, piperazinyl, N-methyl piperazinyl, azetidinyl, N-methyl azetidinyl, thiazolyl, thienyl, triazolyl and the following:

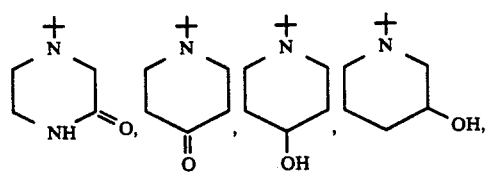

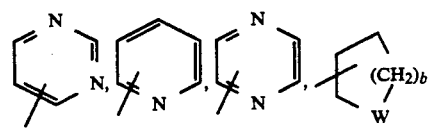

or

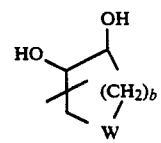

wherein b is 1 or 2 and W is N, NH, O, S, provided that W is the point of connection only when T is N,

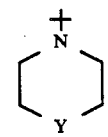

wherein Y is NH, N-loweralkyl, O, S, or $SO_2$, or

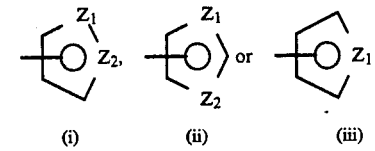

wherein the symbols (i), (ii) and (iii) represent 5-membered heterocycles containing one or more heteroatoms and containing 2 double bonds; wherein $Z_1$ is N, O, or S and not the point of connection and $Z_2$ is N when it is the point of connection and NH, O or S when it is not the point of connection.

The terms "His", "Phe", "HomoPhe", "Ala", "Leu" and "norLeu" as used herein refer to histidine, phenylalanine, homophenylalanine, alanine, leucine and norleucine, respectively.

The compounds of the invention may be prepared as shown in Schemes I-XXIII. The syntheses of segments containing substituents D are described in the Examples or have previously been described (Kempf, et al., J. Med. Chem. 1987, 30, 1978; Luly, et al., J. Med. Chem. 1987, 30, 1609; Buhlmayer, et al., U.S. Pat. No. 4,727,060; Morisawa, et al., European Patent Application No. 0228192; Ten Brink, PCT Patent Application No. W087/02986).

In particular, the process shown in Scheme I discloses the preparation of compounds of the invention having the general structure (1) wherein A is carboxy or alkoxycarbonyl and X is NH. As illustrated in Scheme I, reductive amination of an amino acid ester (I) with an alpha-keto ester (II, R=loweralkyl) provides a diastereomeric mixture which is separated. Each of the diastereomers is hydrolyzed and coupled to the amine (VI) using standard peptide coupling reagents such as N-methylmorpholine (NMM), 1-hydroxybenzotriazole (HOBT) and N-ethyl-N'-(3-dimethylaminopropyl)carbodiimide (EDAC) to give the desired compound (VII).

Compound (VII) can also be prepared using the following method. After reductive amination of (II) with (I), the diastereomeric mixture is hydrolyzed to give (III) and then coupled to amine (VI) as described above. The mixture of diastereomers is then separated, providing two separate isomers. Compound (VII) may be further hydrolyzed to the acid (VIII). The assignment of R or S configuration to the carbon bearing the $R_3$ substitutent in compound (VIII) is based on the fact that the compound derived from the L-isomer is generally a more potent renin inhibitor than the compound derived from the corresponding D-isomer.

The stereochemistry at the chiral carbons of (VIII) can also be established by using chiral starting materials. As illustrated in Scheme II, chiral amino acid ester (XV, R=loweralkyl) is reacted with chiral D-trifluorosulfonyloxy ester (XVI) to give the single isomer (XVII) which is then hydrolyzed and coupled to (VI) to obtain the desired compound (XVIII).

Alternatively, Scheme III illustrates the preparation of compounds (XI). Reductive amination of (IX, $R_2$=loweralkyl) by (X) provides a mixture of diastereomers which can be separated.

A further alternative illustrated by Scheme III involves reductive amination of (IX, $R_2$=loweralkyl) by (XII) followed by separation of the diastereomers (XIII). Each of the diastereomers is then debenzylated and coupled to (VI) as previously described. The methods of Scheme III provide compound (XI) having unknown stereochemistry at the carbon bearing the $R_1$ substituent.

The process of Scheme IV discloses the preparation of compounds of the general structure (1) wherein A is a carboxy derivative $R_5CO$— wherein $R_5$ is an amine and X is NH. Selective hydrolysis of one of the diastereomers (IV) gives the acid derivative (XIX). The acid (XIX) is coupled to the amine $R_5$—H and the resulting amide-ester is hydrolyzed to give (XXI). The acid (XXI) is coupled to amine (VI) to give (XXII). Alternatively, compound (VIII) can be coupled to amine (VI) to provide (XXII).

The process in Scheme V discloses the preparation of compounds of the general structure (XXV) wherein $R_{28}$ is a $C_1$ to $C_4$ straight or branched carbon chain substituted by a substituent selected from carboxy, alkoxycarbonyl, alkylsulfonyl or a substituted or unsubstituted heterocylic. A reaction sequence similar to that used in Scheme I is followed except that compound (XXIII) is employed instead of the amino acid ester (I).

The process in Scheme VI discloses the preparation of compounds of general structure (XXIX) wherein A is alkoxycarbonyl or $R_5CO$— wherein $R_5$ is a substituted amine and X is O or S. The reaction of an alcohol or thiol (XXVI) with the bromo-acid (XXVII) provides a single diastereomer (XXVIII) which is then coupled to the amine (VI) using standard peptide coupling conditions to give the desired product (XXIX). If the racemic form of the bromo-acid (XXVII) is used, diastereomer separation can take place with compound (XXVIII) or (XXIX).

Scheme VII discloses the preparation of compounds of general structure (1) wherein X is $CH_2$ and A is $R_5CO$— wherein $R_5$ is hydroxy, alkoxy, thioalkoxy or an amine. Compound (XXX) (J. Med. Chem. 26, 1277 (1983)) is coupled to amine (VI) to provide the amide ester (XXXI) which is hydrolyzed to give the carboxylic acid (XXXII). Coupling to the appropriate amine provides (XXXIII) wherein $R_5$ is a substituted amine.

The process in Scheme VIII discloses the preparation of compounds of the general structure (1) wherein X is CHOH. Aldol condensation of an aldehyde (XXXIV) (J. Am. Chem. Soc. 103 2876 (1981)) with the chiral oxazolidinone imide (XXXV) (J. Am. Chem. Soc. 103 2127 (1981)) provides (XXXVI). After protection of the secondary alcohol, the benzyl group is removed and the primary alcohol oxidized to the carboxylic acid (XXXVII). The acid is coupled to the appropriate amine $R_5$—H, the imide is hydrolyzed, the resulting acid is coupled to the amine (VI) and the alcohol is deprotected providing the desired compound (XXXVIII).

Schemes IX-XIII disclose the preparation of intermediates used in Schemes I, V and VI, respectively. In Scheme X, R is loweralkyl. In Scheme XI, R is loweralkyl, Ts is p-toluenesulfonyl and P is an N-protecting group. In Scheme XII, R is loweralkyl, $R_5$—H is an amine and X is O or S. In Scheme XIII, $R_5$—H is an amine.

The process in scheme XIV describes the preparation of compounds of the general structure XLII wherein $R_3$ is a $C_1$ to $C_6$ straight or branched alkyl/alkenyl carbon chain or heteroatom substituted carbon chain substituted by O, S, N or substituted by a substitutent selected from a heterocycle or substituted heterocycle. $R_1$ is selected from aryl, substituted aryl, heterocycle, substituted heterocycle, cycloalkyl, unsaturated cycloalkyl, alkylaryl, alkylheterocycle, alkyl cycloalkyl, alkyl unsaturated cycloalkyl. $R_5$ is a cyclic amine, substituted amine, substituted cyclic amine, aryl, substituted aryl, heterocycle, substituted heterocycle. The synthesis of intermediate XL begins by the metalation of the sulfonyl derivative XXXIX with alkyl lithium reagents in THF or THF/HMPA at low temperature according to the procedure sited in European Patent Application No. EP0309841, published Apr. 5, 1989. The subsequent anion is trapped with the appropriate 2-substituted-3-benzyloxypropyl iodide (prepared from the alcohol by the procedure of M. Holladay; J. Med. Chem. 1983, 26, 1277 ), p-toluenesulfonyl chloride and sodium iodide. The resulting diastereomeric sulfonyl ethers XL are deprotected ($H_2$ Pd/C or PdOH) and oxidized to the corresponding carboxylic acids XLI using a variety of oxidants ($KMnO_4$, Jones, PDC, $RuO_4$, $Pt/O_2$). Coupling of the acids with mimics of the Leu-Val cleavage site of angiotensinogen (T-H) using standard coupling procedures gives the diastereomeric amides XLII and XLIII which are separated to give optically active inhibitors.

Scheme XV outlines the synthesis of carboxylic acids of the general formula XLIX wherein $R_1$ is a $C_1$ to $C_6$ straight or branched alkyl/alkenyl carbon chain or heteroatom substituted carbon chain substituted by O, S, N. or substituted by a substitutent selected from a heterocycle or substituted heterocycle. R is selected from aryl, substituted aryl, heterocycle, substituted heterocycle, cycloalkyl, unsaturated cycloalkyl, alkylaryl, alkylheterocycle, alkyl cycloalkyl, alkyl unsaturated cycloalkyl. The cyclic amine ($n''$=1 to 7) is substituted with groups V selected from a $C_1$ to $C_6$ straight or branched alkyl/alkenyl carbon chain or heteroatom substituted carbon chain substituted by O, S, N. The synthesis begins by esterificaton followed by allylation of the 2S-hydroxyacid XLIV. Ester XLV is reduced with lithium aluminum hydride and the resulting alcohol is reacted with ozone. Reductive workup of the ozonide and Collins oxidation ($CrO_3 \cdot 2Pyr$) gives the optically pure lactone XLVI. Reaction of the lactone with LiHMDS in THF or THF/HMPA followed by the addition of $R_1$—I or $R_1$—Br (i.e., an alkyl iodide or arylalkyl iodide or bromide) gives the disubstituted lactone XLVII. The lactone XLVII is reacted with the amino aluminum reagent which is prepared from the secondary amine and trimethylaluminum according to the procedure of Weinreb et. al. Org. Syn. 1980, 59, 49, to give the alcohol XLVIII. Oxidation of the alcohol using a variety of oxidants ($KMnO_4$, Jones, PDC, $RuO_4$, $Pt/O_2$) gives the acid XLIX which is ready for coupling to T-H using known methods.

An alternative synthesis of the disubstituted lactone LIII and related lactone LVII is shown in scheme XVI. The 2(S)-hydroxyacid L is first converted to the ethyl ester by Fisher esterification. Trans esterification with the Z-allylic alcohol and titanium isopropoxide (using the procedure of Seebach et. al. Org. Syn. 1986, 65, 230) gives the hydroxy ester LI. Halo ($I_2$ or NBS) or mercuric trifluoroacetate cyclization of the hydroxy olefin gives the disubstituted lactone LII. Reduction of LII with tributyltinhydride or sodium borohydride affords the reduced lactone intermediate LIII.

Scheme XVII discloses an alternative synthesis of carboxylic acids LVIII and LIX wherein $R_1$ is a $C_1$ to $C_6$ straight or branched alkyl/alkenyl carbon chain or heteroatom substituted carbon chain substituted by O, S, N or substituted by a substitutent selected from a heterocycle or substituted heterocycle. R is selected from aryl, substituted aryl, heterocycle, substituted heterocycle, cycloalkyl, unsaturated cycloalkyl, alkylaryl, alkylheterocycle, alkyl cycloalkyl, alkyl unsaturated cycloalkyl. The cyclic amine ($n''=1$ to 7) is substituted with groups V selected from a $C_1$ to $C_6$ straight or branched alkyl/alkenyl carbon chain or heteroatom substituted carbon chain substituted by O, S, N. The synthetic strategy is similar to that outlined in scheme XV. The lactone LV is prepared from the corresponding amino alcohol LIV. Alkylation of LV with NaHMDS and alkyl iodide or bromide gives the disubstituted lactone LVI. The lactone LVI is hydrolyzed and esterified to hydroxy ester LVII which is converted to the acid LIX as shown in the scheme. Alternatively, LVI is transformed to the acid LVIII. Carboxylic acids LVIII and LIX are converted to final inhibitor compounds LVIIIa and LIXa as previously described.

Scheme XVIIa discloses a synthetic route to inhibitors containing esters of the general formula LVIb and LVIIb wherein R and $R_1$ are the same as previously described for scheme XVII and $R_2$ is selected from $C_1$ to $C_6$ straight or branched carbon chain. T is selected from a variety of mimics of the Leu-Val cleavage site of angiotensinogen. The five step sequence from LVI to LVIb prepares the key acid intermediate from permanganate oxidation which is coupled to give final products. The seven step sequence from LVI to LVIIb produces a similar final product with the R and $R_1$ substituents reversed.

The syntheses of hydroxyethylene dipeptide isosteres are depicted in Schemes XVIII and XIX. The chirality of the valine-mimic isopropyl group is established via a highly diastereoselective aldol condensation. Scheme XVIII details the use of technology developed by D. A. Evans and coworkers (see D. A. Evans, J. Bartroli and T. L. Shih, J. Am. Chem. Soc. 1981, 103, 2127), in which the aldehyde LX (synthesized in analogy to the isobutyl-substituted aldehyde described by S. Thaisrivongs, D. T. Pals, L. T. Kroll, S. R. Turner and F.-S. Han, J. Med. Chem. 1987, 30, 976) is condensed with the norephedrine-derived acyloxazolidinone to produce the aldol product LXI. Barton deoxygenation (D. H. R. Barton and S. W. McCombie, J. Chem. Soc., Perkin Trans. 1, 1975, 1574) provides the diprotected hydroxyethylene dipeptide isostere LXIII. Removal of the chiral auxiliary with basic peroxide (D. A. Evans, T. C. Britton and J. A. Ellman, Tetrahedron Lett. 1987, 28(49), 6141) affords the intermediate carboxylic acid LXIV, which is then coupled to the desired amines ($RNH_2$) to yield amides LXV.

An alternative strategy is outlined in Scheme XIX. Employment of the cysteine-derived thiazolidinethione (C. N. Hsiao, L. Liu and M. J. Miller, J. Org. Chem. 1987, 52, 2201) as chiral auxiliary allows the direct conversion of aldol adduct LXVII to the hydroxy amide LXVIII, thereby avoiding the hydrolysis step in Scheme XVIII. The secondary hydroxyl group is deoxygenated to produce the same protected amides LXV.

The synthesis of $P_2'$ retro-inverted amine derivatives is described in Scheme XX. The intermediate carboxylic acid LXIV is transformed into isocyanate LXX by the action of diphenylphosphorylazide, and the isocyanate is trapped with a range of nucleophiles, including, but not limited to primary and secondary amines, alcohols, thiols and organomagnesium halides. Scheme XX illustrates the synthesis of retro-inverted amides LXXI, ureas LXXII and carbamates LXXIII.

These various hydroxyethylene dipeptide isosteres are then deprotected under the conditions listed in Scheme XXI. The resulting free-base forms of the aminoalcohols LXXIV and LXXV are then available for standard peptide couplings.

Scheme XXII outlines a method for producing analogs of $P_2'$-retro-inverted statine isosteres (an extension of the previous work of S. H. Rosenberg, J. J. Plattner, K. W. Woods, H. H. Stein, P. A. Marcotte, J. Cohen and T. J. Perun, J. Med. Chem. 1987, 30, 1224), in which the protected amino-epoxide LXXVI (J. R. Luly, J. F. Dellaria, J. J. Plattner, J. L. Soderquist and N. Yi, J. Org. Chem. 1987, 52, 1487) is opened with a primary amine to provide aminoalcohols LXXVII. These compounds are then derivatized as sulfonamides, sulfamides, ureas, carbamates, amides or other amine derivatives. Scheme XXII details the example of a sulfonamide or sulfamide. The free aminoalcohol (LXXIX) is provided by simple deprotection of the Boc-group.

Scheme XXIII depicts an alternative strategy for the production of the $P_2'$ retro-inverted amide derivatives. Intermediate aldehyde LX is condensed with a primary amine under standard reductive alkylation conditions, and the resulting amine LXXX is derivatized to the desired protected amine derivative LXXXII. This has been accomplished by the use of the appropriate sulfonyl or sulfamoyl chloride, to yield, respectively, the corresponding sulfonamide or sulfamide. In addition, the catechol sulfamate ester LXXXI can be employed to produce sulfamide derivatives. Deprotection produces aminoalcohols LXXXIII, available for coupling reactions.

SCHEME I
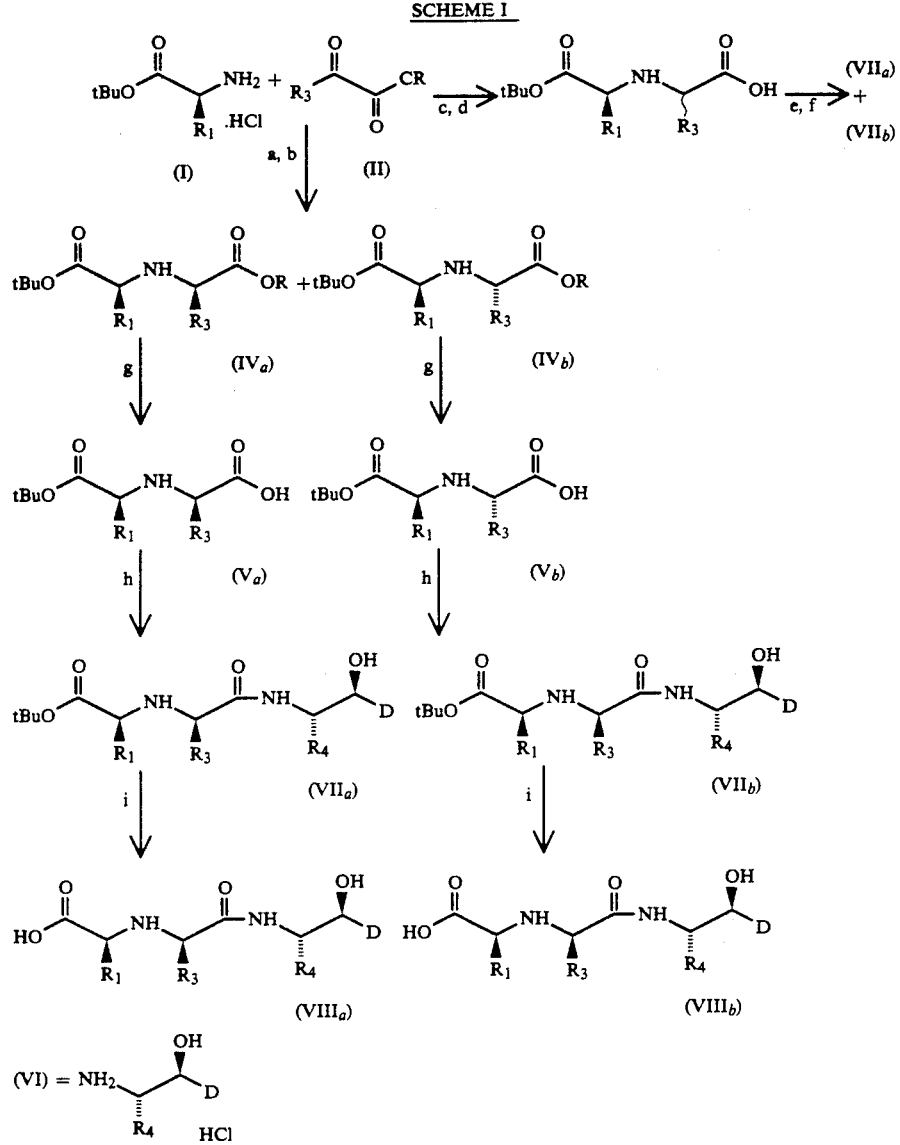
a: NaOAc, NaCNBH₃; b: separate diastereomers; c: as a; d: LiOH, H₂O, dioxane; e: (VI), NMM, HOBT, EDAC; f: as b; g: as d; h: as e; i: dioxane/HCl.
SCHEME II
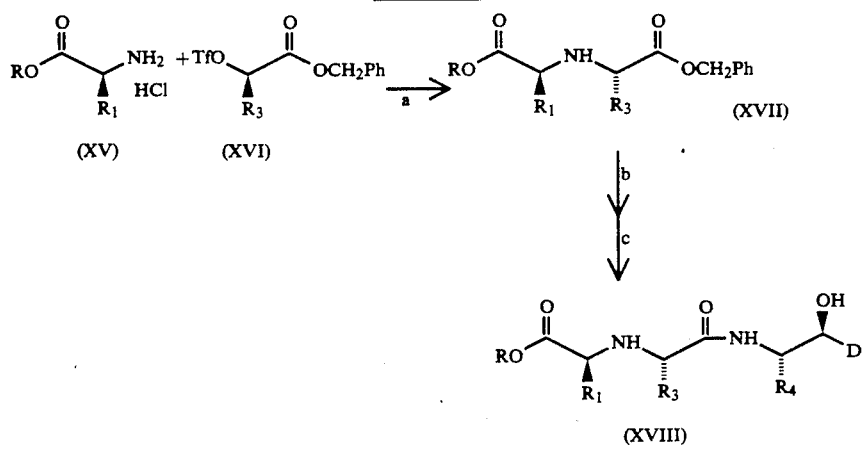

SCHEME II
a: 2 eq TEA, CH$_2$Cl$_2$, 0-25°; b: selective hydrolysis:
C: coupled to (VI).
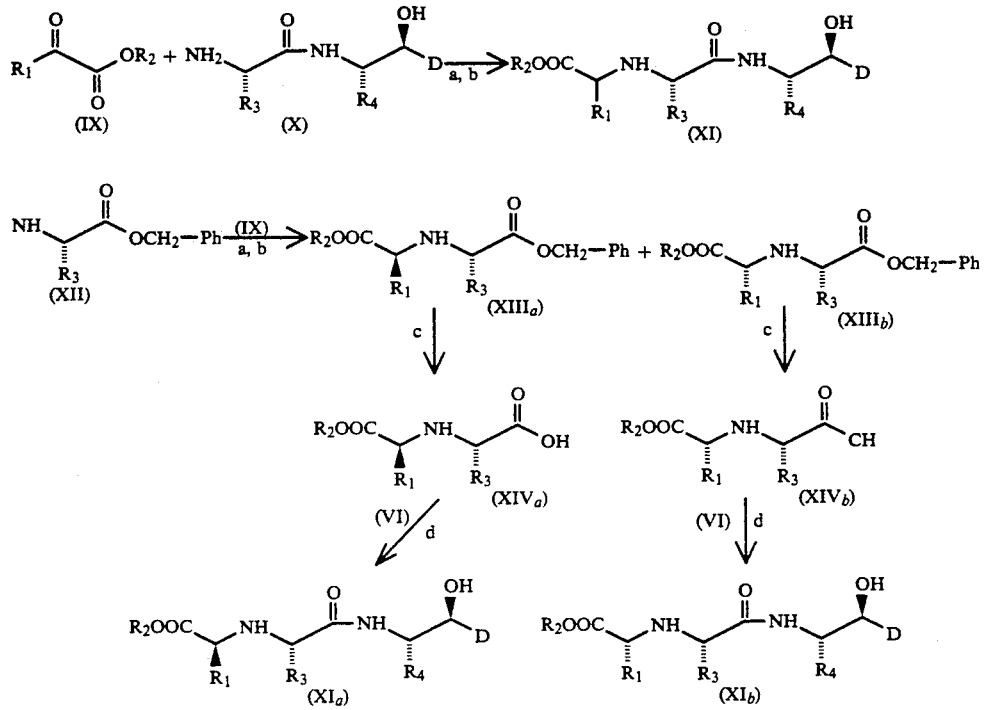
a: NaOAc, NaCNBH$_3$; b: separate diasteromers; c: H$_2$, Pd/C; d: NMM, HOBT, EDAC.
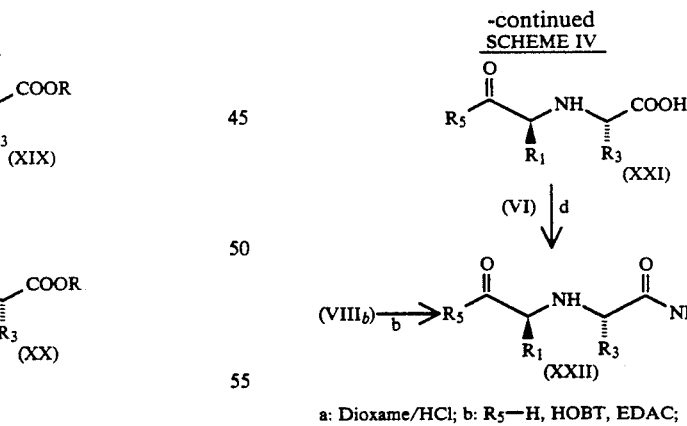
a: Dioxame/HCl; b: R$_5$—H, HOBT, EDAC;
c: H$_2$, Pd/C or LiOH/H$_2$O; d: NMM, HOBT, EDAC.
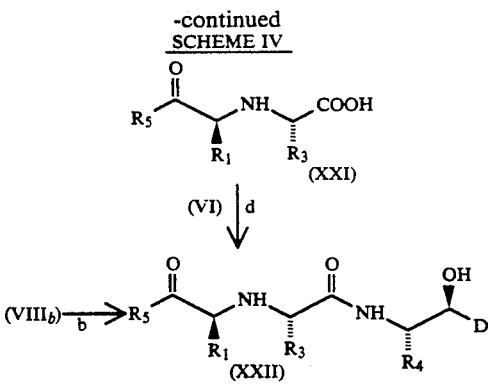

SCHEME V
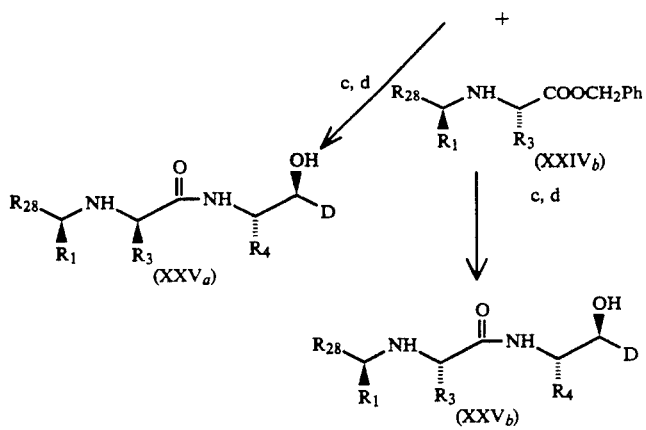
a: NaOAc, NaCNBH₃; b: separate diasteromers; c: H₂, Pd/C;
d: (VI), NMM, HOBT, EDAC.
SCHEME VI
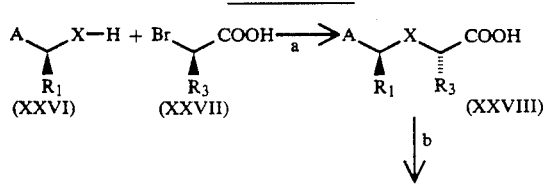
-continued
SCHEME VI
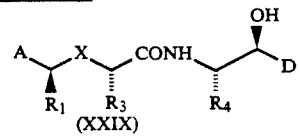
a: NaH, THF; b: (VI), NMM, HOBT, EDAC.
SCHEME VII
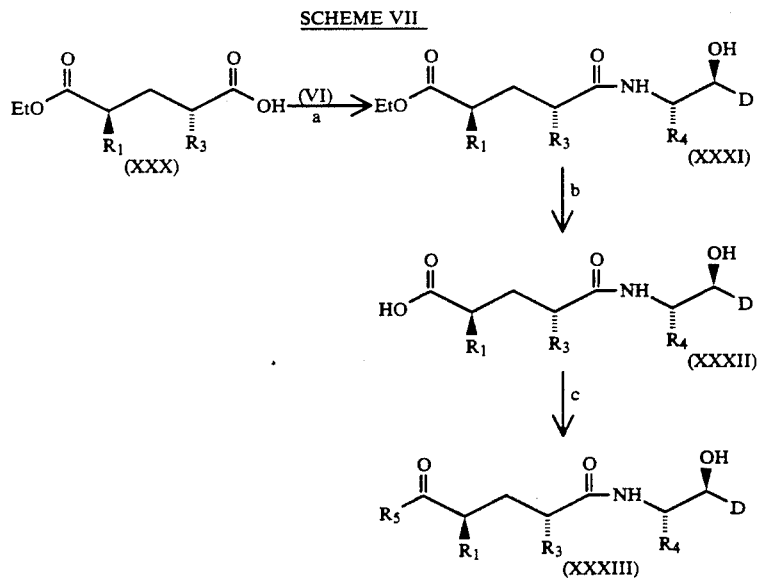
a: NMM, HOBT, EDAC; b: LiOH/H₂O/dioxane; c: R₅—H, HOBT, EDAC.

5,268,374
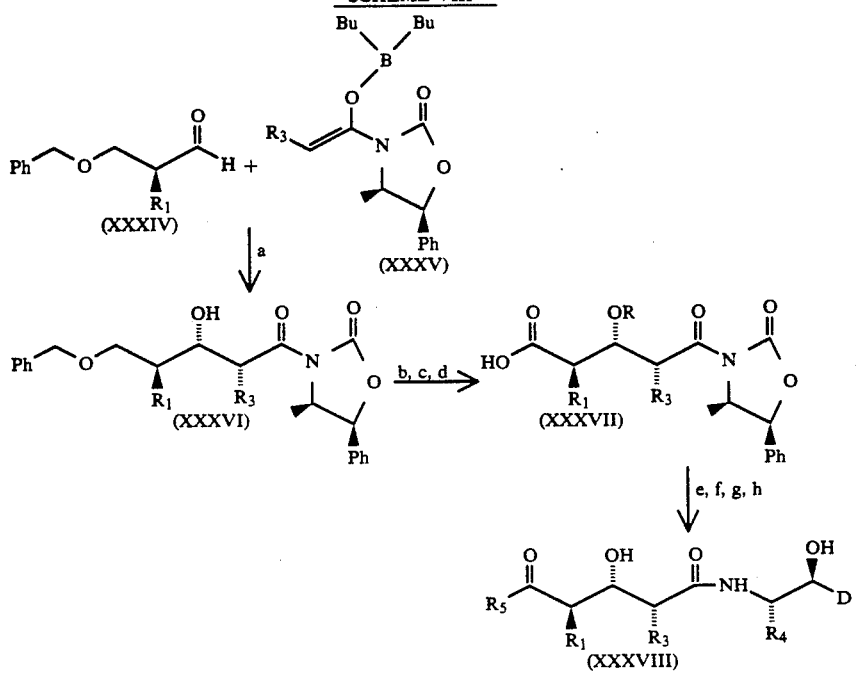
a: $CH_2Cl_2$, $-72°$ C.; b: protect; c: $H_2$, Pd/C;
d: Jones [O]; e: $R_5$—H, HOBT, EDAC; f: $LiOH/H_2O$;
g: (VI), HOBT, EDAC; h: deprotect.
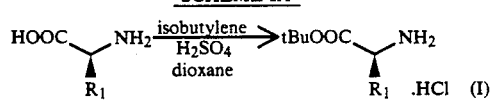
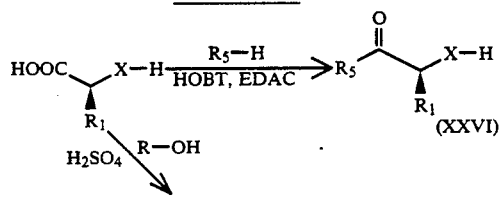
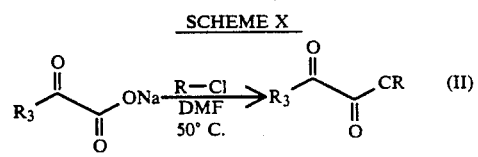
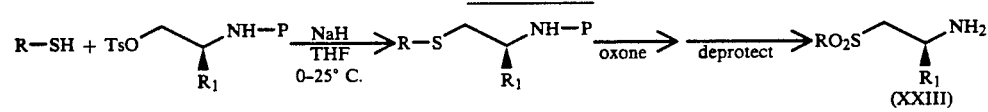
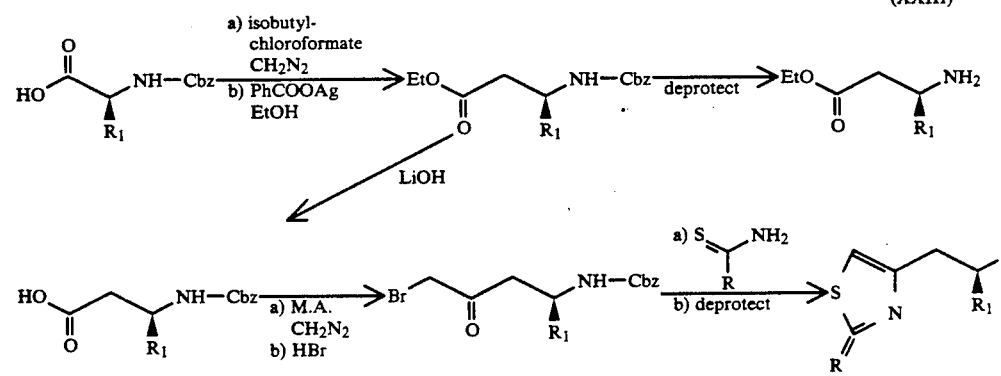

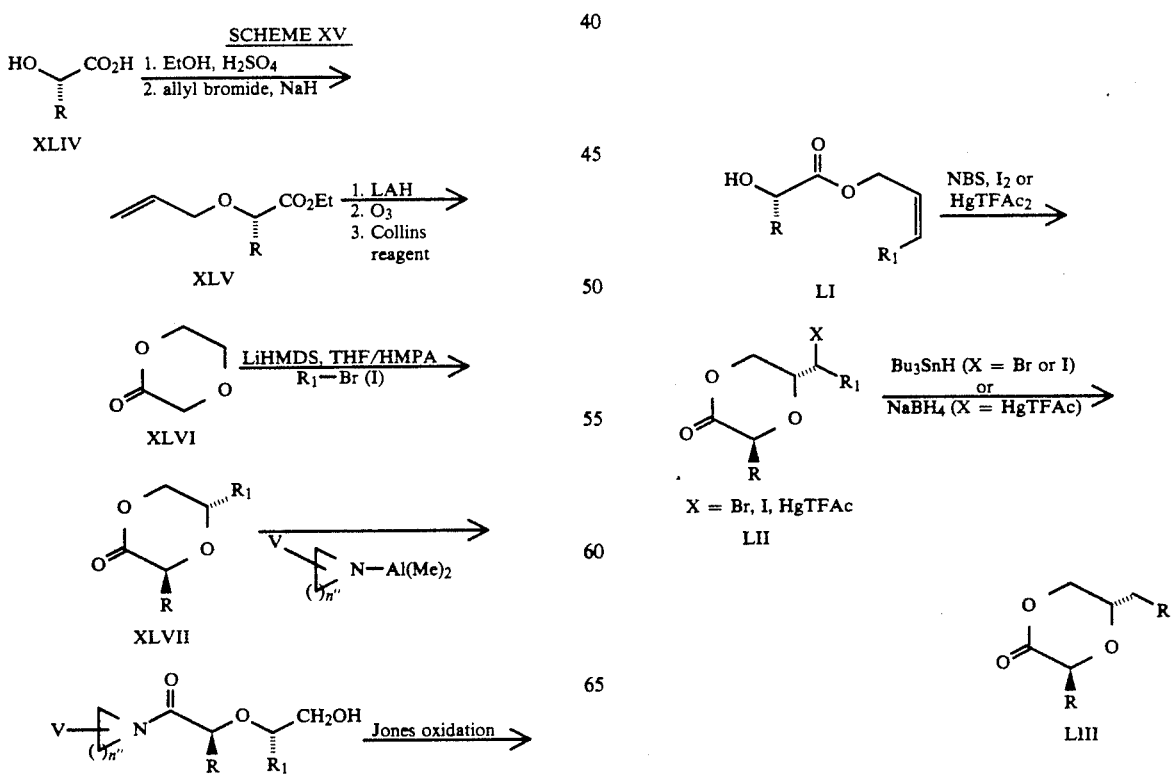

SCHEME XVII
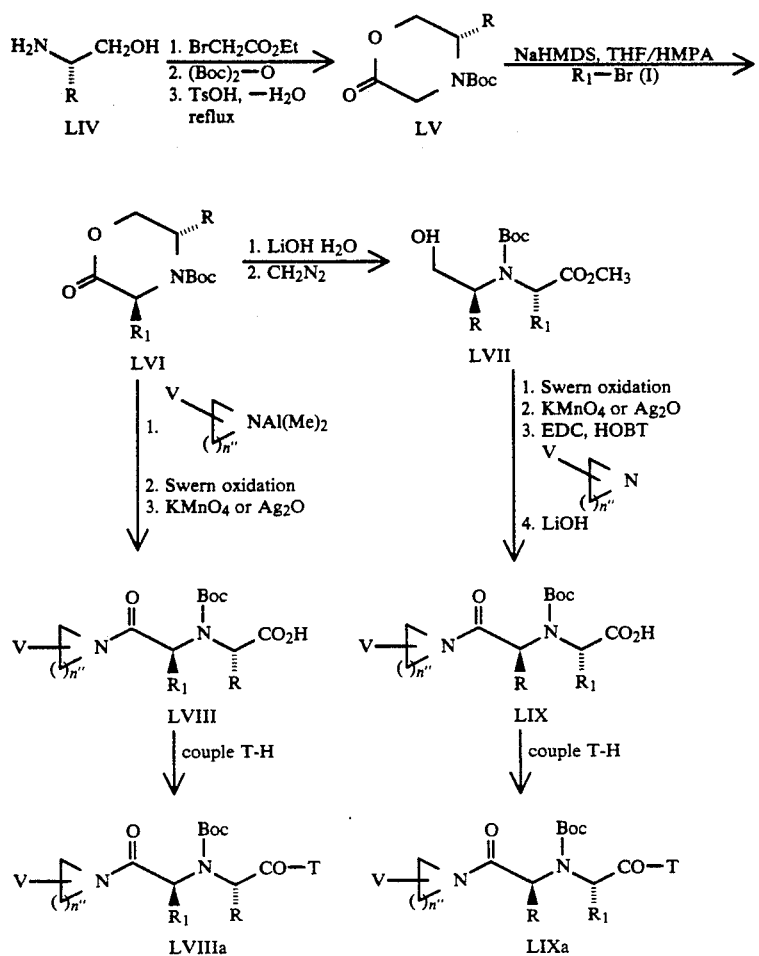
SCHEME XVIIa
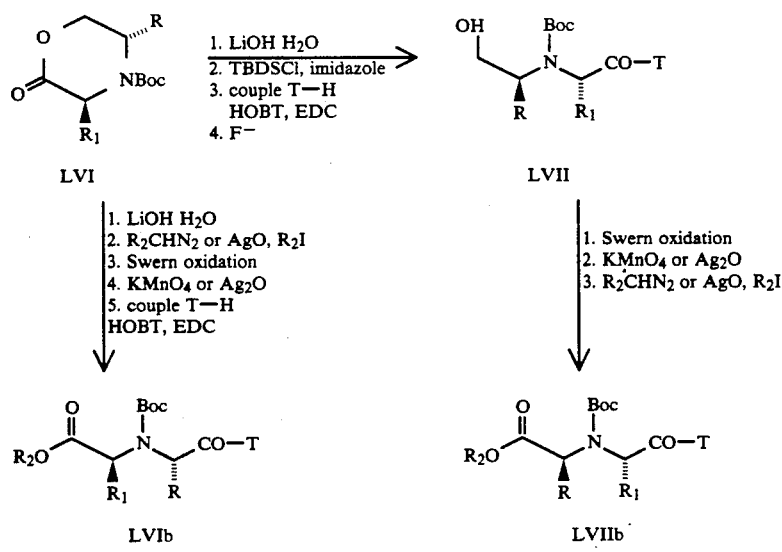

SCHEME XVIII
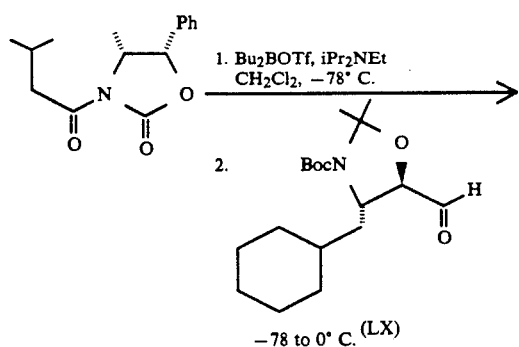
(LX)
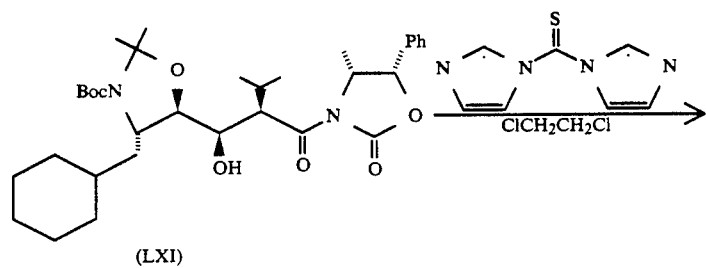
(LXI)
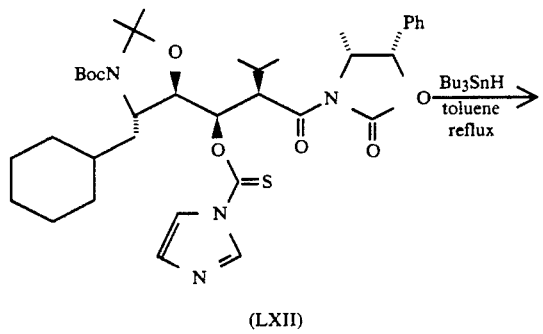
(LXII)
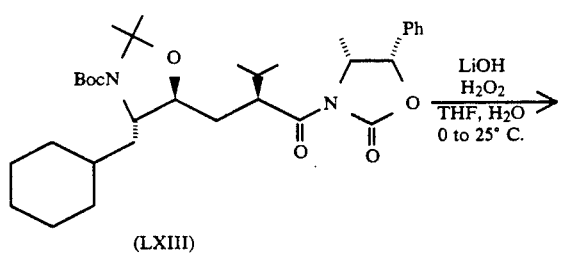
(LXIII)
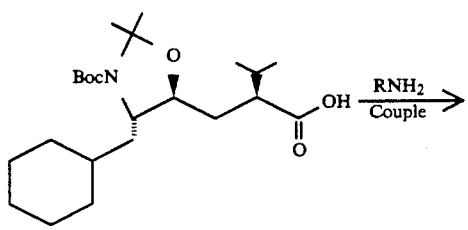

SCHEME XVIII
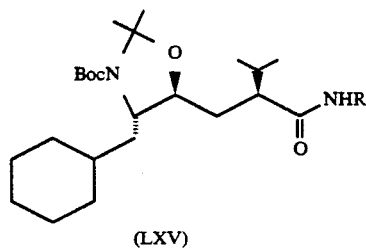
SCHEME XIX
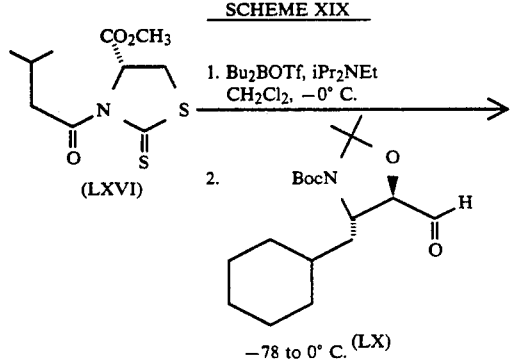
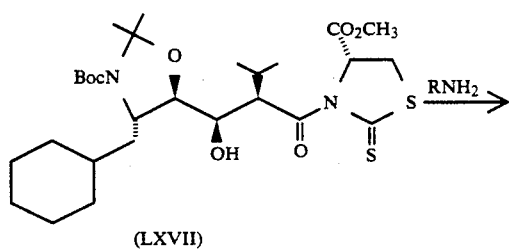
-continued
SCHEME XIX
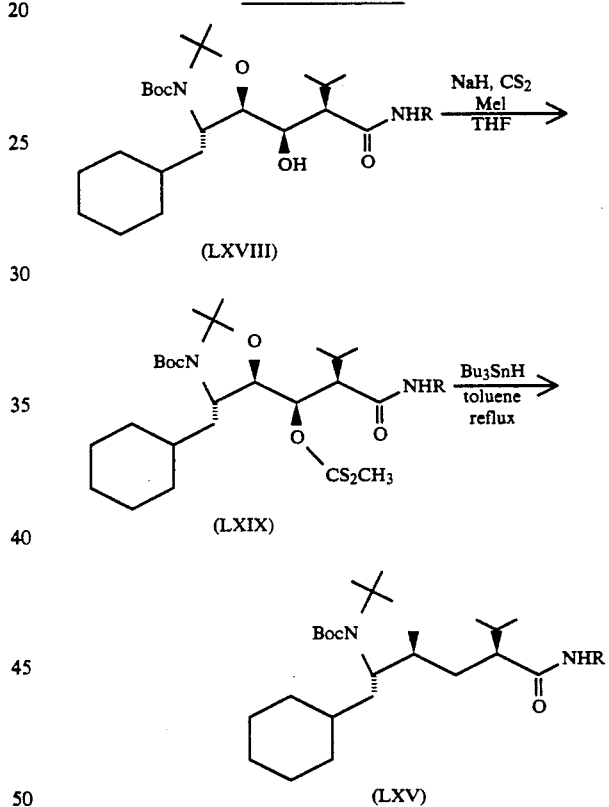
SCHEME XX
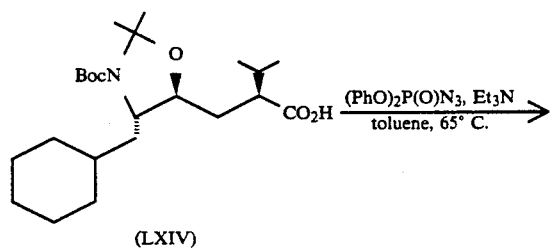

-continued
SCHEME XX
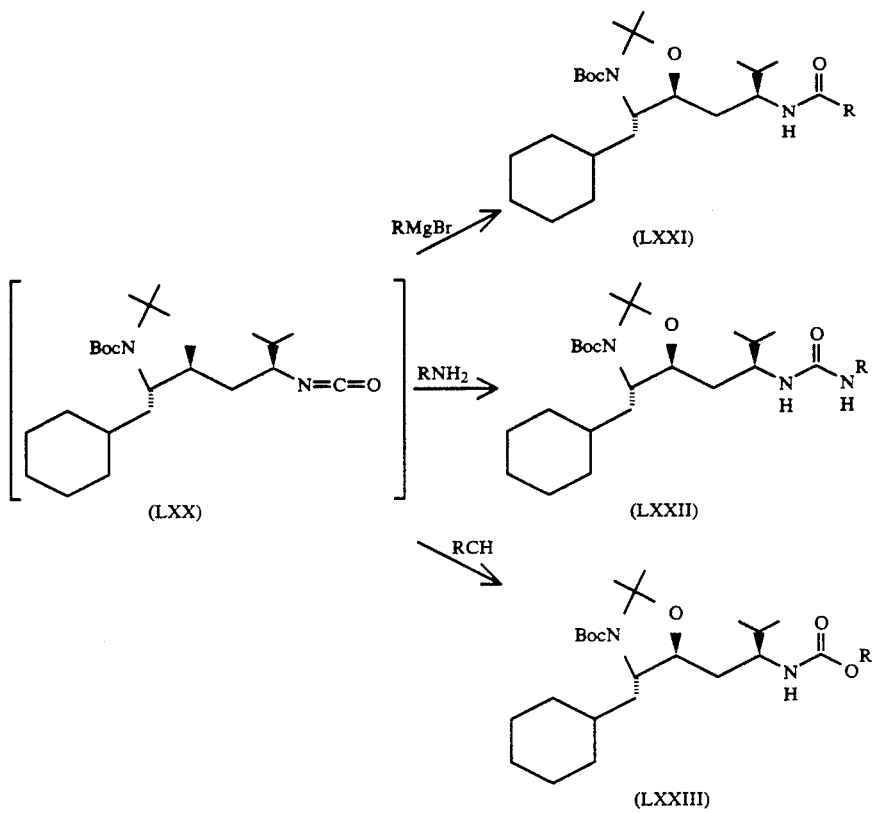
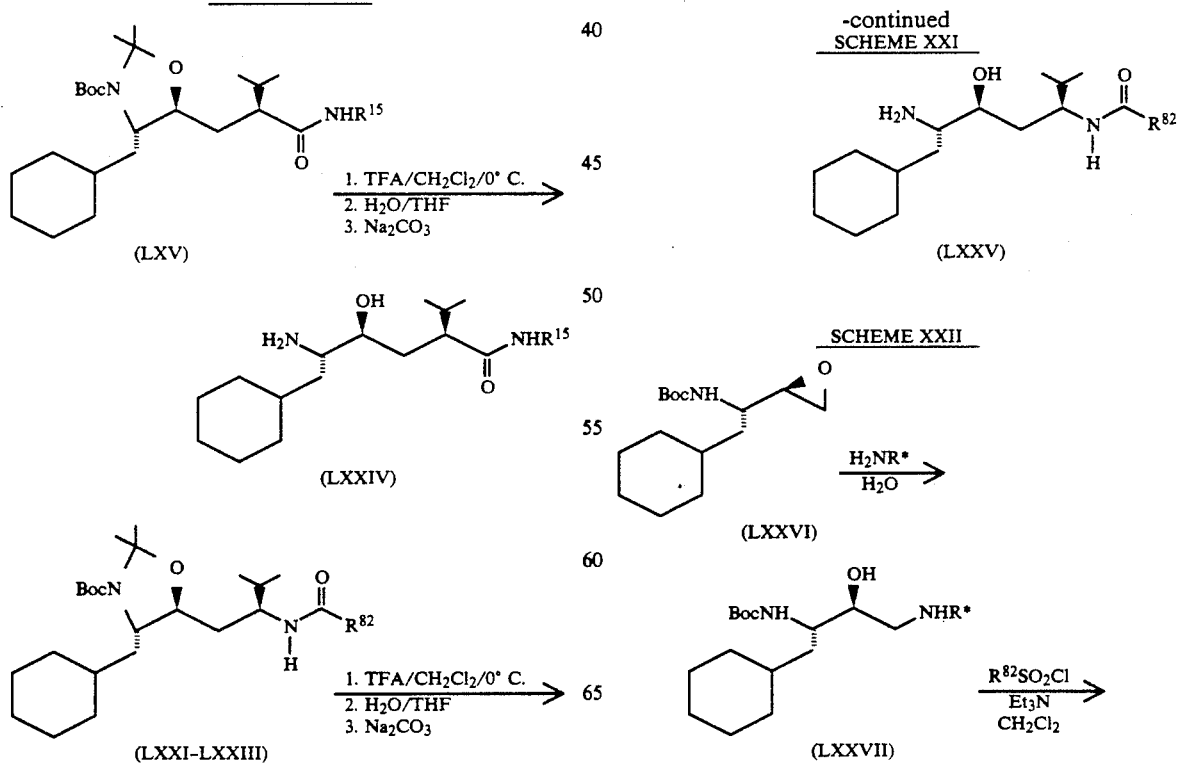

-continued
SCHEME XXII

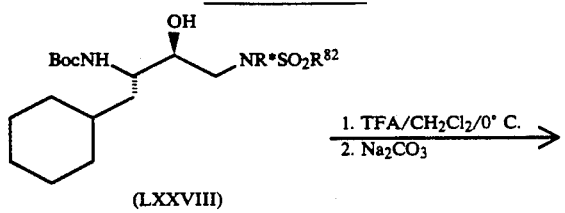

(LXXVIII)

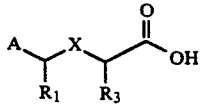

(LXXIX)
R* = H, loweralkyl

SCHEME XXIII

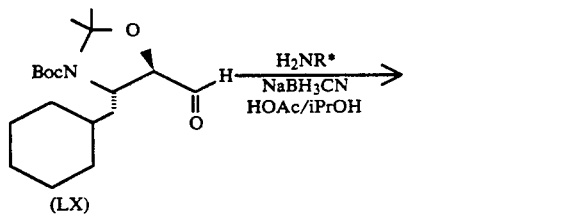

(LX)

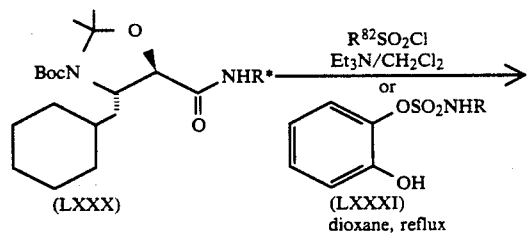

(LXXX)   (LXXXI)
dioxane, reflux

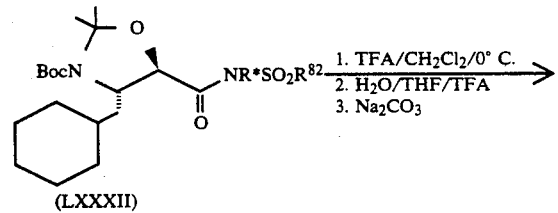

(LXXXII)

[structure]

(LXXXIII)

R* = H, loweralkyl

In the above schemes, optically active or racemic starting materials can be used to obtain products of known or mixed stereochemistry.

Particularly useful intermediates for the preparation of the novel compounds of this invention are compounds of the formula:

[structure with A-CH(R₁)-X-CH(R₃)-COOH]

or an acid halide or activated ester derivative thereof.

A is
(I) $R_5C(O)-(CH_2)_w-$ wherein
 1) w is 0 to 4 and
 2) $R_5$ is
  i) hydroxy,
  ii) alkoxy,
  iii) thioalkoxy,
  iv) amino or
  v) substituted amino;
(II) alkylsulfonyl, (aryl)sulfonyl or (heterocyclic)sulfonyl;
(III) aryl, arylalkyl, heterocyclic or (heterocyclic)alkyl; or
(IV) $R_{90}-$ or $R_{90}NHC(O)-$ wherein $R_{90}$ is a $C_1$ to $C_4$ straight or branched carbon chain substituted by a substituent selected from
 1) carboxy,
 2) alkoxycarbonyl,
 3) alkylsulfonyl,
 4) aryl,
 5) arylsulfonyl,
 6) heterocyclic or
 7) (heterocyclic)sulfonyl).

$R_1$ is
(I) hydrogen,
(II) loweralkyl,
(III) loweralkenyl,
(IV) cycloalkylalkyl,
(V) cycloalkenylalkyl,
(VI) aryloxyalkyl,
(VII) thioaryloxyalkyl,
(VIII) arylalkoxyalkyl,
(IX) arylthioalkoxyalkyl or
(X) a $C_1$ to $C_3$ straight or branched carbon chain substituted by a substituent selected from
 1) alkoxy,
 2) thioalkoxy,
 3) aryl and
 6) heterocyclic.

X is
(I) $CH_2$,
(II) CHOH,
(III) C(O),
(IV) NH,
(V) O,
(VI) S,
(VII) S(O),
(VIII) $SO_2$,
(IX) N(O) or
(X) $-P(O)O-$.

$R_3$ is
(I) loweralkyl,
(II) haloalkyl,
(III) loweralkenyl,
(IV) cycloalkylalkyl,
(V) cycloalkenylalkyl,
(VI) alkoxyalkyl,
(VII) thioalkoxyalkyl,
(VIII) (alkoxyalkoxy)alkyl,
(IX) hydroxyalkyl, (X) —$(CH_2)_{ee}NHR_{12}$
wherein
 1) ee is 1 to 3 and
 2) $R_{12}$ is
  i) hydrogen,
  ii) loweralkyl or
  iii) an N-protecting group;
(XI) arylalkyl or
(XII) (heterocyclic)alkyl.

Acid halide derivatives of the above intermediates include the acid chloride. Activated ester derivatives of the above intermediates include activated esters commonly used by those skilled in the art for activating carboxylic acid groups for coupling with an amine to form a peptide bond, including, but not limited to formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 4-nitrophenol derived esters, 2,4,5-trichlorophenol derived esters and the like.

Compounds of the invention include the following.

| Example Number | A | $R_1$ | X | $R_3$ | $R_4$ | D |
|---|---|---|---|---|---|---|
| 51 | tBuOC(O)— | 2-phenethyl | NH | isobutyl | cyclohexylmethyl | —CH(OH)CH$_2$CH(CH$_3$)$_2$ |
| 57 | tBuOC(O)— | benzyl | NH | isobutyl | cyclohexylmethyl | —CH(OH)CH$_2$CH(CH$_3$)$_2$ |
| 58 | EtOC(O)— | 2-phenethyl | NH | methyl | cyclohexylmethyl | —CH(OH)CH$_2$CH(CH$_3$)$_2$ |
| 60 | EtOC(O)— | 2-phenethyl | NH | 4-imidazolyl-methyl | cyclohexylmethyl | —CH(OH)CH$_2$CH(CH$_3$)$_2$ |
| 65 | morpholin-1-yl-carbonyl | benzyl | NH | isobutyl | cyclohexylmethyl | —CH(OH)CH$_2$CH(CH$_3$)$_2$ |
| 66 | tBuOC(O)— | benzyl | NH | methyl | cyclohexylmethyl | —CH(OH)CH$_2$CH(CH$_3$)$_2$ |
| 67 | EtOC(O)—(CH$_2$)$_3$NHC(O)— | benzyl | NH | methyl | cyclohexylmethyl | —CH(OH)CH$_2$CH(CH$_3$)$_2$ |
| 68 | morpholin-1-yl-carbonyl | benzyl | NH | methyl | cyclohexylmethyl | —CH(OH)CH$_2$CH(CH$_3$)$_2$ |
| 69 | morpholin-1-yl-carbonyl | benzyl | NH | n-butyl | cyclohexylmethyl | —CH(OH)CH$_2$CH(CH$_3$)$_2$ |
| 71 | morpholin-1-yl-carbonyl | benzyl | NH | isobutyl | cyclohexylmethyl | —CH(OH)CH$_2$CH(CH$_3$)$_2$ |
| 76 | tBuS(O)$_2$CH$_2$— | benzyl | NH | methyl | cyclohexylmethyl | —CH(OH)CH$_2$CH(CH$_3$)$_2$ |
| 84 | morpholin-1-yl-carbonyl | benzyl | O | n-butyl | cyclohexylmethyl | —CH(OH)CH$_2$CH(CH$_3$)$_2$ |
| 85 | morpholin-1-yl-carbonyl | benzyl | O | n-hexyl | cyclohexylmethyl | —CH(OH)CH$_2$CH(CH$_3$)$_2$ |
| 86 | morpholin-1-yl-carbonyl | benzyl | O | methyl | cyclohexylmethyl | —CH(OH)CH$_2$CH(CH$_3$)$_2$ |
| 87 | azetidin-1-yl-carbonyl | benzyl | O | methyl | cyclohexylmethyl | —CH(OH)CH$_2$CH(CH$_3$)$_2$ |
| 88 | pyrrolidin-1-ylcarbonyl | benzyl | O | methyl | cyclohexylmethyl | —CH(OH)CH$_2$CH(CH$_3$)$_2$ |
| 89 | piperidin-1-ylcarbonyl | benzyl | O | methyl | cyclohexylmethyl | —CH(OH)CH$_2$CH(CH$_3$)$_2$ |
| 90 | 4-(methoxycarbonyl)-piperidin-1-ylcarbonyl | benzyl | O | methyl | cyclohexylmethyl | —CH(OH)CH$_2$CH(CH$_3$)$_2$ |
| 91 | morpholin-1-yl-carbonyl | benzyl | O | methyl | cyclohexylmethyl | —CH$_2$CH(CH(CH$_3$)$_2$)—C(O)NH-n-butyl |
| 92 | EtOC(O)— | hydrogen | S | methyl | cyclohexylmethyl | —CH(OH)CH$_2$CH(CH$_3$)$_2$ |
| 93 | 4-(methoxymethoxy)-piperidin-1-ylcarbonyl | benzyl | O | n-butyl | cyclohexylmethyl | —CH(OH)CH$_2$CH(CH$_3$)$_2$ |
| 94 | 4-(methoxymethoxy)-piperidin-1-ylcarbonyl | benzyl | O | methyl | cyclohexylmethyl | —CH(OH)CH$_2$CH(CH$_3$)$_2$ |
| 95 | 4-(methoxymethoxy)-piperidin-1-ylcarbonyl | benzyl | CH$_2$ | methyl | cyclohexylmethyl | —CH(OH)CH$_2$CH(CH$_3$)$_2$ |
| 96 | 4-(methoxymethoxy)-piperidin-1-ylcarbonyl | benzyl | O | n-butyl | cyclohexylmethyl | —CH$_2$CH(CH(CH$_3$)$_2$)—C(O)NH-n-butyl |
| 97 | 4-(methoxymethoxy)-piperidin-1-ylcarbonyl | methyl | CH(OH) | methyl | cyclohexylmethyl | —CH(OH)CH$_2$CH(CH$_3$)$_2$ |
| 104 | 4-(methoxymethoxy)-piperidin-1-ylcarbonyl | benzyl | O | n-butyl | cyclohexylmethyl | 4-methyltetrahydrofur-2-yl |
| 105 | 4-(methoxymethoxy)-piperidin-1-ylcarbonyl | benzyl | NH | n-butyl | cyclohexylmethyl | —CH(OH)CH$_2$CH(CH$_3$)$_2$ |
| 106 | 4-(methoxymethoxy)-piperidin-1-ylcarbonyl | benzyl | NH | n-butyl | cyclohexylmethyl | —CH$_2$CH(CH(CH$_3$)$_2$)—C(O)NH-n-butyl |
| 107 | 4-(methoxymethoxy)-piperidin-1-ylcarbonyl | benzyl | NH | n-butyl | cyclohexylmethyl | 4-methyltetrahydrofur-2-yl |
| 108 | 4-(methoxymethoxy)-piperidin-1-ylcarbonyl | benzyl | NH | n-butyl | cyclohexylmethyl | 3-ethyloxazolidin-2-on-5-yl |
| 116 | 4-(methoxymethoxy)-piperidin-1-ylcarbonyl | benzyl | O | n-butyl | cycohexylmethyl | —CH$_2$CH(CH(CH$_3$)$_2$)—C(O)NH(CH$_2$)$_3$-imidazol-1-yl |
| 117 | 4-(methoxymethoxy)-piperidin-1-ylcarbonyl | benzyl | O | n-butyl | cycohexylmethyl | —CH$_2$CH(CH(CH$_3$)$_2$)—C(O)NH(CH$_2$)$_3$—N(CH$_3$)$_2$ |
| 118 | 4-(methoxymethoxy)-piperidin-1-ylcarbonyl | benzyl | O | n-butyl | cycohexylmethyl | —CH$_2$CH(CH(CH$_3$)$_2$)—C(O)NH(CH$_2$)$_3$-morpholin-1-yl |
| 119 | 4-(methoxymethoxy)-piperidin-1-ylcarbonyl | benzyl | NH | n-butyl | cycohexylmethyl | —CH$_2$CH(CH(CH$_3$)$_2$)—C(O)NH(CH$_2$)$_3$-imidazol-1-yl |

-continued

| Example Number | A | R₁ | X | R₃ | R₄ | D |
|---|---|---|---|---|---|---|
| 120 | 4-(methoxymethoxy)-piperidin-1-ylcarbonyl | benzyl | NH | n-butyl | cyclohexylmethyl | —CH₂CH(CH(CH₃)₂)—C(O)NH(CH₂)₃-morpholin-1-yl |
| 122 | 4-(methoxymethoxy)-piperidin-1-ylcarbonyl | benzyl | O | n-butyl | cyclohexylmethyl | —CH₂N(CH₃)SO₂NHCH₃ |
| 129 | 4-(methoxymethoxy)-piperidin-1-ylcarbonyl | benzyl | O | n-butyl | cyclohexylmethyl | —CH₂CH(CH(CH₃)₂)NH—C(O)OCH₂CH₂NMe₂ |
| 130 | 4-(methoxymethoxy)-piperidin-1-ylcarbonyl | benzyl | NH | n-butyl | cyclohexylmethyl | —CH₂CH(CH(CH₃)₂)NH—C(O)OCH₂CH₂morpholin-1-yl |
| 131 | 4-(methoxymethoxy)-piperidin-1-ylcarbonyl | benzyl | O | n-butyl | cyclohexylmethyl | —CH₂CH(CH(CH₃)₂)NH—C(O)OCH₂CH₂pyrid-2-yl |
| 132 | 4-(methoxymethoxy)-piperidin-1-ylcarbonyl | benzyl | O | n-butyl | cyclohexylmethyl | —CH₂CH(CH(CH₃)₂)NH—C(O)-n-butyl |
| 133 | 4-(methoxymethoxy)-piperidin-1-ylcarbonyl | benzyl | O | n-butyl | cyclohexylmethyl | —CH₂CH(CH(CH₃)₂)NH—C(O)OCH₂-imidazol-2-yl |
| 134 | 4-(methoxymethoxy)-piperidin-1-ylcarbonyl | benzyl | O | n-butyl | cyclohexylmethyl | —CH₂CH(CH(CH₃)₂)NH—C(O)OCH₂CH₂SCH₃ |
| 135 | 4-(methoxymethoxy)-piperidin-1-ylcarbonyl | benzyl | O | n-butyl | cyclohexylmethyl | —CH₂CH(CH(CH₃)₂)NH—C(O)OCH₂CH₂S(O)₂CH₃ |
| 136 | 4-(methoxymethoxy)-piperidin-1-ylcarbonyl | benzyl | O | n-butyl | cyclohexylmethyl | —CH₂CH(CH(CH₃)₂)C(O)—NHCH₂CH₂N(O)Me₂ |
| 139 | 4-(methoxymethoxy)-piperidin-1-ylcarbonyl | benzyl | O | n-butyl | cyclohexylmethyl | —CH(OH)CH₂N(CH₃)(OCH₃) |
| 142 | 4-(methoxymethoxy)-piperidin-1-ylcarbonyl | benzyl | O | n-butyl | cyclohexylmethyl | —CH₂N(CH(CH₃)₂)S(O)₂—NHCH₃ |
| 143 | 4-(methoxymethoxy)-piperidin-1-ylcarbonyl | benzyl | O | n-butyl | cyclohexylmethyl | —CH=C(Et)C(O)NHCH₂CH(CH₃)₂ |
| 144 | 4-(methoxymethoxy)-piperidin-1-ylcarbonyl | benzyl | O | n-butyl | isobutyl | —CH₂CH(CH(CH₃)₂)C(O)—Ile—His—NH₂ |
| 145 | 4-(methoxymethoxy)-piperidin-1-ylcarbonyl | benzyl | O | n-butyl | isobutyl | —CH₂CH(CH(CH₃)₂)S(O)₂—morpholin-1-yl |
| 146 | 4-(methoxymethoxy)-piperidin-1-ylcarbonyl | benzyl | O | n-butyl | cyclohexylmethyl | —(CH(OH))—D = —C(O)—C(O)-n-Pr |
| 147 | 4-(methoxymethyox)-piperidin-1-ylcarbonyl | benzyl | O | n-butyl | cyclohexylmethyl | imidazol-2-yl |
| 148 | 4-(methoxymethoxy)-piperidin-1-ylcarbonyl | benzyl | O | n-butyl | cyclohexylmethyl | —CH(OH)—D = —C(O)CF₂CH₂NH—C(O)CH(CH(CH₃)₂)C(O)—NHCH₂Ph |
| 149 | 4-(methoxymethoxy)-piperidin-1-ylcarbonyl | benzyl | O | n-butyl | cyclohexylmethyl | (structure: 3,3-dimethyl-5-methyl-2-oxopyrrolidin-1-yl with N—CH₂CH₂N(CH₂Ph)(Et₂)⁺ —OAc) |
| 150 | 4-(methoxymethoxy)-piperidin-1-ylcarbonyl | benzyl | O | n-butyl | cyclohexylmethyl | —CH₂CH₂NHCH(CH₂CH(CH₃)₂)—C(O)NHCH₂Ph |
| 151 | 4-(methoxymethoxy)-piperidin-1-ylcarbonyl | benzyl | O | n-butyl | isobutyl | —CH₂N(CH(CH₃)₂)C(O)—Ile—His—OCH₃ |
| 152 | 4-(methoxymethoxy)-piperidin-1-ylcarbonyl | benzyl | O | n-butyl | isobutyl | —CH(OH)—D = —CH(NH₂)CH₂C(O)—NCHC(CH(CH₃)CH₂CH₃))—C(O)NHCH₂pyrid-2-yl |
| 163 | morpholin-1-yl-carbonyl | benzyl | NH | 3-propenyl | cyclohexylmethyl | —(CH(OH)CH₂CH(CH₃)₂ |
| 164 | 4-(methoxymethoxy)-piperidin-1-ylcarbonyl | benzyl | O | n-butyl | cyclohexylmethyl | —CH₂CH(CH₃)CH₂S(O)₂CH(CH₃)₂ |
| 165 | 4-(methoxymethoxy)-piperidin-1-ylcarbonyl | benzyl | O | n-butyl | cyclohexylmethyl | —CH₂CH(CH(CH₃)₂)CH₂S(O)₂—CH(CH₃)₂ |
| 166 | 4-(methoxymethoxy)-piperidin-1-ylcarbonyl | benzyl | O | n-butyl | cyclohexylmethyl | —C(O)OCH(CH₃)₂ |
| 167 | 4-(methoxymethoxy)-piperidin-1-ylcarbonyl | benzyl | O | n-butyl | cyclohexylmethyl | —CH₂C(O)NHCH₂CH₂—morpholin-1-yl |
| 168 | 4-(methoxymethoxy)-piperidin-1-ylcarbonyl | benzyl | O | n-butyl | cyclohexylmethyl | —CH₂CH(CH(CH₃)₂)CH=CH₂ |
| 169 | 4-(methoxymethoxy)-piperidin-1-ylcarbonyl | benzyl | O | n-butyl | cyclohexylmethyl | —CF₂C(O)NHCH(CH₃)CH₂CH₃ |
| 170 | 4-(methoxymethoxy)-piperidin-1-ylcarbonyl | benzyl | O | n-butyl | cyclohexylmethyl | —CF₂CH₂SCH(CH₃)₂ |
| 171 | 4-(methoxymethoxy)-piperidin-1-ylcarbonyl | benzyl | O | n-butyl | cyclohexylmethyl | —CF₂CH₂S(O)₂CH(CH₃)₂ |
| 179 | 4-(methoxymethoxy)-piperidin-1-ylcarbonyl | benzyl | O | n-butyl | cyclohexylmethyl | —CF₂CH(OH)CH(CH₃)₂ |
| 180 | 4-(methoxymethoxy)-piperidin-1-ylcarbonyl | benzyl | O | n-butyl | isobutyl | —CH₂C(O)NHCH₂CH(CH₃)CH₂CH₃ |
| 181 | 4-(methoxymethoxy)-piperidin-1-ylcarbonyl | benzyl | NH | n-butyl | cyclohexylmethyl | —CH₂CH(CH(CH₃)₂)C(O)Ile— |

-continued

| Example Number | A | R₁ | X | R₃ | R₄ | D |
|---|---|---|---|---|---|---|
| 182 | piperidin-1-ylcarbonyl 4-(methoxymethoxy)-piperidin-1-ylsulfonyl | benzyl | CH₂ | n-butyl | cyclohexylmethyl | NHCH₂-pyrid-2-yl —CH₂CH(CH(CH₃)₂)C(O)— NH(CH₂)₃-morpholin-1-yl |

Preferred compounds of the invention include:

2(S)-(1(S)-(4-(methyoxymethoxy)piperidin-1-yl)carbonyl)-2-phenylethoxyhexanoic acid amide of 3-(1-imidazolyl)propyl 5(S)-amino-6-cyclohexyl-4(S)-hydroxy-2(S)-isopropylhexanamide;

2(S)-(1(S)-(4-(methyoxymethoxy)piperidin-1-yl)carbonyl)-2-phenylethoxyhexanoic acid amide of 3-(dimethylamino)propyl 5(S)-amino-6-cyclohexyl-4(S)-hydroxy-2(S)-isopropylhexanamide;

2(S)-(1(S)-(4-(methyoxymethoxy)piperidin-1-yl)carbonyl)-2-phenylethoxyhexanoic acid amide of 3-(4-morpholinyl)propyl 5(S)-amino-6-cyclohexyl-4(S)-hydroxy-2(S)-isopropylhexanamide;

N-(1(S)-(4-(Methoxymethoxy)piperidin-1-yl)carbonyl)-2-phenylethyl-L-noreucyl amide of 3-(1-imidazolyl)propyl 5(S)-amino-6-cyclohexyl-4(S)-hydroxy-2(S)-isopropylhexanamide; and N-(1(S)-(4-(Methoxymethoxy)piperidin-1-yl)carbonyl)-2-phenylethyl-L-norleucyl amide of 3-(4-morpholinyl)propyl 5(S)-amino-6-cyclohexyl-4(S)-hydroxy-2(S)-isopropylhexanamide.

The following examples will serve to further illustrate preparation of the novel compounds of the invention.

EXAMPLE 1

4-Methyl-2-oxo-pentanoic acid, benzyl ester

A mixture of 2-Oxo-4-methyl pentanoic acid sodium salt (10 g, 65.7 mmol) and benzyl chloride (8 g, 63 mmol) in 300 ml DMF was stirred at 40°–50° C. for 5 h. It was filtered, and the filtrate was evaporated under reduced pressure to provide an oil. The oil was dissolved in chloroform, washed with water, dried, filtered, and evaporated to provide the desired product (13 g, 94%). ¹H NMR (CDCl₃, TMS) δ0.95 (d,6H), 2.15 (m,1H), 2.7 (d,2H), 5.28 (s,2H), 7.4 (m,5H). Mass spectrum: (M+H)⁺=221.

EXAMPLE 2

Pyruvic acid, benzyl ester

Using the procedure of Example 1, but replacing 2-Oxo-4-methyl pentanoic acid sodium salt with pyruvic acid sodium salt gave the desired compound. ¹H NMR (CDCl₃, TMS) δ2.4 (s,3H), 5.3 (s,2H). Mass spectrum: (M+H)⁺=179.

EXAMPLE 3

Hexanoic acid, benzyl ester

Using the procedure of Example 1, but replacing 2-Oxo-4-methyl pentanoic acid sodium salt with 2-oxohexanoic acid sodium salt gave the desired compound. ¹H NMR (CDCl₃, TMS) δ0.91 (t,3H), 1.35 (m,2H), 1.6 (m,2H), 2.85 (t,2H), 5.29 (s,2H), 7.4 (m,5H). Mass spectrum: (M+H)⁺=221.

EXAMPLE 4

D-Phenylalanine, tert-butyl ester.HCl 6.07 ml of concentrated sulfuric acid was added to a solution of 5 g (0.03 mol) of D-phenylalanine in 80 ml of dioxane. The solution was saturated with isobutylene. After 18 h at room temperature the solution was added to 500 ml of ice water containing sodium hydroxide sufficient to neutralize all acids. The aqueous dioxane solution was extracted with a large quantity of ether. The ether portion was washed with water, saturated sodium chloride, dried, and filtered. The filtrate was evaporated to an oil. Hexane and etherial hydrogen chloride were added sequentially. A white solid precipitated out to give the desired compound in 65% yield. ¹H NMR (CDCl₃, TMS) δ1.29 (s,9H), 3 (dd,1H), 3.25 (dd,1H), 4.1 (dd,1H), 7.4 (m,5H). Mass spectrum: (M+H)⁺=222.

EXAMPLE 5

L-Homophenylalanine, tert-butyl ester.HCl

Using the procedure of Example 4, but replacing D-Phe with L-HomoPhe gave the desired compound. ¹H NMR (DMSO, TMS) δ1.5 (s,9H), 2.05 (m,2H), 2.75 (m,2H), 3.9 (t,1H), 7.3 (m,5H). Mass spectrum: M⁺=235, R$_f$=0.6 (5 CHCl₃:1 CH₃OH).

EXAMPLE 6

D-Homophenylalanine, tert-butyl ester.HCl

Using the procedure of Example 4, but replacing D-Phe with D-HomoPhe gave the desired compound. ¹H NMR (DMSO, TMS) δ1.5 (s,9H), 2.05 (m,2H), 2.75 (m,2H), 3.89 (t,1H), 7.25 (m,5H). R$_f$=0.6 (5 CHCl₃: 1 CH₃OH).

EXAMPLE 7

N-(1(S)-(tert-Butyloxycarbonyl)-2-phenylethyl)-L-leucine, benzyl ester

TEA (triethylamine) (140 μl, 0.94 mmol) was added to the cooled suspension of L-Phe-t-Bu ester.HCl (0.243 g, 0.94 mmol) in 3 ml of methylene chloride at 0° C. and the mixture was stirred at 0°–5° C. for a half hour. The mixture was added to a solution of 4-methyl-2(R)-(trifluorosulfonyloxy)-pentanoic acid, benzyl ester (0.288 g, 0.81 mmol) and TEA (120 μl, 0.82 mmol) in 2 ml of methylene chloride and the mixture was allowed to stir at 15° C. for 2 h, then warmed to room temperature and stirred for one hour. The clear liquid was then allowed to stand in a refrigerator for 18 h and then concentrated. The clear liquid was dissolved in EtOAc and washed with H₂O, dried, and filtered. The filtrate was evaporated to an oil which was chromatographed, eluting with ether:hexane (1:9) to obtain the desired product in 25% yield. ¹H NMR (CDCl₃, TMS) δ0.87 (t,6H), 1.33 (s,9H), 1.46 (d,2H), 1.67 (m,1H), 2.89 (bd,2H), 3.37 (bt,1H), 3.41 (bt,1H), 5.11 (d,2H). Mass spectrum: (M+H)⁺=426.

EXAMPLE 8

N-(1(S)-(tert-Butyloxycarbonyl)-2-phenylethyl)-L-leucine, benzyl ester and its D-leucine isomer To L-Phe-t-Bu ester.HCl (0.25 g, 0.96 mmol) in 10 ml of absolute ethanol, 2-oxo-4-methyl pentanoic acid benzyl ester (0.25 g, 1.15 mmol) and sodium acetate (0.16 g, 1.92 mmol) were added sequentially at 5° C. The suspension was cooled at 5° C. for 30 min, followed by dropwise addition of sodium cyanoborohydride (0.07 g, 1.15 mmol) in 6 ml of absolute ethanol. The reaction mixture was stirred at 0°–5° C. for 1 h and at room temperature for 15 h. The mixture was filtered and the filtrate was evaporated under reduced pressure to give a solid which was taken up into chloroform and washed with 5% sodium bicarbonate, water, and brine. The organic phase was dried and evaporated to a yellow oil. The crude product was chromatographed on silica gel eluting with ether:hexane (1:9) to give two separate diastereomers (26% total yield).

Less polar (S,R) isomer: $^1$H NMR (CDCl$_3$, TMS) δ0.8 (dd,6H), 1.33 (2,9H) 1.43 (bt,2H), 1.62 (m,1H), 2.87 (bt,2H), 3.22 (bt,1H), 3.37 (bt,1H), 5.1 (s,2H). Mass spectrum: (M+H)$^+$ = 426.

More polar (S,S) isomer: $^1$H NMR (CDCl$_3$, TMS) δ0.87 (t,6H), 1.33 (s,9H), 1.46 (d,2H), 1.67 (m,1H), 2.89 (bd,2H). 3.37 (bt,1H), 3.41 (bt,1H), 5.11 (d,2H). Mass spectrum: (M+H)$^+$ = 426. R$_f$ value is identical to the resultant compound of Example 7.

EXAMPLE 9

N-(1(R)-(tert-Butyloxycarbonyl)-3-phenylpropyl)-L-leucine, benzyl ester and its D-leucine isomer Using the procedure of Example 8, but replacing L-Phe-t-Bu ester.HCl with D-HomoPhe-t-Bu ester.HCl gave a mixture of two diastereomers which were separated by chromatography on silica gel eluting with ethyl acetate:hexane (1:4).

Less polar (R,S) isomer: $^1$H NMR (CDCl$_3$, TMS) δ0.89 (d,3H), 0.91 (d,3H), 1.45 (s,9H), 1.85 (m,3H), 2.7 (m,2H), 3.15 (t,1H), 3.3 (t,1H), 5.1 (q,2H), 7.3 (m,5H). Mass spectrum: (M+H)$^+$ = 440.

More polar (R,R) isomer: $^1$H NMR (CDCl$_3$, TMS) δ0.89 (d,3H), 0.91 (d,3H), 1.45 (s,9H), 2.65 (m,2H), 3.15 (t,1H), 3.36 (t,1H), 5.15 (s,2H), 7.2 (m,5H). Mass spectrum: (M+H)$^+$ = 440.

EXAMPLE 10

N-(1(S)-(tert-Butyloxycarbonyl)-3-phenylpropyl)-L-leucine, benzyl ester and its D-leucine isomer Using the procedure of Example 8, but replacing L-Phe-t-Bu ester.HCl with L-HomoPhe-t-Bu ester.HCl gave a mixture of two diastereomers which were separated by chromatography to give the desired compounds.

Less polar (S,R) isomer: $^1$H NMR (CDCl$_3$, TMS) δ0.9 (dd,6H), 1.45 (s,9H), 1.8 (dd,1H), 1.9 (m,2H), 2.69 (m,2H). 3.25 (t,1H), 3.39 (t,1H), 5.11 (d,2H), 7.27 (m,5H). Mass spectrum: (M+H)$^+$ = 440.

More polar (S,S) isomer: $^1$H NMR (CDCl$_3$, TMS) δ0.89 (d,3H), 0.92 (d,3H), 1.46 (s,9H), 2.64 (m,2H), 3.15 (t,1H), 3.36 (dd,1H), 7.26 (m,5H). Mass spectrum: (M+H)$^+$ = 440.

EXAMPLE 11

N-(1(S)-(tert-Butyloxycarbonyl)-2-phenylethyl)-L-alanine benzyl ester and its D-alanine isomer Using the procedure of Example 8, but replacing 2-oxo-4-methyl pentanoic acid benzyl ester with pyruvic acid benzyl ester gave the desired compounds.

Less polar (S,S) isomer: $^1$H NMR (CDCl$_3$, TMS) δ1.27 (d,3H), 1.33 (s,9H), 2.91 (dd,2H), 3.35 (dd,1H), 3.45 (bt,1H), 5.12 (d,2H). Mass spectrum: (M+H)$^+$ = 384.

More polar (S,R) isomer: $^1$H NMR (CDCl$_3$, TMS) δ1.3 (d,3H), 1.34 (s,9H), 2.91 (d,2H), 3.44 (dd,1H), 3.42 (bt,1H), 5.12 (s,2H). Mass spectrum: (M+H)$^+$ = 384.

EXAMPLE 12

Hexanoic acid, benzyl ester

Alternatively, the compound of Example 3 was prepared by the Grignard reaction of n-butylmagnesium chloride with excess benzyloxalate to obtain desired product in 27% yield. $^1$H NMR (CDCl$_3$, TMS) δ0.91 (t,3H), 1.35 (m,2H), 1.6 (m,2H), 2.85 (t,2H), 5.29 (s,2H), 7.4 (m,5H). R$_f$ value is identical to Example 3.

EXAMPLE 13

N-(1R)-(tert-Butyloxycarbonyl)-2-phenylethyl)-L-alanine benzyl ester and its D-alanine isomer Using the procedure of Example 11, but replacing L-Phe-t-Bu ester.HCl with D-Phe-t-Bu ester.HCl gave the desired compounds.

Less polar isomer: $^1$H NMR (CDCl$_3$, TMS) δ1.27 (d,3H), 1.32 (s,9H), 2.91 (dd,2H), 3.34 (dd,1H), 3.45 (t,1H), 5.12 (d,2H). Mass spectrum: (M+H)$^+$ = 384.

More polar isomer: $^1$H NMR (CDCl$_3$, TMS) δ1.3 (d,3H), 1.33 (s,9H), 2.91 (d,2H), 5.12 (s,2H). Mass spectrum: (M+H)$^+$ = 384.

EXAMPLE 14

N-(1(S)-(tert-Butyloxycarbonyl)-2-phenylethyl)-L-norleucine, benzyl ester and its D-norleucine isomer Using the procedure of Example 8, but replacing the 2-oxo-4-methyl pentanoic acid benzyl ester with 2-oxohexanoic acid benzyl ester gave the desired compounds.

Less polar (S,R) isomer: $^1$H NMR (CDCl$_3$, TMS) δ0.8 (bt,3H), 1.18 (m,2H), 1.34 (s,9H), 2.89 (bt,2H), 3.19 (t,1H), 3.37 (t,1H), 5.12 (d,2H). Mass spectrum: (M+H)$^+$ = 426.

More polar (S,S) isomer: $^1$H NMR (CDCl$_3$, TMS) δ0.85 (m,3H), 1.33 (s,9H), 2.9 (d,2H), 3.31 (t,1H), 3.41 (t,1H), 5.11 (s,2H). Mass spectrum: (M+H)$^+$ = 426.

EXAMPLE 15

N-(1(R)-(tert-Butyloxycarbonyl)-2-phenylethyl)-L-leucine, benzyl ester

Using the procedure of Example 8, but replacing the L-Phe-t-Bu ester.HCl with D-Phe-t-Bu ester.HCl to give the desired less polar L-isomer. $^1$H NMR (CDCl$_3$, TMS) δ0.8 (dd,6H), 1.34 (s,9H), 1.42 (t,2H), 2.88 (t,2H), 3.21 (bt,1H), 3.48 (bt,1H), 5.1 (s,2H). Mass spectrum: (M+H)$^+$ = 426.

EXAMPLE 16

N-(1(S)-(tert-Butyloxycarbonyl)-3-phenylpropyl)-L-leucine

A solution of the more polar (S,S) diastereomer (45 mg, 0.1 mmol) of Example 10 in 2 ml of methanol was treated with 20 mg of 10% palladium on carbon and stirred under a hydrogen atmosphere for 2 h. After filtration through celite, the solution was concentrated under reduced pressure to give the desired product (35 mg, 98%). $^1$H NMR (CDCl$_3$, (TMS) δ0.92 (dd,6H), 1.49 (s,9H), 2.68 (m,2H), 3.19 (dd,1H), 3.28 (t,1H), 7.24 (m,5H). Mass spectrum: (M+H)$^+$ = 350.

EXAMPLE 17

4(S)-t-Butyloxycarbonylamino-5-cyclohexyl-3(R,S)-hydroxy-1-pentene

To a stirred −78° C. solution of Boc-cyclohexylalanine methyl ester (10.2 g, 35.8 mmol) in dry toluene (60 ml) was added diisobutylaluminum hydride (34 ml of a 1.5M solution in toluene). After 30 min, vinyl magnesium bromide (108 ml of 1M solution in tetrahydrofuran (THF)) was added. After stirring for 15 h at 0° C., the mixture was carefully quenched with methanol, treated with Rochelle salts (22 ml of saturated aqueous solution in 140 ml $H_2O$), and filtered. After extracting the solids 5 times with ethyl acetate, the extracts and filtrate were combined and the organic phase was washed with brine, dried, filtered and evaporated to an oil (10.2 g). Chromatography on silica gel eluting with hexane/ethyl acetate mixtures provided 6.1 g (60%) of the desired product.

Anal. Calcd. for $C_{16}H_{29}NO_3 \cdot \frac{1}{4}H_2O$: C, 66.8; H, 10.3; N, 4.9.

Found: C, 66.9, H, 10.2; N, 4.7.

EXAMPLE 18

4(S)-Cyclohexylmethyl-5(R,S)-vinyl-2-oxazolidinone

The resultant product of Example 17 (2.80 g, 9.88 mmol) in dry dimethylformamide (OMF) (50 ml) was added to a stirred suspension of NaH (593 mg of a 60% dispersion in oil, 14.8 mmol, hexane washed) in dry DMF (50 ml). After 3 h, the mixture was quenched (750 ml water+100 ml brine) and extracted with ether (5×100 ml). The combined organic phase was washed with brine (3×50 ml), dried ($MgSO_4$), filtered and evaporated to an oil (2.23 g). The NMR spectrum of the crude product revealed an 82:18 mixture of 5S:5R diastereomers. Silica gel chromatography gave 80% recovery of pure diastereomers. 5S:

Anal Calcd. for $C_{12}H_{19}NO_2$: C. 68.9; H, 9.1; N, 6.7. Found: C, 68.4; H, 9.2; N, 6.5. Mass spectrum: $(M+1)^+ = 210$. 5R: Mass spectrum: $(M+1)^+ = 210$.

EXAMPLE 19

(3S,4S)-3-Hydroxy-4-amino-5-cyclohexyl-1-pentene

To the resultant 5S-diastereomer from Example 18 (2.06 g, 9.84 mmol) in dioxane (180 ml) and water (120 ml) was added barium hydroxide octahydrate (6.24 g, 19.8 mmol). The mixture was refluxed for 18 h, cooled, filtered, concentrated, taken up in water and extracted with ethyl acetate which was dried over $Na_2SO_4$ and evaporated to afford 1.64 g (91%) of the desired product, m.p.: 59°–61° C.

Anal. Calcd. for $C_{11}H_{21}NO$: C, 72.08; H, 11.55., N, 7.64. Found: C, 71.67; H, 11.68; N, 7.36.

EXAMPLE 20

(3S,4S)-3-Hydroxy-4-tert-butyloxycarbonylamino-5-cyclohexyl-1-pentene

To the resultant compound from Example 19 (1.62 g, 8.84 mmol) in methylene chloride (20 ml) was added di-tertbutyldicarbonate (1.93 g, 8.84 mmol). The mixture was stirred for 14 h, diluted with ethyl acetate, washed sequentially with 0.5M $H_3PO_4$, saturated $NaHCO_3$ solution and brine, then dried over $Na_2SO_4$ and evaporated to afford 2.51 g (100%) of the desired compound.

EXAMPLE 21

(3S,4S)-3-Methoxyethoxymethoxy-4-tertbutyloxycarbonylamino-5-cyclohexyl-1-pentene To the resultant compound from Example 20 (2.51 g, 8.84 mmol) in methylene chloride (20 ml) was added diisopropylethylamine (4.60 ml, 26.4 mmol) and methoxyethoxychloromethane (3.00 ml, 26.3 mmol). After stirring at room temperature for 24 h the mixture was concentrated, diluted with ethyl acetate, washed with 0.5M $H_3PO_4$, saturated $NaHCO_3$ solution, then brine, dried over $Na_2SO_4$, and evaporated. Chromatography on silica gel with ethyl acetate/hexane mixtures afforded 2.63 g (80%) of the desired product as an oil. EI-MS: $M^+ = 371$.

EXAMPLE 22

(2RS,3R,4S)-3-Methoxyethoxymethoxy-4-tertbutyloxycarbonylamino-5-cyclohexyl-1,2-oxopentane To the resultant compound from Example 21 (5.41 g, 14.56 mmol) in methylene chloride (50 ml) was added 3-chloroperbenzoic acid (6.28 g). After stirring at room temperature for 60 h the mixture was concentrated, diluted with ethyl acetate, washed with cold 1:1 15% aqueous $Na_2SO_3$ solution/saturated $NaHCO_3$ solution (2×200 ml), saturated $NaHCO_3$ solution (3×100 ml) then brine (1×100 ml), dried over $Na_2SO_4$, and evaporated to afford 4.57 g (81%) product as an oil. EI-MS: $M^+ = 387$.

EXAMPLE 23

(2'S,1'R,5S)-3-Ethyl-5-(1'-methoxyethoxymethoxy-2'-tert-butyloxycarbonylamino-3'-cyclohexylpropyl)oxazolidin-2-one To the resultant compound from Example 22 (310 mg, 0.80 mmol) in isopropanol (5 ml) was added ethylamine (200 mg, 4 mmol). The mixture was heated at 70° C. for 48 h, evaporated and dissolved in methylene chloride (5 ml). To this solution was added triethylamine (0.34 ml, 2.4 mmol) and phosgene in toluene (1.0 ml, 1.2 mmol, 12.5% solution). After 2 h the mixture was diluted with ethyl acetate, washed with 0.5M $H_3PO_4$, saturated $NaHCO_3$ solution then brine, dried over $Na_2SO_4$ and evaporated. Chromatography of the residue on silica gel with 1:1 ethyl acetate/hexane provided 14.3 mg (4%) of the 5R isomer followed by 63.0 mg (17%) of the desired 5S isomer, both as oils.

5S-Isomer: $^1$H-NMR ($CDCL_3$,TMS) δ4.83 (d,1H), 4.80 (d,1H), 4.58 (m,1H), 3.49 (s,3H), 1.43 (s,9H), 1.15 (t,3H).

5R-Isomer: MS $(M+H)^+ = 459$.

EXAMPLE 24

(2'S,1'R,5S)-3-Methoxy-5-(1'-methoxyethoxymethoxy-2'-tert-butyloxycarbonylamino-3'-cyclohexylpropyl)oxazolidin-2-one Using the procedure of Example 23 but replacing the ethyl amine with equal parts of methoxyamine hydrochloride and sodium bicarbonate gives the desired compound.

EXAMPLE 25

(2RS,3R,4S)-1,2-Dihydroxy-3-methoxyethoxymethoxy-4-tert-butyloxycarbonylamino-5-cyclohexylpentane To the resultant compound from Example 21 (1.00 g, 2.69 mmol) in tetrahydrofuran (20 ml) at 0° C. was added osmium tetroxide (0.75 ml of a 2.5% solution in tert-butanol) and N-methylmorpholine N-oxide (347 mg, 2.95 mmol). The mixture was stirred at room temperature 16 h, diluted with ethyl acetate, washed with $NaHSO_3$ solution, saturated $NaHCO_3$ solution and brine, then dried over $Na_2SO_4$ and evaporated. Chromatography of the residue on silica gel with methanol-/methylene chloride mixtures provided 887 mg (81%) of the desired product.

Anal. Calcd. for $C_{20}H_{39}NO_7.0.3\ H_2O$: C, 58.46; H, 9.71; N, 3.41.

Found: C, 58.69, H, 9.53., N, 3.41.

EXAMPLE 26

(2'S,1'R,5S)-2-Oxo-4-(1'-methoxyethoxymethoxy-2'-tert-butyloxycarbonylamino-3'-cyclohexylpropyl)dioxolane The resultant compound of Example 25 in methylene chloride at 0° C. was treated with triethylamine then phosgene in toluene. The mixture was stirred at 0° C. for 1 h, then at room temperature for 3 h, poured into ethyl acetate, washed with 0.5M $H_3PO_4$, saturated $NaHCO_3$ solution and brine, then dried over $Na_2SO_4$ and evaporated to afford the desired product as an oil.

EXAMPLE 27

(2R,3R,4S)-1-Benzyloxycarbonylethylamino-2-hydroxy-3-methoxyethoxymethoxy-4-tert-butyloxycarbonylamino-5-cyclohexylpentane Using the procedure of Example 23 with the resultant compound from Example 22 and replacing the phosgene with benzyl chloroformate provided the desired 2R isomer preceded by the 2S isomer.

2R-Isomer: $^1$H-NMR ($CDCL_3$,TMS) δ7.34 (m,5H), 5.13 (s,2H), 4.95 (d,1H), 4.79 (m.2H), 3.37 (s,3H), 1.43 (s.9H), 1.14 (m,3H).

2S-Isomer: $^1$H-NMR ($CDCL_3$, TMS) δ7.35 (m,5H), 5.14 (d,1H), 5.12 (d,1H), 4.93 (d,1H), 4.80 (m,2H), 3.38 (s,3H), 1.43 (s,9H), 1.13 (t,3H).

EXAMPLE 28

(2S,3R,4S)-1-Benzyloxycarbonylethylamino-2-azido-3-methoxyethoxymethoxy-4-tert-butyloxycarbonylamino-5-cyclohexylpentane To triphenylphosphine (100.0 mg, 0.381 mmol) in tetrahydrofuran (THF, 0.6 ml) at −78° C. was added diethyl azodicarboxylate (60 μl, 0.38 mmol) in THF (1 ml). To this mixture was added a solution of hydrazoic acid (0.46 mmol) in benzene (1 ml) then the resultant compound from Example 27 (180.0 mg, 0.318 mmol) in THF (1.4 ml) was added. After one hour the mixture was warmed to room temperature, stirred for 16 h, evaporated and chromatographed on silica gel with 20% ethyl acetate in hexane to afford 103.5 mg (55%) of the desired product as an oil. $^1$H-NMR ($CDCL_3$, TMS) δ7.35 (m,5H), 5.15 (m,2H), 3.38 (s,3H), 1.45 (s,9H), 1.15 (m,3H).

EXAMPLE 29

(2'S,1'R,5S)-3-Ethyl-5-(1'-methoxyethoxymethoxy-2'-tert-butyloxycarbonylamino-3'-cyclohexylpropyl)imidazolidin-2-one To the resultant compound from Example 28 (99.0 mg, 0.167 mmol) in methanol (2 ml) was added triethylamine (75 μl, 0.54 mmol) and propane 1,3-dithiol (50 μl, 0.50 mmol). After 72 h the mixture was filtered and evaporated, and the crude amino compound was dissolved in toluene (5 ml) and heated to reflux for 72 h. Evaporation and chromatography on silica gel with ethyl acetate/hexane mixtures provided the desired product as an oil. $^1$H NMR ($CDCl_3$) δ1.12 (t,3H), 1.43 (s,9H), 3.23 (m,2H), 3.39 (s,3H), 3.64 (m,1H), 3.78 (m,1H),, 3.94 (m,1H), 4.58 (d,1H), 4.74 (d,1H), 5.47 (s,1H).

EXAMPLE 30

(3S,4S)-3-tert-Butyldimethylsilyloxy-4-tertbutoxycarbonylamino-5-cyclohexyl-1-pentene.

To the resultant compound from Example 20 (0.264 g, 0.932 mmol) in DMF (4 ml) was added tert-butyldimethylsilyl chloride (0.300 g, 1.99 mmol) and imidazole (0.269 g, 3.95 mmol). The mixture was stirred at room temperature for 12 hours, poured into ethyl acetate and washed sequentially with 0.5M $H_3PO_4$, saturated $NaHCO_3$ solution and brine, then dried over $Na_2SO_4$ and evaporated to afford 0.355 g (96%) of the desired compound. Mass spectrum: $(M+H)^+=398$.

EXAMPLE 31

(2RS,3R,4S)-3-tert-Butyldimethylsilyloxy-4-tertbutoxycarbonylamino-5-cyclohexyl-1,2-oxopentane The resultant compound from Example 30 (0.355 g, 0.893 mmol) in methylene chloride (8 ml) was treated with m-chloroperbenzoic acid (0.758 g, 3.51 mmol) and stirred at ambient temperature for 14 hours. The mixture was concentrated, dissolved in ethyl acetate, washed sequentially with cold 10% aqueous $Na_2SO_3$ solution, saturated $NaHCO_3$ solution and brine, and then dried over $Na_2SO_4$ and evaporated to afford 0.374 g (100%) of the desired compound Mass spectrum: $(M+H)^+=404$.

EXAMPLE 32

(2RS,3R,4S)-3-Hydroxy-4-tert-butoxycarbonylamino-5-cyclohexyl-1,2-oxopentane.

The resultant compound from Example 31 (2.10 g, 5.07 mmol) was treated with 1M tetrabutylammonium fluoride in tetrahydrofuran (10 ml). The mixture was stirred at 0° C. for 1 hour, poured into ethyl acetate, washed with water and brine, then dried over $Na_2SO_4$ and evaporated. Chromatography on silica gel (0.5% methanol in chloroform) afforded 1.3 g (74%) of the desired compound. Mass spectrum $(M+H)^+=300$.

EXAMPLE 33

(2S,3R,4S)-1-Azido-2,3-dihydroxy-4-tertbutoxycarbonylamino-5-cyclohexylpentane

The resultant compound from Example 32 (1.12 g, 3.74 mmol), ammonium chloride (0.374 g, 6.98 mmol) and sodium azide (0.580 g, 8.92 mmol) were refluxed in methanol (25 ml) for 12 hours. The mixture was concentrated, then taken up in ethyl acetate, washed with water and brine, dried over $Na_2SO_4$ and evaporated.

Chromatography on silica gel (20% ether in hexane) afforded 0.461 g (36%) of the desired compound followed by 0.323 g (25%) of the 4-R isomer. 4S-Diasteriomer: m.p. 93°-94° C. 4R-Diasteriomer: mass spectrum: (M+H)+ = 343.

EXAMPLE 34

N-(3-Methylbutyl)-4-hydroxy-5-t-butyloxycarbonylamino-6-cyclohexylhex-1-ene-2-carboxamide A solution of N-(3-methylbutyl)-2-methylpropenamide (643 mg, 4.15 mmol) in 25 ml of dry tetrahydrofuran was cooled under an $N_2$ atmosphere to −78° C. and treated dropwise with 3.28 ml (8.5 mmol) of n-butyllithium in hexane. The resulting solution was warmed to 0° C. for 20 min, recooled to −78° C. and treated with 6.2 ml (6.2 mmol) of chlorotitanium triisopropoxide in hexane. After again warming to 0° C. for 5 min, the dark solution was recooled to −78° C. treated with a solution of N-t-butyloxycarbonylcyclohexylalininal (670 mg, 2.3 mmol) in 5 ml of tetrahydrofuran, stirred for 5 min at −78° C., warmed to 0° C. for 20 min and quenched with saturated aqueous ammonium chloride. The resulting suspension was treated with ca. 50 ml of ether, stirred until the salts became white, extracted with two 100 ml portions of ether, dried over $MgSO_4$ and concentrated in vacuo. The crude mixture was separated by flash column chromatography using 4:1 chloroform/ethyl acetate to give 249 mg (26%) of the (4S,5S) product ($R_f$.44), 292 mg (31%) of the (4R,5S) product ($R_f$.36. 3:2 chloroform/ethyl acetate) and 184 mg (20%) of a ca. 1:1 mixture of the two products.

(4S,5S)-Isomer: $^1$H NMR (CDCl$_3$) δ0.8–1.9 (m,16H), 0.94 (d,J=6Hz,6H), 1.43 (s,9H), 2.42 (m,2H), 3.32 (br q,J=7Hz,2H), 3.62, (m,1H), 3.68 (m,1H), 4.79 (br d,J=9Hz,1H), 5.08 (br s,1H), 5.43 (s,1H), 5.56 (s,1H), 6.03 (br t,1H). Mass spectrum: M+=410.

EXAMPLE 35

2(S)-t-Butyloxycarbonylamino-1-cyclohexyl-6-methylhept-3-ene

To a stirred −78° C. solution of Boc-cyclohexylalanine methyl ester (40 g, 140 mmol) in anhydrous toluene (250 ml) was added diisobutylaluminum hydride (130M%, 1.5M solution in toluene, 121.4 ml) at a rate to keep the internal temperature below −60° C. After stirring for an additional 20 minutes at −78° C., the aldehyde solution is used immediately as described below.

To a potassium hydride (35% dispersion in oil, 32.09 g) suspension in a 0° C. mixture of anhydrous THF/DMSO (1000 ml/200 ml) under dry $N_2$ was added 1,1,1,3,3,3-hexamethyldisilazane (209M%, 49.07 g) dropwise. After stirring at 0° C. for 1 hour, the resulting solution was added via cannula to a 0° C. flask containing isopentyltriphenylphosphonium bromide (209M%, 125.66 g). The mixture was stirred vigorously for 1 hour at which time it was cooled to −78° C. The −78° C. aldehyde solution prepared above was then added via cannula. After stirring at −78° C. for 15 minutes, the mixture was allowed to slowly warm to room temperature and then heated to 40° C. for 12 hours. The mixture was then cooled to room temperature and quenched with methanol (7.65 ml) followed by aqueous Rochelle salts (100 ml saturated solution and 500 ml H$_2$O). The mixture was then extracted with ethyl acetate (2×). The combined extracts were washed with water and brine. Drying (MgSO$_4$) and evaporating provided crude alkene which was chromatographed on silica gel (ether/hexane) to give 16.5 g (38%) of the desired compound as an 85:15 mixture of cis:trans isomers. Mp=53°-55° C. Mass spectrum: M+=309.

Anal. Calcd. for C$_{19}$H$_{35}$NO$_2$: C, 73.7; H, 11.4., N, 4.5. Found: C, 73.8; H, 11.4; N, 4.5.

EXAMPLE 36

2(S)-t-Butyloxycarbonylamino-1-cyclohexyl-3,4-dihydroxy-6-methylheptane:

The 3(R)4(S),3(S)4(S), 3(R)4(R), and 3(S)4(R) Diastereomers

To a solution of the resultant compound of Example 35 (8.50, 27.5 mmol) in dry THF (150 ml) were added OsO$_4$ (2.8 ml of a 2.5% solution in t-butanol and N-methylmorpholine N-oxide (9.28 g, 68.7 mmol). After 4 days the mixture was partitioned between ether (200 ml) and brine (100 ml). The aqueous layer was back-extracted with ether (2×100 ml), and the combined organic phase was washed with 10% Na$_2$SO$_3$, 0.1M H$_3$PO$_4$, and brine. Drying (MgSO$_4$) and evaporating provided a residue (10.81 g) which was chromatographed on silica gel to elute a 60% yield of the 4 diols in the following order.

3(R),4(S) Mass spectrum: (M+H)+ = 344.
Anal Calcd. for C$_{19}$H$_{37}$NO$_4$: C. 66.4; H, 10.9; N, 4.1. Found: C, 66.4; H, 10.8; N, 3.9.
3(S),4(S) Mass spectrum: (M+H)+ = 344.
Anal Calcd. for C$_{19}$H$_{37}$NO$_4$: C, 66.4; H, 10.9; N, 5.1. Found: C, 66.4; H, 11.1; N. 4.0.
3(R),4(R) Mass spectrum: (M+H)+ = 344.
3(S),4(R) Mass spectrum: (M+H)+ = 344.
Anal Calcd. for C$_{19}$H$_{37}$NO$_4$: C, 66.4; H, 10.9; N, 4.1. Found: C, 66.0; H, 10.7; N, 4.0.

EXAMPLE 37

2-t-Butyloxycarbonylamino-1-cyclohexylbut-3-ene

To a stirred suspension of methyltriphenyl phosphonium bromide (10.97 g, 30.70 mmol) in anhydrous tetrahydrofuran (200 ml) at −78° C. (dry ice/acetone bath) under an argon atmosphere, was added n-butyl lithium (19.8 ml of a 1.55M hexane solution) dropwise over the course of 5 min. After 10 min, the −78° C. bath was replaced with a 0° C. bath for 0.5 h, at which time the resulting orange solution was cooled again to −78° C. The solution was then added dropwise by cannula to a stirred −78° C. solution of Boc-cyclohexylalaninal (27.91 mmol) in anhydrous tetrahydrofuran (30 ml) over the course of 0.5 h. The mixture was then allowed to warm to room temperature during a 3 h period after which water (150 ml) was added. Extraction with hexane (4×100 ml) provided a combined organic phase which was washed with brine (100 ml), dried (Na$_2$SO$_4$), and concentrated. Chromatography with ether/hexane (1/9) provided the desired compound. Mass spectrum: (M+H)+ = 254.

EXAMPLE 38

3-t-Butyloxycarbonylamino-4-cyclohexyl-1,2-oxobutane

To a stirred solution of the resultant compound of Example 37 (2.0 mmol) in dichloromethane (20 ml) was added m-chloroperbenzoic acid (MCPBA, 1.51 g of 80% MCPBA, 7.0 mmol). After 68 h the reaction mixture was cooled to 0° C., and 0° C. 10% Na$_2$SO$_3$ (5 ml)

was added with stirring. After 15 min, the solid was filtered off and extracted with dichloromethane. The combined organic phase was washed sequentially with 0° C. 10% Na₂SO₃ (6 ml), saturated NaHCO₃ (2×6 ml), and water (5 ml). Drying (MgSO₄), filtering, concentrating and chromatography on 50 g of SiO₂ (hexane/ether, 3/1) gave the desired compound. Mass spectrum: (M+H)⁺ =270.

EXAMPLE 39

3-t-Butyloxycarbonylamino-4-cyclohexyl-2-hydroxy-1-isopropylmercaptobutane

To a stirred solution of the resultant compound of Example 38 (0.37 mmol) in methanol (8.7 ml) was added isopropyl mercaptan (0.87 mmol) and triethylamine (0.87 mmol). The resultant solution was refluxed for 2 h and then evaporated to give a residue which was chromatographed on 15 g of 40 μ SiO₂ (7/3, hexane/ether) to give the desired compound. Mass spectrum: (M+H)⁺ =346.

EXAMPLE 40

3-t-Butyloxycarbonylamino-4-cyclohexyl-2-hydroxy-1-isopropylsulfonylbutane

Treating the resultant compound of Example 39 with 2.5 equivalents of 3-chloroperoxybenzoic acid in dichloromethane, gave the desired compound after work-up as described in Example 38. Mass spectrum: (M+H)⁺ =418.

Anal Calcd. for $C_{21}H_{33}NO_5S \cdot 0.5\ H_2O$: C, 59.10; H, 9.45; N, 3.28. Found: C, 58.90; H, 9.46; N, 3.03.

EXAMPLE 41

2(S)-Amino-1-cyclohexyl-3(R),4(S)-dihydroxy-6-methylheptane Hydrochloride

To 0.17 g (0.50 mmol) of the resultant compound of Example 36 was added 5 ml of 4M HCl in dioxane. After being allowed to stand for 1 h at ambient temperature, the solution was concentrated with two chloroform chasers to give a white solid which was used without further purification.

EXAMPLE 42

Boc-His Amide of 2(S)-Amino-1-cyclohexyl-3(R),4(S)-dihydroxy-6-methylheptane

To a stirred suspension of Boc-His-OH (72 mg, 0.23 mmol) in dry dimethylformamide (3 ml) −23° C. was added a solution of the resultant compound of Example 41 (0.23 mmol) in dry dimethylformamide (2 ml) containing N-methylmorpholine (29 mg, 0.28 mmol). Hydroxybenzotriazole (HOBT, 58 mg, 0.43 mmol) and N,N'-dicyclohexylcarbodiimide (DCC, 59 mg, 0.28 mmol) were then added sequentially. After 2 h the mixture was allowed to warm to room temperature. After 22 h the mixture was filtered, evaporated, and partitioned between ethyl acetate (18 ml) and saturated aqueous NaHCO₃ (6 ml). The layers were separated, and the organic phase was washed with brine (5 ml), dried (Na₂SO₄), filtered, and evaporated to a solid which was chromatographed on SiO₂ to give the desired compound. Mass spectrum: M⁺ =480.

Anal Calcd. for $C_{25}H_{44}N_4O_5 \cdot \frac{3}{4}H_2O$: C, 60.8; H, 9.1; N, 11.3. Found: C, 60.9., H. 9.2, N, 11.0.

EXAMPLE 43

3-Amino-4-cyclohexyl-2-hydroxy-1-isopropylsulfonylbutane Hydrochloride.

Using the procedure of Example 41 with the resultant compound of Example 40 gave the desired compound which was used without further purification.

EXAMPLE 44

His Amide of 2(S)-Amino-1-cyclohexyl-3-(R),4(S)-dihydroxy-6-methylheptane Dihydrochloride Using the procedure of Example 41 with the resultant compound of Example 42 gave the desired compound which was used without further purification.

EXAMPLE 45

(4S,5S)-N-(3-Methylbutyl)-5-amino-4-hydroxy-6-cyclohexylhex-1-ene-2-carboxamide Hydrochloride Using the procedure of Example 41 with the resultant compound of Example 34 gave the desired compound which was used without further purification.

EXAMPLE 46

(2S,3R,4S)-1-Azido-2,3-dihydroxy-4-amino-5-cyclohexylpentane Hydrochloride

Using the procedure of Example 41 with the resultant compound of Example 33 gave the desired compound which was used without further purification.

EXAMPLE 47

(2'S,1'R,5S)-3-Ethyl-5-(2'-amino-3-cyclohexyl-1'-hydroxypropyl)imidazolidin-2-one Hydrochloride.

Using the procedure of Example 41 with the resultant compound of Example 29 gave the desired compound which was used without further purification.

EXAMPLE 48

(2'S,1'R,5S)-2-Oxo-4-(2'-amino-3'-cyclohexyl-1'-hydroxypropyl)dioxolane Hydrochloride.

Using the procedure of Example 41 with the resultant compound of Example 26 gave the desired compound which was used without further purification.

EXAMPLE 49

(2'S,1'R,5S)-3-Methoxy-5-(1'-hydroxy-2'-amino-3'-cyclohexylpropyl)oxazolidin-2-one Hydrochloride.

Using the procedure of Example 41 with the resultant compound of Example 24 gave the desired compound which was used without further purification.

EXAMPLE 50

(2'S,1'R,5S)-3-Ethyl-5-(1'-hydroxy-2'-amino-3'-cyclohexylpropyl)oxazolidin-2-one Hydrochloride Using the procedure of Example 41 with the resultant compound of Example 23 gave the desired compound which was used without further purification.

EXAMPLE 51

N-(1(S)-(tert-Butyloxycarbonyl)-3-phenylpropyl)-L-leucyl Amide of 2(S)-Amino-1-cyclohexyl-3(R),4(S)-dihydroxy-6-methylheptane To a mixture of the resultant compound of Example 16 (33.2 mg, 0.095 mmol) and 2(S)-amino-1-cyclohexyl-3(R),4(S)-dihydroxy-6-methylheptane hydrochloride (26.6 mg, 0.095 mmol, Example 41) in 2 ml of anhydrous DMF was added 1-hydroxybenzotriazole hydrate (38.5 mg, 0.285 mmol), N-methyl morpholine (11 mg, 0.114 mmol) and EDAC (21.9 mg, 0.114 mmol) sequentially at $-23°$ C. After stirring for 2 h, the mixture was allowed to warm to room temperature. After another 17 h, the mixture was poured into ethyl acetate, washed with dilute sodium bicarbonate, water, and brine. The organic phase was dried and concentrated under reduced pressure to a crude product which was chromatographed on silica gel eluting with ethyl acetate:-hexane (1.5:8.5) to obtain the desired compound (29.2 mg, 54%) as a white solid. $^1$H NMR (CDCl$_3$, TMS) $\delta$0.9 (d,3H), 0.94 (d,3H), 0.95 (d,3H), 0.97 (d,3H), 1.49 (s,9H), 2.73 (m,2H). 3.05 (br t,1H), 3.11 (dd,1H), 3.20 (m,2H), 4.31 (m,1H), 7.22 (m,5H). Mass spectrum: $(M+H)^+ = 575$.

EXAMPLE 52

N-(1(S)-(tert-Butyloxycarbonyl)-3-phenylpropyl)-D-leucyl Amide of 2(S)-Amino-1-cyclohexyl-3(R),4(S)-dihydroxy-6-methylheptane The resultant less polar (S,R) diastereomer of Example 10 was hydrogenated using the procedure of Example 16. The resultant product was coupled to the resultant product of Example 41 according to the procedure of Example 51 to give the desired compound. $^1$H NMR (CDCl$_3$, TMS) $\delta$0.9 (dd,6H), 0.95 (dd,6H), 1.59 (s,9H), 1.94 (m,3H), 2.6 (m,2H), 3.2 (m,4H), 4.29 (m,1H), 7.24 (m,5H). Mass spectrum: $(M+H)^+ = 575$.

EXAMPLE 53

N-(1(R)-(tert-Butyloxycarbonyl)-3-phenylpropyl)-D,L-leucyl Amide of 2(S)-Amino-1-cyclohexyl-3(R),4(S)-dihydroxy-6-methylheptane The resultant diastereomeric mixture of Example 9 was hydrogenated according to the procedure of Example 16. The resultant acid was coupled to the resultant product of Example 41 according to the procedure of Example 51 to give desired compound. $^1$H NMR (CDCl$_3$, TMS) $\delta$0.85 (dd,6H), 0.95 (dd,6H), 1.5 (2s,9H), 3.1 (m,2H), 7.2 (m,5H). Mass spectrum: $(M+H)^+ = 575$.

EXAMPLE 54

N-(1(S)-tert-Butyloxycarbonyl)-2-phenylethyl)-L-leucyl Amide of 2(S)-Amino-1-cyclohexyl-3(R),4(S)-dihydroxy-6-methylheptane The resultant more polar diastereomer of Example 8 was hydrogenated according to the procedure of Example 16. The resultant acid was coupled to the resultant product of Example 41 according to the procedures of 51 to give the desired compound. $^1$H NMR (CDCl$_3$, TMS) $\delta$0.83 (dd,6H), 0.89 (dd,6H), 1.37 (s,9H), 1.93 (m,1H), 2.45 (d,2H), 4.28 (br dd,1H), 4.52 (br dd,1H), 7.24 (m,5H), 7.41 (br d,1H). Mass spectrum: $(M+H)^+ = 561$.

EXAMPLE 55

N-(1(S)-(tert-Butyloxycarbonyl)-2-phenylethyl)-D-leucyl Amide of 2(S)-Amino-1-cyclohexyl-3(R),4(S)-dihydroxy-6-methylheptane Using the procedure of Example 54, but replacing the resultant more polar diastereomer of Example 8 with the less polar diastereomer of Example 8 gave the desired compound. $^1$H NMR (CDCl$_3$, TMS) $\delta$0.91 (dd,6H), 0.96 (dd,6H), 1.38 (s,9H), 2.83 (br dd,2H), 4.16 (br m,1H), 4.5 (br,1H), 6.8 (br,1H), 7.28 (m,5H). Mass spectrum: $(M+H)^+ = 561$.

EXAMPLE 56

N-(1(R)-tert-Butoxycarbonyl)-2-phenylethyl)-D-leucyl Amide of 2(S)-Amino-1-cyclohexyl-3(R),4(S)-dihydroxy-6-methylheptane Using the procedure of Example 52, but replacing the resultant (S,R) less polar diastereomer of Example 10 with the resultant product of Example 15 gave the desired compound.

$^1$H NMR (CDCl$_3$, TMS) $\delta$0.73 (dd,6H), 0.88 (dd,6H), 1.41 (s,9H), 2.8 (dd,1H), 2.97 (dd,1H), 3.12 (bm,3H), 3.43 (dd,1H), 4.3 (m,1H), 4.86 (bm,1H), 7.95 (bd,1H). Mass spectrum: $(M+H)^+ = 561$.

EXAMPLE 57

N-(1-(Ethoxycarbonyl)-3-phenylpropyl)-L-alanine, benzyl ester (More polar and Less polar isomers)

2-Oxo-4-phenylbutyric acid, ethyl ester (Syn. Comm., 11(12), 943–946, 1981) was treated with L-Ala benzyl ester.HCl according to the procedure of Example 8. The crude product was chromatographed eluting with 15% EtOAc/Hex to give two separate diastereomers. Less polar isomer (18% yield). $^1$H NMR (CDCl$_3$, TMS) $\delta$1.25 (t,3H), 1.32 (d,3H), 1.94 (m,2H), 2.37 (bs,1H), 2.71 (t,2H), 3.27 (bt,1H), 3.38 (q,1H), 4.12 (m,2H), 5.13 (dd,2H). Mass spectrum: $(M+H)^+ = 370$.

More polar isomer (20% yield) $^1$H NMR (CDCl$_3$, TMS) $\delta$1.28 (t,3H), 1.35 (d,3H), 1.93 (m,2H), 2.71 (m,2H), 3.35 (dd,1H), 3.43 (q,1H), 4.15 (m,2H), 5.15 (dd,2H), $(M+H)^+ = 370$.

EXAMPLE 58

N-(1(R or S)-(Ethoxycarbonyl)-3-phenylpropyl)-L-alanyl Amide of 2(S)-Amino-1-cyclohexyl-3(R),4(S)-dihydroxy-6-methylheptane.

The more polar resultant product of Example 57 was hydrogenated according to the procedure of Example 16. The resultant acid was coupled to the resultant product of Example 41 according to the procedure of Example 51 to give the desired compound in 80% yield. $^1$H NMR (CDCl$_3$, TMS) $\delta$0.9 (dd,6H), 1.27 (t,3H), 1.29 (d,3H), 2.3 (bd,1H), 2.69 (bt,2H), 3.12 (m,3H), 3.34 (t,1H), 4.15 (m,2H), 4.3 (m,1H), 4.63 (b,1H), 7.67 (bd,1H). Mass spectrum: $(M+H)^+ = 505$.

EXAMPLE 59

N-(1(R or S)-(Ethoxycarbonyl)-3-phenylpropyl)-L-alanyl Amide of 2(S)-Amino-1-cyclohexyl-3(R),4(S)-dihydroxy-6-methylheptane Using the procedure of Example 58, but replacing the more polar resultant product of Example 57 with the less polar product of Example 57 gave the desired compound. $^1$H NMR (CDCl$_3$, TMS) a 0.9 (dd,6H), 1.26 (t,3H), 1.28 (d,3H), 2.3 (bd,1H), 2.68 (t,2H), 3.12 (m,3H), 4.17 (q,2H), 4.3 (m,1H), 7.67 (bd,1H). Mass spectrum: (M+H)$^+$=505.

EXAMPLE 60

N-(1(R or S)-(Ethoxycarbonyl)-3-phenylpropyl)-L-His Amide of 2(S)-Amino-1-cyclohexyl-3(R),4(S)-dihydroxy-6-methylheptane and its isomer Using the procedure of Example 57, but replacing L-Ala benzyl ester.HCl with the resultant compound of Example 44 gave a mixture of two diastereomers which were separated on silica gel chromatography eluting with 5% CH$_3$OH/CHCl$_3$ Less polar isomer (a) $^1$H NMR (CDCl$_3$, TMS) δ0.9 (dd,6H), 1.25 (t,3H), 1.1–1.9 (m,19H), 2.6 (bt,3H), 3.1 (m.3H), 4.1 (m,2H), 4.3 (m,1H), 6.9 (s,1H), 7.2 (m,5H), 7.58 (s,1H). Mass spectrum: (M+H)$^+$=571. More polar isomer (b) $^1$H NMR (CDCl$_3$, TMS) δ0.9 (dd,6H), 1.2 (t,3H), 4.1 (q,2H), 4.3 (m,1H). 6.9 (s,1H), 7.3 (m,5H), 7.6 (s,1H). Mass spectrum: (M+H)$^+$=571.

EXAMPLE 61

N-(1(R)-(4-Morpholinylcarbonyl)-3-phenyl propyl)-L-leucine benzyl ester

The resultant less polar (S,S) isomer of Example 9 (770 mg, 1.76 mmol) was stirred in 7 ml of 4M HCl/dioxane for 16 h. The solvent was evaporated off under reduced pressure to provide a solid. The residual solid (400 mg, 0.95 mmol) was coupled to morpholine (0.96 mmol) using NMM, HOBT, and EDAC according to the procedure of Example 51 to give the desired compound in 70% overall yield. $^1$H NMR (CDCl$_3$, TMS) δ0.9 (dd,6H), 2.75 (m,2H), 3.2 (t,2H), 3.35 (t,2H), 3.5 (m,2H), 3.6 (m,2H), 5.05 (s,2H), 7.4 (m,5H).

EXAMPLE 62

N-(1(S)-(4-Morpholinylcarbonyl)-2-phenylethyl)-L-alanine, benzyl ester

Using the procedure of Example 61, the resultant less polar isomer of Example 11 was hydrolyzed and coupled to morpholine to give the desired compound. $^1$H NMR (CDCl$_3$, TMS) δ1.35 (d,3H), 2.5 (m,2H), 2.8 (m,2H), 3.1 (m,1H), 3.3 (m,2H), 3.5 (m,2H), 3.8 (q,1H), 5.2 (s,2H), 7.25 (m,5H).

EXAMPLE 63

N-(1(R)-(4-Morpholinylcarbonyl)-2-phenylethyl)-L-alanine, benzyl ester

Using the procedure of Example 61, the resultant less polar isomer of Example 13 was hydrolyzed and coupled to morpholine to give the desired compound in 32% yield. $^1$H NMR (CDCl$_3$, TMS) δ0.82 (d,3H), 2.73 (m,3H), 3.03 (m,2H), 3.36 (m,4H), 3.56 (m,1H), 3.64 (m,1H), 3.78 (dd,1H), 5.12 (s,2H). Mass spectrum: (M+H)$^+$=397.

EXAMPLE 64

N-(1(S)-(4-Morpholinylcarbonyl)-2-phenylethyl)-L-norLeu, benzyl ester

Using the procedure of Example 61, the resultant more polar (S,S) isomer of Example 14 was hydrolyzed and coupled to morpholine to give the desired compound in 65% yield. $^1$H NMR (CDCl$_3$, TMS) δ0.86 (m,3H), 1.27 (m,4H), 2.44 (m,2H), 2.77 (m,2H), 2.99 (dd,1H), 3.13 (m,2H), 3.32 (m,2H). 3.53 (m,2H), 3.7 (dd,1H), 5.18 (s,2H). Mass spectrum: (M+H)$^+$=439.

EXAMPLE 65

N-(1(S)-(4-Morpholinylcarbonyl)-2-phenylethyl)-L-leucyl Amide of 2(S)-Amino-1-cyclohexyl-3(R),4(S)-dihydroxy-6-methylheptane Using the procedure of Example 61, but replacing the resultant product of Example 9 with the more polar (S,S) resultant product of Example 54 gave the desired compound in 71% yield. $^1$H NMR (CDCl$_3$, TMS) δ0.87 (dd,6H), 0.93 (dd,6H), 2.88 (m,6H), 3.16 (m,4H), 3.62 (m,4H). 4.22 (bm,1H), 4.52 (bd,1H), 7.09 (bd,1H). Mass spectrum: (M+H)$^+$=574.

EXAMPLE 66

N-(1(S)-(tert-Butyloxycarbonyl)-2-phenylethyl)-L-alanyl Amide of 2(S)-Amino-1-cyclohexyl-3(R),4(S)-dihydroxy-6-methylheptane Using the procedure of Example 58, but replacing the more polar resultant product of Example 57 with the less polar (S,S) resultant product of Example 11 gave the desired compound in 76% yield. $^1$H NMR (CDCl$_3$, TMS) δ0.92 (dd,6H), 1.42 (d,2H), 1.42 (s,9H), 1.4 (m,1H), 2.72 (dd,2H), 2.95 (dd,1H), 3.09 (m,3H), 4.11 (m,1H), 4.45 (b,1H), 6.78 (bd,1H). Mass spectrum: (M+H)$^+$=519.

EXAMPLE 67

N-(1(S)-(3-(Ethoxycarbonyl)propylcarbamoyl)-2-phenylethyl)-L-alanyl Amide of 2(S)-Amino-1-cyclohexyl-3(R),4(S)-dihydroxy-6-methylheptane Using the procedure of Example 61, the resultant compound of Example 66 was hydrolyzed and coupled to 3-(ethoxycarbonyl)-propyl amine according to the procedure of Example 51 gave the desired compound in 33% yield. $^1$H NMR (CD$_3$OD, TMS) δ0.92 (dd,6H), 1.24 (d,3H), 1.25 (t,3H), 2.15 (t,2H), 2.88 (m,2H). 4.12 (q,2H), 7.23 (m.5H). Mass spectrum: (M+H)$^+$=576.

EXAMPLE 68

N-(1(S)-(4-Morpholinylcarbonyl)-2-phenylethyl)-L-alanyl Amide of 2(S)-Amino-1-cyclohexyl-3(R),4(S)-dihydroxy-6-methylheptane Using the procedure of Example 52, but replacing the resultant (S,R) less polar product of Example 10 with the resultant product of Example 62 gave the desired compound. $^1$H NMR (CDCl$_3$, TMS) δ0.8 (d,3H), 0.95 (d,3H), 1.25 (t.3H), 2.7–3.0 (m,4H), 3.15 (m,2H), 3.5 (m,2H), 3.7 (m.2H). 7.3 (m,5H). Mass spectrum: (M+H)$^+$=532.

EXAMPLE 69

N-(1(S)-(4-Morpholinylcarbonyl)-2-phenylethyl)-L-norleucyl Amide of 2(S)-Amino-1-cyclohexyl-3(R),4(S)-dihydroxy-6-methylheptane Using the procedure of Example 52, but replacing the resultant (S,R) less polar product of Example 10 with the resultant product of Example 64 gave the desired compound in 50% yield. $^1$H NMR (CDCl$_3$, TMS) δ0.88 (dd,6H), 0.9 (t,3H), 1.87 (m,1H) 2.85(m,5H), 3.15 (m,3H), 3.4 (m,2H), 3.62 (m,3H), 4.24 (bt,1H), 4.51 (bd,1H), 7.06 (bd,1H). Mass spectrum: (M+H)$^+$=574.

EXAMPLE 70

N-(1(R)-(4-Morpholinylcarbonyl)-2-phenylethyl)-L-alanyl Amide of 2(S)-Amino-1-cyclohexyl-3(R),4(S)-dihydroxy-6-methylheptane Using the procedure of Example 52, but replacing the resultant (S,R) less polar product of Example 10 with the resultant product of Example 63 gave the desired compound in 57% yield. $^1$H NMR (CDCl$_3$, TMS) δ0.9 (dd,6H), 1.3 (d,3H), 2.92 (m,4H), 3.2 (m,3H), 3.37 (m,3H), 3.64 (m,2H), 3.88 (b dd,1H), 4.3 (m,1H), 4.74 (bd,1H), 7.8 (bd,1H). Mass spectrum: (M+H)$^+$=532.

EXAMPLE 71

N-(1(R)-(4-Morpholinylcarbonyl)-3-phenylpropyl)-L-leucyl Amide of 2(S)-Amino-1-cyclohexyl-3(R),4(S)-dihydroxy-6-methylheptane Using the procedure of Example 52, but replacing the resultant (S,R) less polar product of Example 10 with the resultant product of Example 61 gave the desired compound. $^1$H NMR (CDCl$_3$, TMS) δ0.8–1.0 (3d,12H), 2.6–3.6 (m,10H), 7.3 (m,5H). Mass spectrum: (M+H)$^+$=572.

EXAMPLE 72 tert-Butyl (2(S)-2-(tert-butyloxycarbamoyl)-3-phenylpropyl)sulfide

Tert-butyl mercaptan (0.52 ml, 416 mg, 4.61 mmol) was added to a suspension of sodium hydride (111 mg, 4.62 mmol) in 8 ml of THF, cooled to 0° C. under a nitrogen atmosphere. The resulting suspension was stirred at 0° C. for 1 h, and for an additional 3 h at room temperature. To the resulting thick white suspension, cooled to 0° C., was added dropwise via cannula, a solution of 1-phenyl-3-p-toluenesulfonyloxy-2(S)-t-butyloxyamidopropane (1.63 g, 4.02 mmol) in 10 ml of THF. The resultant mixture was allowed to stir and slowly warm to room temperature over 18 h. The mixture was partitioned between 75 ml Et$_2$O and 50 ml water. The organic phase was extracted with 50 ml saturated NaHCO$_3$, then the combined aqueous phases were extracted with 2×50 ml Et$_2$O. All organic phases were combined, washed with 50 ml brine, dried (MgSO$_4$), and the filtrate concentrated under reduced pressured to afford 1.40 g of orangish solid. Purification by recrystallization (hexanes, three crops) gave 1.16 g (89%) of white crystals; m.p. 67°–69° C. $^1$H NMR (CDCl$_3$) δ1.31 (s,9H), 1.43 (s,9H), 2.57 (dd,1H), 2.66 (dd,1H), 2.84 (m,2H). 4.04 (bm,1H), 4.79 (bm,1H), 7.16–7.4 (m,5H).

EXAMPLE 73 tert-Butyl (2(S)-2-(tert-butyloxycarbamoyl)-3-phenylpropyl)sulfone

The resultant compound from Example 72 (863 mg, 2.67 mmol) was dissolved in 5 ml absolute ethanol and 5 ml THF, and 2.5 ml water and 5 ml pH 4.5 aqueous phosphate buffer was added. The mixture was cooled in ice and treated with OXONE (2.45 g, 8.00 mmol KHSO$_5$). The mixture was stirred and allowed to warm to room temperature. After 60 h, the mixture was partitioned between 50 ml water and 50 ml CH$_2$Cl$_2$. The aqueous phase was further extracted with 3×50 ml CH$_2$Cl$_2$, and the combined organic extracts were washed with brine, dried (MgSO$_4$), filtered, and the filtrate concentrated under reduced pressure to give 942 mg of white solid. Recrystallization from CH$_2$Cl$_2$/Et$_2$O (three crops) afforded 839 mg (88%) of white crystals; m.p. 169°–170.5° C. $^1$H NMR (CDCl$_3$) δ1.38 (s,9H), 1.42 (s,9H), 3.1–3.3 (m,4H), 4.30 (bm,1H), 5.26 (bs,1H), 7.21–7.42 (m,5H). High resolution mass spectrum; calcd. for C$_{13}$H$_{30}$NO$_4$S (M+H)$^+$: 356.1895. Found: 356.1894.

EXAMPLE 74 tert-butyl (2(S)-2-amino-3-phenylpropyl) sulfone hydrochloride

The resultant compound from Example 73 (741 mg, 2.09 mmol) was treated with 2.5 ml of 4.5M HCl in dioxane at room temperature. After 24 h the volatiles were removed under reduced pressure, and the residue placed under high vacuum overnight, to afford 614 mg (100%) of the desired compound: m.p. >220° C. $^1$H NMR (CDCl$_3$) δ1.34 (s,9H), 3.20 (dd,1H), 3.26 (dd,1H), 3.70 (dd,1H), 3.89 (dd,1H), 4.25 (bm,1H), 7.25–7.35 (m,5H), 8.7 (bs,1H+H$_2$O).

EXAMPLE 75

N-(1(S)-(tert-Butylsulfonylmethyl)-2-phenylethyl)-D,L-alanine ethyl ester

A suspension of the resultant compound from Example 74 (200 mg, 0.685 mmol) in 5 ml of isopropanol was cooled to 0° C., then ethyl pyruvate (96 mg, 0.822 mmol) and sodium acetate (140 mg, 1.03 mmol) were added. Sodium cyanoborohydride (49 mg, 0.780 mmol) was added as a solution in 1.2 ml of isopropanol, and the reaction mixture was allowed to warm slowly to room temperature and stir for 48 h. The mixture was stirred with 5 ml of 1M sodium carbonate for 1 h at room temperature, then the mixture was concentrated under reduced pressure. The residue was partitioned between 40 ml of water and 50 ml of CH$_2$Cl$_2$. The aqueous phase was further extracted (4×25 ml CH$_2$Cl$_2$), then the combined organic phases were washed (50 ml sat. aq. NaHCO$_3$, 50 ml brine), dried (Na$_2$SO$_4$), and the filtrate concentrated under reduced pressure. Purification by column chromatography (Et$_2$O-hexanes 5:1) gave the two isomeric products, 70 mg (29%) of the less polar isomer, and 124 mg (51%) of the more polar isomer, as colorless, viscous oils.

Data for the less polar isomer: $^1$H NMR (CDCl$_3$) δ1.27 (dd,3H), 1.3 (d,3H), 1.57 (bm,1H), 2.74–3.04 (m,4H), 3.50 (b q,1H), 3.62 (m,1H), 4.20 (qd,2H), 7.2–7.33 (m,5H).

Data for more polar isomer: $^1$H NMR (CDCl$_3$) δ1.23 (t,3H), 1.30 (d,3H), 2.89–3.16 (m,4H), 3.54 (q,1H), 3.58 (m,1H), 4.12 (qd,2H), 7.21–7.35 (m,5H).

EXAMPLE 76

N-(1(S)-(tert-Butylsulfonylmethyl)-2-phenylethyl)-L-alanyl Amide of 2(S)-amino-1-cyclohexyl-3(R),4(S)-dihydroxy-6-methylheptane The resultant compound from Example 75 (51 mg 0.143 mmol, more polar isomer) was treated with lithium hydroxide (160 ul, 1.0M in H$_2$O, 0.160 mmol) in 1.0 ml of THF. After 20 h, the solution was concentrated under reduced pressure and the residue was placed under high vacuum, affording 49.3 mg of the corresponding lithium carboxylate. The carboxylate salt was then suspended in 1.4 ml of dry DMF, cooled to 0° C., and hydroxybenzotriazole monohydrate (22.6 mg, 0.148 mmol), ethyl (dimethylaminopropyl)carbodiimide hydrochloride (38 mg, 0.198 mmol) and N-methylmorpholine (36 mg, 0.355 mmol) were added. After stirring for 5 min, the resultant compound from Example 41 (40.2 mg, 0.144 mmol) was added, and the resulting mixture allowed to slowly warm to room temperature and stir for 48 h. Concentration under high vacuum was followed by partitioning of the residue between 15 ml of EtOAc, 5 ml of sat. aqueous NaHCO$_3$ and 2 ml of water. The aqueous phase was further extracted with 2×10 ml of EtOAc, and the combined organic extracts were washed with 10 ml of brine, dried (Na$_2$SO$_4$), and the filtrate was concentrated under reduced pressure to give 69.3 mg of yellow oil. Column chromatography on silica gel (EtOAc-hexane 5:2) afforded 33.8 mg (69%) of the desired product as a glassy solid. $^1$H NMR (CDCl$_3$) δ0.74 (d,3H), 0.90 (d,3H+m,4H), 1.1–1.75 (several m,11H), 1.32 (s,9H), 1.39 (d,3H), 1.87 (m,1H), 2.74 (dd,1H), 2.78 (dd,1H), 3.06 (m,2H), 3.17 (bs,1H), 3.43 (bq,1H), 3.55 (bm,1H), 4.2 (bm,2H), 4.57 (bm,1H), 7.18–7.38 (m,5H), 7.52 and 7.71 (2m,1H). High resolution mass spectrum: calcd. for C$_{30}$H$_{53}$N$_2$O$_5$S (M+H)$^+$: 553.3675. Found: 553.3677.

EXAMPLE 77

1(S)-(4-Morpholinylcarbonyl)-2-phenylethanol

Morpholine (0.48 ml, 5.47 mmol) was added to a mixture of L-phenyllactic acid (1 g, 6.02 mmol) and HOBT (2 g, 14.77 mmol) in DMF (30 ml). The clear solution was cooled to −23° C. and then treated with EDAC (1.648 g, 6.02 mmol). The mixture was stirred at −23° C. for 2 h and then allowed to warm to room temperature and stirred for another 18 h. The resultant yellow liquid was concentrated and then taken up into EtOAc, washed consecutively with 5% NaHCO$_3$, H$_2$O, and brine. The crude product obtained after concentration was chromatographed on SiO$_2$ column, eluted with 50% EtOAc/Hexane. The desired product was obtained as white needles (1.0972 g, 85%). $^1$H NMR (CDCl$_3$, TMS) δ1.59 (b,1H), 2.93 (t,2H), 3.07 (dd,1H), 3.3 (b dd,2H), 3.58 (m,4H), 4.59 (bt,1H). Mass spectrum: (M+H)$^+$=236.

Analogous to the preparation of Example 77 the following compounds were prepared.

EXAMPLE 78

1(S)-(N-Azetidinylcarbonyl)-2-phenylethanol (60%)

$^1$H NMR (CDCl$_3$, TMS) δ2.19 (m,2H), 2.91 (dd,2H), 3.42 (m, 1H), 4.03 (m,3H), 4.22 (t,1H). Mass spectrum: (M+H)$^+$=206.

EXAMPLE 79

1(S)-(N-Pyrolidinylcarbonyl)-2-phenylethanol $^1$H NMR (CDCl$_3$, TMS) δ1.82 (m,4H), 2.91 (m,3H), 3.4 (m,1H), 3.56 (m,2H), 4.39 (t,1H). Mass spectrum: (M+H)$^+$=220.

EXAMPLE 80

1(S)-(N-Piperidinylcarbonyl)-2-phenylethanol,(84% yield)

$^1$H NMR (CDCl$_3$, TMS) δ1.52 (m,6H), 2.88 (dd,2H), 3.16 (m,1H), 3.31 (m,1H), 3.5 (m,1H), 3.64 (m,1H), 3.82 (b,1H), 4.59 (b dd,1H). Mass spectrum: (M+H)$^+$=234.

EXAMPLE 81

1(S)-(4-(Methoxycarbonyl)piperidin-1-yl-carbonyl)-2-phenylethanol (84% yield)

$^1$H NMR (CDCl$_3$, TMS) δ0.9 (m,1H), 1.64 (m,1H), 1.88 (m,2H), 2.52 (m,1H), 2.88 (d,2H), 2.92 (m,2H), 3.64 (m,2H), 3.7 (s,3H), 4.35 (m,1H), 4.6 (dd,1H). Mass spectrum: (M+H)$^+$=292.

EXAMPLE 82(a)

4-(Methoxymethoxy)-piperidine

A solution of 200 g (1.98 mol) of 4-hydroxypiperidine (Aldrich) and 160 mL (2.59 mol) was allowed to stir first at ice-water bath temperature for 30 min then at rt for 2 h. Excess methyl formate and methanol were removed by rotary evaporation under vacuum then submitted to high vacuum (0.5 mm Hg) for 18 h. The crude formamide was used without further purification.

The crude formamide was dissolved into 1 L dichloromethane, 700 mL of diisopropylethylamine, and cooled in an ice-water bath. MOMCl (200 g) was added dropwise and the reaction stirred to rt over 8 h. Another 250 mL portion of diisopropylethylamine was added and the reaction mixture recooled in an ice-water bath. MOMCl (100 g) was added dropwise and the reaction mixture stirred to rt over 18 h. TLC (2% CH$_3$OH/EtOAc) showed complete reaction. Saturated sodium bicarbonate solution was added (2 L) and the dichloromethane layer separated. The aqueous layer extracted once with dichloromethane. The combined dichloromethane solutions were combined, dried (MgSO$_4$) and evaporated at 65 0∞C using a rotary evaporator to remove excess diisopropylethylamine, then kept at rt (0.5 mm Hg) for 1 h. The crude ether was used in the next step without purification.

The crude residue was stirred rapidly at rt for 24 h with a solution of 300 g KOH (85%) in 1.5 L of water. The aqueous suspension was extracted four times with diethyl ether, dried (MgSO$_4$) and concentrated under reduced pressure. The product was isolated by short path distillation as a water white liquid. Yield 190 g (66% from 4-hydroxypiperidine): bp 68°–70° C. at 0.7 mm Hg.

$^1$H NMR (CDCl$_3$, TMS) δ1.65 (m,2H), 1.95 (m,2H), 2.8 (m,2H), 3.15 (m,2H), 3.4 (s,3H), 4.7 (s,2H). Mass spectrum : (M+H)$^+$=146.

EXAMPLE 82(b)

1(S)-(4-(Methoxymethoxyl)piperidin-1-yl-carbonyl)-2-phenylethanol

A solution of 176 g (1.3 mol) of 1-hydroxybenzotriazole (Aldrich), 80 g (0.48 mol) of L-3-phenyllactic acid (prepared from L-phenylalanine) 76 g (0.52 mol) of 4-(methoxymethoxy)piperidine in 800 mL of DMF was cooled to −25 0° C. (internal temperature) while 132 g EDC HCl (Saber Labs) was added (mechanical stirring). After addition the reaction was stirred to rt over 24 h. Excess DMF was removed under high vacuum and the residue dissolved into 1.5 L of ethyl acetate. The ethyl acetate solution was washed with 4 L of saturated sodium bicarbonate. The ethyl acetate layer was separated, dried (MgSO$_4$) and evaporated to give approximately 138 g of crude amide. The product was isolated by silica gel chromatography using ethyl acetate/hexane as eluant. Yield 120 g (79%).

$^1$H NMR (CDCl$_3$, TMS) δ1.61 (m,2H), 1.81 (m,2H), 2.89 (m,2H), 3.38 (s,3H), 3.5 (m,2H), 3.79 (m,2H), 3.96 (m,1H), 4.62 (t,1H), 4.68 (s,2H).

EXAMPLE 83

2(S)-(1(S)-(4-(Methoxymethoxy)piperidin-1-yl-carbonyl)-2-phenylethoxy)hexanoic acid The resultant compound of Example 82(b) (1.45 g, 4.95 mmol), in 10 ml THF was added dropwise to the cooled suspension of sodium hydride (60% dispersion in oil, 0.5 g, 11.2 mmol) in 4 ml THF (0°–5° C.). The suspension was stirred for 20 mins at 0°–5° C. and then warmed up to room temperature and stirred for additional 1 h. Solution of D-2-bromohexanoic acid in 6 ml THF was added dropwise to the cooled suspension (0°–5° C.) at N$_2$ atmosphere. It was then allowed to warm up to room temperature and stirred overnight. Quenched with cold H$_2$O and extracted with ethylacetate to remove undesired starting material. It was acidified with 1M sodium hydrogen sulfate and extracted with chloroform. After filtration and evaporation, the crude product was purified on silica gel, eluted with CH$_2$Cl$_2$: CH$_3$OH: AcOH (19.4=0.3:0.3) to obtain 0.79 g of desired acid (43% yield).

$^1$H NMR (CDCl$_3$, TMS) δ0.88 (t,3H), 3.35 (s,3H), 3.98 (bt,1H), 4.6 (m,1H), 4.64 (s,2H), 7.38 (m,5H). Mass spectrum: (M+H)$^+$=408.

EXAMPLE 84 (Method A)

2(S)-(1(S)-(4-Morpholinylcarbonyl)-2-phenylethoxy)-hexanoic acid Amide of 2(S)-Amino-1-cyclohexyl-3(R),4(S)-dihydroxy-6-methylheptane The resultant compound of Example 77 (110 mg, 0.468 mmol), in 5 ml of dry THF, was added dropwise to sodium hydride (60% dispersion in oil, 39 mg, 0.93 mmol) in 6 ml of dry THF at 5° C. The mixture was stirred at 5° C. for half hour and at room temperature for another half hour. Then the mixture was cooled to 5° C and D-2-bromohexanoic acid (91 mg, 0.468 mmol) in 5 ml of dry THF was added dropwise. The mixture was stirred at 5° C for 5 h and at room temperature for 16 h. 3 ml of dry DMF was added and the mixture was stirred for another day. The mixture was evaporated to provide a solid which was partitioned between ethyl acetate and water. The aqueous portion was acidified with citric acid and extracted with ethyl acetate. The organic portion was dried and filtered, and the filtrate was evaporated to a solid which, without purification, was coupled to the aminoglycol of Example 41 according to the procedure of Example 51 (except that only one equivalent of HOBT was used). After isolation, the crude product was chromatographed eluting with ethyl acetate:hexane (5:2) to obtain the desired compound in 37% yield.

$^1$H NMR (CDCl$_3$, TMS) δ0.8 (d,3H), 0.95 (m,5H), 1.2–1.9 (m,22H), 3.0 (q,2H), 3.2 (m,4H), 3.55 (m,2H), 3.65 (m,2H), 3.8 (t,1H), 4.4 (q,1H), 7.3 (m,5H). R$_f$=0.30 (EtOAc 5:Hexane 2).

EXAMPLE 84 (Method B)

2(S)-(1(S)-(4-Morpholinylcarbonyl)-2-phenylethoxy)-hexanoic acid Amide of 2(S)-Amino-1-cyclohexyl-3(R),4(S)-dihydroxy-6-methylheptane and the 2(R) isomer The resultant compound of Example 77 (1.1 g, 4.68 mmol), in 10 ml of dry THF, was added dropwise into sodium hydride (60% dispersion in oil, 390 mg, 9.3 mmol) in 6 ml of dry THF at 5° C. The mixture was stirred at 5° C for a half hour and at room temperature for another half hour. Then the mixture was cooled to 5° C and D,L-2-bromohexanoic acid (910 mg, 4.68 mmol) in 10 ml of dry THF was added dropwise. The mixture was stirred at 5° C. for 5 h and at room temperature for 16 h. 3 ml of dry DMF was added and the mixture was stirred for another day. The mixture was evaporated to a solid which was partitioned between ethyl acetate and water. The aqueous portion was acidified with citric acid and extracted with ethyl acetate. The organic portion was dried and filtered, and the filtrate was evaporated to a solid which, without purification, was coupled to the aminoglycol of Example 41 according to the procedure of Example 51 (except that only one equivalent of HQBT was used). After isolation, the crude product was chromatographed eluting with ethyl acetate:hexane (5:2) to obtain two compounds: the less polar diastereomer (150 mg, 22.4% (2 steps)) and the more polar diastereomer (130 mg, 19.4% (2 steps)).

Less polar 1(S),2(R) isomer (a) $^1$H NMR (CDCl$_3$, TMS) δ0.85 (m,5H), 0.95 (d,3H), 1.2–1.9 (m,22H), 3.0 (q,3H), 3.2 (m,4H), 3.5 (m,2H), 3.65 (m,2H), 4.2 (m,1H), 4.45 (t,1H), 7.25 (m,5H). Mass spectrum: (M+H)$^+$=575.

More polar 1(S),2(S) isomer (b) $^1$H NMR (CDCl$_3$, TMS) δ0.8 (d,3H), 0.95 (m,5H), 1.2–1.9 (m,22H), 3.0 (1,2H), 3.2 (m,4H), 3.55 (m,2H), 3.65 (m,2H), 3.8 (t,1H), 4.4 (q,1H), 7.3 (m,5H). Mass spectrum: (M+H)$^+$=575. R$_f$=0.30 (EtOAc 5:Hexane 2).

EXAMPLE 85

2(S)-(1(S)-(4-Morpholinylcarbonyl)-2-phenylethoxy)octanoic acid Amide of 2(S)-Amino-1-cyclohexyl-3(R),4(S)-dihydroxy-6-methylheptane and the 2(R) isomer The resultant compound of Example 77 (0.2 g, 0.85 mmol), in 10 ml of dry THF, was added dropwise into sodium hydride (60% dispersion in oil, 0.04 g, 0.85 mmol) in 6 ml of dry THF at 5° C. The mixture was stirred at 5° C for a half hour and at room temperature for another half hour. Then the mixture was cooled to 5° C and D,L-2-bromooctanoic acid (0.19 g, 0.85 mmol) in 10 ml of dry THF was added dropwise. The mixture was stirred at 5° C for 5 h and at room temperature for 16 h. 3 ml of dry DMF was added and the mixture was stirred for another day. Without isolation, the resultant crude product in the mixture was coupled to the aminoglycol of Example 41 according to the procedure of Example 51 (except that only one equivalent of HOBT was used). After isolation, the crude product was chromatographed on silica gel eluting with ethyl acetate:-hexane (3:1) to obtain two separate diastereomers. Total yield of the two isomers=26.5% (two steps).

Less polar 1(S),2(R) isomer: $^1$H NMR (CDCl$_3$, TMS) δ0.9 (m,5H), 0.95 (d,3H), 1.2-1.9 (m,26H), 3.0 (q,2H), 3.2 (m,4H), 3.5 (m,2H), 3.7 (m,2H), 4.25 (bq,1H), 4.45 (t,1H), 7.3 (m,5H). Mass spectrum: (M+H)+ =603.

More polar 1(S),2(S) isomer: $^1$H NMR (CDCl$_3$, TMS) δ0.8 (d,3H), 0.9 (t,3H), 0.95 (d,3H), 1.1-1.9 (m,26H), 3.0 (q,2H), 3.1 (m,4H), 3.5 (m,2H), 3.6 (m,2H), 3.8 (t,1H), 3.9 (q,1H), 7.3 (m,5H). Mass spectrum: (M+H)+ =603.

Analogous to the preparation of Example 83 the following compounds were prepared.

EXAMPLE 86

2(S)-(1(S)-(4-Morpholinylcarbonyl)-2-phenylethoxy)-propionic acid Amide of
2(S)-Amino-1-cyclohexyl-3(R),4(S)-dihydroxy-6-methylheptane (30% yield)

$^1$H NMR (CDCl$_3$, TMS) δ0.89 (dd,6H), 1.43 (d,3H), 1.87 (m,1H), 3.04 (dd,2H), 3.1 (m,2H), 3.3 (bm,2H), 3.44 (m,1H), 3.61 (m,6H), 3.89 (q,1H), 4.14 (m,2H), 4.42 (dd,1H), 6.01 (bd,1H). Mass spectrum: (M+H)+ =533.

EXAMPLE 87

2(S)-(1(S)-(N-Azetidinylcarbonyl)-2-phenylethoxy)propionic acid Amide of
2(S)-Amino-1-cyclohexyl-3(R),4(S)-dihydroxy-6-methylheptane (26% yield)

$^1$H NMR (CDCl$_3$, TMS) δ0.9 (dd,6H), 1.43 (d,3H), 1.88 (m,1H), 2.2 (m,2H), 3.02 (m,2H), 3.78 (m,1H), 3.9 (q,1H), 4.07 (m,5H), 6.03 (bd,1H). Mass spectrum: (M+H)+ =503.

EXAMPLE 88

2(S)-(1(S)-(N-Pyrolidinylcarbonyl)-2-phenylethoxy)-propionic acid Amide of
2(S)-Amino-1-cyclohexyl-3(R),4(S)-dihydroxy-6-methylheptane (26% yield)

$^1$H NMR (CDCl$_3$, TMS) δ0.9 (dd,6H), 1.44 (d,3H), 3.02 (m,5H), 3.37 (m,1H), 3.51 (m,2H), 3.89 (q,1H), 4.24 (dd,1H), 6.01 (bd,1H). Mass spectrum: (M+H)+ =517.

EXAMPLE 89

2(S)-(1(S)-(N-Piperidinylcarbonyl)-2-phenylethoxy)-propionic acid Amide of
2(S)-Amino-1-cyclohexyl-3(R),4(S)-dihydroxy-6-methylheptane (39% yield)

$^1$H NMR (CDCl$_3$, TMS) δ0.89 (dd,6H), 1.43 (d,3H), 1.86 (m,1H), 3.0 (m,2H), 3.05 (m,2H), 3.38 (m,2H), 3.87 (q,1H), 4.43 (dd,1H), 5.94 (bd,1H). Mass spectrum: (M+H)+ =531.

EXAMPLE 90

2(S)-(1(S)-(4-(Methoxycarbonyl)piperidin-1-yl-carbonyl)-2-phenylethoxy)propionic acid Amide of
2(S)-Amino-1-cyclohexyl-3(R),4(S)-dihydroxy-6-methylheptane (16% yield)

$^1$H NMR (CDCl$_3$, TMS) δ0.89 (dd,6H), 1.42 (d,3H), 2.53 (m,1H), 3.7 (s,3H), 3.86 (q,1H), 4.42 (m,1H). Mass spectrum: (M+H)+ =589.

EXAMPLE 91

2(S)-(1(S)-(4-Morpholinylcarbonyl)-2-phenylethoxy)-propionic acid Amide of
2(S)-Amino-1-cyclohexyl-3(S)-hydroxy-5(S)-n-butyl-carbamoyl-6-methylheptane The title compound was prepared using the method of Example 84(method A) but replacing the D-2-bromohexanoic acid and amino glycol of Example 41 with the D-2-bromopropionic acid and the appropriate amino derivative (Buhlmayer, et al., U.S. Pat. No. 4,727,060, issued Feb. 23, 1988).

$^1$H NMR (CDCl$_3$, TMS) δ0.9 (m,9H), 1.43 (d,3H), 0.7-1.9 (several bm,20H), 2.01 (m,1H), 2.9-3.25 (several m,4H), 3.35 (q,2H), 3.45 (bm,3H), 3.55-3.62 (bm,5H), 3.79 (q,1H), 4.49 (dd,1H), 5.72 (bt,1H), 5.82 (bd,1H), 7.33 (bm,5H); $^{13}$C NMR (CDCl$_3$, TMS) 13.78, 19.84, 20.13, 21.24, 26.11, 26.43, 30.22, 31.71, 32.21, 33.82, 34.16, 34.34, 37.15, 39.11, 39.25, 42.55, 45.79, 51.16, 52.30, 66.55, 66.89, 71.11, 76.09, 76.83, 77.22, 77.88, 127.47, 128.92, 129.81, 136.59, 169.36, 173.82, 175.36. Analysis Calcd. for C$_{35}$H$_{57}$N$_3$O$_6$.0.5 H$_2$O: C, 67.28; H, 9.36; N, 6.73. Found C, 67.44; H, 9.28; N, 6.91.

EXAMPLE 92

2(S)-((Ethoxycarbonyl)methylthio)propionic acid Amide of
2(S)-Amino-1-cyclohexyl-3(R)-4(S)-dihydroxy-6-methylheptane The title compound was prepared using the method of Example 86, but replacing the resultant compound of Example 77 with commercially available ethylthioacetate.

$^1$H NMR (CDCl$_3$, TMS) δ0.9 (dd,6H), 1.28 (t,3H), 1.49 (d,3H), 1.92 (m,1H), 3.35 (dd,2H), 3.59 (q,1H), 4.2 (m,2H), 4.34 (m,1H), 6.84 (bd,1H). Mass spectrum: (M+H)+ =418.

EXAMPLE 93

2(S)-(1(S)-(4-(Methoxymethoxy)piperidin-1-yl-carbonyl)-2-phenylethoxy)hexanoic acid Amide of
2(S)-Amino-1-cyclohexyl-3(R),4(S)-dihydroxy-6-methylheptane (41% yield)

The resultant compound of Example 83 was coupled to the aminoglycol of Example 41 according to the procedure of Example 51 to obtain the desired compound in 41% yield.

$^1$H NMR (CDCl$_3$, TMS) δ0.89 (dd,6H), 0.9 (t,3H), 2.98 (m,2H), 3.08 (m,2H), 3.35 (s,3H), 4.44 (m,1H), 4.66 (s,2H), 5.98 (dd,1H). Mass spectrum: (M+H)+ =633.

Similarly, the following compound was prepared.

EXAMPLE 94

2(S)-(1(S)-(4-(Methoxymethoxy)piperidinyl-1-yl-carbonyl)-2-phenylethoxy)propionic acid Amide of 2(S)-Amino-1-cyclohexyl-3(R),4(S)-dihydroxy-6-methylheptane (16%) yield)

$^1$H NMR (CDCl$_3$, TMS) δ0.9 (dd,6H), 1.44 (d,3H), 3.04 (m,4H), 3.37 (s,3H) 3.88 (m,1H), 4.43 (m,1H), 4.6 (s,2H), 6.0 (dd,1H). Mass spectrum: (M+H)$^+$ = 591.

EXAMPLE 95

2(R)-Methyl-4(R)-(4-(methoxymethoxy)piperidin-1-yl(carbonyl)-6-phenylhexanoic acid Amide of 2(S)-Amino-1-cyclohexyl-3(R),4(S)-dihydroxy-6-methylheptane The title compound can be prepared according to the procedure of Scheme VII in which R$_5$ is 4-(methoxymethoxy)piperidin-1-yl R$_1$ is benzyl, R$_3$ is methyl, and (VI) is the aminoglycol of Example 41. As illustrated in Scheme VII), compound (XXX) (J. Med. Chem. 1983, 26, 1277) is coupled to the aminoglycol of Example 41 according to the procedure of Example 51 to afford the amide (XXXI) which is hydrolyzed to the acid (XXXII) with LiOH/H$_2$O/dioxane. The resulting acid is then coupled to 4-(methyoxymethoxy)piperidine (HOBT, EDAC) to obtain the desired compound (XXXIII).

EXAMPLE 96

2(S)-(1(S)-(4-(Methoxymethoxy)piperidin-1-yl-carbonyl)-2-phenylethoxy)hexanoic acid Amide of 2(S)-Amino-1-cyclohexyl-3(S)-hydroxy-5(S)-n-butyl-carbamoyl-6-methylheptane Using the procedure of Example 93, but replacing the resultant glycol of Example 41 with 2(S)-amino-1-cyclohexyl-3(S)-hydroxy-5(S)-n-butylcarbamoyl-6-methylheptane (see Example 93) gave the desired product.

$^1$H NMR (CDCl$_3$, TMS) δ2.04 (m,1H), 2.97 (m,1H), 3.17(m,2H), 3.38 (s,3H), 3.4 (m,4H), 3.84 (m,4H), 4.47 (m,1H), 4.68 (s,1H), 5.7 (bm,1H), 5.8 (bd,1H). Mass spectrum: (M+H)$^+$ = 716.

EXAMPLE 97

2(R)-Methyl-3(R)-hydroxy-4(R)-(4-(methoxymethoxy)-piperidin-1-yl-carbonyl)pentanoic acid Amide of 2(S)-Amino-1-cyclohexyl-3(R),4(S)-dihydroxy-6-methylheptane The title compound can be prepared according to the process of Scheme VIII in which R$_5$ is 4-(methoxymethoxy)piperidin-1-yl, R$_1$ and R$_3$ are methyl and (VI) is the aminoglycol of Example 41. The dibutylboryl enolate (XXXV) (Evans, D. A., Bartroli, J., Shih, T., J. Am. Chem. Soc. 1981, 103, 2127–2129) undergoes condensation with the aldehyde (XXXIV) (Evans D. A., McGee, L. R., J. Am. Chem. Soc. 1981, 103, 2876. Also Tetrahedron Lett. 1980, 21, 3975) under standard conditions (see references above) to provide a diastereomeric adduct. The secondary alcohol is converted to the silyl ether (Me$_3$SiNEt$_2$, DMAP, CH$_2$Cl$_2$) followed by debenzylation with palladium/carbon in an nitrogen atmosphere and Jones' oxidation to provide an acid (XXXVII). The resulting acid is then coupled to 4-(methoxymethoxy)piperidine and the chiral auxiliary is removed by hydrolysis (LiOH/H$_2$O). The resulting acid is then coupled to the aminoglycol (VI) of Example 41 according to the procedure of Example 51 to provide a product which is deprotected (oxalic acid, NaOH, r.t.) to afford the desired compound.

EXAMPLE 98

3-(t-Butyloxycarbonyl)-4-(cyclohexylmethyl)-2,2-dimethyl-5-vinyloxazolidine.

The procedure of S. Thaisrivong (J. Med. Chem. 1987, 30, 976) was employed. A solution of 40 g of the resultant compound of Example 17 and 102 g of 2-methoxypropene in 250 ml of dichloromethane was stirred at room temperature. Solid pyridinium p-toluenesulfonate (PPTS) (177 g) was added slowly to the reaction mixture. After addition was complete, the reaction was stirred for 1 h and neutralized by addition of solid sodium bicarbonate. The solids were filtered and the filtrate was concentrated. Flash chromatography on silica gel gave 57 g of the desired compound. IR (CDCl$_3$) 1690 (C=O carbamate) cm$^{-1}$; $^1$H NMR (CDCl$_3$) δ5.95 (m,1H), 5.32 (m,1H), 5.20 (dt,1H), 4.27 (dd,1H), 1.47 (s,9H).

Anal. Calcd. for C$_{19}$H$_{33}$NO$_3$: C, 70.55; H, 10.28; N, 4.33. Found: C, 70.47; H, 10.27; N, 4.09.

EXAMPLE 99

3-(t-Butyloxycarbonyl)-4-(cyclohexylmethyl)-2,2-dimethyloxazolidine-5-carboxaldehyde A solution of 10 g of the resultant compound of Example 98 in 150 ml of 2:1 dichloromethane: methanol was cooled in an dry-ice acetone bath. Ozone was bubbled through the solution until a blue color persisted (1 h). Dry nitrogen was then bubbled through the reaction mixture to remove excess dissolved ozone. The reaction mixture was cannulated into a suspension of 8 g zinc dust, 8 ml glacial acetic acid, 200 ml water, and 200 ml of methanol cooled to −45° C. After 5 min the bath was removed and the mixture allowed to warm to room temperature overnight. 100 ml of saturated sodium chloride was added and the entire reaction mixture extracted with two 300 ml portions of dichloromethane. The combined dichloromethane extracts were decanted, dried (MgSO$_4$), filtered, and evaporated. The crude aldehyde was purified by flash chromatography (1:4) ethyl acetate:hexane to give 9.7 g of the desired compound as a mixture of diastereomers (3:1 trans:cis) as judged by the integrated resonances of the two aldehyde protons. IR (CDCl$_3$) 1735 (C=O aldehyde), 1690 (C=O carbamate) cm$^{-1}$; $^1$H NMR (CDCl$_3$) δ9.83 (s,1H,CHO), 9.73 (d,1H,CHO cis diastereomer), 4.14 (m,1H), 1.46 (s,9H).

Anal. Calcd. for C$_{18}$H$_{31}$NO$_4$: C, 66.43; H, 9.60; N, 4.30. Found: C, 65.27; H, 9.79; N, 4.20.

Equilibration of Aldehyde Isomers

A suspension of 25 g of the above aldehyde in 300 ml of methanol and powdered potassium carbonate (10.7 g) was stirred at room temperature for 6 h. The reaction mixture was cooled in an ice-water bath and treated with 9.3 g of glacial acetic acid for 5 min. A solution of 0.5M sodium dihydrogen phosphate (300 ml) was added to the mixture. After 30 min, the solution was concentrated to one-half the volume under reduced pressure and extracted with ether (600 ml). The combined ether extracts were dried (MgSO$_4$), filtered, and concentrated. The aldehyde was purified by flash chromatography using (1:4) ethyl acetate:hexane to give 19.5 g of the desired compound as an 8:1 mixture of trans:cis diastereomers.

EXAMPLE 100

(5S,4'S,5'R)-5-(3-(t-Butyloxycarbonyl)-4-(cyclohexylmethyl)-2,2-dimethyloxazolidin-5-yl)-3-methylenedihydrofuran-2(4H)-one A solution of 16.52 g (51 mmol) of the resultant compound of Example 99 in 15 ml of anhydrous tetrahydrofuran was treated with 3.98 g (61 mmol) of freshly activated zinc dust. With vigorous stirring, the mixture was treated with 10 g (56 mmol) of methyl 2-(bromomethyl)acrylate at a rate which maintained the temperature at 50°–60° C. Upon completion of the addition, the mixture was stirred at 50° C for 1 h. After being allowed to cool, the mixture was poured into 100 ml of cold 1M HCl and extracted with dichloromethane (3×100 ml). The combined organic layers were washed successively with saturated aqueous NaHCO$_3$ and H$_2$O, dried over Na$_2$SO$_4$, and concentrated. Silica gel chromatography using 9:1 hexane:ethyl acetate provided 10.83 g (61%) of the desired compound.

$^1$H NMR (CDCl$_3$) δ0.8–2.0 (br envelope), 1.49 (s,9H), 1.54 (s,3H), 1.57 (s,3H), 2.93 (ddt,J=18,6,3Hz,1H), 3.05 (m,1H), 3.70 (m,1H), 4.07 (m,1H), 4.47 (ddd,J=13,9,6Hz,1H), 5.70 (br t,J=3Hz,1H), 6.28 (t,J=3Hz,1H). Mass spectrum: (M+H)$^+$=394.

Anal. Calcd. for C$_{22}$H$_{35}$NO$_5$: C, 67.15; H, 8.96; N, 3.56. Found: C, 67.66; H, 9.11; N, 3.60.

EXAMPLE 101

(3S,5S,4'S,5'R)-5-(3-(t-Butyloxycarbonyl)-4-(cyclohexylmethyl)-2,2-dimethyloxazolidin-5-yl)-3-methyldihydrofuran-2(3H)-one A mixture of 8.03 g (20 mmol) of the resultant compound of Example 100 and 0.81 g of 10% palladium on carbon in 200 ml of ethyl acetate was shaken under 4 atmospheres of H$_2$. After filtration, concentration of the filtrate gave 7.58 g (94%) of the desired compound.

$^1$H NMR (CDCl$_3$) δ0.8–2.0 (br envelope), 1.31 (s,3H), 1.48 (s,9H), 1.54 (s,3H), 1.58 (s,3H), 2.57 (m,1H), 2.68 (m,1H), 3.74 (m,1H), 4.04 (m,1H), 4.31 (ddd,J=13,9,6Hz,1H). Mass spectrum: (M+H)$^+$=396.

EXAMPLE 102

3-(t-Butylcarbonyl-4-(cyclohexylmethyl)-5-(1,4-dihydroxy-3-methylbutyl)-2,2-dimethyloxazolidine A mixture of 0.50 g (1.26 mmol) of the resultant compound of Example 101 and 0.15 g (4 mmol) of sodium borohydride in 50 ml of tetrahydrofuran was heated at reflux under N$_2$ atmosphere for 48 h. After being allowed to cool, the mixture was treated cautiously with aqueous NH$_4$Cl, extracted with ether, washed with saturated brine, dried over MgSO$_4$, and concentrated in vacuo. Silica gel chromatography using 2:1 chloroform/ethyl acetate gave 0.37 g (73%) of the desired compound.

$^1$H NMR (CDCl$_3$) δ0.7–2.0 (br envelope), 0.94 (d,J=7Hz,3H), 1.49 (s,9H), 1.52 (s,3H), 1.55 (s,3H), 3.43 (dd,J=11,8Hz,1H), 3.55–3.7 (m,3H), 4.09 (br d,1H). Mass spectrum: (M+H)$^+$=400.

EXAMPLE 103

3-(t-Butyloxycarbonyl)-4-(cyclohexylmethyl)-2,2-dimethyl-5-(4-methylhydrofuran-2-yl)oxazolidine A solution of 51 mg (0.13 mmol) of the resultant compound of Example 102 and 0.037 ml (0.27 mmol) of triethylamine in 2 ml of dichloromethane was cooled to 0° C under N$_2$ atmosphere and treated with 0.012 mol (0.15 mmol) of methanesulfonyl chloride. After 1 h, the solution was diluted with dichloromethane, washed successively with 10% citric acid, water and saturated aqueous NaHCO$_3$, dried over Na$_2$SO$_4$, and concentrated in vacuo. The crude mesylate thus produced (59 mg) was taken up in 8 ml of dry detrahydrofuran, treated with 20 mg (0.50 mmol) of sodium hydride (60% dispersion in oil), and heated at reflux for 2 h. After being allowed to cool, the solution was treated cautiously with saturated aqueous NH$_4$Cl, extracted with ether, dried over MgSO$_4$ and concentrated. Silica gel chromatography using 9:1 hexane/ethyl acetate gave 30 mg (75%) of the desired compound.

$^1$H NMR (CDCl$_3$) δ0.7–2.4 (br envelope), 1.06 (d,J=7Hz,3H),1.48 (s,9H),1.52 (s,3H), 1.56 (s,3H),3.30 (t,J=9Hz,1H), 3.66 (m,1H), 3.9–4.0 (m,3H). Mass spectrum: (M+H)$^+$=382.

EXAMPLE 104

2(S)-(1(S)-(4-(Methoxymethoxy)piperidin-1-yl-carbonyl)-2-phenylethoxy)hexanoic acid Amide of 2(S)-(2(S)-Amino-3-cyclohexyl-1(R)-hydroxy)propyl-4(S)-methyltetrahydrofuran Using the procedure of Example 93, but replacing the resultant glycol of Example 41 with 2(S)-(2(S)-amino-3-cyclohexyl-1(R)-hydroxy)propyl-4(S)-methyltetrahydrofuran (obtained from deprotection of the resultant compound of Example 103 according to the procedure of Example 41) gave the desired compound in 30% yield.

$^1$H NMR (CDCl$_3$, TMS) δ0.9 (t,3H), 1.02 (d,3H), 1.99 (m,1H), 2.3 (m,1H), 3.31 (t,1H), 3.37 (s,3H), 3.9 (t,2H), 4.5 (m,1H), 4.67 (S,2H). Mass spectrum: (M+H)$^+$=631.

EXAMPLE 105

N-(1(S)-(4-Methoxymethoxy)piperidin-1-yl-carbonyl)-2-phenylethyl-L-norleucyl Amide of 2(S)-Amino-1-cyclohexyl-3(R),4(S)-dihydroxy-6-methylheptane Using the procedure of Example 64, but replacing the morpholine with 4-(methoxymethoxy) piperidine gave the desired intermediate. The resultant benzyl ester was hydrogenated using the procedure of Example 16 and followed by coupling to the resultant product of Example 41 according to the procedure of Example 51 to give the desired compound in 69% yield.

$^1$H NMR (CDCl$_3$, TMS) δ0.9 (dd,6H), 0.9, (t,3H), 2.81 (m,2H), 3.1(m,2H), 3.35 (s,3H), 3.67 (b,1H), 4.63 (s,2H). (M+H)$^+$=632.

EXAMPLE 106

N-(1(S)-4-(Methoxymethoxy)piperidin-1-yl-carbonyl)-2-phenylethyl)-L-norleucyl Amide of 2(S)-amino-1-cyclohexyl-3(S)-hydroxy-5(S)-n-butylcarbamoyl-6-methylheptane The title compound can be obtained according to the procedure of Example 105, but replacing the resultant product of Example 41 with 2(S)-amino-1-cyclohexyl-3(S)-hydroxy-5(S)-n-butylcarbamoyl-6-methylheptane.

EXAMPLE 107

N-(1(S)-(4-(Methoxymethoxy)piperidin-1-yl-carbonyl)-2-phenylethyl)-L-norleucyl Amide of 2(S)-(2(S)-Amino-3-cyclohexyl-1(R)-hydroxy)propyl-4(S)-methyltetrahydrofuran The title compound can be obtained according to the procedure of Example 105, but replacing the resultant product of Example 41 with 2(S)-(2(S)-amino-3-cyclohexyl-1(R)-hydroxy)propyl-4(S)-methyltetrahydrofuran (see Example 104).

EXAMPLE 108

2(S)-(1(S)-(4-(Methoxymethoxy)piperidin-1-yl-carbonyl)-2-phenylethoxy)hexanoic acid Amide of (2's,1'R,5S)-3-Ethyl-5-(1'-hydroxy-2'-amino-3'-cyclohexylpropyl)oxazolidin-2-one Using the procedure of Example 93, but replacing the resultant glycol of Example 41 with the resultant compound of Example 50 gave the desired product.

$^1$H NMR (CDCl$_3$, TMS) δ0.9 (t,3H) 1.18 (t,3H), 1.3–1.7 (m,22H), 3.4 (s,3H), 4.7 (s,3H), 7.4 (m,5H). Mass spectrum: $(M+H)^+ = 660$.

EXAMPLE 109

3-(3(R)-(3-(tert-Butyloxycarbonyl)-2,2-dimethyl-4(S)-cyclohexylmethyl-5(R)-oxazolidinyl)-3-hydroxy-2(R)-isopropyl-1-oxopropyl)-4(R)-methyl-5(S)-phenyl-2-oxazolidinone The title compound was prepared in analogy to the procedure of S. Thaisrivongs, D. T. Pals, L. T. Kroll, S. R. Turner and F. S. Han, J. Med. Chem. 1987, 30, 976–82, from the resultant compound of Example 99, in 63% yield. M. p. 97° C. $^1$H NMR (CDCl$_3$) δ0.91 (d, 3H), 1.06 (d, 3H), 1.1 (d, 3H), 1.48 (s, 9H), 0.9–1.9 (several bm, 12 H total), 2.12 (bd, 1H), 2.3 (m, 1H), 3.81 (dd, 1H), 3.94 (td, 1H), 4.04 (bm, 1H), 4.22 (dd, 1H), 4.84 (dq, 1H), 5.61 (d, 1H), 7.31–7.45 (m, 5H). High resolution mass spectrum. Calcd. for $(M+H)^+$ of $C_{33}H_{51}N_2O_7$: 587.3698. Found: 587.3696.

Analysis. Calcd. for $C_{33}H_{50}N_2O_7$: C, 67.55; H, 8.59; N, 4.77. Found: C, 67.41; H, 8.61; N, 4.77.

EXAMPLE 110

3-(3(R)-(3-(tert-Butyloxycarbonyl)-2,2-dimethyl-4(S)-cyclohexylmethyl-5(R)-oxazolidinyl)-3-((1-imidazolyl)thionyloxy)-2(R)-isopropyl-1-oxopropyl)-4(R)-methyl-5(S)-phenyl-2-oxazolidinone The resultant compound of Example 109 (1.840 g, 3.136 mmol) and 1,1'-thiocarbonyldiimidazolide (1.128 g, 6.330 mmol) were refluxed in 8 mL dry 1,2-dichloroethane under a nitrogen atmosphere for 24 h. The mixture was concentrated and the residue purified by flash chromatography (2.5% MeOH-CH$_2$Cl$_2$) to afford 1.896 g (87%) of the title compound. $^1$H NMR (CDCl$_3$) δ0.93 (d, 3H), 1.04 (d, 3H), 1.08 (d, 3H), 1.5 (bs, 9H), 0.9–1.9 (several bm, 13H total), 2.05 (m, 1H), 4.13 (bm, 1H), 4.23 (dd, 1H), 4.81 (dd, 1H), 4.94 (dq, 1H), 5.70 (d, 1H), 6.33 (dd, 1H), 7.06 (bs, 1H), 7.3–7.5 (m, 5H), 7.61 (bs, 1H), 8.40 (bs, 1H). High resolution mass spectrum. Calcd. for $(M+H)^+$ of $C_{37}H_{53}N_4O_7S$: 697.3635. Found: 697.3629.

Analysis. Calcd. for $C_{37}H_{52}N_4O_7S$: C, 63.77; H, 7.52; N, 8.04. Found: C, 63.58; H, 7.44; N, 7.94.

EXAMPLE 111

3-(3-(3-tert-Butyloxycarbonyl)-2,2-dimethyl-4(S)-cyclohexylmethyl-5(S)-oxazolidinyl)-2(R)-isopropyl-1-oxopropyl)-4(R)-methyl-5(S)-phenyl-2-oxazolidinone A solution of the resultant product from Example 110 (6.50 g, 9.33 mmol) in 275 ml of dry toluene was degassed with argon for 30 min, then warmed to reflux (under argon). A solution of tri-n-butyltin hydride (5.43 g, 18.6 mmol) in 75 ml of dry, degassed toluene was added dropwise over 15 min. After an additional 2 h of reflux, the reaction was cooled, concentrated and purified by flash chromatography (5% EtOAc-hexanes) to afford 4.82 g (90%) of the title compound as a white foam. $^1$H NMR (CDCl$_3$) δ0.90 (d, 3H), 0.92 (d, 3H), 0.9–1.1 (bm, 3H), 1.06 (d, 3H), 1.15–1.35 (bm, 3H), 1.51 (s, 9H), 1.57–2.14 (several bm, 16H total), 3.84 (m, 1H), 3.97 (m, 1H), 4.85 (dq, 1H), 5.68 (d, 1H), 7.3–7.46 (m, 5H). Mass spectrum: $(M+H)^+ = 571$.

Analysis. Calcd. for $C_{33}H_{50}N_2O_6$: C, 69.44; H, 8.83; N, 4.91. Found: C, 69.31; H, 8.82; N, 4.89.

EXAMPLE 112

2(S)-((3-(tert-Butyloxycarbonyl-2,2-dimethyl-4(S)-cyclohexylmethyl-5(S)-oxazolidinyl)methyl)-3-methylbutanoic acid Using the procedure of D. A. Evans, T. C. Britton and J. A. Ellman, Tetrahedron Lett. 1987, 28(49), 6141–44, the resultant product from Example 111 (6.10 g, 10.7 mmol) was hydrolyzed with aq. LiOH and hydrogen peroxide in THF. The crude material was purified by flash chromatography (15% EtOAc-0.5% HOAc-hexanes) to provide 3.53 g (90%) of the title compound as a viscous colorless oil. 1H NMR (CDCl$_3$) δ0.96 (d, 3H, ), 1.00 (d, 3H), 1.1–1.3 (bm, 5H), 1.48 (s, 9H), 1.5–1.9 (several bm, 15H total), 2.0 (m, 1H), 2.66 (m, 1H), 3.7 (bm, 1H), 3.90 (m, 1H). Mass spectrum: $(M+H)^+ = 412$.

Analysis. Calcd. for $C_{23}H_{41}NO_5 \cdot 0.25\ H_2O$: C, 66.39; H, 10.05; N, 3.37. Found: C, 66.46; H, 9.84; N, 3.36.

EXAMPLE 113

3-(1-Imidazolyl)propyl 2(S)-((3-tert-butyloxycarbonyl)-2,2-dimethyl-4(S)-cyclohexylmethyl-5(S)-oxazolidinyl)methyl)-3-methylbutanamide The procedure of P. Buhlmayer, et. al., J. Med. Chem. 1988, 31 (9), 1839–46 is adapted. The resultant compound from Example 112 (75 mg, 0.182 mmol), HOBt (42.0 mg, 0.274 mmol) and N-methylmorpholine (55 mg, 0.55 mmol) were dissolved in 1.0 ml dry DMF, and the solution was cooled to −20° C. (under nitrogen). EDAC (53 mg, 0.28 mmol) was added as a solid, and the resulting mixture was stirred at −20° to 0° C. for 1 h. The mixture was sealed, and allowed to react at 0° C. (in refrigerator) for 48 h. To the resulting solution was added 1-(3-aminopropyl)imidazole (28 mg, 0.23 mmol). The resulting solution was stirred at 0° C. for 4 h, and for a further 20 h, allowing it to warm slowly to room temperature. The volatiles were removed by high vacuum distillation, and the residue was partitioned between CH$_2$Cl$_2$ and aq. NaHCO$_3$. The aqueous phase was extracted 3× with CH$_2$Cl$_2$, and the combined organic phases were washed with brine, dried (Na$_2$SO$_4$) and concentrated to a viscous oil. Purification by flash chromatography (4% MeOH-CH$_2$Cl$_2$) provided 90.2 mg (95%) of a colorless glass. $^1$H NMR (CDCl$_3$) δ0.93 (d, 3H), 0.95 (d, 3H), 1.48 (s, 9H), 1.58 (s, 6H), 0.8–1.9 (several bm, 16H total), 2.05 (m, 2H), 3.28 (ddd, 2H), 3.64 (bm, 1H), 3.72 (m, 1H), 4.01 (t, 1H), 5.70 (bt, 1H), 6.96 (t, 1H), 7.08 (s, 1H), 7.58 (s, 1H). High resolution mass spectrum. Calcd. for (M+H)$^+$ of C$_{29}$H$_{51}$N$_4$O$_4$: 519.3910. Found: 519.3915.

EXAMPLE 114

3-(Dimethylamino)propyl 2(S)-((3-tert-butyloxycarbonyl)-2,2-dimethyl-4(S)-cyclohexylmethyl-5(S)-oxazolidinyl)methyl-3-methylbutanamide The procedure of Example 113 is followed, substituting 3-dimethylaminopropyl amine for 1-(3-aminopropyl)imidazole, which provided the title compound in 97% yield. $^1$H NMR (CDCl$_3$) δ0.93 (d, 3H), 0.935 (d, 3H), 1.48 (s, 12H), 1.58 (bs, 3H), 0.8–1.8 (several bm, 18H total), 2.05 (m, 1H), 2.37 (bs, 6H), 2.53 (bm, 2H), 3.37 (2×dd, 2H), 3.63 (bm, 1H), 3.75 (m, 1H), 6.60 (bm, 1H). Mass spectrum: (M+H)$^+$=496.

Analysis. Calcd. for C$_{28}$H$_{53}$N$_3$O$_4$·H$_2$O: C, 65.46; H, 10.79; N, 8.18. Found: C, 65.6; H, 10.18; N, 8.23.

EXAMPLE 115

3-(4-Morpholinyl)propyl 2(S)-((3-(tert-butyloxycarbonyl)-2,2-dimethyl-4(S)-cyclohexylmethyl-5(S)-oxazolidinyl)methyl)-3-methylbutanamide Using the procedure of Example 113, substituting 4-(3-aminopropyl)morpholine for 1-(3-aminopropyl)imidazole, the title compound was obtained in 96% yield. $^1$H NMR (CDCl$_3$) δ0.92 (d, 3H), 0.95 (d, 3H), 1.46 (s) and 1.48 (s, 12H total), 1.57 (bs, 3H), 0.8–1.8 (several bm, 18H total), 2.01 (m, 1H), 2.46 (bm, 6H), 3.37 (m, 2H), 3.64 (bm, 1H), 3.75 (bm, 5H), 6.80 (bt, 1H). High resolution mass spectrum. Calcd. for (M+H)$^+$ of C$_{30}$H$_{56}$N$_3$O$_5$: 538.4220. Found: 538.4220.

EXAMPLE 116

2(S)-(1(S)-(4-(Methoxymethoxy)piperidin-1-yl)carbonyl-2-phenyl)ethoxyhexanoic acid amide of 3-(1-imidazolyl)propyl 5(S)-amino-6-cyclohexyl-4(S)-hydroxy-2(S)-isopropylhexanamide The resultant compound from Example 113 (83.5 mg, 0.161 mmol) was deprotected by dissolving in 1.0 ml dry CH$_2$Cl$_2$, cooling the solution to −10° C. (under nitrogen), and treating with 1.0 ml of trifluoroacetic acid. The resulting solution was stirred at −10° to 0° C. for 4 h. The solvents were largely removed with a stream of nitrogen, and the residue (as a concentrated solution in trifluoroacetic acid) was dissolved in 1.0 ml THF and 0.3 ml water at 0 ° C. The solution was allowed to warm slowly to ambient temperature over 18 h. The crude aminoalcohol was isolated by basifying the reaction with an excess of 1.0M aq. Na$_2$CO$_3$, saturating the solution with NaCl, and extracting with 5×10 ml of 5% EtOH-CHCl$_3$. The combined organic phases were washed with brine, dried (Na$_2$SO$_4$), concentrated, and the residue placed under high vacuum overnight to yield 66.2 mg (>100%) of yellow viscous oil.

Coupling was acheived by combining the resultant compound from Example 83 (72 mg, 0.177 mmol), the above aminoalcohol (63.8 mg, 0.168 mmol), HOBt (34 mg, 0.22 mmol) and N-methylmorpholine (25 mg, 0.25 mmol) in 1.0 ml dry DMF. The resulting solution was cooled to −20° C. (under argon), and EDAC (45 mg, 0.23 mmol) was added. The reaction was allowed to slowly warm to room temperature as the ice bath melted, for a total of 24 h. The solvent was removed by high vacuum distillation, and the residue was partitioned between 15 ml CH$_2$Cl$_2$, 9 ml sat. aq. NaHCO$_3$ and 1 ml H$_2$O. The aqueous phase was further extracted (3×10 ml CH$_2$Cl$_2$), and the combined organic phases were washed with 10 ml brine, dried (Na$_2$SO$_4$) and concentrated. Purification by flash chromatography (6% MeOH-0.5% conc. aq. NH$_4$OH-CH$_2$Cl$_2$) yielded 92.3 mg (72%) of the title compound as a hygroscopic glassy solid, m.p. 49°–56° C. $^1$H NMR (CDCl$_3$) δ0.9 (m, 9H), 1.97 (m, 3H), 0.65–1.9 (several bm, approx. 26H total), 2.88–3.07 (m, 2H), 3.13 (bm, 1H), 3.25 (m, 2H), 3.37 (s, 3H), 3.2–3.5 (bm, 3H), 3.6–3.9 (bm, 4H), 4.0 (bm, 3H), 4.50 (m, 1H), 4.68 (s, 2H), 5.70 (m, 1H), 5.78 (d) and 5.85 (d, 1H total), 6.96 (s, 1H), 7.08 (s, 1H), 7.3 (m, 5H), 7.58 (m, 1H). Mass spectrum: (M+H)$^+$=768.

Analysis. Calcd. for C$_{43}$H$_{69}$N$_5$O$_7$·1.25 H$_2$O: C, 65.33; H, 8.86; N, 8.86. Found: C, 65.28; H, 8.78; N, 8.91.

EXAMPLE 117

2(S)-(1(S)-(4-(Methoxymethoxy)piperidin-1-yl)carbonyl-2-phenyl)ethoxyhexanoic acid amide of 3-(dimethylamino)propyl 5(S)-amino-6-cyclohexyl-4(S)-hydroxy-2(S)-isopropylhexanamide The procedure of Example 116 was used, with the substitution of the resultant compound from Example 114 for the resultant compound from Example 113, to provide the title compound in 77% yield as a white foamy solid, m. p. 49°–54° C. $^1$H NMR (CDCl$_3$) δ0.90 (m), 0.92 (d) and 0.94 (d, 9H total), 0.65–1.95 (several bm, approx. 28H total), 2.02 (m, 1H), 2.26 (bs, 6H), 2.42 (m, 2H), 2.96 (m, 1H), 3.05 (dd, 1H), 3.1–3.48 (several bm) and 3.36 (s, 8H total), 3.54 (bm, 1H), 3.60–4.0 (several bm, 5H total), 4.52 (dd, 1H), 4.67 (s, 2H), 5.83 (d) and 5.90 (d, 1H total), 6.93 (bm, 1H), 7.30 (bm, 5H). High resolution mass spectrum. Calcd. for C$_{42}$H$_{73}$N$_4$O$_7$: 745.5479. Found: 745.5471.

EXAMPLE 118

2(S)-(1(S)-(4-(Methoxymethoxy)piperidin-1-yl)carbonyl-2-phenyl)ethoxyhexanoic acid amide of 3-(4-morpholinyl)propyl 5(S)-amino-6-cyclohexyl-4(S)-hydroxy-2(S)-isopropylhexanamide The procedure of Example 116 was used, substituting the resultant product from Example 115 for the resultant compound from Example 113, to provide the title compound in 68% yield as a hygroscopic glassy solid, m.p. 49°–51° C. $^1$H NMR (CDCl$_3$) δ0.90 (m), 0.91 (d) and 0.92 (d, 9H total), 0.65–1.90 (several bm, approx. 28H total), 2.02 (m, 1H), 2.45 (bm, 6H), 2.95 (m, 1H), 3.05 (dd, 1H), 3.20 (bm, 2H), 3.36 (s, 3H), 3.45 (m, 2H), 3.6–4.0 (several bm) and 3.71 (m, 10H total), 4.48 (dd, 1H), 4.68 (s, 2H), 5.80 (d) and 5.88 (d, 1H total), 6.87 (bt, 1H), 7.3 (bm, 5H). Mass spectrum: (M+H)$^+$=787.

EXAMPLE 119

N-(1(S)-(4-(Methoxymethoxy)piperidin-1-yl)carbonyl-2-phenyl)ethyl-L-norleucyl amide of 3-(1-imidazolylpropyl 5(S)-amino-6-cyclohexyl-4(S)-hydroxy-2(S)-isopropylhexanamide The procedure of Example 116 was followed, with the substitution of the intermediate amino acid from Example 105 for the resultant compound from Example 83, providing the title compound in 89% yield as a hygroscopic foamy solid, m.p. 66°–71° C. $^1$H NMR (CDCl$_3$) δ0.90 (d) and 0.91 (d) and 0.93 (d, 9H total), 0.65–1.90 (several bm, approx. 26H total), 2.0 (bm, 3H), 2.22 (m, 1H), 2.29 (bm, 2H), 2.35 (bm, 1H), 3.25 (m, 2H), 3.36 (s, 3H), 2.9–3.5 (several bm, 4H total), 3.5–4.0 (several bm, 6H total), 4.0 (m, 2H), 4.66 (2 s, 2H), 5.70 (m, 1H), 6.96 (m, 1H), 7.07 (s, 1H), 7.2–7.35 (bm, 5H), 7.57 (d, 1H). Mass spectrum: (M+H)$^+$ = 767.

Analysis. Calcd. for C$_{43}$H$_{70}$N$_6$O$_6$.H$_2$O: C, 65.79; H, 9.24; N, 10.70. Found: C, 65.46; H, 8.95; N, 10.54.

EXAMPLE 120

N-(1(S)-(4-(Methoxymethoxy)piperidin-1-yl)carbonyl-2-phenyl)ethyl-L-norleucyl amide of 3-(4-morpholinyl)propyl 5(S)-amino-6-cyclohexyl-4(S)-hydroxy-2(S)-isopropylhexanamide The procedure of Example 118 was used, with the substitution of the intermediate amino acid from Example 105 for the resultant compound from Example 83, providing the title compound in 81% yield as a hygroscopic foamy solid, m.p. 60°–65° C. $^1$H NMR (CDCl$_3$) δ0.89 (t), 0.93 (d, 9H total), 0.65–1.94 (several bm, approx. 28H total), 2.06 (m, 1H), 2.33 (bm, 1H), 2.46 (bm, 6H), 2.67–2.85 (m, 3H), 3.0 (bm, 1H), 3.25 (m, 3H), 3.35 (s, 3H), 3.35–3.60 (bm, 3H), 3.71 (bm, 4H), 3.6–3.9 (several bm, 5H total), 4.65 (2 s, 2H), 6.75 (m, 1H), 6.80 (d) and 6.87 (d, 1H total), 7.2–7.4 (bm, 5H). Mass spectrum: (M+H)$^+$ = 786.

EXAMPLE 121

(2S,3S)-3-((tert-Butyloxycarbonyl)amino)-4-cyclohexyl-2-hydroxy-1-(methyl(methylsulfamoyl)amino)butane A solution of (1R,S)-(1'S-((tert-Butyloxycarbonyl)amino)-1-cyclohexylmethyl)oxirane (1.29 g, 4.79 mmol, prepared according to J. R. Luly, J. F. Dellaria, J. J. Plattner, J. L. Soderquist and N. Yi, J. Org. Chem. 1987, 52, 1487) in 20 ml methanol was treated with 40% aq. methylamine (4.1 ml, 1.48 g, 47.6 mmol). After 24 h at ambient temperature, the solvent was removed in vacuo to provide 1.53 g (100%) of (2S,3S)-3-((tertbutloxycarbonyl)- amino)-4-cyclohexyl-2-hydroxy-1-(methylamino)butane as a viscous oil. $^1$H NMR (CDCl$_3$) δ0.75–1.57 (several bm) and 1.45 (s, approx. 17H total), 1.66 (bm, 5H), 1.86 (bd, 1H), 1.9–2.5 (vbm, 2H), 2.42 (s, 3H), 2.5–2.68 (m, =2H), 3.6 (bm, 2H), 4.70 (bd, 1H). Mass spectrum: (M+H)$^+$ = 301.

A sample of the crude N-methylamine above (896 mg, 2.98 mmol) was dissolved in 13 ml CH$_2$Cl$_2$ and treated sequentially with triethylamine (602 mg, 5.93 mmol) and methylsulfamoyl chloride (450 mg, 3.46 mmol) at −35° C. The resulting solution was stirred at −35° C. for 3 h, at which time tlc (15% MeOH-CH$_2$Cl$_2$) indicated complete consumption of starting amine. The reaction was quenched with 20 ml of sat. aq. NaHCO$_3$ and extracted with 3×30 ml CH$_2$Cl$_2$. The combined organic extracts were combined, washed with brine, dried (Na$_2$SO$_4$) and concentrated in vacuo. The crude was purified by column chromatography (EtOAc-hexane-toluene 4:4:1) to provide 534 mg (49%) of the title compound as glassy solid; $^1$H NMR (CDCl$_3$) δ0.75–1.90 (several bm) and 1.45 (s, 22H total), 2.74 (d, 3H), 2.86 (m, 1H), 2.93 (s, 3H), 3.14 (dd, 1H), 3.38 (dd, 1H), 3.64 (m, 1H), 3.79 (m, 1H), 4.33 (m, 1H), 4.69 (m, 1H). Mass spectrum: (M+H)$^+$ = 394; (M+NH$_4$)$^+$ = 411.

EXAMPLE 122

2(S)-(1(S)-(4-(Methoxymethoxy)piperidin-1-yl)carbonyl-2-phenyl)ethoxyhexanoic acid amide of (2S,3S)-3-amino-4-cyclohexyl-2-hydroxy-1-(methyl(methylsulfamoyl)amino)butane A sample of the resultant compound from Example 121 (501 mg, 1.27 mmol) was dissolved in 3 ml CH$_2$Cl$_2$, cooled to 0° C. under a dry nitrogen atmosphere, and treated with 3 ml trifluoroacetic acid. The solution was stirred for 5.5 h, then the solvents were removed under reduced pressure, and the residue was basified with 1.0M aq. Na$_2$CO$_3$. The product was extracted with 4×20 ml CH$_2$Cl$_2$. The combined extracts were washed with brine, dried (Na$_2$SO$_4$) and concentrated under reduced pressure to yield 332 mg (89%) of (2S,3S)-3-amino-4-cyclohexyl-2-hydroxy-1-(methyl(methylsulfamoyl)amino)butane as a white powder. $^1$H NMR (CDCl$_3$) δ0.8–1.45 (several bm, 8H), 1.6–1.8 (bm, 5H), 1.9 (vbm, 3H), 2.75 (s, 3H), 2.85 (m, 1H), 2.94 (s, 3H), 3.21 (dd, 1H), 3.30 (dd, 1H), 3.48 (m, 1H). Mass spectrum: (M+H)$^+$ = 294.

The above crude aminoalcohol (35.4 mg, 0.121 mmol) was combined with the resultant compound from Example 83 (53.1 mg, 0.130 mmol), HOBt (23.2 mg, 0.152 mmol) and 4-methyl- morpholine (14 mg, 0.136 mmol) in 1.2 ml DMF. The solution was cooled to −15° C. and EDC (36 mg, 0.19 mmol) was added. The resulting mixture was stirred and allowed to slowly warm to room temperature (24 h total). The solvent was removed under reduced pressure, and the residue partitioned between aq. NaHCO$_3$ and CH$_2$Cl$_2$. The aqueous phase was extracted (3×10 ml CH$_2$Cl$_2$), and the combined organic extracts were washed with 10 ml brine, dried (Na$_2$SO$_4$) and concentrated under reduced pressure. Column chromatography (3% MeOH-CH$_2$Cl$_2$) provided 41.3 mg (50%) of the title compound as a colorless solid, m.p. 55°–60° C. $^1$H NMR (CDCl$_3$) δ0.6–1.9 (several bm, approx. 26H), 2.68 (d, 3H), 2.8 (dd, 1H), 2.92 (s, 3H), 3.0–3.2 (m, 2H), 3.31 (m, 1H), 3.38 (2s, 3H), 3.4–3.6 (bm, 2H), 3.85 (bm, 4H), 3.94 (bm, 1H), 4.51 (dd, 1H), 4.69 (2s, 2H), 5.65 (bm, 1H), 5.87 (2d, 1H), 7.25–7.38 (m, 5H). Mass spectrum: (M+H)$^+$ = 683.

Analysis. Calcd. for C$_{34}$H$_{58}$N$_4$O$_8$S.0.5 H$_2$O: C, 59.02; H, 8.59; N, 8.10. Found: C, 58.98; H, 8.31; N, 7.94.

EXAMPLE 123

1-(3-(tert-Butyloxycarbonyl)-2,2-dimethyl-4(S)-cyclohexylmethyl-5(S)-oxazolidinyl)-2(S)-((dimethylaminoethoxycarbonyl)amino)-3-methylbutane A solution of the resultant compound from Example 112 (2.27 g, 5.52 mmol) in 17 ml dry toluene was treated with triethylamine (0.85 ml, 6.07 mmol) and diphenylphosphorylazide (1.67 g, 6.07 mmol). The solution was warmed to 65° C. for 2 h, then N,N-dimethylethanolamine (2.46 g, 27.6 mmol) was added, and the resulting solution was refluxed for 24 h. The solvent was evaporated under reduced pressure and the residue was dissolved in 450 ml EtOAc and extracted (1×400 ml of 1N HCl, 1×400 ml water, 1×400 ml sat. aq. NaHCO$_3$, 1×450 ml brine). The organic phase was dried (MgSO$_4$) and concentrated under reduced pressure. Flash chromatography (6% MeOH-CH$_2$Cl$_2$) provided 1.88 g (68%) of a colorless glass.

$^1$H NMR (CDCl$_3$) δ0.9 (d, 6H), 0.8–1.9 (several bm) and 1.47 (s, approx. 31H total), 2.29 (s, 6H), 2.54 (bt, 2H), 3.7 (bm, 2H), 3.97 (m, 1H), 4.16 (m, 2H), 4.90 (bd, 1H). Mass spectrum: (M+H)+ =498.

Analysis. Calcd. for C$_{27}$H$_{51}$N$_3$O$_5$,0.5 H$_2$O: C, 64.00; H, 10.34; N, 8.29. Found: C, 64.13; H, 10.13; N, 8.35.

EXAMPLE 124

1-(3-(tert-Butyloxycarbonyl)-2,2-dimethyl-4(S)-cyclohexylmethyl-5(S)-oxazolidinyl)-2(S)-((4-morpholinoethoxycarbonyl)amino)-3-methylbutane The procedure of Example 123 was followed, with the substitution of 2-(hydroxyethyl)morpholine for N,N-dimethylethanolamine, to provide the title compound in 65% yield. 1H NMR (CDCl3) δ0.93 (2d, 6H), 0.8–1.9 (several bm), 1.48 (s) and 1.60 (s, approx. 31 H total), 2.50 (bm, 6H), 2.61 (bt, 2H), 3.65 (bm) and 3.72(m, 6H total), 3.99 (m, 1H), 4.2 (m, 2H), 4.9 (bm, 1H). Mass spectrum: (M+H)+ =540.

EXAMPLE 125

1-(3-(tert-Butyloxycarbonyl)-2,2-dimethyl-4(S)-cyclohexylmethyl-5(S)-oxazolidinyl)-2(S)-((2-pyridyl)ethoxycarbonyl)amino)-3-methylbutane The procedure of Example 123 was followed, with the substitution of 2-(2-hydroxyethyl)pyridine for N,N-dimethylethanolamine, to provide the title compound in 64% yield after flash chromatography (3% MeOH-CH$_2$Cl$_2$). $^1$H NMR (CDCl$_3$) δ0.9 (bd, 6H), 1.47 (s), 1.54 (bs) and 0.75–1.85 (several bm, approx. 31 H total), 3.11 (bt, 2H), 3.63 (bm, 2H), 3.97 (bd, 1H), 4.45 (m, 2H), 4.82 (bs, 1H), 7.14 (ddd, 1H), 7.19 (bd, 1H), 7.60 (td, 1H), 8.55 (ddd, 1H).

EXAMPLE 126

1-(3-(tert-Butyloxcarbonyl)-2,2-dimethyl-4(S)-cyclohexylmethyl-5(S)-oxazolidinyl)-2(S)-((2-(1H-imidazolyl))methoxycarbonyl)amino)-3-methylbutane The procedure of Example 123 is employed, with the substitution of (2-hydroxymethyl)imidazole hydrochloride for N,N-dimethylethanolamine, and the inclusion of an additional equivalent of triethylamine, to provide the title compound.

EXAMPLE 127

1-(3-(tert-Butyloxycarbonyl)-2,2-dimethyl-4(S)-cyclohexylmethyl-5(S)-oxazolidinyl)-2(S)-((2-methylthio)ethoxycarbonyl)amino)-3-methylbutane The procedure of Example 123 is employed, with the substitution of 2-methylthioethanol for N,N-dimethylethanolamine, to provide the desired compound in 25% yield, after flash chromatography (10% EtOAc-hexanes). $^1$H NMR (CDCl$_3$) δ0.92 (bd) and 0.8–1.05 (bm, 8H total), 1.48 (s), 1.60 (bs) and 1.1–1.9 (several bm, approx 31 H total), 2.16 (s, 3H), 2.71 (bt, 2H), 3.65 (bm, 2H), 3.99 (m, 1H), 4.23 (m, 2H), 4.87 (bm, 1H). Mass spectrum: (M+H)+ =501.

EXAMPLE 128

1-(3-(tert-Butyloxycarbonyl)-2,2-dimethyl-4(S)-cyclohexylmethyl-5(S)-oxazolidinyl)-2(S)-(pentanoyl)amino)-3-methylbutane A solution of the resultant compound from Example 112 (200 mg, 0.486 mmol) in 1.5 ml dry toluene was treated with triethylamine (0.075 ml, 0.54 mmol) and diphenylphosphoryl- azide (0.115 ml, 0.54 mmol). The solution was warmed to 65° C. for 2.5 h, then was cooled to 0° C. and treated with a solution of butylmagnesium chloride (0.668 ml, 2.0M in THF, 1.34 mmol). The solution was allowed to slowly warm to room temperature and stir for 14 h. The mixture was partitioned between EtOAc and water, and the organic phase was washed (1×25 ml 1N HCl, 2×75 ml water, 1×75 ml sat. aq. NaHCO$_3$, 1×100 ml brine), then concentrated in vacuo. Flash chromatography (20% EtOAc-hexanes) gave 202 mg (84%) of the title compound as a white solid. $^1$H NMR (CDCl$_3$) δ0.93 (m) and 0.8–1.05 (bm, 11H total), 1.48 (s) and 1.1–1.9 (several bm, approx. 35H total), 2.16 (dd, 2H), 3.63 (bm, 1H), 3.95 (bm) and 4.0 (m, .2H total), 5.25 (bm, 1H). Mass spectrum: (M+H)+ =467.

EXAMPLE 129

2(S)-(1(S)-(4-Methoxymethoxy)piperidin-1-yl)carbonyl-2-phenyl)ethoxyhexanoic acid amide of 2(S)-amino-1-cyclohexyl-5-(S)-(2-(dimethylamino)ethoxycarbonyl)amino-3(S)-hydroxy-6-methylheptane Using the procedure of Example 116, the resultant product from Example 123 is deprotected and coupled, to provide the desired product in 68% yield after flash chromatography (5% MeOH-CH$_2$Cl$_2$), m.p. 55°–60° C. $^1$H NMR (CDCl$_3$) δ0.88 (m) and 0.7–1.0 (bm, approx 11H total), 1.0–1.9 (several bm, approx. 24H total), 2.25 (bs, 3H), 2.31 (bs, 3H), 2.57 (bm, 2H), 2.6–3.25 (bm, 4H), 3.32 (m, 4H), 3.4–4.0 (several bm, 8H), 4.2 (bm, 2H), 4.4–4.9 (bm, 4H), 6.04 (bd), 6.18 (bd) and 6.7 (2 overlapping bd, 1H total), 7.2–7.4 (bm, 5H). Mass spectrum: (M+H)+ =747.

Analysis. Calcd. for C$_{41}$H$_{70}$N$_4$O$_8$: C, 65.92; H, 9.44; N, 7.50. Found: C, 65.77; H, 9.45; N, 7.47.

EXAMPLE 130

2(S)-(1(S)-(4-(Methoxymethoxy)piperidin-1-yl)carbonyl)-2-phenyl)ethoxyhexanoic acid amide of 2(S1-amino-1-cyclohexyl-5-(S)-((2-(4-morpholino)ethoxycarbonyl)amino-3(S)-hydroxy-6-methylheptane Using the procedure of Example 116, the resultant product from Example 124 is deprotected and coupled, to provide the desired product in 73% yield after flash chromatography (3% MeOH-CH$_2$Cl$_2$), m.p. 57°–60° C. $^1$H NMR (CDCl$_3$) δ0.9 (overlapping t and 2d) and 0.6–1.05 (bm, 11H total), 1.05–1.9 (several bm, approx. 24H), 2.50 (m, 4H), 2.64 (bt, 2H), 2.97–3.25 (bm, 3H), 3.34 (s) and 3.25–3.45 (bm, 4H total), 3.47 (bm), 3.75 (m) and 3.45–4.0 (12H total), 4.25 (m, 2H), 4.4–4.7 (bm) and 4.63(s) and 4.65 (s, 3H total), 4.77 (bd, 1H), 6.02 (bd), 6.16 (bd), 6.50 (m) and 6.05 (m, 1H total), 7.28 (bm, 5H). Mass spectrum: (M+H)+ =789.

Analysis. Calcd. for C$_{43}$H$_{72}$N$_4$O$_9$: C, 65.45; H, 9.20; N, 7.09. Found: C, 65.10; H, 9.10; N, 7.09.

EXAMPLE 131

2(S)-(1(S)-(4-(Methoxymethoxy)piperidin-1-yl)carbonyl-2-phenyl)ethoxyhexanoic acid amide of 2(S)-amino-1-cyclohexyl-5(S)-((2-(2-pyridyl)ethoxycarbonyl)amino-3(S)-hydroxy-6-methylheptane Using the procedure of Example 116, the resultant product from Example 125 is deprotected and coupled, to provide the desired product in 64% yield after flash chromatography (3% MeOH-CH$_2$Cl$_2$), m.p. 51°-54° C. $^1$H NMR (CDCl$_3$) δ0.88 (overlapping t and 2d) and 0.6–1.0 (bm, 11H total), 1.0–1.9 (several bm, approx. 24H), 3.14 (bt), 3.35 (s) and 2.96–3.4 (several bm, 9H total), 3.54 (bd), 3.73 (bt) and 3.4–4.4 (several bm, approx 9H total), 4.52 (bm, 4H), 4.65 (2s, 2H), 5.99 (bd) and 6.12 (bd, 1H total), 7.1–7.3 (m, 7H), 7.61 (m, 1H), 8.56 (m, 1H). Mass spectrum: (M+H)$^+$ =781.

Analysis. Calcd. for C$_{44}$H$_{68}$N$_4$O$_8$.0.5 H$_2$O: C, 66.89; H, 8.80; N, 7.09. Found: C, 66.68; H, 8.59; N, 7.13.

EXAMPLE 132

2(S)-1(S)-4-(Methoxymethoxy)piperidin-1-yl)carbonyl-2-phenyl)ethoxyhexanoic acid amide of 2(S)-amino-1-cyclohexyl-5(S)-((2-(pentanoyl)amino-3(S)-hydroxy-6-methylheptane Using the procedure of Example 116, the resultant product from Example 128 is deprotected and coupled, to provide the desired product in 35% yield after flash chromatography (1% MeOH-CH$_2$Cl$_2$), m.p. 55°-65° C. $^1$H NMR (CDCl$_3$) δ0.9 (overlapping t and 2d) and 0.6–1.0 (bm, 11H total), 1.0–1.9 (several bm, approx. 28H), 2.27 (t, 2H), 2.9–3.6 (several bm) and 3.33 (s, 10H total), 3.65 (bm, 1H), 3.72 (bt, 2H), 3.9 (bm, 3H), 4.14 (bm, 1H), 4.52 (bq, 1H), 4.64 (2s, 2H), 5.50 (dd, 1H), 6.19 (d) and 6.30 (d, 1H total), 7.28 (bm, 5H). Mass spectrum: (M+H)$^+$ =716.

Analysis. Calcd. for C$_{41}$H$_{69}$N$_3$O$_7$.0.75 H$_2$O: C, 67.50; H, 9.74; N, 5.76. Found: C, 67.13; H, 9.36; N, 5.80.

EXAMPLE 133

2(S)-(1(S)-(4-Methoxymethoxy)piperidin-1-yl)carbonyl-2-phenyl)ethoxyhexanoic acid amide of 2(S)-amino-1-cyclohexyl-5(S)-((1H-imidazol-2-yl)methoxycarbonyl)amino-3(S)-hydroxy-6-methylheptane Using the procedure of Example 116, the resultant product from Example 126 is deprotected and coupled, to provide the desired product.

EXAMPLE 134

2(S)-(1(S)-(4-(Methoxymethoxy)piperidin-1-yl)carbonyl-2-phenyl)ethoxyhexanoic acid amide of 2(S)-amino-1-cyclohexyl-5(S)-(2-(methylthio)ethoxycarbonyl)amino-3(S)-hydroxy-6-methylheptane Using the procedure of Example 116, the resultant product from Example 127 is deprotected and coupled, to provide the desired product.

EXAMPLE 135

2(S)-(1(S)-(4-(Methoxymethoxy)piperidin-1-yl)carbonyl-2-phenyl)ethoxyhexanoic acid amide of 2(S)-amino-1-cyclohexyl-5(S)-(2-(methylsulfonyl)ethoxycarbonyl)amino-3(S)-hydroxy-6-methylheptane Using the procedure of B. M. Trost and D. P. Curran, Tetrahedron Lett. 1981, 22, 1287–1290, the resultant product from Example 134 is oxidized to provide the desired product.

EXAMPLE 136

2(S)-(1(S)-(4-(Methoxymethoxy)piperidin-1-yl)carbonyl-2-phenyl)ethoxyhexanoic acid amide of 3-(dimethyl-N-oxyamino)propyl) 5(S)-amino-6-cyclohexyl-4(S)-hydroxy-2(S)-isopropylhexanamide A sample of the resultant product from Example 117 (50 mg, 0.067 mmol) was dissolved in 0.35 ml MeOH and treated with 30% aq. hydrogen peroxide solution (0.027 ml), added in three portions over 3 days. After 4 days at room temperature, the solvent was removed, and the residue purified by column chromatography (9.5% MeOH-0.5% conc. aq. NH$_4$OH—CH$_2$Cl$_2$) to provide 18 mg (37%) of the desired compound. $^1$H NMR (CDCl$_3$) δ0.88 (d, 3H), 0.9 (bt, 3H), 0.93 (d, 3H), 0.65–2.7 (several bm, approx. 28H total), 2.9–3.25 (several bm) and 3.14 (s, 7H total), 3.25–3.6 (several bm), 3.34 (s), 3.36 (s) and 3.37 (s, approx. 10H), 3.6–3.8 (bm, 4H), 3.88 (bm, 1H), 4.0–4.2 (bm, 2H), 4.62 (bm, 1H), 4.67 (2s, 2H), 5.84 (bt, 1H), 7.2–7.4 (bm, H), 8.28 (bm, 1H). Mass spectrum: (M+H)$^+$ =761.

EXAMPLE 137

(2S,3R,4S)-4-(tert-Butyloxycarbonyl)amino-5-cyclohexyl-2-hydroxy-1-(N-methoxy-N-methylamino)-3-(methoxyethoxymethoxy)pentane The resultant compound from Example 22 (454.7 mg, 1.17 mmol) in dioxane (4 mL) was treated with N-methyl-O-methylhroxylamine hydrochloride (1.14 g, 11.7 mmol) in water (4 mL). Solid NaHCO$_3$ (1.00 g, 11.9 mmol) was added, the reaction was sealed and heated at 90° C. for 60 h. The reaction was cooled, poured into saturated NaHCO$_3$ solution and extracted into ethyl acetate which was dried over Na$_2$SO$_4$ and evaporated. Chromatography of the residue on silica gel (60 g) with 60% ethyl acetate in hexane afforded 306.0 mg (58%) of the 2S-isomer (followed by the 2R-isomer). TLC (5% methanol/95% chloroform) R$_f$=0.53; $^1$H NMR (CDCl$_3$) δ4.89 (d, 1H), 4.77 (s,2H), 4.02–4.12 (m, 1H), 3.02 (s, 3H), 3.39 (s, 3H), 2.91 (dd, 1H), 2.63 (s, 3H), 1.45 (s, 9H).

EXAMPLE 138

(2S,3R,4S)-4-Amino-5-cyclohexyl-2,3-dihydroxy-1-(N-methoxy-N-methylamino)pentane The resultant compound from Example 137 (1.00 mmol) was stirred for 1 h in 4M HCl/ethanol. The mixture was evaporated and the residue was dissolved in water which was made basic with solid K$_2$CO$_3$ and was then saturated with NaCl. The mixture was extracted with chloroform which was dried over Na$_2$SO$_4$ and evaporated to afford the desired product.

EXAMPLE 139

2(S)-(1(S)-(4-(Methoxy)piperidin-1-yl)carbonyl-2-phenyl)ethoxyhexanoic acid amide of (2S,3R,4S)-4-Amino-5-cyclohexyl-2,3-dihydroxy-1-(N-methoxy-N-methylamino)pentane The resultant compounds from Examples 138 and 83 were coupled according to the procedure of Example 93 to give the desired product. High resolution mass spectrum. Calcd. for (M+H)$^+$ of C$_{35}$H$_{60}$N$_3$O$_8$: 650.4380. Found: 650.4388.

EXAMPLE 140

N-((3-(tert-Butoxycarbonyl)-2,2-dimethyl-4(S)-cyclohexylmethyl-5(R)-oxazolidinyl)methyl)isopropylamine The resultant aldehyde from Example 99 (479 mg, 1.47 mmol, 8:1 mixture of epimeric aldehydes) was dissolved in 5 ml iPrOH, and isopropylamine (0.15 ml, 1.76 mmol) was added, and the pH was adjusted to 6 with acetic acid and sodium acetate as buffer. The solution was cooled in an ice bath, and a solution of sodium cyanoboro-hydride (119 mg, 1.89 mmol) in 2 ml iPrOH was added. After stirring the resultant solution at 0° C. for 6 h, it was allowed to warm to room temperature and stir an additional 0.5 h. The reaction was made basic with 1.0M aq. $Na_2CO_3$ (5 ml) and the isopropanol was removed under reduced pressure. The residue was partitioned between water and EtOAc, and the organic extracts washed with brine, dried ($Na_2SO_4$) and concentrated. Purification by flash chromatography (3% MeOH-$CH_2Cl_2$) provided 262 mg (48%) of the title compound as a colorless oil, (as well as 18 mg (3%) of diastereomeric amine). $^1$H NMR ($CDCl_3$) δ0.9–1.35 (several bm) and 1.08 (2d, 13H total), 1.48 (s, 9H), 1.51 (s), 1.58 (s) and 1.35–1.86 (several bm, approx. 12H total), 2.70 (m, 2H), 2.82 (m, 1H), 3.7 (bm, 1H), 4.0 (ddd, 1H). Mass spectrum: $(M+H)^+ = 369$.

EXAMPLE 141

N-((3-tert-Butyloxycarbonyl)-2,2-dimethyl-4(S)-cyclohexylmethyl-5(R)-oxazolidinyl)methyl)-N-(methylsulfamoyl)isopropylamine The resultant product from Example 140 is reacted with methylsulfamoyl chloride according to the procedure of Example 121, to produce the title compound as a low melting solid in 86% after flash chromatography (EtOAc-hexanes 1:4). 1H NMR ($CDCl_3$) δ0.98 (bm, 2H), 1.25 (2d) and 1.1–1.35 (bm, 10H total), 1.48 (s, 9H), 1.63 (bs) and 1.37–1.87 (several bm, approx. 13H total), 2.70 (d, 3H), 3.25 (m, 2H), 3.83 (dt, 1H), 4.01 (septet, 1H), 4.10 (m, 1H), 4.25 (bm, 1H). Mass spectrum: $(M+H)^+ = 462$.

Analysis. Calcd. for $C_{22}H_{43}N_3O_5S$: C, 57.24; H, 9.39; N, 9.10. Found: C, 57.54; H, 9.50; N, 8.95.

EXAMPLE 142

2(S)-(1(S)-(4-(Methoxymethoxy)piperidin-1-yl)carbonyl-2-phenyl)ethoxyhexanoic acid amide of (2S,3S)-3-amino-4-cyclohexyl-2-hydroxy-1-(isopropyl(-methylsulfamoyl)amino)butane The resultant compound from Example 141 was deprotected and coupled according to the procedure of Example 116 to provide the desired product in 51% yield after preparative thin-layer chromatography (4% MeOH-$CH_2Cl_2$) as a foam, m.p. 45°–52° C. $^1$H NMR ($CDCl_3$) δ0.94 (2t, 3H), 1.21 (2d, 6H), 0.65–1.9 (several bm, approx. 21H), 2.66 (2d, 3H), 2.9–3.15 (bm, 5H), 3.2–3.4 (bm, 2H), 3.37 (2s, 3H), 3.5 (bm, 3H), 3.72 (bm, 5H), 4.0 (bm overlapping septet, 2H), 4.55 (dd, 1H), 4.69 (2s, 2H), 5.58 (bm, 1H), 5.64 (2bd, 1H), 7.35 (bm, 5H). Mass spectrum: $(M+H)^+ = 711$.

Analysis. Calcd. for $C_{36}H_{62}N_4O_8S.0.25\ H_2O$: C, 60.44; H, 8.80; N, 7.83. Found: C, 60.82; H, 8.57; N, 7.80.

EXAMPLE 143

2(S)-(1(S)-(4-(Methoxymethoxy)piperidin-1-yl)carbonyl-2-phenyl)ethoxyhexanoic acid amide of (4S,5S)-5-amino-4-hydroxy-7-methyl-2(E)-octenoic acid isobutylamide The title compound is prepared according to the procedure of Example 116, with the substitution of (4S,5S)-5-amino-4-hydroxy-7-methyl-2(E)-octenoic acid isobutylamide (prepared according to the procedure described in Example 2, part 3, European Patent Application EP0272583, published Jun. 29, 1988) for 2(S)amino-1-cyclohexyl-3(R),4(S)-dihydroxy-6-methylheptane as the amine component.

EXAMPLE 144

2(S)-(1(S)-(4-(Methoxymethoxy)piperidin-1-yl)carbonyl-2-phenyl)ethoxyhexanoic acid amide of N-((2R,4S,5S)-5-amino-4-hydroxy-2-isopropyloctanoyl)-isoleucylhistadinamide The title compound is prepared according to the procedure of Example 116, with the substitution of N-((2R,4S,5S)-5-amino-4-hydroxy-2-isopropyloctanoyl)isoleucylhistadinamide (prepared according to the procedure described in Example 1(i), U.S. Pat. No. 4,719,288, issued Jan. 12, 1988) for 2(S)-amino-1-cyclohexyl-3(R),4(S)-dihydroxy-6-methylheptane as the amine component.

EXAMPLE 145

2(S)-(1(S)-(4-(Methoxymethoxy)piperidin-1-yl)carbonyl-2-phenyl)ethoxyhexanoic acid amide of (1R,3S,4S)-4-amino-5-cyclohexyl-3-hydroxy-1-isopropylpentanesulfonic acid morpholinoamide The title compound is prepared according to the procedure of Example 116, with the substitution of (1R,3S,4S)-4-amino-5-cyclohexyl-3-hydroxy-1-isopropylpentanesulfonic acid morpholinoamide (prepared according to the procedure described in Example 2, European Patent Application No. EP0309841, published Apr. 5, 1989) for 2(S)-amino-1-cyclohexyl-3(R),4(S)-dihydroxy-6-methylheptane as the amine component.

EXAMPLE 146

2(S)-(1(S)-(4-(Methoxymethoxy)piperidin-1-yl)carbonyl-2-phenyl)ethoxyhexanoic acid amide of (2S)-2-amino-1-cyclohexyl-3,4-dioxoheptane The procedure of Example 116 is utilized, with the substitution of 2-((1RS,2S)-2-amino-3-cyclohexyl-1-hydroxypropyl)-2-propyl-1,3-dithiane hydrochloride (prepared according to the procedure described in Example 1, European Patent Application No. EP0296581, published Dec. 28, 1988) for 2(S)-amino-1-cyclohexyl-3(R),4(S)-dihydroxy-6-methylheptane as the amine component. The resulting amide was transformed into the title compound by hydrolysis of the thioketal and Dess-Martin oxidation of the secondary hydroxyl group according to the procedures described in the above citation.

EXAMPLE 147

2(S)-(1(S)-(4-Methoxymethoxy)piperidin-1-yl)carbonyl)-2-phenyl)ethoxyhexanoic acid amide of 2-((1R,2S)-2-amino-3-cyclohexylpropyl)-1H-imidazole The procedure of Example 116 is employed, with the substitution of 1-benzyloxymethyl-2-((1R,2S)-2-amino-3-cyclohexylpropyl)-imidazole (prepared according to the procedure described in Example 1, European Patent Application No. EP0231919, published Aug. 12, 1987) for 2(S)-amino-1-cyclohexyl-3(R),4(S)-dihydroxy-6-methylheptane as the amine component. The title compound is then produced by hydrogenolysis of the resultant amide over palladium hydroxide on carbon, according to the procedure in the citation above.

EXAMPLE 148

2(S)-(1(S)-(4-(Methoxymethoxy)piperidin-1-yl)carbonyl-2-phenyl)ethoxyhexanoic acid amide of (4S)-N$^1$-((2S)-(2-benzylaminocarbonyl-3-methylbutanoyl))-2,2-difluoro-3-oxo-6-methyl-1,4-heptanediamine The title compound is prepared according to the procedure of Example 116, with the substitution of (3RS,4S)-N$^1$-((2S)-2-benzylaminocarbonyl-3-methylbutanoyl))-2,2-difluoro-3-hydroxy-6-methyl-1,4-heptanediamine (prepared according to the procedure described in Example 32, European Patent Application No. 275101, published Jul. 20, 1988) for 2(S)-amino-1-cyclohexyl-3(R),4(S)-dihydroxy-6-methylheptane as the amine component. Subsequent Collins oxidation, according to the procedure of Example 8 of the above citation, produces the title compound.

EXAMPLE 149

2(S)-(1(S)-(4-(Methoxymethoxy)piperidin-1-yl)carbonyl-2-phenyl)ethoxyhexanoic acid amide of (3S)-3-((1S,2S)-2-amino-3-cyclohexyl-1-hydroxypropyl)-1-(N-benzyl-2-(diethylaminoethyl))-5,5-dimethyl-2-pyrrolidinone acetate The procedure of Example 116 is employed, with the substitution of (3S)-3-((1S,2S)-2-amino-3-cyclohexyl-1-hydroxypropyl)-1-(2-(diethylaminoethyl))-5,5-dimethyl-2-pyrrolidinone (prepared according to the procedure described in Examples 2 and 3, European Patent Application NO. 312283, published Apr. 19, 1989) for 2(S)-amino-1-cyclohexyl-3(R),4(S)-dihydroxy-6-methylheptane as the amine component. The C-terminal tertiary amine is quaternized by the action of benzyl bromide in the presence of ethyldiisopropylamine, followed by anion exchange, according to the procedure of Example 3, part Q, of the above citation, thereby producing the desired compound.

EXAMPLE 150

2(S)-(1(S)-(4-(Methoxymethoxy)piperidin-1-yl)carbonyl-2-phenyl)ethoxyhexanoic acid N$^4$-amide of (3S,4S)-N$^1$-((1S)-1-(benzylaminocarbonyl)-3-methylbutyl)-3-hydroxy-6-methyl-1,4-heptanediamine The title compound is prepared according to the procedure of Example 116, with the substitution of (3S,4S)-N$^1$-((1S)-1-(benzylaminocarbonyl)-3-methylbutyl)-3-hydroxy-6-methyl-1,4-heptanediamine (prepared according to the procedure described in Example 2, U.S. Pat. No. 4,609,641, issued Sep. 2, 1986) for 2(S)-amino-1-cyclohexyl-3(R),4(S)-dihydroxy-6-methylheptane as the amine component.

EXAMPLE 151

2(S)-(1(S)-(4-(Methoxymethoxy)piperidin-1-yl)carbonyl-2-phenyl)ethoxyhexanoic acid amide of N-(N-(((2S,3S)-3-amino-2-hydroxy-5-methylhexyl)-(1-methylethyl)amino)carbonyl)-L-isoleucyl)-L-histidine, methyl ester The title compound is prepared according to the procedure of Example 116, with the substitution of N-(N-((((2S,3S)-3-amino-2-hydroxy-5-methylhexyl)-(1-methylethyl- amino)carbonyl)-L-isoleucyl-L-(N$^{im}$-benzyloxymethyl)-histidine, methyl ester (prepared according to the procedure described in Example 4g, U.S. Pat. No. 4,757,050, issued Jul. 12, 1988) for 2(S)-amino-1-cyclohexyl-3(R),4(S)-dihydroxy-6-methylheptane as the amine component. The title compound is obtained by standard hydrogenolysis of the above resultant compound.

EXAMPLE 152

2(S)-(1(S)-(4-(Methoxymethoxy)piperidin-1-yl)carbonyl-2-phenyl)ethoxyhexanoic acid N$^4$-amide of ((3S,4S)-3,4-diamino-6-methylheptanoyl-L-isoleucyl-2-pyridylmethylamine The title compound is prepared according to the procedure of Example 116, with the substitution of ((3S,4S)-3-(4-methoxyphenyl)amino-4-amino-6-methylheptanoyl)-L-isoleucyl-2-pyridyl-methylamine (prepared according to the procedures described in H. J. Schostarez, J. Org. Chem. 1988, 53, 3628, and S. Thaisrivongs, H. J. Schostarez, D. T. Pals and S. R. Turner, J. Med. Chem. 1987, 30, 1837) for 2(S)-amino-1-cyclohexyl-3(R),4(S)-dihydroxy-6-methylheptane as the amine component. The title compound is obtained by oxidative deprotection of the methoxyphenyl group with ceric ammonium nitrate as described in the citations above.

EXAMPLE 153

4-(tert-Butoxycarbonyl)-5S-(benzyl)-2H-1,4-oxazin-2-one

To suspension of 10.0 g (66 mmol) of L-phenylalaninol in 120 mL of dry THF and 16 mL, 11.5 g (114 mmol) triethylamine cooled in an ice-water bath was added 11 mL, 16.5 g (98 mmol) of ethyl bromoacetate (freshly filtered through basic alumina). The reaction mixture was stirred to room temperature over 18 h, recooled in an ice-water bath, and filtered. Remaining unfiltered solids were washed with cold THF and filtered. Di-tert-butyl dicarbonate (20g, 92 mmol) was added to the combined filtrates and the THF was slowly removed under reduced pressure (30 min) at 50°-70° C. The crude residue was dissolved in 300 mL toluene, washed with dilute HCl, saturated sodium bisulfate, dried (MgSO$_4$) and filtered. p-Toluenesulfonic acid monohydrate, 500 mg, was added to the toluene solution. Excess toluene (250 mL) was removed by distillation. The toluene solution was cooled, washed with saturated sodium bisulfate, dried (MgSO$_4$) and filtered, total volume 100 mL. Hexane (150 mL) was added and the product crystallized at room temperature to give 10.00 g of a white solid. A second recrystallization gave 1.75 g of a white solid. The mother liquors were purified by flash chromatography using ethyl acetate:hexane (1:4) to give another 1.13 g. Total combined yield 12.88 g (67%): mp 98°-100° C.; $[\alpha]^{25}_D = -13.7°$ (C=2.45 CHCl$_3$); IR (CDCl$_3$) 1750 (lactone C=O), 1690 (carbamate C=O) cm$^{-1}$; $^1$H NMR (CDCl$_3$) 7.4-7.2 (m, 5H, Ph), 4.35-4.1 (m, 5H, O—CH$_2$, COCH$_2$ and CH—N), 3.0 (dd, 1H, J=5 and 12 Hz, CH$_2$—Ph), 2.82 (dd,1H, J=10 and 12 Hz, CH$_2$—Ph), 1.45 (s, 9H, t-butyl); MS, m/e (M+) 291; Anal. Calcd for C$_{16}$H$_{21}$NO$_4$: C, 65.97; H, 7.21; N, 4.81. Found: C, 65.67; H, 7.21; N, 4.75.

EXAMPLE 154

4-(tert-Butoxycarbonyl)-5S-(cyclohexylmethyl)-2H-1,4-oxazin-2-one

Using the procedure of Example 1 and 14.0 g (71 mmol) of amino alcohol hydrochloride (prepared from 20 g of L-Boc-cyclohexylalaninol and 4M HCl dioxane), 200 mL THF, 28 mL (193 mmol) triethylamine, 17.9 g (106 mmol) ethyl bromoacetate, 18.5 g (85 mmol) di-tert-butyl dicarbonate, 500 mg p-toluenesulfonic acid monohydrate gave crude lactone. Product was purified by flash chromatography using a 1:4, 3:7 and 4:6 ethyl acetate : hexane step gradient to give 11.7 grams of pure lactone. Yield 55%: mp 73°-74° C.; $[\alpha]^{25}_D = +1.09°$ (C=0.82 CHCl$_3$); IR (CDCl$_3$) 1750 (lactone C=O), 1690 (carbamate C=O) cm$^{-1}$; $^1$H NMR (CDCl$_3$) 4.5-4.2 (m, 4H, O—CH2, COCH and CH—N), 3.97 (d, 1H, 18 Hz, COCH), 1.9-0.9 (br m, 13H, cyclohexylmethyl), 1.49 (s, 9H, t-butyl); MS m/e (M+H)+298; Anal. Calcd for C$_{16}$H$_{27}$NO$_4$: C, 64.64; H, 9.09; N, 4.71. Found: C, 64.73; H, 9.00; N, 4.71.

EXAMPLE 155

4-(tert-Butoxycarbonyl)-5S-(methyl)-2H-1,4-oxazin-2-one

Using the procedure of Example 1 and 9.5 g (126 mmol) of 2S-amino-1-propanol, 100 mL THF, 30 mL (214 mmol) triethylamine, 31 g (190 mmol) ethyl bromoacetate, 33 g (151 mmol) di-tert-butyl dicarbonate, 500 mg p-toluenesulfonic acid monohydrate gave crude lactone. Product was purified by flash chromatography using a 1:4 and a 3:7 ethyl acetate : hexane step gradient. The lactone was obtained as a white crystalline solid (8.0 g) in 30% yield: mp 85°-86° C.; $[\alpha]^{25}_D = +6.96°$ (C=2.21 CHCl$_3$); IR (CDCl$_3$) 1750 (lactone C=O), 1690 (carbamate C=O) cm$^{-1}$;$^1$H NMR (CDCl$_3$) 4.46 (dd, 1H, J=3 and 10 Hz, O—CH), 4.30 (d, 1H, 18 Hz, COCH), 4.18 (br dd, 2H, J=3 and 12 Hz, O—CH and CH—N), 4.08 (d, 1H, J =18 Hz, COCH), 1.48 (s, 9H, t-butyl), 1.29 (d, 3H, J=7Hz, CH$_3$); MS m/e (M+H)+216; Anal. Calcd for C$_{10}$H$_{17}$NO$_4$: C, 55.81; H, 7.90; N, 6.51. Found: C, 55.98; H, 7.93; N, 6.55.

EXAMPLE 156

4-(tert-Butoxycarbonyl)-5S-(n-butyl)-2H-1,4-oxazin-2-one

Using the procedure of Example 1 and 16 g of 2S-amino-1-hexanol hydrochloride (prepared from 26 g ,119 mmol of L-Boc-norlucinol and 4M HCl dioxane), 250 mL THF, 45 mL (320 mmol) triethylamine, 30 g (180 mmol) ethyl bromoacetate, 31 g (142 mmol) di-tert-butyl dicarbonate, 500 mg p-toluenesulfonic acid monohydrate gave crude lactone. Product was purified by flash chromatography using a 1:4 and a 3:7 ethyl acetate : hexane step gradient. The lactone was obtained as a clear oil (13.0 g) in 45% yield: $[\alpha]^{25}_D = +3.45°$ (C=2.95 CHCl$_3$); IR (Film) 1760 (lactone C=O), 1700 (carbamate C=O) cm$^{-1}$;$^1$H NMR (CDCl$_3$) 4.46 (dd, 1H, J=3 and 10 Hz, O—CH), 4.41-4.26 (br m, 2H, O—CH and COCH), 4.12 (br s, 1H, CH—N), 4.00, 1.74-1.56 (11 line m, 2H, CH$_2$), 1.48 (s, 9H, t-butyl), 1.42-1.21 (m, 4H, CH$_2$CH$_2$), 0.92 (d, 3H, J=6Hz, CH$_3$); MS m/e (M+H)+258; Anal. Calcd for C$_{13}$H$_{23}$NO$_4$: C, 60.70; H, 8.95; N, 5.45. Found: C, 60.56; H, 8.88; N, 5.42.

EXAMPLE 157

4-(tert-Butoxycarbonyl)-5S-(isopropyl)-2H-1,4-oxazin-2-one

Using the procedure of Example 1 and 10 g (97 mmol) of 2S-3-methyl-1-butanol, 100 mL THF, 23 mL (145 mmol) triethylamine, 23 g (145 mmol) ethyl bromoacetate, 25 g (116 mmol) di-tert-butyl dicarbonate, 500 mg p-toluenesulfonic acid monohydrate gave crude lactone. Product was purified by flash chromatography using a 1:4 and a 3:7 ethyl acetate : hexane step gradient. The lactone was obtained as a clear oil (14.9 g) which solidified at −25° C. Yield 66%: mp 38°-40° C. $[\alpha]^{25}_D = -30.55°$ (C=3.22 CHCl$_3$); IR (Film) 1750 (lactone C=O), 1700 (carbamate C=O) cm$^{-1}$;$^1$H NMR (CDCl$_3$) 4.50 (br d, 2H, O—CH and COCH), 4.40 (d d, 1H, J=3 and 10 Hz, O—CH), 3.95 (br d, 2H, CH—N and COCH), 1.99 (14 line m, 1H, CH), 1.48 (s, 9H, t-butyl), 1.04 (d, 3H, J=7Hz, CH$_3$), 0.96 (d, 3H, J=7Hz, CH$_3$); MS m/e (M+H)+244; Anal. Calcd for C$_{12}$H$_{21}$NO$_4$: C, 59.25; H, 8.64; N, 5.76. Found: C, 58.88; H, 8.72; N, 5.71.

EXAMPLE 158

3S-(Prop-2-en-1-yl)-4-tert-butoxycarbonyl)-5S-(benzyl)-2H-1,4-oxazin-2-one

To a solution of 7.0 mL (1M, 7 mmol) of sodium bis (hexamethyl-silyl) amide in THF cooled to −70° C. (limited liquid nitrogen-diethyl ether bath) was added 2.1 g (7.2 mmol) of lactone (example 1) in 10 mL THF. After addition was complete 2.5 mL of dry HMPA was added. The reaction was stirred for 15 min between −70° and −80° C. and 1.5 mL of allyl bromide (freshly filtered through basic alumina) was added. The reaction was stirred from −80° to −50° C. over a 20 min period. A dilute solution of sodium bisulfate was added and the reaction warmed to room temperature, poured into chloroform and the aqueous layer separated. The aqueous layer was extracted once with chloroform. The combined chloroform extracts were washed once with water, dried (MgSO$_4$) and evaporated to give 2.02 g of a crystalline solid (85%). An analytical sample was prepared by recrystalization from ethyl acetate:hexane at 0° .C.: mp 125°-127° C.; $[\alpha]^{25}_D = +40.1°$ (C=0.96 CHCl$_3$); IR (CDCl$_3$) 1750 (lactone C=O), 1690 (carbamate C=O); 1H NMR (CDCl$_3$, 55° C.) 7.37-7.18 ( br m, 5H, C$_6$H5), 5.90-5.74 (11 line m, 1H, CH=C), 5.22-5.10 (m, 2H, C=CH$_2$), 4.61-4.48 (br s, 1H, COCH), 4.38-4.30 (m, 1H, O—CH), 4.17-4.10 (br d, 2H, O—CH and CH—N), 3.13-3.00 (br d, 1H, CHPh), 2.8-2.58 (m, 3H, CH$_2$—C=C and CHPh), 1.55 (s, 9H, t-butyl); MS m/e (M+H)+332; Anal. Calcd for C$_{19}$H$_{25}$NO$_4$: C, 68.88; H, 7.55; N, 4.22. Found: C, 68.49; H, 7.56; N, 4.17.

EXAMPLE 159

3S-(Butyl)-4-(tert-butoxycarbonyl)-5S-(benzyl)-2H-1,4-oxazin-2-one

Using the procedure in Example 6 but replacing allyl bromide with butyl iodide and raising the reaction temperature to −60° C. gave the alkylated product in 43% yield. 1H NMR (DMSO) 7.37–7.18 (br m, 5H, C6H5), 4.48 (dd, 1H, COCH), 4.22 (dd, 1H, O—CH), 4.13–3.97 (br d, 2H, C—CH and CH—N), 2.90 (dd, 1H, CHPh), 2.65 (dd, 1H, CHPh), 1.45 (s, 9H, t-butyl), 0.86 (t, 3H, CH3); MS m/e (M+H)+348; Anal. Calcd for C20H29NO4: C, 69.14; H, 8.41; N, 4.03. Found: C, 69.43; H, 8.46; N, 3.89.

EXAMPLE 160

Methyl 3-Aza-4(S)-benzyl-3-(tert-butoxycarbonyl)-2(S)-butyl-5-hydroxypentanoate

A solution of lithium hydroxide (966 mg, 22.8 mmol) in 7 mL water and lactone (2.0 g, 5.7 mmol) from example 7 in 16 mL THF was stirred at room temperature for 18 h. The reaction mixture was acidified with a saturated solution of sodium bisulfate and extracted with dichloromethane. A solution of diazomethane in ether was added to the dichloromethane extract until the yellow color persisted. Excess diazomethane and solvent was removed under a nitrogen ebullition. The crude methyl ester was purified by column chromatography using ethyl acetate:hexane (3:7) as eluant. The pure ester was obtained as a clear oil (2.05 g) in 94% yield.1H NMR (CDCl3) 7.26 (br m, 5H, C6H5), 4.31 (br, m, 2H, CH2OH), 3.78 (s, 3H, O—CH3),1.46 (s, 9H, t-butyl), 0.90 (t, 3H, CH3); MS m/e (M+H)+380.

EXAMPLE 161

Methyl 3-Aza-3-(tert-butoxycarbonyl)-2(S)-butyl-4(S)-(4-methoxymethoxypiperidinocarbonyl)-5-phenylpentanoate The hydroxy ester from example 8 ( 600 mg, 1.58 mmol) in dichloromethane is added to a solution of oxalyl chloride (152 mcL) and DMSO (0.27 mL) at −25° C. After stirring for 15 min, triethylamine (1.1 mL) was added and the reaction stirred to room temperature. The crude aldehyde was obtained as a yellow oil and directly oxidized to the carboxylic acid using the procedure of Masmune et al. (Tetrahedron Letters 1986, 27, 4537) gives the carboxylic acid. The crude acid couples with the amine from example 82a using the procedure in example 93 to give the product.

EXAMPLE 162

Methyl 3-Aza-3-(tert-butoxycarbonyl)-2(S)-(prop-2-en-1-yl)-4(S)-morpholinocarbonyl-5-phenylpentanoate The lactone from example 6 (520 mg, 1.5 mmgl) was hydrolyzed using the procedure in example 8 to give the hydroxy ester which was oxidized in 1.6 mL of DMF with 1.5 g of PDC. Standard workup gave the crude acid. Coupling of the crude acid with 0.6 mL morpholine, 318 mg HOBT, 450 mg EDC HCl in 5 mL DMF at −20° C. to room temperature over 18 h gave the amide. Mass Spectrum: (M+H)+ =447.

EXAMPLE 163

3-Aza-2(S)-(prop-2-en-1-yl)-4(S)-morpholinocarbonyl-5-phenylpentanoic acid amide of 2(S)-amino-1-cyclohexyl-3(R),4(S)-dihydroxy-6-methylheptane The ester from example 10 ( 90 mg) was hydrolyzed using 50 mg LiOH in 2.5 mL of 1.5:1 (dioxane: water) at room temperature for 2 days gave 67 mg of the crude acid which was coupled with 2(S)-amino-1-cyclohexyl-3(R),4(S)dihydroxy-6-methylheptane using the procedure in example 93 gave the Boc amide which was purified by silica gel chromatography. The Boc amide was stirred in TFA: dichloromethane (1:1) for 24h. The solvents were removed under reduced pressure, the residue made basic with saturated sodium bicarbonate and the free base extracted with dichloromethane. The product was purified by preparative TLC using 4:1 ethyl acetate:hexane. Concentration of the solvent gave the product as a white solid. Mass Spectrum: (M+H)+ =558.

EXAMPLE 164

2(S)-(1(S)-(4-Methoxymethoxypiperidin-1-yl carbonyl)-2-phenylethoxy)hexanoic acid amide of 5-amino-6-cyclohexyl-4-hydroxy-1-isopropylsulfonyl-2-methylhexane Using the acid from example 83, 5-amino-6-cyclohexyl-4-hydroxy-1-isopropylsulfonyl-2-methylhexane (Tetrahedron Letters 1989, 30, 2653) and the procedure from example 93 gives the desired product.

EXAMPLE 165

2(S)-(1(S)-(4-Methoxymethoxypiperdin-1-yl carbonyl)-2-phenylethoxy)hexanoic acid amide of 5-amino-6-cyclohexyl-4-hydroxy-1-isopropylsulfonyl-2-isopropylhexane Using the acid from example 83, 5-amino-6-cyclohexyl-4-hydroxy-1-isopropylsulfonyl-2-isopropylhexane (European Patent Application No. EP0273893, published Jul. 6, 1988) and the procedure from example 93 gives the desired product.

EXAMPLE 166

2(S)-(1(S)-(4-Methoxymethoxypiperidin-1-yl carbonyl)-2-phenylethoxy)hexanoic acid amide of isopropyl 3-amino-4cyclohexyl-2-hydroxybutrate Using the acid from example 83, 3-amino-4-cyclohexyl-2-hydroxy-butyrate (Japanese Patent Application No. JP63275552, published Nov. 14, 1988) and the procedure from example 93 gives the desired product.

EXAMPLE 167

2(S)-(1(S)-(4-Methoxymethoxypiperidin-1-yl carbonyl)-2-phenylethoxy)hexanoic acid amide of N-(2-Morpholinoethyl)-4-Amino-5-cyclohexyl-3-hydroxypentamide Using the acid from example 83, N-(2-morpholinoethyl) 4-amino-5-cyclohexyl-3-hydroxypentamide (Japanese Patent Application No. JP62246546A, published Oct. 27, 1987; European Patent Application No. EP0274259, published Jul. 13, 1988) prepared from BocACHPA amide of 2-morpholinoethylamine by acid treatment, and the procedure from example 93 gives the desired product.

EXAMPLE 168

2(S)-1(S)-(4-Methoxymethoxypiperidin-1-yl carbonyl)-2-phenylethoxy)hexanoic acid amide of 6-Amino-7-cyclohexyl-5-hydroxy-3-isopropyl-1-heptene Using the acid from example 83, 6-amino-7-cyclohexyl-5-hydroxy-3-isopropyl-1-heptene (European Patent Application No. EP0310918, published Apr. 12, 1989) and the procedure from example 93 gives the desired product.

EXAMPLE 169

2(S)-(1(S)-(4-Methoxymethoxypiperidin-1-yl carbonyl)-2-phenylethoxy)hexanoic acid amide of N-isobutyl 4-amino-5-cyclohexyl-2,2-difluoro-3-hydroxypentamide Using the acid from example 83, N-isobutyl 4-amino-5-cyclohexyl-2,2-difluor-3-hydroxypentamide, prepared from Boc cyclomethylalinal according to the procedure of Thaisrivong (J. Med. Chem. 1986, 29, 2080; see also U.S. Pat. No. 4,857,507, issued Aug. 15, 1989, example 69), and the procedure from example 93 gives the desired product.

EXAMPLE 170

2(S)-(1(S)-(4-Methoxymethoxypiperidin-1-yl carbonyl)-2-phenylethoxy)hexanoic acid amide of 4-amino-5-cyclohexyl-2,2-difluoro-3-hydroxy-1-isopropylmercapto-1-pentane Using the acid from example 83, 4-amino-5-cyclohexyl-2,2-difluor-3-hydroxy-1-isopropylmercapto-1-pentane, prepared from the oxazolidinone (U.S. Pat. No. 4,857,507, issued Aug. 15, 1989, example 74, according to the procedure of example 76 in U.S. Pat. No. 4,857,507, issued Aug. 15, 1989), and the procedure from example 93 gives the desired product.

EXAMPLE 171

2(S)-(1(S)-(4-Methoxymethoxypiperidin-1-yl carbonyl)-2-phenylethoxy)hexanoic acid amide of 4-amino-5-cyclohexyl-2,2-difluoro-3-hydroxy-1-isopropylsulfonyl-1-pentane To the resultant compound from example 36 (10 mmol) in 5 mL of $CH_2Cl_2$ is added 30 mmol of m-chloroperbenzoic acid. Standard workup and chromatography on silica gel gives the title compound.

EXAMPLE 172

Ethyl 4(S)-((t-butyloxycarbonyl)amino)-5-cyclohexyl-2,2-difluoro-3(R,S)-hydroxypentanoate.

To a suspension of 1.2 g (17 mmole) of activated zinc in 5 ml of tetrahydrofuran under argon in a sonicating bath was added slowly a solution of 1.7 g (6.8 mmole) of Boc-L-cyclohexylalaninal and 2.34 ml (18.4 mmole) of ethyl bromodifluoroacetate in 30 ml of tetrahydrofuran. After complete addition, the solution was sonicated for an additional 30 min. The mixture was then added to 1M $KHSO_4$ and extracted with dichloromethane (3×100 ml), dried with $Na_2SO_4$, filtered and concentrated in vacuo. The residual oil was purified by silica gel column chromatography (15–30% ethyl acetate in hexane) to give 1.22 g (75%) of two diasteromers. 3(R) diastereomer: $^1H$ NMR ($CDCl_3$) $\delta 1.37$ (t,3H, J=7.0 Hz), 1.46 (S,9H), 4.35 (q,2H, J=7.0 Hz). m.p. 73°–74.5° C.

Anal. ($C_{18}H_{31}NO_5F_2$)C,H,N. 3(S) diastereomer: $^1H$ NMR ($CDCl_3$) $\delta 1.37$ (t,3H, J=7.5 Hz), 1.45 (S,9H), 4.31 (q, 2H, J=7.5 Hz); m p. 115°–117° C.

Anal. ($C_{18}H_{31}NO_5F_2$)C,H,N.

EXAMPLE 173

2-Oxazolidinone derivative of Ethyl 4(S)-amino-5-cyclohexyl-2,2-difluoro-3(R)-hydroxypentanoate To 50 mg of the 3(R) isomer from Example 172 was added 1 ml of 4M HCl in dioxane. The solution was stirred at RT for 30 min. The concentrated residue was dissolved in dichloromethane and treated with 0.1 ml of triethylamine and excess phosgene in toluene (10% solution). After stirring at RT for 1 hr, the crude product was purified by silica gel column chromatography (10% ethyl acetate in hexane) to give 32 mg of desired product. $^1H$ NMR ($CDCl_3$) $\delta 1.38$ (t,3H, J=7 Hz), 4.08 (m,1H), 4.38 (q, 2H, J=7 Hz), 4.58 (ddd,1H, J=4.5,6.0,15 Hz), 6.05 (br S,1H). Anal. ($C_{14}H_{21}NO_4F_2$)C,H,N.

EXAMPLE 174

23-Oxazolidinone derivative of Ethyl 4(S)-amino-5-cyclohexyl-2,2-difluoro-3-(S)hydroxypentanoate Using the same procedure as in Example 173, and using the 3(S) isomer from Example 1 as the starting material provided the desired product $^1H$ NMR ($CDCl_3$) $\delta 1.38$ (t,3H,J=7.5 Hz), 4.28 (ddd, 1H, J=3,7.5,12 Hz), 4.38 (q,2H, J=7.5 Hz), 5.02 (ddd,1H,J=6,9,19.5 Hz), 5.63 (br S,1H).

Anal. ($C_{14}H_{21}NO_4F_2$)C,H,N.

EXAMPLE 175

4(S)-cyclohexylmethyl-5(R)-(4'(4',4'-difluoro-3'-oxo-2'-methyl-butyl))-2-oxazolidinone The hydrolysis of 2.5 g of the product in Example 174 by lithium hydroxide in aqueous methanol provided 2.3 g of the corresponding carboxylic acid. The acid was dissolved in 40 ml of THF and cooled to −78° C. To the vigorously stirred solution was added 18 ml of isopropyl lithium solution in pentane (12.4% by wt.). After 30 min, the solution was slowly warmed to 0° C. and stirred for an additional 30 min. The reaction was carefully quenched with water and extracted with ethyl acetate (3×100 ml), dried and concentrated in vacuo. The crude product was purified by silica gel column chromatography (20% ethyl acetate in hexane) to give 1.36 g of desired product. $^1H$ NMR ($CDCl_3$) $\delta 1.20$ (t,6H, J=6.3 Hz), 3.17 (d of heptet, 1H, J=1.8,6.6 Hz), 4.06 (m,1H), 4.62 (ddd,1H, J=4.5,6.0,20.4 Hz), 5.63 (br S,1H). Anal. ($C_{14}H_{23}NO_3F_2$)C,H,N.

EXAMPLE 176

4(S)-cyclohexylmethyl-5-(R)(4'-(4',4'-difluoro-3(R,S)-hydroxy-2'-methylbutyl))-2-oxazolidinone To the product of Example 175 (1.0 g, 3.4 mmole) in 20 ml of methanol at 0° C. was added 125 mg of sodium borohydride. After 10 min the reaction was quenched by addition of excess acetone. The solution was concentrated and the residual oil was dissolved in ethyl acetate and washed with brine. The aqueous layer was extracted with ethyl acetate (2×50 ml). The combined ethyl acetate solution was dried with MgSO$_4$ and concentrated to give a mixture of 3'(R) and 3'(S) diastereomers. 3'(R) isomer: $^1$H NMR (CDCl$_3$): δ1.04 (t,6H, J=7.5 Hz), 2.12 (m,1H), 3.82 (m,1H), 4.10 (m,1H), 4.63 (dd,1H, J=4.5,22.5 Hz), 5.38 (br S,1H).

Anal. (C$_{14}$H$_{25}$NO$_3$F$_2$)C,H,N.

3'(S) isomer: $^1$H NMR (CDCl$_3$): δ1.01 (d,3H, J=6Hz), 1.07 (d,3H, J=2.10 (m,1H), 3.80 (m,1H), 4.15 (m,1H), 4.40 (td, 1H, J=6,15.5 Hz), 5.62 (br S,1H).

Anal. (C$_{14}$H$_{25}$NO$_3$F$_2$)C,H,N.

EXAMPLE 177

2(S)-Benzyloxycarbonylamino-1-cyclohexyl-4,4-difluoro-3(R),5(R)-dihydroxy-6-methylheptane.

To a solution of 0.9 g (3.0 mmole) of the 3'(R) isomer in Example 176 in 50 ml of dioxane and water was added 1.05 g (2.1 eq) of barium hydroxide hydrate. The reaction mixture was heated to reflux for 18 hr. and cooled to RT and filtered. The filtrate was concentrated in vacuo and the crude product was dissolved in 50 ml of dichloromethane and 1.0 g of N-(benzyloxycarbonyloxy)succinimide was added. After 1 hr. at RT the solution was washed with satd. NaHCO$_3$ and extracted with dichloromethane (3×50 ml), dried with Na$_2$SO$_4$ and filtered. The filtrate was concentrated in vacuo to give a pale yellow oil which was purified by silica gel column chromatography (10% EtOAc in CH$_2$Cl$_2$) to give 900 mg of the desired product. $^1$H NMR (CDCl$_3$) δ1.01 (d,3H, J=5Hz), 1.03 (d,3H, J=5Hz), 2.07 (m,1H), 2.42 (br d,1H), 3.70–3.95 (m,3H), 4.07 (m,1H), 5.02 (br d,1H), 5.11 (S,2H), 7.30–7.36 (m,5H).

Anal. (C$_{22}$H$_{33}$NO$_4$F$_2$)C,H,N.

EXAMPLE 178

2(S)-Amino-1-cyclohexyl-4,4-difluoro-3(R),5(R)-dihydroxy-6-methylheptane

A solution of 700 mg of the product from Example 177 in 10 ml of methanol was stirred vigorously under a hydrogen atmosphere using 10% Pd/C as catalyst. After 30 min, the catalyst was filtered off and the solution concentrated to give 470 mg the desired product. Mass spectrum: M$^+$=279.

EXAMPLE 179

2(S)-(1(S)-(4-(Methoxymethoxy)piperidin-1-yl-carbonyl)-2-phenylethoxy)hexanoic acid Amide of (2(S)-Amino-1-cyclohexyl-4,4-difluoro-3(R),5(R)-dihydroxy-6-methylheptane Using the procedure of Example 93, but replacing the resultant glycol of Example 41 with the resultant product of Example 178 gave the desired product.

$^1$H NMR (CDCl$_3$, TMS) δ0.9 (bt,1H), 1.02 (dd,6H), 2.92 (m,2H), 3.37 (s,3H), 4.46 (dd,1H), 4.67 (s,2H), 6.0 (bdd, 1H), 7.32 (m,5H). Mass spectrum: (M+H)$^+$=669.

EXAMPLE 180

2(S)-(1(S)-(4-Methoxymethoxy)piperidin-1-yl-carbamoyl)-2-phenylethoxy)hexanoic acid Amide of 4(S)-Amino-5(S)-hydroxy-2-methyl-6-(2(S)-methylcarbonyl)hexane Using the procedure of Example 93, but replacing the resultant glycol of Example 41 with 4(S)-Amino-5(S)-hydroxy-2-methyl-6-(2(S)-methylcarbamoyl)hexane (Buhlmayer, et al., U.S. Pat. No. 4,727,060, issued Feb. 23, 1988) gave the desired product.

$^1$H NMR (CDCl$_3$, TMS) δ0.84 (m,15H), 2.2 (m,2H), 3.36 (s,3H), 3.77 (t,1H), 3 9 (bt,1H), 4.53 (bdd,1h), 4.66 (s,2H), 6.08 (bdd,1H), 6.28 (bm,1H), 7.28 (m,5H). Mass spectrum: (M+H)$^+$=634.

EXAMPLE 181

N-(1(S)-(4-(Methoxymethoxy)piperidin-1-yl-carbonyl)-2-phenyl-L-norleucyl Amide of 5(S)-Amino-6-cyclohexyl-4(R)-hydroxy-2-isopropylhexanoyl)-L-isoleucyl)-2-pyridylmethylamine Using the procedure of Example 105, but replacing the resultant product of Example 41 with 5(S)-Amino-6-cyclohexyl-4(R)-hydroxy-2-isopropylhexanoyl)-L-isoleucyl)-2-pyridylmethylamine (PCT Patent Application No. W087/02986, published May 21, 1987), gave the desired product.

$^1$H NMR (CDCl$_3$, TMS) δ0.9 (m,15H), 1.1–1.6 (m,29H), 3 (s,3H), 4.55 (d,2H), 7.4 (m,10H). Mass spectrum: (M+H)$^+$=864.

EXAMPLE 182

2(R)-Butyl-4(R)-(4(Methoxymethoxy)piperidin-1-yl-sulfonyl)-5-phenylpentanoic acid Amide of 3-(4-morpholinyl)-propyl-5(S)-amino-6-cyclohexyl-4(S)-hydroxy-2(S)-isopropyl hexanamide The title compound can be prepared according to the procedure of Scheme XIV in which R$_5$ is 4-(methoxymethoxy)piperidin-1-yl, R$_1$ is phenyl, R$_3$ is n-butyl and D is the deprotected resultant product of Example 115.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The compounds of the present invention can also be used in the form of prodrugs which include esters. Examples of such esters include a hydroxyl-substituted compound of formula (1) which has been acylated with a blocked or unblocked amino acid residue, a phosphate function, or a hemisuccinate residue. The amino acid esters of particular interest are glycine and lysine; however, other amino acid residues can also be used. Other esters include the compounds of formula (1) wherein a carboxylic acid group has been esterified to provide esters which include, but are not limited to, methyl, ethyl or benzyl esters. These esters serve as prodrugs of the compounds of the present invention and serve to increase the solubility of these substances in the gastrointestinal tract. The prodrugs are metabolically converted in vivo to the parent compound of formula (1). The preparation of the pro-drug esters is carried out by reacting a hydroxyl-substituted compound of formula.(1) with an activated amino acyl, phosphoryl or hemisuccinyl derivative. The resulting product is then deprotected to provide the desired prodrug ester. Prodrugs which are esters of carboxylic acid group containing compounds of formula (1) are prepared by methods known in the art.

The novel compounds of the present invention possess an excellent degree of activity and specificity in treating hypertension in a host. The novel compounds of the present invention are also useful for treating congestive heart failure. The ability of the compounds of the invention to inhibit human renal renin can be demonstrated in vitro by reacting a selected compound at varied concentrations with human renal renin, free from acid proteolytic activity, and with renin substrate (human angiotensinogen) at 37 degrees C and pH of 6.0. At the end of the incubation, the amount of angiotensin I formed is measured by radioimmunoassay and the molar concentration required to cause 50% inhibition, expressed as the $IC_{50}$ is calculated. When tested in accordance with the foregoing procedure, the compounds of the invention demonstrated $IC_{50}$'s in the range of $10^{-7}$ to $10^{-9}$ M as seen in Table I.

TABLE I

| Example | $IC_{50}$ (nM) |
| --- | --- |
| 69 | 9.0 |
| 87 | 5.5 |
| 88 | 12 |
| 89 | 15 |
| 91 | 3.9 |
| 93 | 1.1 |
| 94 | 1.3 |
| 96 | 1.5 |
| 108 | 0.87 |
| 116 | 1.3 |
| 117 | 2.5 |
| 118 | 0.84 |
| 119 | 3.0 |
| 120 | 2.0 |
| 122 | 2.5 |
| 129 | 2.7 |
| 130 | 1.4 |
| 131 | 0.88 |
| 132 | 3.2 |
| 136 | 1.4 |
| 139 | 2.7 |
| 142 | 1.3 |
| 179 | 4.6 |
| 180 | 3.8 |
| 181 | 1.8 |

The ability of the compounds of the invention to decrease blood pressure and plasma renin activity in vivo can be determined using the following method.

In Vivo Activity

Male cynomolgous monkeys housed under constant temperature and lighting conditions and weighing 3–5 kg were instrumented with chronic indwelling arterial and venous catheters. Following pretreatment by saltdepletion, the monkeys were dosed by nasogastric tube with 3 mg/kg of the compound of Example 118. The results with two monkeys are shown in Table II.

TABLE II

Effect of the Compound of Example 118 on Blood Pressure (BP, mmHg) and Plasma Renin Activity (PRA, ng/ml/hr) in Two Salt Depleted Monkeys Following Oral Dosing (3 mg/kg)

| Time (min) | Monkey 1 | | Monkey 2 | | Mean | |
| --- | --- | --- | --- | --- | --- | --- |
| | BP | PRA | BP | PRA | BP | PRA |
| 0 | 107 | 29.1 | 120 | 18.7 | 114 | 23.9 |
| 5 | 112 | 5.8 | 121 | 13.5 | 117 | 9.7 |
| 15 | 105 | 0.1 | 117 | 2.9 | 111 | 1.5 |
| 30 | 113 | 0.4 | 110 | 0.4 | 112 | 0.4 |
| 45 | 95 | 0.0 | 112 | 0.3 | 104 | 0.2 |
| 60 | 102 | 0.0 | 115 | 0.3 | 109 | 0.2 |
| 90 | 90 | 0.0 | 106 | 0.0 | 98 | 0.0 |
| 120 | 84 | 0.2 | 103 | 0.4 | 94 | 0.3 |
| 180 | 84 | 0.2 | 103 | 0.4 | 94 | 0.3 |
| 360 | 94 | 0.0 | 103 | 0.3 | 99 | 0.2 |

These results indicate that the compound caused a decrease in blood pressure accompanied by suppression of PRA when administered orally.

The compounds of the invention may also be used with one or more antihypertensive agents selected from the group consisting of diuretics, and/or β-adrenergic blocking agents, central nervous system -acting agents, adrenergic neuron blocking agents, vasodilators, angiotensin I converting enzyme inhibitors, and other antihypertensive agents.

Total daily dose administered to a host in single or divided doses may be in amounts, for example, from 0.001 to 10 mg/kg body weight daily and more usually 0.01 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The present invention also relates to the use of novel compounds, pharmaceutical compositions containing the novel compounds and the use of the compounds and compositions to inhibit renin for treating glaucoma or reducing and/or controlling intraocular pressure. The present invention also relates to the use of novel compounds and pharmaceutical compositions which inhibit renin in combination with a beta-adrenergic antagonist agent or an angiotensin converting enzyme inhibiting compound for treating glaucoma or reducing and/or controlling intraocular pressure.

The present invention also relates to pharmaceutical compositions for treating the increase in intraocular pressure associated with the administration of steroidal antiinflammatory agents comprising novel renin inhibiting compounds in combination with a steroidal antiinflammatory compound in a pharmaceutically acceptable vehicle.

The present invention also relates to a kit comprising in individual containers in a single package a novel renin inhibiting compound in a suitable pharmaceutical vehicle and a steroidal antiinflammatory compound in a suitable pharmaceutical vehicle and/or a beta-adrenergic antagonist agent in a suitable pharmaceutical vehicle or an angiotensin converting enzyme inhibiting compound in a suitable pharmaceutical vehicle.

The compositions of the invention are administered as topical or systemic pharmaceutical compositions when used for treating or reducing and/or controlling intraocular pressure.

These compositions are preferably administered as topical pharmaceutical compositions suitable for ophthalmic administration, in a pharmaceutically acceptable vehicle such as pharmaceutically acceptable sterile aqueous or nonaqueous solutions, suspensions, emulsions, ointments and solid inserts.

Examples of suitable pharmaceutically acceptable vehicles for ophthalmic administration are water, propylene glycol and other pharmaceutically acceptable alcohols, sesame or peanut oil and other pharmaceutically acceptable vegetable oils, petroleum jelly, water soluble ophthalmologically acceptable non-toxic polymers such as methyl cellulose, carboxymethyl cellulose salts, hydroxyethyl cellulose, hydroxypropyl cellulose; acrylates such as polyacrylic acid salts; ethylacrylates; polyacrylamides; natural products such as gelatin, alginates, pectins, tragacanth, karaya, agar, acacia; starch derivatives such as starch acetate, hydroxyethyl starch ethers, hydroxypropyl starch; as well as other synthetic derivatives such as polyvinyl alcohol, polyvinyl pyrrolidone, polyvinyl methyl ether, polyethylene oxide, carbopol and xantham gum; and mixtures of these polymers. Such compositions may also contain adjuvants such as buffering, preserving, wetting, emulsifying, and dispersing agents. Suitable preserving agents include antibacterial agents such as quaternary ammonium compounds, phenylmercuric salts, benzyl alcohol, phenyl ethanol; and antioxidants such as sodium metabisulfite, butylated hydroxyanisole and butylated hydroxytoluene. Suitable buffering agents include borate, acetate, gluconate and phosphate buffers.

The pharmaceutical ophthalmic compositions of the invention may also be in the form of a solid insert. A solid water soluble or water swellable polymer such as dextran, hydroxyloweralkyl dextran, carboxymethyl dextran, hydroxyloweralkyl cellulose, loweralkyl cellulose, carboxymethyl cellulose, polyvinyl alcohol, dextrin, starch, polyvinyl pyrrolidone and polyalkylene glycols may be used as the carrier for the drug.

Dosage levels of the active compound in the compositions for treating glaucoma or reducing and/or controlling intraocular pressure may be varied so as to obtain a desired therapeutic response to a particular composition. Generally, the active compound will be administered as an isotonic aqueous solution of from 0.00001 to 1.0 (w/v) percent concentration. More preferably the active compound will be administered as an isotonic aqueous solution of from 0.00001 to 0.1 (w/v) percent concentration.

The term "controlling intraocular pressure" as used herein means the regulation, attenuation and modulation of increased intraocular tension. The term also means that the decrease, in the otherwise elevated intraocular pressure, obtained by the methods and compositions of the invention is maintained for a significant period of time as, for example, between consecutive doses of the composition of the invention.

The novel renin inhibiting compounds of the invention may be the only active ingredient for controlling intraocular pressure in the methods and compositions of the invention or may be used in combination with other ingredients which control intraocular pressure such as beta-adrenergic antagonist compounds. The term "beta-adrenergic antagonist" as used herein means a compound which by binding to betaadrenergic plasma membrane receptors reduces or eliminates sympathetic activity or blocks the effects of exogenously administered catecholamines or adrenergic drugs. Examples of beta-adrenergic antagonists are atenolol, metopropol, nadolol, propranolol, timolol, labetalol, betaxolol, carteolol and dilevalol and pharmaceutically acceptable salts thereof. Most preferably the beta-adrenergic antagonist is timolol.

Timolol is currently used for treating glaucoma or reducing and/or controlling intraocular pressure, but it has a number of adverse side effects. Accordingly, administration of a composition comprising a combination of a beta-adrenergic antagonist and a novel renin inhibiting compound of the invention could produce a reduction in intraocular pressure equivalent to that produced by a beta-adrenergic antagonist alone, but at a reduced dose level of the beta-adrenergic antagonist. This will result in a reduced level of the beta-adrenergic antagonist related adverse side effects.

The combination composition is administered as a single dosage form containing both the novel renin inhibitor and the beta-adrenergic antagonist. The beta adrenergic antagonist may comprise from 5 mg to about 125 mg of the composition of the invention. The preferred ranges of the components in the composition of the invention in unit dosage form are:
Renin inhibitor: 1 ng to 0.1 mg
Beta-adrenergic antagonist: 5 ug to 125 ug When the beta-adrenergic antagonist and the novel renin inhibitor are administered as separate compositions the present invention relates to a kit comprising in two separate containers a pharmaceutically acceptable beta-adrenergic antagonist composition and a pharmaceutically acceptable novel renin inhibitor composition, in a single package. A preferred kit comprises a beta-adrenergic antagonist composition and a topical novel renin inhibitor composition. A most preferred kit comprises a topical ophthalmological beta-adrenergic antagonist composition and a topical ophthalmological novel renin inhibitor composition.

The novel renin inhibiting compounds of the invention may also be administered in combination with an angiotensin converting enzyme (ACE) inhibiting compound. Examples of tensin converting enzyme inhibiting compounds are captopril and enalapril. As was previously mentioned, ACE inhibitors have some undesirable side effects. Accordingly, administration of an ACE inhibitor in combination with a renin inhibitor could produce a reduction in intraocular pressure greater than or equivalent to that of an ACE inhibitor alone, but at a reduced dose level of the ACE inhibitor. This will result in a reduced level of the ACE inhibitor related adverse side effects.

The combination composition is administered as a single dose form containing both the novel renin inhibitor and the angiotensin converting enzyme inhibitor. The ACE inhibitor may comprise from 5 ng to about 50 ug of the composition of the invention. The preferred ranges of the components in the composition of the invention in unit dosage form are:
Renin inhibitor: 1 ng to 0.1 mg
ACE inhibitor: 5 ng to 50 ug When the ACE inhibitor and the novel renin inhibitor are administered as separate compositions the present invention relates to a kit comprising in two separate containers a pharmaceutically acceptable ACE inhibitor composition and a pharmaceutically acceptable novel renin inhibitor composition, in a single package. A preferred kit comprises an ACE inhibitor composition and a topical novel renin inhibitor composition. A most preferred kit comprises a topical ophthalmological ACE inhibitor composition and a topical novel renin inhibitor composition.

Dosage levels of the active compounds in the compositions of the invention may be varied so as to obtain a desired therapeutic response depending on the route of administration, severity of the disease and the response of the patient.

Topical, ophthalmic and systemic administration of steroidal antiinflammatory agents can cause an increase in intraocular pressure. The increase in intraocular pressure can be reduced by the administration of a novel renin inhibiting compound of the invention. Steroidal antiinflammatory agents include hydrocortisone, cortisone, prednisone, prednisolone, dexamethasone, methylprednisolone, triamcinolone, betamethasone, alclometasone, flunisolide, beclomethasone, clorocortolone, diflorasone, halcinonide, fluocinonide, fluocinolone, desoximetasone, medrysone, paramethasone, and fluorometholone, and their pharmaceutically acceptable salts and esters. Preferred steroidal antiinflammatory agents are hydrocortisone, prednisolone, dexamethasone, medrysone and fluorometholone and their pharmaceutically acceptable salts and esters. The novel renin inhibitor is administered after use of a steroidal antiinflammatory agent or at the same time, causing reduction and/or control of intraocular pressure.

Various combinations of a topical or oral or injectible dosage form of a steroidal antiinflammatory agent and a topical or oral dosage form of the novel renin inhibitor may be used. A preferred combination comprises a topical stercidal antiinflammatory and a topical novel renin inhibitor. More preferred is a topical ophthalmic dosage form comprising both a steroidal antiinflammatory and a novel renin inhibitor.

When the steroidal antiinflammatory agent and the novel renin inhibitor are administered as separate compositions the present invention relates to a kit comprising in two separate containers a pharmaceutically acceptable steroidal antiinflammatory agent composition and a pharmaceutically acceptable novel renin inhibitor composition, in a single package. A preferred kit comprises a steroidal antiinflammatory composition and a topical novel renin inhibitor composition. A most preferred kit comprises a topical ophthamological steroidal antiinflammatory composition and a topical ophthamological novel renin inhibitor composition.

The combination composition of the invention may contain from about 0.00001 to 1.0 (w/v) percent of the novel renin inhibitor for combined or separate topical administration. More preferably the amount of the novel renin inhibitor is about 0.00001 to 0.1 (w/v) percent of the composition. The amount of the novel renin inhibitor in a unit dosage form for topical administration to the eye is from about 5 ng to about 0.5 mg, preferably from about 5 ng to about 25 ng. The dose required will depend on the potency of the particular novel renin inhibitor, the severity of the intraocular pressure increase and the response of the individual patient.

The combination composition of the invention may contain from about 0.05 to 1.5 (w/v) percent of the steroidal antiinflammatory for combined or separate topical administration. The amount of the steroidal antiinflammatory in a unit dosage form for topical administration to the eye is from about 20 ug to about 600 ug. The dose required will depend on the potency of the particular steroidal antiinflammatory, the severity of the disease and the response of the individual patient.

When the steroidal antiinflammatory agent of the combination therapeutic method of the invention is administered other than ophthalmically, appropriate doses are well known in the art.

The compositions of the invention may include other therapeutic agents in addition to the novel renin inhibitor, and other agents which reduce and/or control intraocular pressure.

The effect on intraocular pressure of the novel compounds of the invention can be determined in rabbits by using the following method.

Effects of Typically Administered Renin Inhibiting Compounds on Intraocular Pressure of Rabbits a. Method The antiglaucoma activity of the compounds was tested by measuring the effect on intraocular pressure in rabbits as described by Tinjum, A.M., Acta Ophthalmologica, 50, 677 (1972). Male albino, New Zealand rabbits were placed in restraining devices and the intraocular pressure was measured with an applamatic tonometer. Exactly 0.1 ml of an isotonic saline solution containing a test compound was instilled into the conjuctival sac and the intraocular pressure was measured at 5, 15, 30, 60, 90, 120 and 180 minutes afterwards.

The present invention is also directed to the use of compounds of the formula I in combination with one or more antihypertensive agents independently selected from diuretics, adrenergic blocking agents, vasodilators, calcium channel blockers, angiotensin converting enzyme (ACE) inhibitors, potassium channel activators and other antihypertensive agents.

Representative diuretics include hydrochlorothiazide, chlorothiazide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside and the like or a pharmeceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Other representative antihypertensive agents include sympatholytic agents such as methyldopa, clonidine, guanabenz, reserpine and the like or a pharmaceutically acceptable salt thereof.

Synergistic combinations of a compound of formula I with one or more of the above-mentioned antihypertensive agents are useful for the treatment of hypertension or congestive heart failure.

The compound of formula I and the antihypertensive agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

In addition, the present invention is directed to the use of a compound of formula I to inhibit retroviral proteases and in particular to inhibit HIV-1 protease and HIV-2 protease. Compounds of formula I are useful for treatment or prophylaxis of diseases caused by retroviruses, especially acquired immune deficiency syndrome or an HIV infection.

The antiviral activity of compounds of the invention can be demonstrated using the following method.

A mixture of 0.1 ml ($4 \times 10^6$ cells/ml) of H9 cells and 0.1 ml (100 infectious units) of HIV-13B was incubated on a shaker for 2 h. The resulting culture was washed three times, resuspended into 2 ml of medium, and treated with 10 $\mu$l of the compound of the invention (5 mM in dimethylsulfoxide). The control culture was treated in an identical manner except the last step was omitted. After incubation of the culture for eight days without change of medium, an aliquot (0.1 ml) of the supernatent was withdrawn and incubated with fresh H9 cells on a shaker for 2 h. The resulting culture was washed three times, resuspended into 2 ml of medium, and incubated. Virus infectivity was determined using the Abbott HTLV-III antigen E.I.A. method (Paul, et al., J. Med. Virol., 22 357 (1987)).

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. 2(S)-(1(S)-(4-(methoxymethoxy)piperidin-1-yl)carbonyl)-2-phenylethoxyhexanoic acid amide of 3-(4-morpholinyl)propyl 5(S)-amino-6-cyclohexyl-4(S)-hydroxy-2(S)-isopropylhexanamide; or a pharmaceutically acceptable salt thereof.

2. N-(1(S)-(4-(Methoxymethoxy)piperidin-1-yl)carbonyl)-2-phenylethyl-L-norleucyl amide of 3-(4-morpholinyl)propyl 5(S)-amino-6-cyclohexyl-4(S)-hydroxy-2(S)-isopropylhexanamide;
or a pharmaceutically acceptable salt thereof.

3. A compound of the formula:

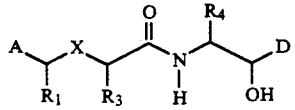

wherein

A is (I) $R_5C(O)—(CH_2)_w—$ wherein
  1) w is 0 to 4 and
  2) $R_5$ is

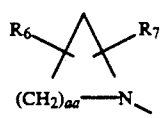

wherein aa is 1 to 5 and $R_6$ and $R_7$ are independently selected from
1) hydrogen,
2) hydroxy,
3) alkoxy wherein alkoxy is $—OR_{30}$ wherein $R_{30}$ is $C_1-C_6$-loweralkyl or $C_3-C_7$-cycloalkyl,
4-thioalkoxy wherein thioalkoxy is $—SR_{30}$ wherein $R_{30}$ is $C_1-C_6$-loweralkyl or $C_3-C_7$-cycloalkyl,
5) alkoxyalkoxy wherein alkoxy is as defined above,
6) —COOH,

137

7) R$_{41}$—C(O)— wherein R$_{41}$ is alkoxy as defined above,
8) halogen,
9) amino,
10) C$_1$-C$_6$-alkylamino,
11) di-C$_1$-C$_6$-alkylamino,
12) C$_1$-C$_6$-alkylsulfonylamino,
13) phenylsulfonylamino, naphthylsulfonylamino, tetrahydronaphthylsulfonylamino or indanylsulfonylamino wherein the phenyl, naphthyl, tetrahydronaphthyl or indanyl group is unsubstituted or substituted with one, two or three substituents independently selected from C$_1$-C$_6$-loweralkyl, C$_1$-C$_6$-haloalkyl, alkoxy as defined above, thioalkoxy as defined above, amino, C$_1$-C$_6$-alkylamino, di-C$_1$-C$_6$-alkylamino, hydroxy, halo, mercapto, nitro, —CHO, —COOH and —C(O)NH$_2$,
14) C$_1$-C$_6$-alkylaminocarbonylamino,
15) C$_1$-C$_6$-alkylaminocarbonyloxy,
16) R$_{80}$OC(O)O— wherein R$_{80}$ is C$_1$-C$_6$-loweralkyl, 17)
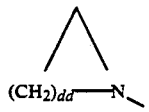

wherein dd is 1 to 5,
and
18) R$_8$—Z— wherein
Z is O, S or NH and R$_8$ is a C$_1$ to C$_6$ straight or branched carbon chain substituted by a substituent selected from hydroxy, alkoxy as defined above, thioalkoxy as defined above, alkoxyalkyl as defined above, amino, C$_1$-C$_6$-alkylamino, di-C$_1$-C$_6$-alkylamino, —COOH, R$_{41}$—C(O)— wherein R$_{41}$ is alkoxy as defined above, phenyl and substituted phenyl as defined above; or (ii)
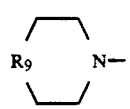

wherein R$_9$ is C=O;
R$_1$ is
(I) hydrogen,
(II) C$_1$-C$_6$-loweralkyl,
(III) C$_3$-C$_7$-cycloalkyl-C$_1$-C$_6$-alkyl,
(IV) phenoxyethyl,
(V) phenylthioethyl,
(VI) benzyloxyethyl,
(VII) benzylthioethyl or
(VIII) a C$_1$ to C$_3$ straight or branched carbon chain substituted by a substituent selected from
1) phenyl,
2) 1-naphthyl or
3) 2-naphthyl wherein the phenyl or naphthyl ring is unsubstituted or substituted with one, two or three substituents independently selected from C$_1$-C$_6$-loweralkyl, C$_1$-C$_6$-haloalkyl, alkoxy as defined above, thioalkoxy as defined above, amino, C$_1$-C$_6$-alkylamino, di-

138

C$_1$-C$_6$-alkylamino, hydroxy, halo, mercapto, nitro, —CHO, —COOH and —C(O)NH$_2$;
X is
(I) NH,
(II) O,
(III) S,
(IV) S(O) or
(V) S(O)$_2$;
R$_3$ is
(I) C$_1$-C$_6$-loweralkyl,
(II) C$_1$-C$_6$-haloalkyl,
(III) C$_2$-C$_6$-loweralkenyl,
(IV) alkoxy-C$_1$-C$_6$-alkyl wherein alkoxy is as defined above,
(V) thioalkoxy-C$_1$-C$_6$-alkyl wherein thioalkoxy is as defined above,
(VI) (alkoxyalkoxy)-C$_1$-C$_6$-alkyl wherein alkoxyalkoxy is as defined above,
(VII) —CH$_2$OH,
(VIII) —(CH$_2$)$_{ee}$NHR$_{12}$ wherein
1) ee is 1 to 3 and
2) R$_{12}$ is
i) hydrogen,
ii) C$_1$-C$_6$-loweralkyl or
iii) an N-protecting group selected from the group consisting of —CHO, acetyl, pivaloyl, t-butylacetyl, trichloroethoxycarbonyl, t-butyloxy-carbonyl, benzyloxycarbonyl or benzoyl; or
(IX) benzyl;
R$_4$ is
(I) C$_1$-C$_6$-loweralkyl,
(II) C$_3$-C$_7$-cycloalkylmethyl or
(III) benzyl; and
D is —CH$_2$CH(R$_{22}$)C(O)NHR$_{23}$ wherein
1) R$_{22}$ is
i) C$_1$-C$_6$-loweralkyl or
ii) C$_3$-C$_7$-cycloalkylalkyl and
2) R$_{23}$ is

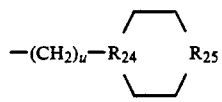

wherein
a) u is 1 to 3,
b) R$_{24}$ is N and
c) R$_{25}$ is O; or a pharmaceutically acceptable salt thereof.

4. The compound of claim 3 wherein R$_6$ is hydrogen, R$_7$ is alkoxyalkoxy, R$_1$ is benzyl, R$_3$ is C$_1$-C$_6$-loweralkyl, R$_4$ is C$_3$-C$_7$-cycloalkylmethyl and R$_{22}$ is C$_1$-C$_6$-loweralkyl.

5. The compound of claim 3, wherein R$_6$ is hydrogen, R$_7$ is methoxymethoxy, R$_1$ is benzyl, R$_3$ is n-butyl, R$_4$ is cyclohexylmethyl and R$_{22}$ is isopropyl.

6. A compound of the formula:

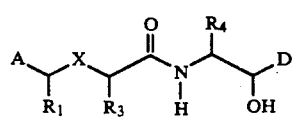

wherein
A is
(I) R$_5$C(O)—(CH$_2$)$_w$— wherein 1) w is 0 to 4 and
2) $R_5$ is

wherein as is 1 to 5 and $R_6$ and $R_7$ are independently selected from
1) hydrogen,
2) hydroxy,
3) alkoxy wherein alkoxy is $-OR_{30}$ wherein $R_{30}$ is $C_1$-$C_6$-loweralkyl or $C_3$-$C_7$-cycloalkyl,
4) thioalkoxy wherein thioalkoxy is $-SR_{30}$ wherein $R_{30}$ is $C_1$-$C_6$-loweralkyl or $C_3$-$C_7$-cycloalkyl and
5) alkoxyalkoxy wherein alkoxy is as defined above, $R_1$ is
(I) hydrogen,
(II) $C_1$-$C_6$-loweralkyl,
(III) $C_3$-$C_7$-cycloalkyl-$C_1$-$C_6$-alkyl or
(IV) a $C_1$ to $C_3$ straight or branched carbon chain substituted by a substituent selected from
  1) phenyl,
  2) 1-naphthyl or
  3) 2-naphthyl wherein the phenyl or naphthyl ring is unsubstituted or substituted with one, two or three substituents independently selected from $C_1$-$C_6$-loweralkyl, $C_1$-$C_6$-haloalkyl, alkoxy as defined above, thioalkoxy as defined above, amino, $C_1$-$C_6$-alkylamino, di-$C_1$-$C_6$-alkylamino, hydroxy, halo, mercapto, nitro, $-CHO$, $-COOH$ and $-C(O)NH_2$;

X is
(I) NH
(II) O or
(III) S;

$R_3$ is
(I) $C_1$-$C_6$-loweralkyl,
(II) $C_1$-$C_6$-haloalkyl,
(III) $C_2$-$C_6$-loweralkenyl,
(IV) alkoxy-$C_1$-$C_6$-alkyl wherein alkoxy is as defined above,
(V) thioalkoxy-$C_1$-$C_6$-alkyl wherein thioalkoxy is as defined above, or
(VI) (alkoxyalkoxy)-$C_1$-$C_6$-alkyl wherein alkoxyalkoxy is as defined above
(VII) $-CH_2OH$, $R_4$ is
(I) $C_1$-$C_6$-loweralkyl,
(II) $C_3$-$C_7$-cycloalkylmethyl or
(III) benzyl; and D is $-CH_2CH(R_{22})C(O)NHR_{23}$ wherein
1) $R_{22}$ is
  i) $C_1$-$C_6$-loweralkyl or
  ii) $C_3$-$C_7$-cycloalkyl-$C_1$-$C_6$-alkyl and
2) $R_{23}$ is

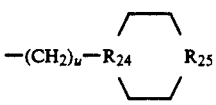

wherein
a) u is 1 to 3,
b) $R_{24}$ is N and
c) $R_{25}$ is O; or a pharmaceutically acceptable salt thereof.

7. The compound of claim 6 wherein $R_6$ is hydrogen, $R_7$ is alkoxyalkoxy, $R_1$ is benzyl, $R_3$ is $C_1$-$C_6$-loweralkyl, $R_4$ is $C_3$-$C_7$-cycloalkylmethyl and $R_{22}$ is $C_1$-$C_6$-loweralkyl.

8. The compound of claim 6 wherein $R_6$ is hydrogen, $R_7$ is methoxymethoxy, $R_1$ is benzyl, $R_3$ is n-butyl, $R_4$ is cyclohexylmethyl and $R_{22}$ is isopropyl.

9. A compound of the formula:

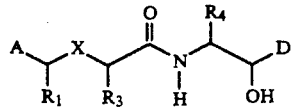

wherein
A is
(I) $R_5C(O)-(CH_2)_w-$ wherein
1) w is 0 to 4 and
2) $R_5$ is

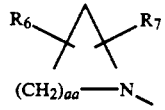

wherein aa is 4 and $R_6$ is hydrogen and $R_7$ is alkoxyalkoxy wherein alkoxy is $-OR_{30}$ wherein $R_{30}$ is $C_1$-$C_6$-loweralkyl or $C_3$-$C_7$-cycloalkyl;

$R_1$ is benzyl;
X is
(I) NH,
(II) O or
(III) S;

$R_3$ is
(I) $C_1$-$C_6$-loweralkyl,
(II) $C_1$-$C_6$-haloalkyl,
(III) $C_2$-$C_6$-loweralkenyl,
(IV) alkoxy-$C_1$-$C_6$-alkyl wherein alkoxy is as defined above,
(V) thioalkoxy-$C_1$-$C_6$-alkyl wherein thioalkoxy is $-SR_{30}$ wherein $R_{30}$ is $C_1$-$C_6$-loweralkyl or $C_3$-$C_7$-cycloalkyl,
(VI) (alkoxyalkoxy)-$C_1$-$C_6$-alkyl wherein alkoxyalkoxy is as defined above or
(VII) $-CH_2OH$, $R_4$ is $C_1$-$C_6$-loweralkyl; and
D is $-CH_2CH(R_{22})C(O)NHR_{23}$ wherein
1) $R_{22}$ is
  i) $C_1$-$C_6$-loweralkyl or
  ii) $C_3$-$C_7$-cycloalkyl-$C_1$-$C_6$-alkyl and
2) $R_{23}$ is

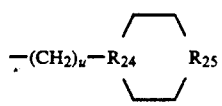

wherein
a) u is 1 to 3,
b) $R_{24}$ is N and
c) $R_{25}$ is O; or a pharmaceutically acceptable salt thereof.

10. The compound of claim 9 wherein $R_7$ is methoxymethoxy, $R_1$ is benzyl, $R_3$ is n-butyl, $R_4$ is cyclohexylmethyl and $R_{22}$ is isopropyl.

* * * * *